US012282014B2

(12) United States Patent
Kadoch et al.

(10) Patent No.: US 12,282,014 B2
(45) Date of Patent: Apr. 22, 2025

(54) METHODS OF IDENTIFYING COMPOUNDS THAT INTERFERE WITH ERG-DRIVEN MISGUIDANCE OF BAF COMPLEXES IN TMPRSS2-ERG DRIVEN PROSTATE CANCERS

(71) Applicant: Dana-Farber Cancer Institute, Inc., Boston, MA (US)

(72) Inventors: Cigall Kadoch, Tiburon, CA (US); Gabriel Sandoval, Lemont, IL (US); William C. Hahn, Newton, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 534 days.

(21) Appl. No.: 15/777,428

(22) PCT Filed: Nov. 18, 2016

(86) PCT No.: PCT/US2016/062911
§ 371 (c)(1),
(2) Date: May 18, 2018

(87) PCT Pub. No.: WO2017/087885
PCT Pub. Date: May 26, 2017

(65) Prior Publication Data
US 2018/0328913 A1 Nov. 15, 2018

Related U.S. Application Data

(60) Provisional application No. 62/257,512, filed on Nov. 19, 2015.

(51) Int. Cl.
*G01N 31/00* (2006.01)
*G01N 33/50* (2006.01)
*G01N 33/53* (2006.01)
*G01N 33/574* (2006.01)
*G01N 33/68* (2006.01)

(52) U.S. Cl.
CPC ... *G01N 33/5011* (2013.01); *G01N 33/57434* (2013.01); *G01N 33/6875* (2013.01); *G01N 2333/4703* (2013.01); *G01N 2500/02* (2013.01)

(58) Field of Classification Search
None
See application file for complete search history.

(56) References Cited

U.S. PATENT DOCUMENTS

| 3,717,642 | A | 2/1973 | Von Strandtmann |
| 4,109,496 | A | 8/1978 | Allerman et al. |
| 4,650,796 | A | 3/1987 | George et al. |
| 4,868,103 | A | 9/1989 | Stavrianopoulos et al. |
| 5,223,409 | A | 6/1993 | Ladner et al. |
| 5,225,422 | A | 7/1993 | Nagata et al. |
| 5,283,317 | A | 2/1994 | Saifer et al. |
| 5,631,169 | A | 5/1997 | Lakowicz et al. |
| 5,677,158 | A | 10/1997 | Zhou et al. |
| 5,801,030 | A | 9/1998 | McVey et al. |
| 5,858,358 | A | 1/1999 | June et al. |
| 5,883,223 | A | 3/1999 | Gray |
| 6,180,612 | B1 | 1/2001 | Hockensmith et al. |
| 6,309,634 | B1 | 10/2001 | Bankiewicz et al. |
| 6,352,694 | B1 | 3/2002 | June et al. |
| 6,551,786 | B2 | 4/2003 | Manfredi |
| 6,683,058 | B1 | 1/2004 | Tuszynski |
| 6,692,964 | B1 | 2/2004 | June et al. |
| 6,716,662 | B2 | 4/2004 | Akai |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 6,995,011 | B2 | 2/2006 | Itoh et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,205,103 | B2 | 4/2007 | Emerson |
| 7,232,566 | B2 | 6/2007 | June et al. |
| 7,572,631 | B2 | 8/2009 | Berenson et al. |

(Continued)

FOREIGN PATENT DOCUMENTS

| CN | 103038231 A | 4/2013 |
| CN | 104530013 A | 4/2015 |
| CN | 105473141 A | 4/2016 |
| CN | 107531668 A | 1/2018 |
| EA | 202192101 A1 | 12/2021 |
| EP | 0172096 A1 | 2/1986 |
| EP | 3018123 A1 | 5/2016 |
| JP | 2008-505963 A | 2/2008 |
| JP | 2011-507910 A | 3/2011 |
| JP | 2011-528016 A | 11/2011 |
| JP | 2014-500303 A | 1/2014 |
| JP | 2016-520515 A | 7/2016 |
| JP | 2021-512166 A | 5/2021 |
| JP | 2022-508155 A | 1/2022 |
| WO | 94/10300 A1 | 5/1994 |

(Continued)

OTHER PUBLICATIONS

Tuoc et al. (Developmental Cell, May 13, 2013 (May 13, 2013), vol. 25, pp. 256-269). (Year: 2013).*

(Continued)

*Primary Examiner* — Lisa V Cook
(74) *Attorney, Agent, or Firm* — Foley Hoag LLP; Deann F. Smith; Philip S. Choi

(57) ABSTRACT

The present invention provides methods of screening for compounds that interfere with the interaction between ERG. ETV1, ETV4 or ETV5 and mSWI/SNF (BAF) chromatin remodeling complex proteins. Included are methods of screening for compounds that interfere with the interaction between ERG, ETV1, ETV4 or ETV5 and BAF155. Methods of treating prostate cancer with compounds that interfere with the interaction between ERG, ETV1, ETV4 or ETV5 and mSWI/SNF (BAF) chromatin remodeling complex proteins are also provided.

6 Claims, 63 Drawing Sheets

Specification includes a Sequence Listing.

(56) References Cited

U.S. PATENT DOCUMENTS

| | | | |
|---|---|---|---|
| 8,324,367 | B2 | 12/2012 | Kaemmerer et al. |
| 8,642,660 | B2 | 2/2014 | Goldfarb |
| 8,697,359 | B1 | 4/2014 | Zhang |
| 8,703,761 | B2 | 4/2014 | Forster et al. |
| 8,771,945 | B1 | 7/2014 | Zhang |
| 8,795,965 | B2 | 8/2014 | Zhang |
| 8,865,406 | B2 | 10/2014 | Zhang et al. |
| 8,946,268 | B2 | 2/2015 | Lau et al. |
| 9,072,052 | B2 | 6/2015 | Griffin et al. |
| 9,126,985 | B2 | 9/2015 | Kley et al. |
| 9,353,051 | B2 | 5/2016 | Byrd et al. |
| 9,410,943 | B2 | 8/2016 | Kadoch et al. |
| 9,546,206 | B2 | 1/2017 | Ring et al. |
| 9,546,296 | B2 | 1/2017 | Wang et al. |
| 9,636,323 | B2 | 5/2017 | Lin et al. |
| 9,656,959 | B2 | 5/2017 | Ni et al. |
| 9,694,084 | B2 | 7/2017 | Bradner et al. |
| 9,708,338 | B2 | 7/2017 | Yukimasa et al. |
| 9,708,348 | B2 | 7/2017 | Castro et al. |
| 9,932,340 | B2 | 4/2018 | Dai et al. |
| 2002/0106632 | A1 | 8/2002 | Manfredi |
| 2005/0079512 | A1* | 4/2005 | Emerson ............ C12Q 1/6809 435/6.12 |
| 2007/0105181 | A1* | 5/2007 | Pope ................ G01N 33/57496 435/23 |
| 2012/0034867 | A1* | 2/2012 | Griffin ............. H04W 52/0254 455/41.1 |
| 2012/0035244 | A1* | 2/2012 | Chinnaiyan .......... A61K 31/501 514/44 A |
| 2013/0034867 | A1 | 2/2013 | Bomgarden et al. |
| 2015/0376139 | A1 | 12/2015 | Abdel-Meguid et al. |
| 2016/0032402 | A1 | 2/2016 | Jagani et al. |
| 2016/0039903 | A1 | 2/2016 | Ring et al. |
| 2016/0130663 | A1 | 5/2016 | Kohno et al. |
| 2016/0176916 | A1 | 6/2016 | Bradner et al. |
| 2016/0200721 | A1 | 7/2016 | Yukimasa et al. |
| 2016/0347708 | A1 | 12/2016 | Ebright et al. |
| 2017/0174688 | A1 | 6/2017 | Dai et al. |
| 2018/0086720 | A1 | 3/2018 | Albrecht et al. |
| 2018/0105500 | A1 | 4/2018 | Derbyshire et al. |
| 2018/0140722 | A1 | 5/2018 | Willis et al. |
| 2018/0258491 | A1 | 9/2018 | Jagani et al. |
| 2018/0303808 | A1 | 10/2018 | Agresta |
| 2018/0328913 | A1 | 11/2018 | Kadoch et al. |
| 2020/0069669 | A1 | 3/2020 | Grassian et al. |
| 2020/0206344 | A1 | 7/2020 | Kadoch et al. |
| 2020/0261434 | A1 | 8/2020 | Choe et al. |
| 2021/0009568 | A1 | 1/2021 | Zhou et al. |
| 2021/0038611 | A1 | 2/2021 | Anthony et al. |
| 2021/0171958 | A1 | 6/2021 | Chan et al. |
| 2021/0230154 | A1 | 7/2021 | Vaswani et al. |
| 2021/0230190 | A1 | 7/2021 | Ruppel et al. |
| 2021/0251988 | A1 | 8/2021 | Zhou et al. |
| 2021/0260171 | A1 | 8/2021 | Zhou et al. |
| 2021/0388040 | A1 | 12/2021 | Kadoch et al. |
| 2022/0016083 | A1 | 1/2022 | Centore et al. |
| 2022/0079940 | A1 | 3/2022 | Centore et al. |
| 2022/0098190 | A1 | 3/2022 | Ruppel et al. |
| 2022/0119378 | A1 | 4/2022 | Anthony et al. |
| 2022/0125776 | A1 | 4/2022 | Bearss et al. |
| 2022/0396604 | A1 | 12/2022 | Kadoch et al. |
| 2023/0035235 | A1 | 2/2023 | Kadoch et al. |
| 2023/0079819 | A1 | 3/2023 | Vaswani et al. |
| 2023/0121497 | A1 | 4/2023 | Vaswani et al. |
| 2023/0129003 | A1 | 4/2023 | Vaswani et al. |
| 2023/0138480 | A1 | 5/2023 | Anthony et al. |
| 2023/0145003 | A1 | 5/2023 | Wilson et al. |
| 2023/0149414 | A1 | 5/2023 | Anthony et al. |
| 2024/0101550 | A1 | 3/2024 | Vaswani et al. |
| 2024/0158387 | A1 | 5/2024 | Vaswani et al. |
| 2024/0189318 | A1 | 6/2024 | Huang |

FOREIGN PATENT DOCUMENTS

| | | |
|---|---|---|
| WO | WO-95/30761 A2 | 11/1995 |
| WO | WO-2000/024392 A1 | 5/2000 |
| WO | WO-00/59888 A1 | 10/2000 |
| WO | WO-00/59905 A1 | 10/2000 |
| WO | WO-2005/039643 A2 | 5/2005 |
| WO | WO-2005/112620 A2 | 12/2005 |
| WO | WO-2006/005941 A1 | 1/2006 |
| WO | WO-2006/051063 A1 | 5/2006 |
| WO | WO-2008/022396 A1 | 2/2008 |
| WO | WO-2009/086303 A2 | 7/2009 |
| WO | WO-2010/007046 A2 | 1/2010 |
| WO | WO-2011/115998 A2 | 9/2011 |
| WO | WO-2012/085650 A1 | 6/2012 |
| WO | WO-2013/116663 A1 | 8/2013 |
| WO | WO-2013116682 A1 | 8/2013 |
| WO | WO-2014/150395 A1 | 9/2014 |
| WO | WO-2015/002230 A1 | 1/2015 |
| WO | WO-2015/005473 A1 | 1/2015 |
| WO | WO-2015/103317 A1 | 7/2015 |
| WO | WO-2015/120320 A1 | 8/2015 |
| WO | WO-2015/121688 A1 | 8/2015 |
| WO | WO-2016/054491 A1 | 4/2016 |
| WO | WO-2016/138114 A1 | 9/2016 |
| WO | WO-2016/160718 A1 | 10/2016 |
| WO | WO-2016/207212 A1 | 12/2016 |
| WO | WO-2017/024318 A1 | 2/2017 |
| WO | WO-2017060470 A1 | 4/2017 |
| WO | WO-2017/087885 A1 | 5/2017 |
| WO | WO-2017/118734 A1 | 7/2017 |
| WO | WO-2017/150395 A1 | 9/2017 |
| WO | WO-2017/158381 A1 | 9/2017 |
| WO | WO-2018/148443 A1 | 8/2018 |
| WO | WO-2018/160636 A1 | 9/2018 |
| WO | WO-2018/175324 A1 | 9/2018 |
| WO | WO-2019/040098 A1 | 2/2019 |
| WO | WO-2019/138017 A1 | 7/2019 |
| WO | WO-2019/142192 A1 | 7/2019 |
| WO | WO-2019/152437 A1 | 8/2019 |
| WO | WO-2019/152440 A1 | 8/2019 |
| WO | WO-2019/226915 A1 | 11/2019 |
| WO | WO-2020/035779 A1 | 2/2020 |
| WO | WO-2020/081556 A2 | 4/2020 |
| WO | WO-2020/081588 A1 | 4/2020 |
| WO | WO-2020/106915 A1 | 5/2020 |
| WO | WO-2020/127685 A1 | 6/2020 |
| WO | WO-2020/160100 A1 | 8/2020 |
| WO | WO-2020/160180 A1 | 8/2020 |
| WO | WO-2021/081032 A1 | 4/2021 |
| WO | WO-2021/155262 A1 | 8/2021 |
| WO | WO-2021/155264 A1 | 8/2021 |
| WO | WO-2021/155316 A1 | 8/2021 |
| WO | WO-2021/155320 A1 | 8/2021 |
| WO | WO-2021/155321 A2 | 8/2021 |
| WO | WO-2021/183218 A1 | 9/2021 |
| WO | WO-2021/236080 A1 | 11/2021 |
| WO | WO-2022/192621 A1 | 9/2022 |
| WO | WO-2022/198043 A1 | 9/2022 |
| WO | WO-2023/009834 A2 | 2/2023 |
| WO | WO-2023/196560 A1 | 10/2023 |
| WO | WO-2023/196565 A1 | 10/2023 |
| WO | WO-2023/196567 A2 | 10/2023 |
| WO | WO-2024/024428 A1 | 2/2024 |
| WO | WO-2024/031875 A1 | 2/2024 |
| WO | WO-2024/086577 A1 | 4/2024 |
| WO | WO-2024/216136 A1 | 10/2024 |
| WO | WO-2024/216151 A1 | 10/2024 |

OTHER PUBLICATIONS

Zong et al. (PNAS, Jul. 28, 2009, vol. 106, No. 30, pp. 12465-12470) (Year: 2009).*

Kunderfranco et al. PLos One, May 2010, vol. 5, Issue 5, e10547, pp. 1-17 (Year: 2010).*

Shi et al. (Genes & Development, Nov. 27, 2013, vol. 27, pp. 2648-2662) (Year: 2013).*

Shen et al. (Cancer Research, Dec. 15, 2008, 68(24), pp. 10154-10162) (Year: 2008).*

(56) References Cited

OTHER PUBLICATIONS

Gingras et al. (J.Physiology.563.1, 2005, pp. 11-21) (Year: 2005).*
Machanick, P. et al.(2011) "MEME-ChIP: motif analysis of large DNA datasets," Bioinformatics (Oxford, England). 27:1696-1697.
Mackereth, C.D. et al. (2004) "Diversity in structure and function of the Ets family PNT domains," J Mol Biol. 342:1249-1264.
Madura et al. (1993) "N-recognin/Ubc2 interactions in the N-end rule pathway," J Biol Chem. 268:12046-12054.
McConnell, H.M. et al. (1992) "The cytosensor microphysiometer: biological applications of silicon technology," Science. 257:1906-1912.
Mele, M. et al. (2015) "Human genomics. The human transcriptome across tissues and individuals," Science. 348:660-665.
Mounir, Z. et al. (2016) "ERG signaling in prostate cancer is driven through PRMT5-dependent methylation of the androgen receptor," Elife. 5.
Nagaich, A.K. et al. (2004) "Rapid periodic binding and displacement of the glucocorticoid receptor during chromatin remodeling," Mol Cell. 14:163-174.
Nam et al. (2007) "Expression of the TMPRSS2:ERG fusion gene predicts cancer recurrence after surgery for localised prostate cancer," Br J Cancer. 97(12):1690-1695.
Ong, S.E. et al. (2006) "A practical recipe for stable isotope labeling by amino acids in cell culture (SILAC)," Nat Protoc. 1:2650-2660.
Paulo, P. (2012) "FLI1 is a novel ETS transcription factor involved in gene fusions in prostate cancer," Genes Chromosomes Cancer. 51:240-249.
Petrovics et al. (2005) "Frequent overexpression of ETS-related gene-1 (ERG1) in prostate cancer transcriptome," Oncogene. 24(23):3847-3852.
Pomerantz, M.M. et al. (2015) "The androgen receptor cistrome is extensively reprogrammed in human prostate tumorigenesis," Nat Genet. 47:1346-1351.
Prensner, J.R. et al. (2013) "The long noncoding RNA SChLAP1 promotes aggressive prostate cancer and antagonizes the SWI/SNF complex," Nat Genet. 45:1392-1398.
Quinlan, A.R. et al. (2010) "BEDTools: a flexible suite of utilities for comparing genomic features," Bioinformatics (Oxford, England). 26:841-842.
Rajput et al. (2007) "Frequency of the TMPRSS2:ERG gene fusion is increased in moderate to poorly differentiated prostate cancers," J Clin Pathol. 60(11):1238-1243.
Rappsilber, J. et al. (2007) "Protocol for micro-purification, enrichment, pre-fractionation and storage of peptides for proteomics using StageTips," Nat Protoc. 2:1896-1906.
Rivas, G. et al. (1993) "New Developments In the Study of Biomolecular Associations Via Sedimentation Equilibrium," Trends Biochem Sci. 18:284-7.
Roberts, C.W. et al. (2004) "The SWI/SNF complex—chromatin and cancer," Nat Rev Cancer. 4:133-142.
Scott et al. (1990) "Searching for peptide ligands with an epitope library," Science. 249(4967):386-390.
Shen, H. et al. (2008) The SWI/SNF ATPase Brm is a gatekeeper of proliferative control in prostate cancer. Cancer Res. 68:10154-10162.
Shi et al. (2013) "Role of SWI/SNF in acute leukemia maintenance and enhancer-mediated Myc regulation," Genes & Development. 27:2648-2662.
Siegel, R.L. et al. (2015) "Cancer statistics, 2015," CA Cancer J Clin. 65:5-29.
Sjolander, S. et al. "Integrated fluid handling system for biomolecular interaction analysis," Anal Chem. 63:2338-2345.
Subramanian, A. et al. (2005) "Gene set enrichment analysis: a knowledge-based approach for interpreting genome-wide expression profiles," Proceedings of the National Academy of Sciences USA. 102:15545-15550.
Sun, C. et al. (2008) "TMPRSS2-ERG fusion, a common genomic alteration in prostate cancer activates C-MYC and abrogates prostate epithelial differentiation," Oncogene. 27:5348-5353.
Szabo et al. (1995) "Surface plasmon resonance and its use in biomolecular interaction analysis (BIA)," Curr Opin Struc Biol. 5:699-705.
Tomlins, S.A. et ai. (2008) "Role of the TMPRSS2-ERG gene fusion in prostate cancer," Neoplasia. 10:177-188.
Tomlins, S.A. et al. (2005) "Recurrent fusion of TMPRSS2 and ETS transcription factor genes in prostate cancer," Science. 310:644-648.
Tomlins, S.A. et al. (2006) "TMPRSS2: ETV4 gene fusions define a third molecular subtype of prostate cancer," Cancer Res. 66:3396-3400.
Varambally, S. et al. (2002) "The polycomb group protein EZH2 is involved in progression of prostate cancer," Nature. 419:624-629.
Verger, A. et al. (2001) "Identification of amino acid residues in the ETS transcription factor Erg that mediate Erg-Jun/Fos-DNA ternary complex formation," J Biol Chem. 276:17181-17189.
Wollenick et al. (2011) "Synthetic transactivation screening reveals ETV4 as broad coactivator of hypoxia-inducible factor signaling," Nucleic Acids Research. 40:1928-1943.
Yang, Y.A. et al. (2013) "EZH2, an epigenetic driver of prostate cancer," Protein Cell. 4:331-341.
Yildirim et al. (2011) "Mbd3/NURD complex regulates expression of 5-hydroxymethylcytosine marked genes in embryonic stem cells," Cell. 147:1498-1510.
Yu, J. et al. (2010) "An integrated network of androgen receptor, polycomb, and TMPRSS2-ERG gene fusions in prostate cancer progression," Cancer Cell. 17:443-454.
Yu, M. et al. (2012) "Direct recruitment of polycomb repressive complex 1 to chromatin by core binding transcription factors," Mol Cell. 45:330-343.
Tuoc et al. (2013) "Chromatin regulation by BAF170 controls cerebral cortical size and thickness," Developmental Cell. 25:256-269.
Zervos et al. (1993) "Mxi1, a protein that specifically interacts with Max to bind Myc-Max recognition sites," Cell. 72:223-232.
Zhang, Y. et al. (2008) "Model-based analysis of ChIP-Seq (MACS)," Genome Biology. 9:R137.
Zong, Y. et al. (2009) "ETS family transcription factors collaborate with alternative signaling pathways to induce carcinoma from adult murine prostate cells," Proceedings of the National Academy of Sciences of the United States of America. 106:12465-12470.
Zuckermann et al. (1994). "Discovery of Nanomolar Ligands for 7-Transmembrane G-Protein-Coupled Receptors from a Diverse N-(Substituted)glycine Peptoid Library," J. Med. Chem. 37:2678-2685.
International Search Report with Written Opinion for PCT/US2016/062911 dated Mar. 3, 2017.
International Preliminary Report on Patentability or PCT/US2016/062911 dated May 22, 2018.
Adamo, P. et al. (2016) "The oncogene ERG: a key factor in prostate cancer," Oncogene. 35:403-414.
Anders, S. et al. (2015) "HTSeq—a Python framework to work with high-throughput sequencing data," Bioinformatics (Oxford, England). 31:166-169.
Asangani, I.A. et al. (2014) "Therapeutic targeting of BET bromodomain proteins in castration-resistant prostate cancer," Nature. 510:278-282.
Attard et al. (2008) "Duplication of the fusion of TMPRSS2 to ERG sequences identifies fatal human prostate cancer," Oncogene 27(3):253-263.
Lupien, M. et al. (2008) "FoxA1 translates epigenetic signatures into enhancer-driven lineage-specific transcription," Cell. 132:958-970.
Basuyaux, J.P. et al.(1997) "The Ets transcription factors interact with each other and with the c-Fos/c-Jun complex via distinct protein domains in a DNA-dependent and -independent manner," J Biol Chem. 272:26188-26195.
Bendall, S.C. et al. (2008) "Prevention of amino acid conversion in SILAC experiments with embryonic stem cells," Mol Cell Proteomics. 7:1587-1597.
Berger, R. et al. (2004) "Androgen-induced differentiation and tumorigenicity of human prostate epithelial cells," Cancer Res. 64:8867-8875.

(56) References Cited

OTHER PUBLICATIONS

Borno, S.T. et al. (2012) "Genome-wide DNA methylation events in 25 TMPRSS2-ERG fusion-negative prostate cancers implicate an EZH2-dependent mechanism with miR-26a hypermethylation," Cancer Discov. 2:1024-1035.

Camuzeaux et al. (2005) "Imaging Erg and Jun transcription factor interaction in living cells using fluorescence resonance energy transfer analyses," Biochemical and Biophysical Research Communications. 332:1107-1114.

Cancer Genome Atlas Research, N. (2015) The Molecular Taxonomy of Primary Prostate Cancer, Cell. 163:1011-1025.

Carell et al. (1994) "A Novel Procedure for the Synthesis of Libraries Containing Small Organic Molecules," Angew. Chem. Int. Ed. Engl. 33:2059-2061.

Carell et al. (1994) "A Solution-Phase Screening Procedure for the Isolation of Active Compounds from a Library of Molecules," Angew. Chem. Int. Ed. Engl. 33:2061-2064.

Chen, Y. et al. (2013) "ETS factors reprogram the androgen receptor cistrome and prime prostate tumorigenesis in response to PTEN loss," Nat Med. 19:1023-1029.

Chng, K.R. et al.(2012) "A transcriptional repressor co-regulatory network governing androgen response in prostate cancers," EMBO J. 31:2810-2823.

Cho et al. (1993) "An unnatural biopolymer," Science. 261:1303-1305.

Clark, J. et al. (2008) "Complex patterns of ETS gene alteration arise during cancer development in the human prostate," Oncogene. 27:1993-2003.

Clark, J.P. et al. (2009) "ETS gene fusions in prostate cancer," Nat Rev Urol. 6:429-439.

Cull et al. (1992) "Screening for receptor ligands using large libraries of peptides linked to the C terminus of the lac repressor," Proc Natl Acad Sci U S A. 89(5):1865-1869.

Cwirla et al. (1990) "Peptides on phage: A vast library of peptides for identifying ligands," Proc. Natl. Acad. Sci. USA. 87:6378-6382.

Delattre, O. et al. (1992) "Gene fusion with an ETS DNA-binding domain caused by chromosome translocation in human tumours," Nature. 359:162-165.

Demichelis et al. (2007) "TMPRSS2:ERG gene fusion associated with lethal prostate cancer in a watchful waiting cohort," Oncogene. 26(31):4596-4599.

Devlin (1990) "Random peptide libraries: a source of specific protein binding molecules," Science. 249:404-406.

DeWitt et al. (1993) ""Diversomers": an approach to nonpeptide, nonoligomeric chemical diversity," Proc. Natl. Acad. Sci. U.S.A. 90(15):6909-6913.

Dobin, A. et al. (2013) "STAR: ultrafast universal RNA-seq aligner," Bioinformatics (Oxford, England). 29:15-21.

Donaldson, L.W. et al. (1996) "Solution structure of the ETS domain from murine Ets-1: a winged helix-turn-helix DNA binding motif," EMBO J. 15:125-134.

Erb et al. (1994) "Recursive deconvolution of combinatorial chemical libraries," Proc. Natl. Acad. Sci. USA 91:11422-11426.

Felicia et al. (1991) "Selection of antibody ligands from a large library of oligopeptides expressed on a multivalent exposition vector," J Mol Biol. 222:301-310.

Feng, J. et al. (2012) "GFOLD: a generalized fold change for ranking differentially expressed genes from RNA-seq data," Bioinformatics (Oxford, England). 28:2782-2788.

Fodor et al. (1993) "Multiplexed biochemical assays with biological chips," Nature. 364(6437):555-556.

Gallop et al. (1994) "Applications of combinatorial technologies to drug discovery. 1. Background and peptide combinatorial libraries," J Med Chem. 37:1233-51.

Gene Ontology Consortium. (2015) "Gene Ontology Consortium: going forward," Nucleic Acids Res. 43:1049-1056.

Hage, D.S. et al. (1997) "Recent advances in chromatographic and electrophoretic methods for the study of drug-protein interactions," J Chromatogr B Biomed Sci Appl. 699:499-525.

Heegaard et al. (1998) "Capillary electrophoresis for the study of affinity interactions," J Mol Recognit. 11:141-8.

Helgeson, B.E. et al. (2008) "Characterization of TMPRSS2:ETV5 and SLC45A3:E11/5 gene fusions in prostate cancer," Cancer Res. 68:73-80.

Ho, L. (2009) "An embryonic stem cell chromatin remodeling complex, esBAF, is an essential component of the core pluripotency transcriptional network," Proceedings of the National Academy of Sciences of the United States of America. 106:5187-5191.

Houghten (1992) "The use of synthetic peptide combinatorial libraries for the identification of bioactive peptides," Biotechniques. 13:412-421.

Ichikawa, H. et al. (1994) "An RNA-binding protein 25 gene, TLS/FUS, is fused to ERG in human myeloid leukemia with t(16;21) chromosomal translocation," Cancer Res. 54:2865-2868.

Kadoch, C. et al. (2013) "Proteomic and bioinformatic analysis of mammalian SWI/SNF complexes identifies extensive roles in human malignancy," Nat Genet. 45:592-601.

Kadoch, C. et al. (2015) "Mammalian SWI/SNF chromatin remodeling complexes and cancer: Mechanistic insights gained from human genomics," Sci Adv. 1:e1500447.

Karim et al. (1990) "The ETS-domain a new DNA-binding motif that recognizes a purine-rich core DNA sequence," Genes & Development. 4:1451-1453.

Klezovitch, O. et al.(2008) "A causal role for ERG in neoplastic transformation of prostate epithelium," Proceedings of the National Academy of Sciences of the United States of America. 105:2105-2110.

Kumar-Sinha, C. et al. (2008) "Recurrent gene fusions in prostate cancer," Nat Rev Cancer. 8:497-511.

Kunderfranco, P. et al. (2010) "ETS transcription factors control transcription of EZH2 and epigenetic silencing of the tumor suppressor gene Nkx3.1 in prostate cancer," PLoS One. 5:e10547.

Lam (1991) "A new type of synthetic peptide library for identifying ligand-binding activity," Nature. 354:82-84.

Lam (1997) "Application of combinatorial library methods in cancer research and drug discovery," Anticancer Drug Des. 12(3):145-67.

Langmead, B. et al. (2012) "Fast gapped-read alignment with Bowtie 2," Nature Methods. 9:357-359.

Link, K.A. et al. (2008) "Targeting the BAF57 SWI/SNF subunit in prostate cancer: a novel platform to control androgen receptor activity," Cancer Res. 68:4551-4558.

Love, M.I. et al. (2014) "Moderated estimation of fold change and dispersion for RNA-seq data with DESeq2," Genome Biology. 15:550.

"FLI1 gene", MedlinePlus, published May 1, 2012, <https://medlineplus.gov/genetics/> (3 pages).

Advani et al., "A Phase 1 study of imatinib mesylate in combination with cytarabine and daunorubicin for c-kit positive relapsed acute myeloid leukemia." Leukemia research 34.12 (2010): 1622-1626.

Alazawi, "Foghorn Therapeutics," Blackseed Bio, last updated Mar. 4, 2022, retrieved Jul. 24, 2023, from <https://blackseedbio.com/reports/fhtx#pipeline> (26 pages).

Boulay et al., "Cancer-specific retargeting of BAF complexes by a prion-like domain." Cell 171.1 (2017): 163-178.

CAS RN: 1223164-86-0; STN entry date: May 14, 2010; N-[2-[[4-(3-Fluoro-4-methoxyphenyl)-2- thiazolyl]amino]-2-oxoethyl]-2-methyl-3-furancarboxamide.

CAS RN: 1300403-14-8; STN entry date May 25, 2011; 5-Methyl-N-[2-oxo-2-[ (5-phenyl-2-pyridinyl)amino]ethyl]-2-thiophenecarboxamide.

CAS RN: 924410-17-3; STN entry date: Mar. 2, 2007; 5-Methyl-N-[2-oxo-2-[ (4-phenyl-2-thiazolyl)amino]ethyl]-2-thiophenecarboxamide.

CAS RN: 924420-04-2; STN entry date: Mar. 2, 2007; 5-Methyl-N-[2-oxo-2-[[4-(4-pyridinyl)-2-thiazolyl]amino]ethyl]-2-thiophenecarboxamide.

Centore et al., "Abstract 1224: Discovery of novel BAF inhibitors for the treatment of transcription factor-driven cancers," Poster Presentations—Proffered abstracts, Cancer Research 81(13_Supplement): 1224.

(56) References Cited

OTHER PUBLICATIONS

Chandler et al., "ARID1a-DNA interactions are required for promoter occupancy by SWI/SNF," Mol Cell Biol. 33(2):265-80.
Chattopadhyay et al., "Uveal melanoma: From diagnosis to treatment and the science in between," Cancer. 122(15):2299-2312.
Coban et al., "Synthesis, biological activity screening and molecular modeling study of acylaminoacetamide derivatives," Med Chem Res. 24(10):3710-29.
Danziger et al., "Automated site-directed drug design: a general algorithm for knowledge acquisition about hydrogen-bonding regions at protein surfaces", Proc R Soc Lond B Biol Sci. 236(1283): 101-113.
Database Registry, RN 1004932-80-2, entered Feb. 21, 2008.
Database Registry, RN 1175782-23-6, entered Aug. 26, 2009.
Database Registry, RN 1315743-98-6, entered Aug. 11, 2011.
Database Registry, RN 1323331-37-8, entered Aug. 25, 2011.
Database Registry, RN 1323542-96-6, entered Aug. 26, 2011.
Database Registry, RN 1324163-01-0, entered Aug. 28, 2011.
Database Registry, RN 1327304-26-6, entered Sep. 2, 2011.
Database Registry, RN 878254-76-3, entered Mar. 28, 2006.
Décor et al., "Design, synthesis and biological evaluation of novel aminothiazoles as antiviral compounds acting against human rhinovirus," Bioorg Med Chem Lett. 23(13):3841-7 (2013).
Dominguez et al. "Beyond editing: Repurposing CRISPR-Cas9 for Precision Genome Regulation and Interrogation," available in PMC Jun. 27, 2016, published in final edited form as: Nat Rev Mol Cell Biol. 17(1):5-15 (Jan. 2016).
Extended European Search Report for EP Application No. 19748410.8 dated Sep. 24, 2021.
Extended European Search Report for EP Application No. 19887386.1 dated Dec. 5, 2022.
Extended European Search Report for EP Application No. 20749261.2 dated Oct. 18, 2022.
Extended European Search Report for EP Application No. 21748261.1 dated Jan. 29, 2024.
Fadul et al., "EWS/FLI utilizes NKX2-2 to repress mesenchymal features of Ewing sarcoma," Genes Cancer 6(3-4):129-43 (2015).
Fathi et al., "Differentiation syndrome with lower-intensity treatments for acute myeloid leukemia," Am J Hematol. 96(6):735-46 (Jun. 1, 2021).
Gaj et al. "ZFN, TALEN and CRISPR/Cas-based Methods for Genome Engineering," available in PMC Jul. 1, 2014, published in final edited form as: Trends Biotechnol. 31(7):397-405 (Jul. 2013).
Godwin et al., "Gemtuzumab ozogamicin in acute myeloid leukemia," Leukemia 31(9):1855-68 (Sep. 2017).
Grohar et al., "Ecteinascidin 743 interferes with the activity of EWS-FLI1 in Ewing sarcoma cells," Neoplasia 13(2):145-53 (Feb. 2011).
Herrero-Martin et al., "Stable interference of EWS-FLI1 in an Ewing sarcoma cell line impairs IGF-1/IGF-1R signalling and reveals TOPK as a new target," Br J Cancer 101(1):80-90 (Jul. 7, 2009).
Hohmann et al., "Sensitivity and engineered resistance of myeloid leukemia cells to BRD9 inhibition," Nat Chem Biol. 12(9): 672-679 (Sep. 2016) (12 pages).
Hosler et al. Chapter 8: 199-229, 50 pages (2014).
International Preliminary Report on Patentability for International Application No. PCT/US19/15722 dated Aug. 4, 2020.
International Preliminary Report on Patentability for International Application No. PCT/US19/56312 dated Apr. 14, 2021.
International Preliminary Report on Patentability for International Application No. PCT/US20/33829 dated Nov. 17, 2022.
International Preliminary Report on Patentability for International Application No. PCT/US22/19506 dated Sep. 12, 2023.
International Preliminary Report on Patentability for International Application No. PCT/US22/20943 dated Sep. 12, 2023.
International Search Report and Written Opinion for International Application No. PCT/US18/000339 dated Jan. 28, 2019.
International Search Report and Written Opinion for International Application No. PCT/US19/15722 dated May 31, 2019.
International Search Report and Written Opinion for International Application No. PCT/US19/56312 dated Jan. 14, 2020.
International Search Report and Written Opinion for International Application No. PCT/US19/56365 dated Jan. 30, 2020.
International Search Report and Written Opinion for International Application No. PCT/US19/62525 dated Feb. 18, 2020.
International Search Report and Written Opinion for International Application No. PCT/US20/15605 dated Jun. 16, 2020.
International Search Report and Written Opinion for International Application No. PCT/US20/15723 dated Jul. 2, 2020.
International Search Report and Written Opinion for International Application No. PCT/US20/33829 dated Aug. 17, 2020.
International Search Report and Written Opinion for International Application No. PCT/US21/15876 dated Apr. 7, 2021.
International Search Report and Written Opinion for International Application No. PCT/US21/15878 dated Jun. 4, 2021.
International Search Report and Written Opinion for International Application No. PCT/US22/19506 dated Jun. 7, 2022.
International Search Report and Written Opinion for International Application No. PCT/US22/20943 dated Jun. 14, 2022.
International Search Report and Written Opinion for International Application No. PCT/US23/17821 dated Jun. 30, 2023.
International Search Report and Written Opinion for International Application No. PCT/US23/17829 dated Aug. 23, 2023.
International Search Report and Written Opinion for International Application No. PCT/US23/17839 dated Sep. 6, 2023.
International Search Report and Written Opinion for International Application No. PCT/US23/77088 dated Mar. 4, 2024.
International Search Report and Written Opinion for International Application No. PCT/US24/24407 dated Jun. 24, 2024.
International Search Report and Written Opinion for International Application No. PCT/US24/24428 dated Jul. 16, 2024.
International Search Report and Written Opinion for International Application No. PCT/US24/31875 dated Oct. 18, 2024.
Jones et al., "A novel series of potent and selective ketone histone deacetylase inhibitors with antitumor activity in vivo," J Med Chem. 51(8):2350-3 (Apr. 24, 2008).
Kadoch et al., "Reversible Disruption of mSWI/SNF (BAF) Complexes by the SS18-SSX Oncogenic Fusion in Synovial Sarcoma," available in PMC May 16, 2013, published in final edited form as: Cell. 153(1):71-85 (2013).
Kedage et al., "An Interaction with Ewing's Sarcoma Breakpoint Protein EWS Defines a Specific Oncogenic Mechanism of ETS Factors Rearranged in Prostate Cancer," Cell Rep. 17(5):1289-301 (Oct. 25, 2016).
McBride et al., "Disruption of mammalian SWI/SNF and polycomb complexes in human sarcomas: mechanisms and therapeutic opportunities," J Pathol. 244(5): 638-649 (Apr. 2018).
Michel et al., "Abstract PR15: BRD9 defines a novel mammalian SWI/SNF (BAF) complex configuration which supports proliferation in AML," Clin Cancer Res. 23(24_Suppl) Abstract PR15 (2017).
Mill et al., "RUNX1-targeted therapy for AML expressing somatic or germline mutation in RUNX1," Blood 134(1):59-73 (Jul. 4, 2019).
Office Action for Chinese Patent Application No. 201980023925.9 dated Apr. 20, 2022.
Papillon et al., "Discovery of Orally Active Inhibitors of Brahma Homolog (BRM)/SMARCA2 ATPase Activity for the Treatment of Brahma Related Gene 1 (BRG1)/SMARCA4-Mutant Cancers," J Med Chem. 61(22):10155-72 (Nov. 2018).
Pescatore et al., "Optimization of a series of potent and selective ketone histone deacetylase inhibitors," Bioorg Med Chem Lett. 18(20):5528-32 (Oct. 15, 2008).
PubChem CID 117640569, "N-[2-[[4-(4-Methoxyphenyl)-1,3-thiazol-2-yl]amino]-2-oxoethyl]-1,3-thiazole-5-carboxamide," https://pubchem.ncbi.nlm.nih.gov/compound/117640569, created Feb. 23, 2016 (9 pages).
PubChem CID 56442706, "1-(4-Methoxyphenyl)-N-[2-oxo-2-[4-(1,2,4-triazol-1-yl)anilino]ethyl]pyrazole-3-carboxamide," https://pubchem.ncbi.nlm.nih.gov/compound/56442706, created Jan. 25, 2012 (8pages).

(56) References Cited

OTHER PUBLICATIONS

PubChem CID 91946137, "N-[2-[(1-Ethylpyrazol-3-yl}amino]-2-oxoethyl]-1-methylpyrazole-3-carboxamide," https://pubchem.ncbi.nlm.nih.gov/compound/91946137, created Oct. 22, 2015 (8pages).
PubChem Compound Summary for CID 155037309, dated Dec. 19, 2020 (9 pages).
PubChem Compound Summary for CID No. 136572628, "4-Chloro-N-[2-(cyclopentylamino)-2-oxoethyl]-5-nitro-1H-pyrazole-3-carboxamide," created Jan. 24, 2019, <https://pubchem.ncbi.nlm.nih.gov/compound/136572628>, (7 pages).
PubChem Compound Summary for CID No. 49726797, "N-Methyl-N-(2-oxo-2-((4-(pyridin-3-yl)thiazol-2-yl)amino)ethyl)-1H-indole-3-carboxamide," created Nov. 27, 2010, <https://pubchem.ncbi.nlm.nih.gov/compound/497267 7>, (8 pages).
PubChem Compound Summary for CID No. 91945707, "N-[2-[(4,5-Dimethyl-1,3-thiazol-2-yl)amino]-2-oxoethyl]-1-methylpyrazole-3-carboxamide," created Oct. 22, 2015 <https://pubchem.ncbi.nlm.nih.gov/compound/91945707>, (8 pages).
PubChem Compound Summary for PubChem CID 49726798, "N-(2-((4-(Furan-2-yl)thiazol-2-yl)amino)-2-oxoethyl)-N-methyl-1H-indole-3-carboxamide," created Nov. 27, 2010 <https://pubchem.ncbi.nih.gov/compound/49726798> (8 pages).
PubChem Compound Summary for SID 172131678, dated Dec. 9, 2014 (8 pages).
PubChem, "Compound Summary for CID 108452511," <https://pubchem.ncbi.nlm.nih.gov/compound/108452511>, created Jan. 15, 2016, retrieved Jan. 4, 2021 (7 pages).
PubChem, "Compound Summary for CID 2955118," <https://pubchem.ncbi.nlm.nih.gov/compound/2955118>, created Jul. 29, 2005, retrieved Mar. 22, 2017 (13 pages).
PubChem, "Compound Summary for CID 7325930," <https://pubchem.ncbi.nlm.nih.gov/compound/7325930>, created Jul. 29, 2006, retrieved Mar. 22, 2017 (11 pages).
PubChem, "Compound Summary for CID 970466," <https://pubchem.ncbi.nlm.nih.gov/compound/970466>, created Jul. 9, 2005, retrieved Mar. 22, 2017 (11 pages).
Rago et al., "Exquisite Sensitivity to Dual BRG1/BRM ATPase Inhibitors Reveals Broad SWI/SNF Dependencies in Acute Myeloid Leukemia," Mol Cancer Res. 20(3):361-72 (Mar. 1, 2022).
Ramos et al., "Current Approaches in the Treatment of Relapsed and Refractory Acute Myeloid Leukemia," J Clin Med. 4(4):665-95 (Apr. 2015).
Riggi et al., "EWS-FLI1 utilizes divergent chromatin remodeling mechanisms to directly activate or repress enhancer elements in Ewing sarcoma," Cancer Cell 26(5):668-81 (Nov. 10, 2014) (28 pages).
Sankar et al., "Promiscuous partnerships in Ewing's sarcoma," Cancer Genet. 204(7):351-65 (Jul. 2011) (28 pages).
Schiefer et al., "Design, synthesis, and optimization of novel epoxide incorporating peptidomimetics as selective calpain inhibitors," J Med Chem. 56(15):6054-68 (Feb. 7, 2013).
Simone, Part XIV: Oncology: Introduction, Textbook of Medicine, Bennett et al., 20(1), 1004-1010 (1997).
Spickler et al., "Phosphatidylinositol 4-kinase III beta is essential for replication of human rhinovirus and its inhibition causes a lethal phenotype in vivo," Antimicrob Agents Chemother. 57(7):3358-68 (Jul. 2013).
STN Registry Database, CAS RN 858073-83-3, Albany Molecular Research, Inc., entered Aug. 3, 2005.
STN Registry Database, RN 1010893-05-6, entered Mar. 30, 2008.
STN Registry Database, RN 1049271-26-2, entered Sep. 14, 2008.
STN Registry Database, RN 1081662-32-9, entered Dec. 8, 2008.
STN Registry Database, RN 1209112-42-4, entered Mar. 12, 2010.
STN Registry Database, RN 1246047-75-5, entered Oct. 12, 2010.
STN Registry Database, RN 1308280-67-2, entered Jun. 9, 2011.
STN Registry Database, RN 1351682-19-3, entered Dec. 22, 2011.
STN Registry Database, RN 1401558-47-1, entered Oct. 22, 2012.
STN Registry Database, RN 1455783-72-8, entered Oct. 6, 2013.
STN Registry Database, RN 1576383-94-2, entered Mar. 31, 2014.
STN Registry Database, RN 1586193-45-4, entered Apr. 17, 2014.
STN Registry Database, RN 1827759-12-5, entered Dec. 13, 2015.
STN Registry Database, RN 1831899-24-1, entered Dec. 17, 2015.
STN Registry Database, RN 1839545-15-1, entered Dec. 31, 2015.
STN Registry Database, RN 923768-18-7, entered Feb. 28, 2007.
STN Registry Database, RN 923809-79-4, entered Feb. 28, 2007.
STN Registry Database, RN 931893-54-8, entered Apr. 23, 2007.
STN Registry Database, RN 932130-00-2, entered Apr. 24, 2007.
STN Registry Database, RN 938283-11-5, entered Jun. 22, 2007.
Takigami et al., "Synthetic siRNA targeting the breakpoint of EWS/Fli-1 inhibits growth of Ewing sarcoma xenografts in a mouse model," Int J Cancer 128(1):216-26 (2011).
Tikdari et al., "Reaction of 2-Aminothiazoles with 5-Oxazolones," ChemInform. 18(47): Abstract 199 (1987).
Tikdari et al., "Reaction of 2-Aminothiazoles with 5-Oxazolones," Indian Journal of Chemistry 26B:478-9 (May 1987).
Triandafillidi et al., "tert-Butyl ester or benzylamide of the dipeptide Pro-Gly as organocatalysts for the asymmetric aldol reaction," Tetrahedron 71:932-40 (Feb. 2015).
Tsai et al. "Dimeric CRISPR RNA-guided FokI Nucleases for Highly Specific Genome Editing," available in PMC Dec. 1, 2014, published in final edited form as: Nat Biotechnol. 32(6):569-576 (Jun. 2014).
Vachtenheim et al., "SWI/SNF chromatin remodeling complex is critical for the expression of microphthalmia-associated transcription factor in melanoma cells," Biochemical and Biophysical Research Communications. 392(3):454-459 (2010).
Vela et al., "Discovery of Enhancers of the Secretion of Leukemia Inhibitory Factor for the Treatment of Multiple Sclerosis," J Biomol Screen. 21(5):437-45 (2016).
Wahedy et al., "Facile Synthesis and In-Vitro Antimicrobial Activity of Some Novel 2-Hetroamido-5-Amino Benzimidazoles," Am J PharmTech Res. 3(2):868-82 (2013).
Wu et al., "Targeting the chromatin remodeling enzyme BRG1 increases the efficacy of chemotherapy drugs in breast cancer cells," Oncotarget 7(19):27158-75 (2016).
Zhang et al., "Discovery of novel dual-action antidiabetic agents that inhibit glycogen phosphorylase and activate glucokinase," Eur J Med Chem. 58:624-39 (2012).
Zvarec et al., "5-Benzylidenerhodanine and 5-benzylidene-2-4-thiazolidinedione based antibacterials," Bioorg Med Chem Lett. 22(8):2720-2 (2012).

\* cited by examiner

SILAC Mass-Spec
TMPRSS2-ERG PrCa Cells (VCaP)

| Rank | Gene Names | Razor + unique peptides | Sequence coverage [%] | P. Value |
|---|---|---|---|---|
| 1 | LBR | 8 | 16.4 | 1.35E-05 |
| 2 | ERG | 43 | 92.6 | 2.59E-07 |
| 3 | GSTP1 | 7 | 55.7 | 3.23E-06 |
| 4 | SRI | 7 | 39.9 | 7.73E-07 |
| 5 | TMEM160 | 10 | 37.2 | 9.13E-07 |
| 6 | SYNGR2 | 6 | 17.1 | 8.34E-07 |
| 7 | SUCLG2 | 5 | 14.1 | 3.97E-06 |
| 8 | SMARCC2 | 67 | 45.9 | 1.82E-06 |
| 9 | SMARCA4 | 79 | 41.3 | 2.41E-06 |
| 10 | USP40 | 65 | 55 | 4.19E-06 |
| 11 | ARID1A | 94 | 49.1 | 4.36E-06 |
| 12 | MAP3K4 | 107 | 65 | 8.67E-06 |
| 13 | CTNND2 | 8 | 9.4 | 7.53E-06 |
| 14 | SQSTM1 | 22 | 74.5 | 5.03E-06 |
| 15 | SMARCB1 | 21 | 65.4 | 5.22E-06 |
| 16 | SMARCC1 | 51 | 55.9 | 5.99E-06 |
| 17 | PPAP2A | 6 | 32.7 | 1.40E-05 |
| 18 | OSBPL9 | 21 | 33 | 6.88E-06 |
| 19 | ACTL6A | 20 | 62.5 | 8.14E-06 |
| 20 | CDS2 | 2 | 9 | 8.63E-06 |
| 21 | PDE8A | 27 | 40.2 | 8.69E-06 |
| 22 | SMARCE1 | 16 | 36.7 | 9.78E-06 |
| 23 | SMARCD2 | 24 | 53.9 | 9.94E-06 |
| 24 | DPF2 | 29 | 70.3 | 2.28E-05 |
| 25 | GFPT1 | 37 | 63.2 | 1.30E-05 |
| 26 | EIF4G1 | 53 | 33.1 | 1.40E-05 |
| 27 | OSBPL11 | 15 | 33.2 | 1.55E-05 |
| 28 | OSBPL10 | 18 | 28.4 | 1.62E-05 |
| 29 | BCL7B | 5 | 41.1 | 2.55E-05 |
| 30 | APEH | 13 | 21.8 | 6.08E-05 |
| 31 | BAIAP2 | 31 | 62 | 2.47E-05 |
| 32 | ANXA7 | 19 | 40.2 | 5.57E-05 |
| 33 | SMARCA2 | 33 | 38.1 | 5.06E-05 |
| 34 | HNRNPK | 28 | 59.5 | 3.51E-05 |
| 35 | DAG1 | 17 | 19.8 | 4.84E-05 |
| 36 | FAM120C | 11 | 13.2 | 9.74E-05 |
| 37 | SPOP | 3 | 11.8 | 0.000109 |
| 38 | STAM | 19 | 46.7 | 5.99E-05 |
| 39 | PRKCI | 6 | 13.6 | 7.22E-05 |
| 40 | NDE1 | 9 | 33.8 | 0.000214 |

*Fig. 1D*

| Rank | Gene Names | Razor + unique peptides | Seq. coverage [%] | P. Value |
|---|---|---|---|---|
| 8 | SMARCC2 | 67 | 45.9 | 1.82E-06 |
| 9 | SMARCA4 | 79 | 41.3 | 2.41E-06 |
| 11 | ARID1A | 94 | 49.1 | 4.36E-06 |
| 15 | SMARCB1 | 21 | 65.4 | 5.22E-06 |
| 16 | SMARCC1 | 51 | 55.9 | 5.99E-06 |
| 19 | ACTL6A | 20 | 62.5 | 8.14E-06 |
| 22 | SMARCE1 | 16 | 36.7 | 9.78E-06 |
| 23 | SMARCD2 | 24 | 53.9 | 9.94E-06 |
| 24 | DPF2 | 29 | 70.3 | 2.28E-05 |
| 29 | BCL7B | 5 | 41.1 | 2.55E-05 |
| 33 | SMARCA2 | 33 | 38.1 | 5.06E-05 |
| 48 | SMARCD1 | 18 | 50.7 | 0.000236321 |
| 289 | PBRM1 | 61 | 40.4 | 0.2738417 |
| 693 | ARID2 | 20 | 14.4 | 0.94347732 |
| 1096 | BRD7 | 3 | 4.8 | 0.146731109 |
| N/A | ARID1B | 4 | 3.9 | N/A |
| N/A | BCL7A; BCL7B | 2 | 16.9 | N/A |
| N/A | BCL7C | 4 | 51.2 | N/A |
| N/A | ACTL6B | 2 | 16 | N/A |
| N/A | SS18L1 | 6 | 15.4 | N/A |

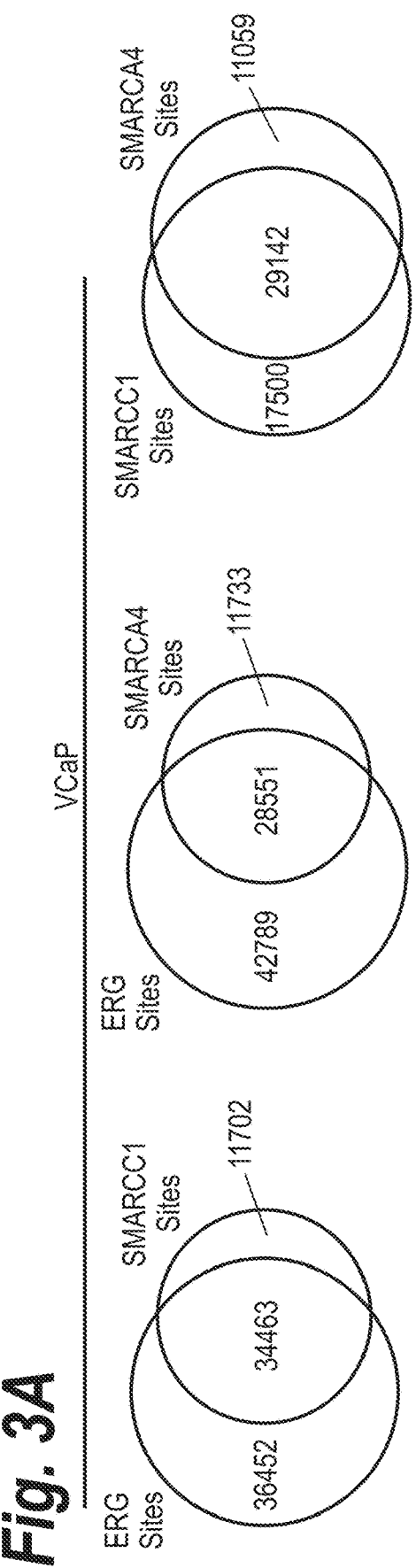
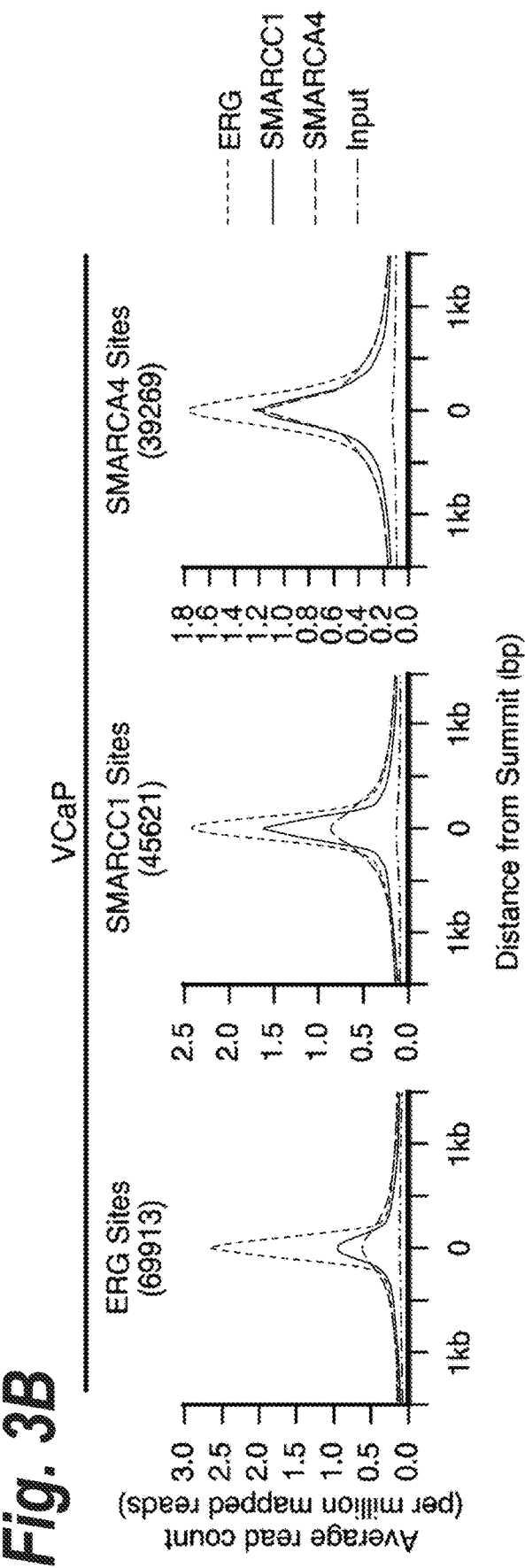
Fig. 3A
Fig. 3B

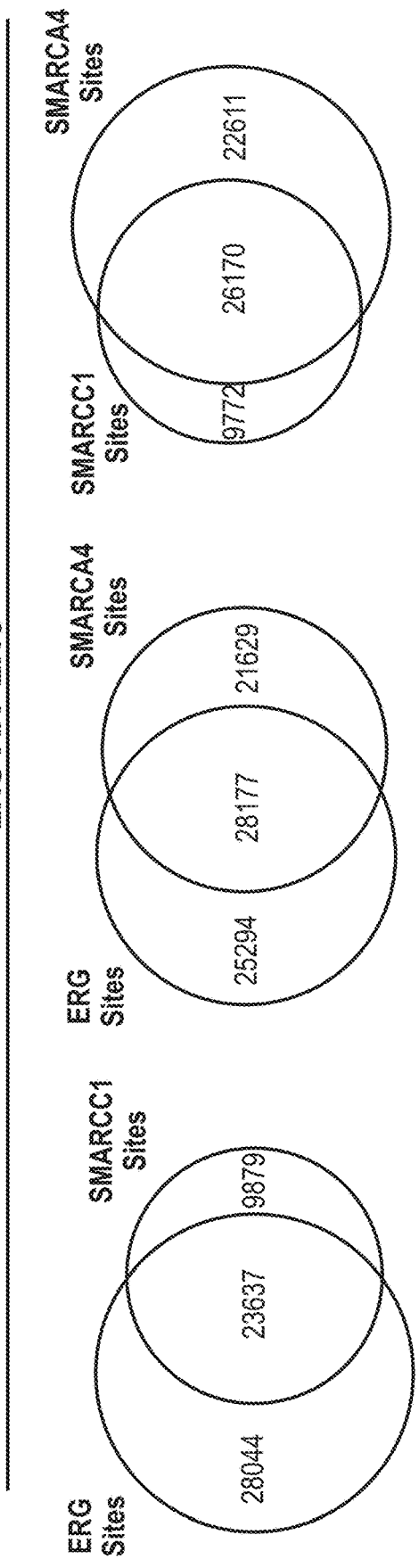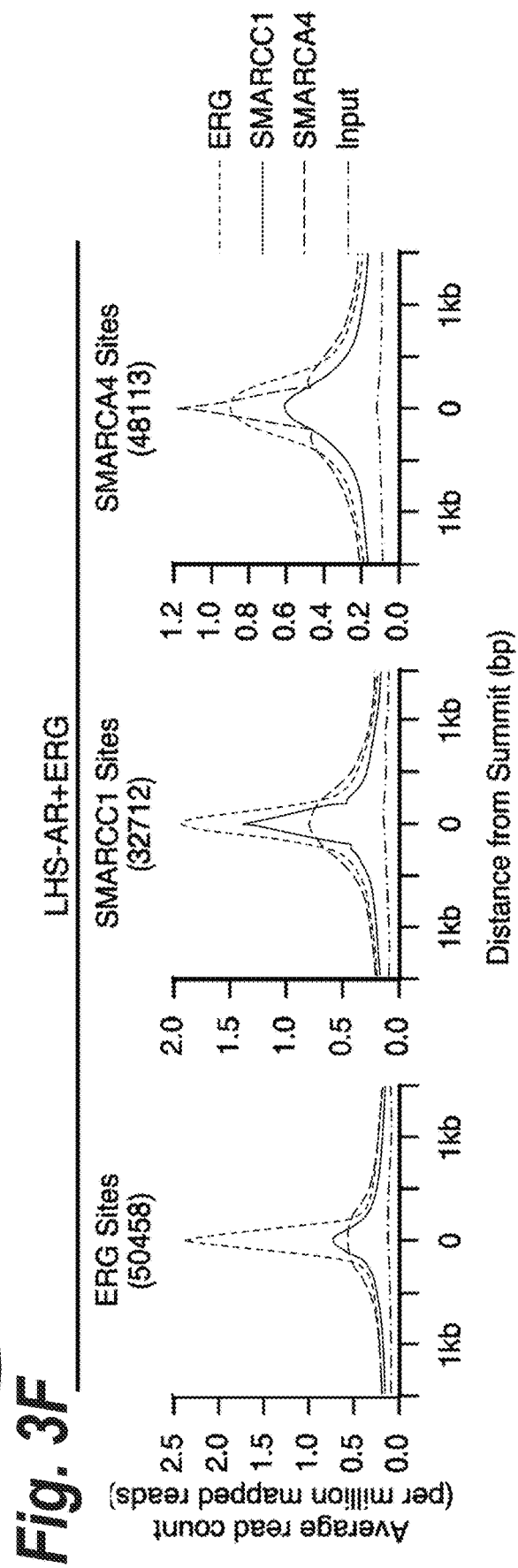

*Fig. 6A*
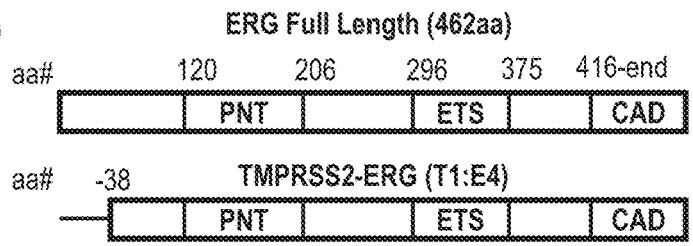
*Fig. 6B*
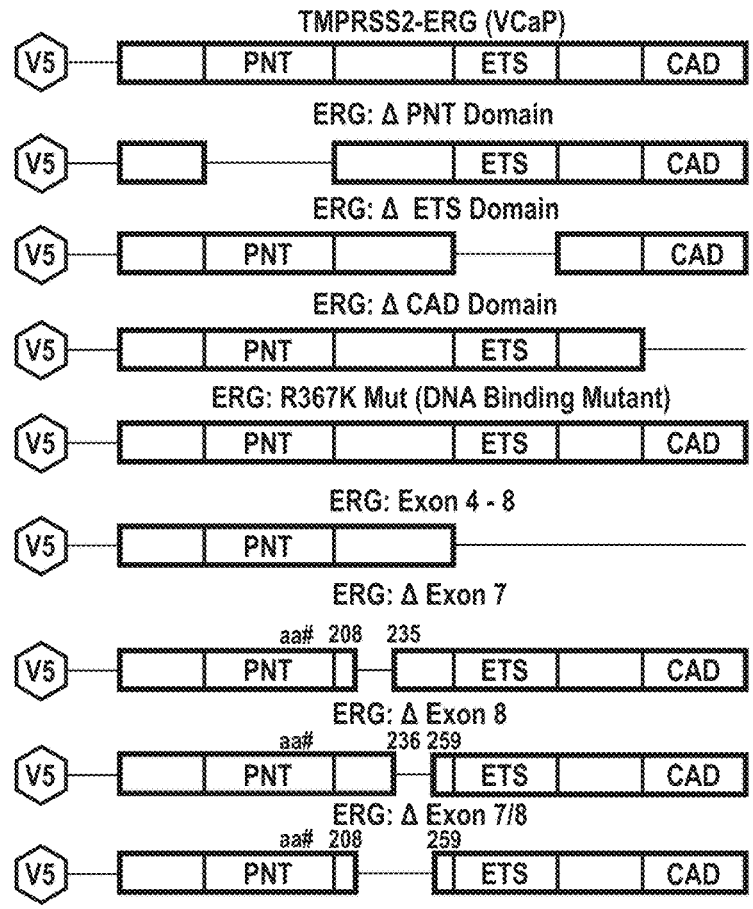
*Fig. 6C*

| Gene Names | Alias | Razor + Unique Peptides | Sequence Coverage (%) | P-Value | Rank (Log2FC) |
|---|---|---|---|---|---|
| ERG | | 29 | 73.4 | 0.00202 | 3 |
| ARID1A | BAF250A | 77 | 46.7 | 0.0087 | 6 |
| SMARCA4 | BRG1 | 71 | 39.3 | 0.00231 | 8 |
| SMARCC1 | BAF155 | 58 | 55 | 0.00237 | 9 |
| SMARCC2 | BAF170 | 46 | 45.4 | 0.00219 | 13 |
| SMARCB1 | BAF47, hSNF5, INI1 | 21 | 65.4 | 0.0016 | 14 |
| SMARCE1 | BAF57 | 17 | 36.7 | 0.00207 | 16 |
| SMARCD2 | BAF60B | 23 | 52.5 | 0.00224 | 21 |
| DPF2 | BAF45D | 25 | 67.5 | 0.00503 | 25 |
| ACTL6A | BAF53A | 18 | 57.6 | 0.00281 | 26 |
| SMARCA2 | BRM | 31 | 36.9 | 0.02118 | 35 |
| BCL7B | | 5 | 41.1 | 0.0072 | 38 |
| SMARCD1 | BAF60A | 16 | 46 | 0.02652 | 49 |

Fig. 8C

| Rank | Gene Names | Log2(FC) | P-Value | Rank | Gene Names | Log2(FC) | P-Value |
|---|---|---|---|---|---|---|---|
| 1 | LBR | 4.558 | 0.033 | 21 | SMARCD2 | 3.078 | 0.0022 |
| 2 | GSTP1 | 4.325 | 0.009 | 22 | SQSTM1 | 3.063 | 0.0029 |
| 3 | ERG | 4.255 | 0.002 | 23 | OSBPL11 | 3.051 | 0.0021 |
| 4 | SRI | 3.697 | 0.0014 | 24 | EIF4G1 | 3.034 | 0.0061 |
| 5 | TMEM160 | 3.658 | 0.0034 | 25 | DPF2 | 3.03 | 0.005 |
| 6 | ARID1A | 3.48 | 0.0087 | 26 | ACTL6A | 3.017 | 0.0028 |
| 7 | MAP3K4 | 3.476 | 0.0161 | 27 | ANXA7 | 2.925 | 0.0068 |
| 8 | SMARCA4 | 3.469 | 0.0023 | 28 | GFPT1 | 2.916 | 0.0032 |
| 9 | SMARCC1 | 3.459 | 0.0024 | 29 | OSBPL10 | 2.833 | 0.0041 |
| 10 | USP40 | 3.442 | 0.0082 | 30 | OSBPL9 | 2.816 | 0.0038 |
| 11 | SUCLG2 | 3.432 | 0.0085 | 31 | DAG1 | 2.796 | 0.0076 |
| 12 | ERG-isoform | 3.366 | 0.005 | 32 | BAIAP2 | 2.751 | 0.0035 |
| 13 | SMARCC2 | 3.362 | 0.0022 | 33 | FAM120C | 2.736 | 0.0229 |
| 14 | SMARCB1 | 3.326 | 0.0016 | 34 | APEH | 2.728 | 0.0224 |
| 15 | CTNND2 | 3.245 | 0.0095 | 35 | SMARCA2 | 2.692 | 0.0212 |
| 16 | SMARCE1 | 3.224 | 0.0021 | 36 | STAM | 2.627 | 0.0088 |
| 17 | SYNGR2 | 3.214 | 0.0019 | 37 | GBAS | 2.588 | 0.0035 |
| 18 | CDS2 | 3.191 | 0.0018 | 38 | BCL7B | 2.58 | 0.0072 |
| 19 | PDE8A | 3.15 | 0.0029 | 39 | PRKCi | 2.575 | 0.006 |
| 20 | PPAP2A | 3.093 | 0.0182 | 40 | KEAP1 | 2.525 | 0.0067 |

ERG Protein expressed in LHS-AR cells
(ERG1c/Isoform 5, CCDS:13658.1)

LHS-AR + V5-ERG

LHS-AR + V5-ERG

ERG Motif Enrichment at LHS-AR+ERG BAF155 Sites p = 2.8e-293

Fig. 12A

| VCaP shCt | Peak B ERG | Peak B BAF155 | Peak B BRG1 |
|---|---|---|---|
| Peak A ERG | 76362 (100%) | 37030 (48.5%) | 32166 (42.1%) |
| Peak A BAF155 | 37700 (78.3%) | 48118 (100%) | 31895 (66.3%) |
| Peak A BRG1 | 32698 (72.4%) | 31851 (70.5%) | 45174 (100%) |

Number (Percent) of Peak A that Overlaps with Peak B

MEME Discovered Motif at ERG Sites

E-value: 7.8e-179

| LHSAR +V5-ERG | | Peak B | |
|---|---|---|---|
| Peak A | V5 | BAF155 | BRG1 |
| V5 | 17845 (100%) | 12254 (68.7%) | 12935 (72.5%) |
| BAF155 | 12111 (29.2%) | 41465 (100%) | 35942 (86.7%) |
| BRG1 | 13039 (20.9%) | 34952 (56.1%) | 62300 (100%) |

Number (Percent) of Peak A that Overlaps with Peak B

Fig. 13K Significantly Changing Genes (p<0.001 and |FC|>2)
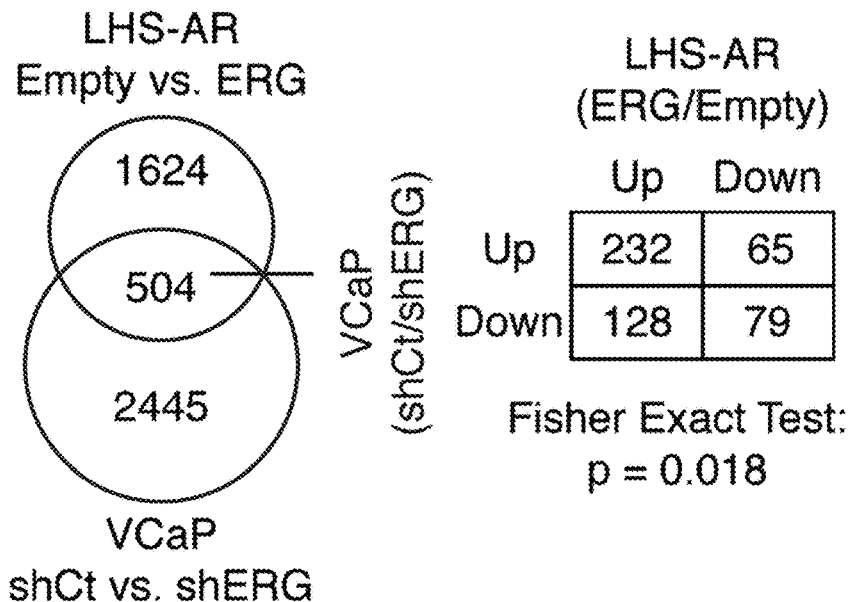
Fig. 13L GO Term Analysis of Upregulated ERG Target Genes (n=232)
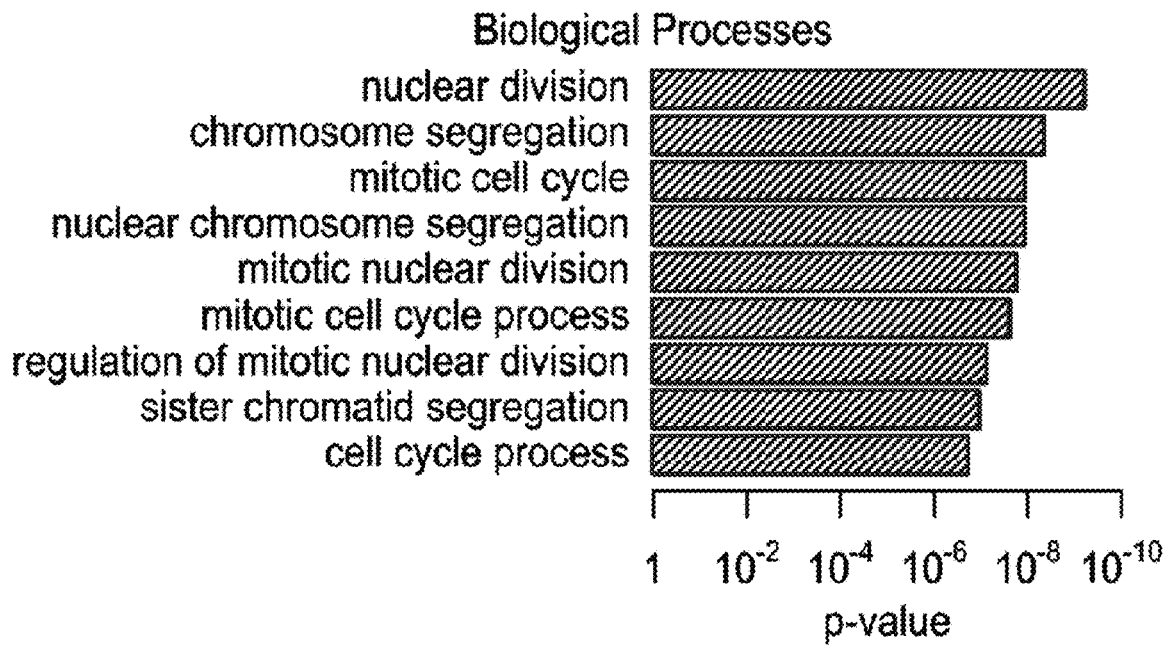

Fig. 15C
```
           aa: 259    264
ERG_Exon8  -------AWTGHG-------------
ETV4       TNAHFIAWTGRGMEFKLIEPEE
ETV1       SNSHFIAWTGRGMEFKLIEPEE
ETV5       ANAHFIAWTGRGMEFKLIEPEE
                  ****.*
```
Fig. 15D
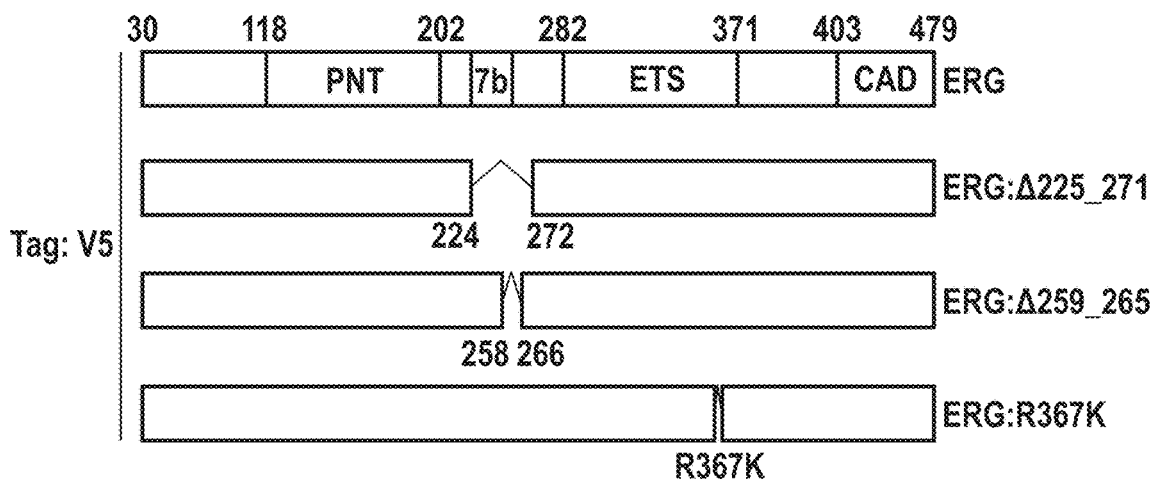
Fig. 15E
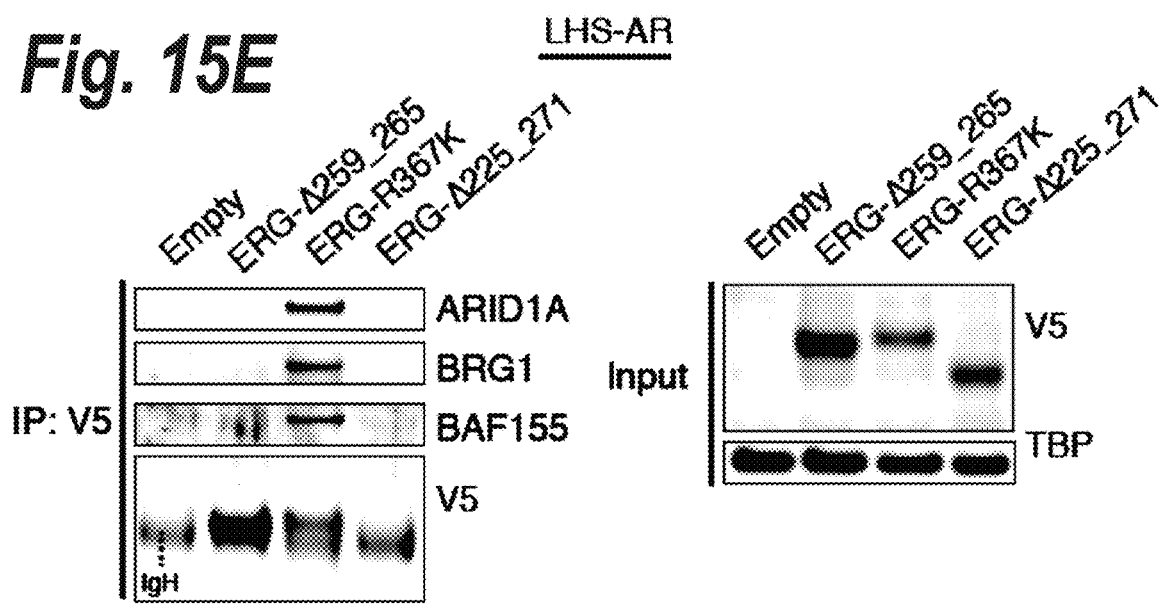

GSEA using ERG Target Gene Signature

*Fig. 16C*

```
ERG_Exon8    1  ------------------------------------------------------------
ETV4         1  MERRMKAGYLDQQVPYTFSSKSPGNGSLREALIGPLGKLMDPGSLPPLDSEDLFQDLSHF
ETV1         1  -----MDGFYDQQVPYMVTNSQRGRNCNEKPTNVRKRKFINRD--LAHDSEELFQDLSQL
ETV5         1  -----MDGFYDQQVPFMVPGKSRSEECRGRPVIDRKRKFLDTD--LAHDSEELFQDLSQL ERG_Exon8    1  ------------------------------------------------------------
ETV4        61  QETWLAEAQVPDSDEQFVPDFHSENLAFHS-PTTRIKKEPQSPRTDPALSCSRKPPLPYH
ETV1        54  QETWLAEAQVPDNDEQFVPDYQAESLAFHG-LPLKIKKEPHSPCSEISSACSQEQPFKFS
ETV5        54  QEAWLAEAQVPD-DEQFVPDFQSDNLVLHAPPPTKIKRELHSPSSELSS-CSHEQALGAN ERG_Exon8    1  ------------------------------------------------------------
ETV4       120  HGEQCLYS-SAYDPPRQIAIKSPAPGALGQSPLQPFPRAE--------------------
ETV1       113  YGEKCLYNVSAYDQKPQVGMRPSNPPTPSSTPVSPLHHAS---------PNSTHTPKP--
ETV5       112  YGEKCLYNYCAYDRKPPSGFKPLTPPT---TPLSPTHQNPLFPPPQATLPTSGHAPAAGP ERG_Exon8    1  ------------------------------------------------------------
ETV4       159  ---------------------QRNFLRSSGTSQPH------PGHGYLGEHSSVFQQPL-DIC
ETV1       162  ---------------------DRAFPAHLPPSQSI------PDSSYPMDHR--FRRQLSEPC
ETV5       169  VQGVGPAPAPHSLPEPGPQQQTFAVPRPPHQPLQMPKMMPENQYPSEQR--FQRQLSEPC ERG_Exon8    1  ------------------------------------------------------------
ETV4       193  HSFTSQGGGREPLPAPYQHQLSEPCPPY----PQQSFKQEYHDPLYEQAGQPAVDQGGVNG
ETV1       195  NSFPPLPTMPREGRPMYQRQMSEPNIPF----PPQGFKQEYHDPVYEHNT--MVGSAASQS
ETV5       227  HPFPPQPGVPGDNRPSYHRQMSEPIVPAAPPPPQGFKQEYHDPLYEHGVPGMPGPPA-HG ERG_Exon8    1  ------------------------DLP-------------------------YEPPRRS---
ETV4       250  HRYPGAGVVIKQEQTDFAYDSDVTGCASMYLHTEGFSG-PSPGDGAMGYGYEKPLRPFPD
ETV1       250  FPPP---LMIKQEPRDFAYDSEVPSCHSIYMRQEGFLAHPSRTEGCM---LEKGPRQFYD
ETV5       286  FQSP---MGIKQEPRDYCVDSEVPNCQSSYMR-GGYFS--SSHEGFS---YEKDPRLYFD
                                         ::.                       :*   *
ERG_Exon8   11  ----------------------------------------AWTGHG--
ETV4       309  DVCVVPEKFEGDIKQEGVGAFREGPPYQRRGALQLWQFLVALLDDPTNAHFIAWTGRGME
ETV1       304  DTCVVPEKFDGDIKQEP-GMYREGPTYQRRGSLQLWQFLVALLDDPSNSHFIAWTGRGME
ETV5       337  DTCVVPERLEGKVKQEP-TMYREGPPYQRRGSLQLWQFLVTLLDDPANAHFIAWTGRGME
                                                                ****.*

ERG_Exon8   17  ------------------------------------------------------------
ETV4       369  FKLIEPEEVARLWGIQKNRPAMNYDKLSRSLRYYYEKGIMQKVAGERYVYKFVCEPEALF
ETV1       363  FKLIEPEEVARRWGIQKNRPAMNYDKLSRSLRYYYEKGIMQKVAGERYVYKFVCDPEALF
ETV5       396  FKLIEPEEVARRWGIQKNRPAMNYDKLSRSLRYYYEKGIMQKVAGERYVYKFVCDPDALF ERG_Exon8   17  -----------------------------------HPTPQSKA---
ETV4       429  SLAFPDNQRPALKAEFDRPVSEEDTVPLSHLDESPAYLPELAGPAQPFGPKGGYSY
ETV1       423  SMAFPDNQRPLLKTDMERHINEEDTVPLSHFDESMAYMPEG-GCCNPHPYNEGYVY
ETV5       456  SMAFPDNQRPFLKAESECHLSEEDTLPLTHFEDSPAYLLDM-DRCSSLPYAEGFAY
```

GO Term Analysis of
Upregulated BAF-Dependent ERG Target Genes
(n=247)

Fig. 19A
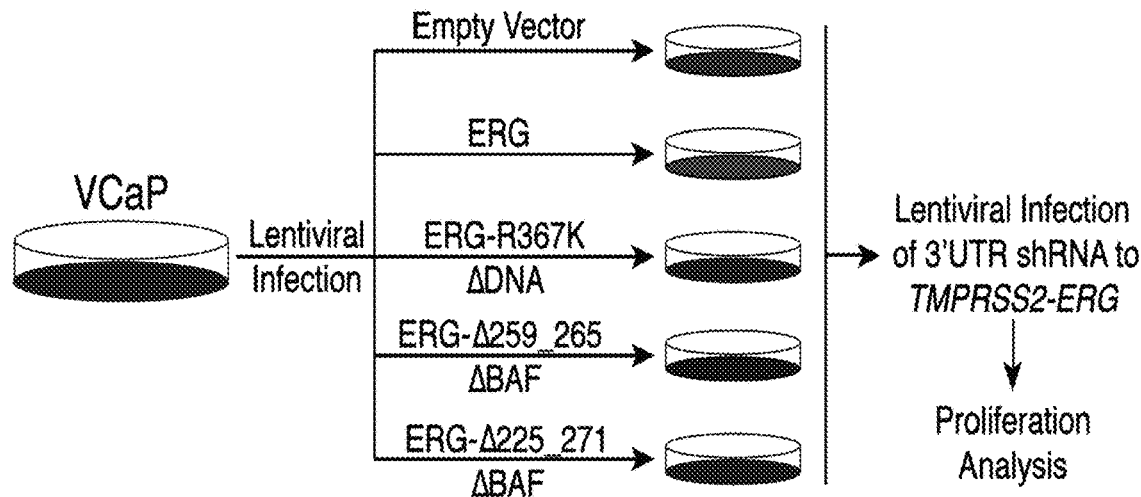
Fig. 19B
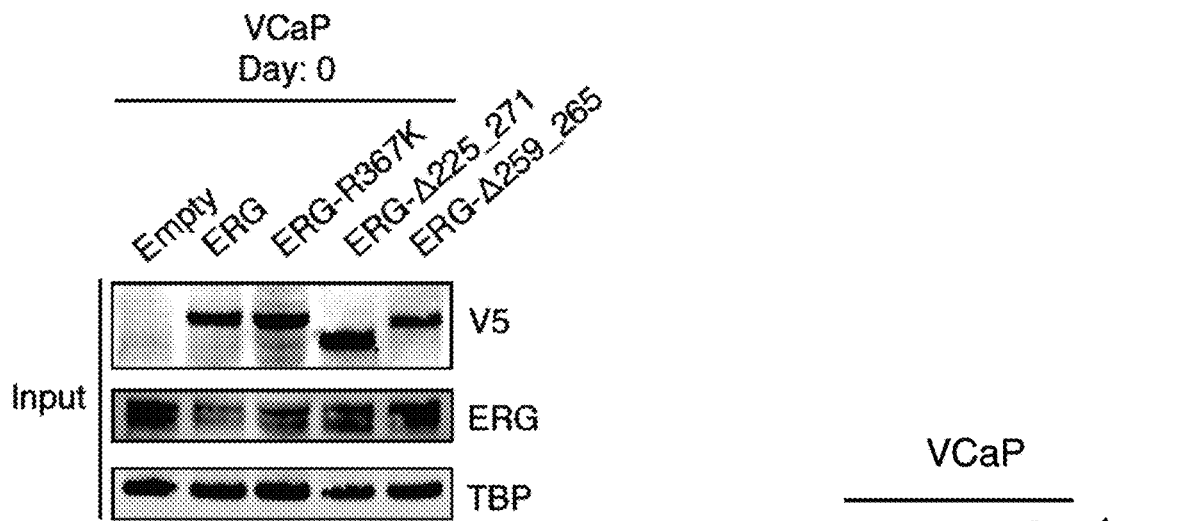
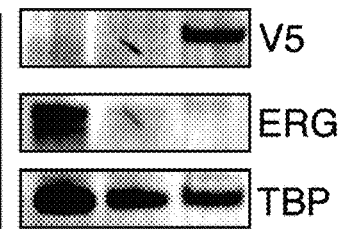
Fig. 19C under grant number W81XWH-15-1-0659 awarded by The
METHODS OF IDENTIFYING COMPOUNDS THAT INTERFERE WITH ERG-DRIVEN MISGUIDANCE OF BAF COMPLEXES IN TMPRSS2-ERG DRIVEN PROSTATE CANCERS

CROSS-REFERENCE TO RELATED APPLICATIONS

This application is a National Stage filing under 35 U.S.C. § 371 of International Patent Application No. PCT/US2016/062911, filed Nov. 18, 2016, which claims the benefit of priority of U.S. Provisional Application No. 62/257,512, filed Nov. 19, 2015, the entireties of which are hereby incorporated herein by reference.

GOVERNMENT RIGHTS

This invention was made with government support under grant number W81XWH-15-1-0659 awarded by The Department of The Army. The government has certain rights in the invention.

FIELD OF THE INVENTION

The present invention relates to the field of screening of compounds that interfere with protein interactions. More specifically, the invention relates to methods of screening for compounds that interfere with interaction between ERG or ETV1, ETV4 or ETV5 and mSWI/SNF (BAF) chromatin remodeling complex proteins.

BACKGROUND

TMPRSS2-ERG was one of the first recurrent translocations discovered in solid tumors, and is known to occur >45% of prostate cancers. As it is often the only genomic event, this provides strong support for its role as an oncogenic driver in this disease. Although several studies have outlined the role of overexpressed ERG in driving aberrant, oncogenic gene expression patterns, the precise mechanism of action has remained largely unknown. There remains a need in the art to determine the mechanism of action and function of ERG and ETV1, ETV4 or ETV5 (and other ETS family members) overexpression in prostate cancer to provide better therapeutics for diagnostics for this cancer.

SUMMARY

The invention utilizes a novel interaction between TMPRSS2-ERG and the mSWI/SNF (BAF) complex. Some embodiments of this interaction use a novel amino acid sequence conserved across ETS factors overexpressed in prostate cancer (i.e. ERG, ETV1, ETV4) that is required for BAF complex binding as well as for the TMPRSS2-ERG gene expression signature. This interaction drives altered global recruitment of the BAF complex in prostate cells, resulting in aberrant gene expression, particularly of genes involved in cell cycle progression and cell signaling genes hallmark to TMPRSS2-ERG tumors. It is likely that the interactions between BAF and other overexpressed ETS factors drives oncogenesis in a similar manner as TMPRSS2-ERG in prostate cancer, irrespective of cell type. ETS factor overexpression can underlie the oncogenic mechanisms driven by EWS-FLI1 in Ewing Sarcoma. TLS-ERG in AML, or any tumor with aberrant ETS factor overexpression. Also considered are novel therapeutic approaches for ETS factor mediated tumorigenesis, as small molecule ligands that have the ability to inhibit the ETS-BAF binding interaction could abrogate the oncogenic effects of ETS overexpression in tumors.

The present disclosure provides a method of identifying a compound that interferes with interaction between an ERG protein or an ETV protein and a mSWI/SNF (BAF) chromatin remodeling complex protein, the method comprising:
a) administering a candidate compound at a first concentration to a sample comprising the ERG protein or the ETV protein and the mSWI/SNF (BAF) chromatin remodeling complex protein under conditions where the proteins interact;
b) determining the strength of the interaction between the ERG protein or the ETV protein and the mSWI/SNF (BAF) chromatin remodeling complex protein; and
c) comparing the strength of the interaction between the ERG protein or the ETV protein and the mSWI/SNF (BAF) chromatin remodeling complex protein to strength of the an interaction of the ERG protein or the ETV protein and the mSWI/SNF (BAF) chromatin remodeling complex protein under the conditions wherein the candidate compound is administered at a second concentration, and wherein the first concentration is higher than the second concentration,
wherein if the strength of the interaction between the ERG protein or the ETV protein and the mSWI/SNF (BAF) chromatin remodeling complex protein administered the first concentration of candidate compound is weaker than the strength of the interaction between the ERG protein or the ETV protein and the mSWI/SNF (BAF) chromatin remodeling complex protein administered the first concentration of candidate compound, then the candidate compound interferes with interaction between the ERG protein or the ETV protein and the mSWI/SNF (BAF) chromatin remodeling complex protein.

In some embodiments, the interaction is between an ERG protein and a mSWI/SNF (BAF) chromatin remodeling complex protein.

In some embodiments, the interaction is between an ETV1 protein and a mSWI/SNF (BAF) chromatin remodeling complex protein.

In some embodiments, the interaction is between an ETV4 protein and a mSWI/SNF (BAF) chromatin remodeling complex protein.

In some embodiments, the interaction is between an ETV5 protein and a mSWI/SNF (BAF) chromatin remodeling complex protein.

In some embodiments, the second concentration is zero.

In some specific embodiments, the interaction between the ERG protein or the ETV protein and the mSWI/SNF (BAF) chromatin remodeling complex protein is at least 20% weaker when the first concentration of the candidate compound is administered than when the second concentration of the candidate compound is administered. In some particular embodiments, the interaction between the ERG protein or the ETV protein and the mSWI/SNF (BAF) chromatin remodeling complex protein is at least 30, 40, 50, 60, 70, 80 or 90% weaker when the first concentration of the candidate compound is administered than when the second concentration of the candidate compound is administered.

In some embodiments, the ERG protein is wild type ERG, TMPRSS2-ERG, ERG: ΔPNT domain, ERG: ΔETS domain, ERG: ΔCAD domain, ERG-Δ225-271, ERG-Δ259-265, or ERG: R367K Mutant (DNA Binding mutant).

In some specific embodiments, the mSWI/SNF (BAF) chromatin remodeling complex protein is BAF170/SMARCC2, BRG1/BAF190A/SMARCA4, ARID1A, BAF47/SNF5/SMARCB1, BAF155/SMARCC1, ACTL6A, SMARCE1, SMARCD2, DPF2, BCL7B, SMARCA2, SMARCD1, PBRM1, ARID2, BRD7, ARID1B, BCL7A: BCL7B, BCL7C, ACTL6B or SS18L1. In some particular embodiments, the mSWI/SNF (BAF) chromatin remodeling complex protein is BAF170/SMARCC2, BRG1/BAF190A/SMARCA4, ARID1A, BAF47/SNF5/SMARCB1, or BAF155/SMARCC1. In some embodiments, the mSWI/SNF (BAF) chromatin remodeling complex protein is BAF155/SMARCC1.

In some embodiments, the interaction of the ERG protein (isoform 1, NCBI Reference Sequence: NP_891548.1, 479 amino acids) and the mSWI/SNF (BAF) chromatin remodeling complex protein occurs among two or more of amino acids 198-272 of the ERG protein and the mSWI/SNF (BAF) chromatin remodeling complex protein. In some specific embodiments, the interaction of the ERG protein and the mSWI/SNF (BAF) chromatin remodeling complex protein occurs among 3, 4, 5, 6, 7, 8, 9, or 10 or more of amino acids 198-272 of the ERG protein and the mSWI/SNF (BAF) chromatin remodeling complex protein.

In some embodiments, the interaction of the ERG protein (isoform 2, NCBI Reference Sequence: NP_004440.1, 462 amino acids) and the mSWI/SNF (BAF) chromatin remodeling complex protein occurs among two or more of amino acids 208-259 of the ERG protein and the mSWI/SNF (BAF) chromatin remodeling complex protein. In some specific embodiments, the interaction of the ERG protein and the mSWI/SNF (BAF) chromatin remodeling complex protein occurs among 3, 4, 5, 6, 7, 8, 9, or 10 or more of amino acids 208-259 of the ERG protein and the mSWI/SNF (BAF) chromatin remodeling complex protein.

In some embodiments, the interaction of the ERG protein (isoform 2, NCBI Reference Sequence: NP_004440.1, 462 amino acids) and the mSWI/SNF (BAF) chromatin remodeling complex protein is among two or more of amino acids 208-235 of the ERG protein and the mSWI/SNF (BAF) chromatin remodeling complex protein. In some specific embodiments, the interaction of the ERG protein and the mSWI/SNF (BAF) chromatin remodeling complex protein occurs among 3, 4, 5, 6, 7, 8, 9, or 10 or more of amino acids 208-235 of the ERG protein and the mSWI/SNF (BAF) chromatin remodeling complex protein.

In some embodiments, the interaction of the ERG protein (isoform 1, NCBI Reference Sequence: NP_891548.1, 479 amino acids) and the mSWI/SNF (BAF) chromatin remodeling complex protein is among two or more of amino acids 224-272 of the ERG protein and the mSWI/SNF (BAF) chromatin remodeling complex protein. In some specific embodiments, the interaction of the ERG protein and the mSWI/SNF (BAF) chromatin remodeling complex protein occurs among 3, 4, 5, 6, 7, 8, 9, or 10 or more of amino acids 224-272 of the ERG protein and the mSWI/SNF (BAF) chromatin remodeling complex protein.

In some embodiments, the interaction of the ERG protein (isoform 1, NCBI Reference Sequence: NP_891548.1, 479 amino acids) and the mSWI/SNF (BAF) chromatin remodeling complex protein is among two or more of amino acids 259-265 of the ERG protein and the mSWI/SNF (BAF) chromatin remodeling complex protein. In some embodiments, the interaction of the ERG protein and the mSWI/SNF (BAF) chromatin remodeling complex protein occurs among 3, 4, 5, 6, or 7 of amino acids 259-265 of the ERG protein and the mSWI/SNF (BAF) chromatin remodeling complex protein.

In some embodiments, the interaction of the ERG protein (isoform 1, NCBI Reference Sequence: NP_891548.1, 479 amino acids) and the mSWI/SNF (BAF) chromatin remodeling complex protein is among two or more of amino acids 198-272 of the ERG protein and BAF155/SMARCC1. In some specific embodiments, the interaction of the ERG protein and the mSWI/SNF (BAF) chromatin remodeling complex protein occurs among 3, 4, 5, 6, 7, 8, 9, or 10 or more of amino acids 198-272 of the ERG protein and BAF155/SMARCC1.

In some embodiments, the interaction of the ERG protein (isoform 2, NCBI Reference Sequence: NP_004440.1, 462 amino acids) and the mSWI/SNF (BAF) chromatin remodeling complex protein is among two or more of amino acids 208-259 of the ERG protein and BAF155/SMARCC1. In some specific embodiments, the interaction of the ERG protein and the mSWI/SNF (BAF) chromatin remodeling complex protein occurs among 3, 4, 5, 6, 7, 8, 9, or 10 or more of amino acids 208-259 of the ERG protein and BAF155/SMARCC1.

In some embodiments, the interaction of the ERG protein (isoform 2, NCBI Reference Sequence: NP_004440.1, 462 amino acids) and the mSWI/SNF (BAF) chromatin remodeling complex protein is among two or more of amino acids 208-235 of the ERG protein and BAF155/SMARCC1. In some specific embodiments, the interaction of the ERG protein and the mSWI/SNF (BAF) chromatin remodeling complex protein occurs among 3, 4, 5, 6, 7, 8, 9, or 10 or more of amino acids 208-235 of the ERG protein and BAF155/SMARCC1.

In some embodiments, the interaction of the ERG protein (isoform 1, NCBI Reference Sequence: NP_891548.1, 479 amino acids) and the mSWI/SNF (BAF) chromatin remodeling complex protein is among two or more of amino acids 224-272 of the ERG protein and BAF155/SMARCC1. In some specific embodiments, the interaction of the ERG protein and the mSWI/SNF (BAF) chromatin remodeling complex protein occurs among 3, 4, 5, 6, 7, 8, 9, or 10 or more of amino acids 224-272 of the ERG protein and BAF155/SMARCC1.

In some embodiments, the interaction of the ERG protein (isoform 1, NCBI Reference Sequence: NP_891548.1, 479 amino acids) and the mSWI/SNF (BAF) chromatin remodeling complex protein is among two or more of amino acids 259-265 of the ERG protein and BAF155/SMARCC1. In some embodiments, the interaction of the ERG protein and the mSWI/SNF (BAF) chromatin remodeling complex protein occurs among 3, 4, 5, 6, or 7 of amino acids 259-265 of the ERG protein and BAF155/SMARCC1.

In some embodiments, the interaction of the ETV1 protein and the mSWI/SNF (BAF) chromatin remodeling complex protein is among two or more of amino acids 355-360 (AWTGRG) of the ETV1 protein and the mSWI/SNF (BAF) chromatin remodeling complex protein. In some embodiments, the interaction of the ETV1 protein and the mSWI/SNF (BAF) chromatin remodeling complex protein occurs among 3, 4, 5, 6, or 7 of amino acids 355-360 (AWTGRG) of the ETV1 protein and the mSWI/SNF (BAF) chromatin remodeling complex protein.

In some embodiments, the interaction of the ETV4 protein and the mSWI/SNF (BAF) chromatin remodeling complex protein is among two or more of amino acids 322-327 (AWTGRG) of the ETV4 protein and the mSWI/SNF (BAF) chromatin remodeling complex protein. In some embodiments, the interaction of the ETV4 protein and the mSWI/SNF (BAF) chromatin remodeling complex protein occurs among 3, 4, 5, 6, or 7 of amino acids 322-327 (AWTGRG) of the ETV4 protein and the mSWI/SNF (BAF) chromatin remodeling complex protein.

In some embodiments, the interaction of the ETV5 protein and the mSWI/SNF (BAF) chromatin remodeling complex protein is among two or more of amino acids 387-392 (AWTGRG) of the ETV5 protein and the mSWI/SNF (BAF) chromatin remodeling complex protein. In some embodiments, the interaction of the ETV5 protein and the mSWI/SNF (BAF) chromatin remodeling complex protein occurs among 3, 4, 5, 6, or 7 of amino acids 387-392 (AWTGRG) of the ETV5 protein and the mSWI/SNF (BAF) chromatin remodeling complex protein.

In some embodiments, the determining the strength of the interaction between the ERG protein or the ETV protein and the mSWI/SNF (BAF) chromatin remodeling complex protein comprises measuring of binding of the ERG protein or the ETV protein to the mSWI/SNF (BAF) chromatin remodeling complex protein. In some specific embodiments, the measuring of binding of the ERG protein or the ETV protein to the mSWI/SNF (BAF) chromatin remodeling complex protein comprises SILAC mass spectrometry. In some particular embodiments, the measuring of binding of the ERG protein or the ETV protein to the mSWI/SNF (BAF) chromatin remodeling complex protein comprises the use of a yeast two hybrid system.

In some specific embodiments, the ETV protein is wild type ETV1.

In some particular embodiments, the interaction of the ETV protein and the mSWI/SNF (BAF) chromatin remodeling complex protein is between wild type ETV1 and BAF155/SMARCC1.

The present disclosure also provides a method of identifying a compound that interferes with interaction between an ERG protein or an ETV protein and a mSWI/SNF (BAF) chromatin remodeling complex protein, the method comprising:
 a) administering a candidate compound at a first concentration to a first set of one or more cells;
 b) determining the strength of the interaction between the ERG protein or the ETV protein and the mSWI/SNF (BAF) chromatin remodeling complex protein in the first set of one or more cells; and
 c) comparing the interaction between the ERG protein or the ETV protein and the mSWI/SNF (BAF) chromatin remodeling complex protein of the first set of one or more cells to the interaction between the ERG protein or the ETV protein and the mSWI/SNF (BAF) chromatin remodeling complex protein of a second set of one or more cells wherein the candidate compound is administered at a second concentration to the second set of one or more cells,
 wherein if the strength of the interaction between the ERG protein or the ETV protein and the mSWI/SNF (BAF) chromatin remodeling complex protein of the first set of cells is weaker than the strength of the interaction between the ERG protein or the ETV protein and the mSWI/SNF (BAF) chromatin remodeling complex protein of the second set of cells, then the candidate compound interferes with interaction between the ERG protein or the ETV protein and the mSWI/SNF (BAF) chromatin remodeling complex protein.

In some embodiments, the interaction is between an ERG protein and a mSWI/SNF (BAF) chromatin remodeling complex protein.

In some embodiments, the interaction is between an ETV1 protein and a mSWI/SNF (BAF) chromatin remodeling complex protein.

In some embodiments, the interaction is between an ETV4 protein and a mSWI/SNF (BAF) chromatin remodeling complex protein.

In some embodiments, the interaction is between an ETV5 protein and a mSWI/SNF (BAF) chromatin remodeling complex protein.

In some embodiments, the one or more cells are normal prostate cells, prostate cancer cells, normal prostate cell line cells, or prostate cancer cell line cells. The one or more cells can be prostate cancer cell line cells. The one or more cells can be VCaP cells. The one or more cells can be normal prostate cells or normal prostate cell line cells. The one or more cells can be PC-3 cells, LHS-AR cells, LHS-AR cells ectopically expressing an ERG protein, or LHS-AR cells ectopically expressing an ETV protein.

In some specific embodiments, the interaction between the ERG protein or the ETV protein and the mSWI/SNF (BAF) chromatin remodeling complex protein of the first set of one or more cells is at least 20% weaker than the ERG protein or the ETV protein and the mSWI/SNF (BAF) chromatin remodeling complex protein of the first set of one or more cells. In some particular embodiments, the interaction between the ERG protein or the ETV protein and the mSWI/SNF (BAF) chromatin remodeling complex protein of the first set of one or more cells is at least 30, 40, 50, 60, 70, 80 or 90% weaker than the ERG protein or the ETV protein and the mSWI/SNF (BAF) chromatin remodeling complex protein of the first set of one or more cells.

In some embodiments, the ERG protein is wild type ERG, TMPRSS2-ERG, ERG: ΔPNT domain, ERG: ΔETS domain, ERG: ΔCAD domain. ERG-Δ225-271, ERG-Δ259-265 or ERG: R367K Mutant (DNA Binding mutant).

In some specific embodiments, the mSWI/SNF (BAF) chromatin remodeling complex protein is BAF170/SMARCC2, BRG1/BAF190A/SMARCA4, ARID1A, BAF47/SNF5/SMARCB1, BAF155/SMARCC1, ACTL6A, SMARCE1, SMARCD2, DPF2, BCL7B, SMARCA2, SMARCD1, PBRM1, ARID2, BRD7, ARID1B, BCL7A: BCL7B, BCL7C, ACTL6B or SS18L1. In some particular embodiments, the mSWI/SNF (BAF) chromatin remodeling complex protein is BAF170/SMARCC2, BRG1/BAF190A/SMARCA4, ARID1A, BAF47/SNF5/SMARCB1, or BAF155/SMARCC1. In some embodiments, the mSWI/SNF (BAF) chromatin remodeling complex protein is BAF155/SMARCC1.

In some particular embodiments, the interaction of the ERG protein (isoform 2, NCBI Reference Sequence: NP_004440.1, 462 amino acids) and mSWI/SNF (BAF) chromatin remodeling complex protein occurs among two or more of amino acids 208-259 of the ERG protein and the mSWI/SNF (BAF) chromatin remodeling complex protein. In some specific embodiments, the interaction of the ERG protein and the mSWI/SNF (BAF) chromatin remodeling complex protein occurs among 3, 4, 5, 6, 7, 8, 9, or 10 or more of amino acids 208-259 of the ERG protein and the mSWI/SNF (BAF) chromatin remodeling complex protein.

In some embodiments, the interaction of the ERG protein (isoform 2, NCBI Reference Sequence: NP_004440.1, 462 amino acids) and the mSWI/SNF (BAF) chromatin remodeling complex protein is among two or more of amino acids 208-235 of the ERG protein and the mSWI/SNF (BAF) chromatin remodeling complex protein. In some specific embodiments, the interaction of the ERG protein and the mSWI/SNF (BAF) chromatin remodeling complex protein occurs among 3, 4, 5, 6, 7, 8, 9, or 10 or more of amino acids 208-235 of the ERG protein and the mSWI/SNF (BAF) chromatin remodeling complex protein.

In some embodiments, the interaction of the ERG protein (isoform 1, NCBI Reference Sequence: NP_891548.1, 479 amino acids) and the mSWI/SNF (BAF) chromatin remodeling complex protein is among two or more of amino acids 224-272 of the ERG protein and the mSWI/SNF (BAF) chromatin remodeling complex protein. In some particular embodiments, the interaction of the ERG protein and the mSWI/SNF (BAF) chromatin remodeling complex protein occurs among 3, 4, 5, 6, 7, 8, 9, or 10 or more of amino acids 224-272 of the ERG protein and the mSWI/SNF (BAF) chromatin remodeling complex protein.

In some embodiments, the interaction of the ERG protein (isoform 1, NCBI Reference Sequence: NP_891548.1, 479 amino acids) and the mSWI/SNF (BAF) chromatin remodeling complex protein is among two or more of amino acids 198-272 of the ERG protein and BAF155/SMARCC1. In some particular embodiments, the interaction of the ERG protein and the mSWI/SNF (BAF) chromatin remodeling complex protein occurs among 3, 4, 5, 6, 7, 8, 9, or 10 or more of amino acids 198-272 of the ERG protein and BAF155/SMARCC1.

In some embodiments, the interaction of the ERG protein (isoform 2, NCBI Reference Sequence: NP_004440.1, 462 amino acids) and the mSWI/SNF (BAF) chromatin remodeling complex protein is among two or more of amino acids 208-259 of the ERG protein and BAF155/SMARCC1. In some particular embodiments, the interaction of the ERG protein and the mSWI/SNF (BAF) chromatin remodeling complex protein occurs among 3, 4, 5, 6, 7, 8, 9, or 10 or more of amino acids 208-259 of the ERG protein and BAF155/SMARCC1.

In some embodiments, the interaction of the ERG protein (isoform 2, NCBI Reference Sequence: NP_004440.1, 462 amino acids) and mSWI/SNF (BAF) chromatin remodeling complex protein is among two or more of amino acids 208-235 of the ERG protein and BAF155/SMARCC1. In some specific embodiments, the interaction of the ERG protein and the mSWI/SNF (BAF) chromatin remodeling complex protein occurs among 3, 4, 5, 6, 7, 8, 9, or 10 or more of amino acids 208-235 of the ERG protein and BAF155/SMARCC1.

In some embodiments, the interaction of the ERG protein (isoform 1, NCBI Reference Sequence: NP_891548.1, 479 amino acids) and the mSWI/SNF (BAF) chromatin remodeling complex protein is among two or more of amino acids 224-272 of the ERG protein and BAF155/SMARCC1. In some particular embodiments, the interaction of the ERG protein and the mSWI/SNF (BAF) chromatin remodeling complex protein occurs among 3, 4, 5, 6, 7, 8, 9, or 10 or more of amino acids 224-272 of the ERG protein and BAF155/SMARCC1.

In some embodiments, the interaction of the ERG protein (isoform 1, NCBI Reference Sequence: NP_891548.1, 479 amino acids) and the mSWI/SNF (BAF) chromatin remodeling complex protein is among two or more of amino acids 259-265 of the ERG protein and the mSWI/SNF (BAF) chromatin remodeling complex protein. In some embodiments, the interaction of the ERG protein and the mSWI/SNF (BAF) chromatin remodeling complex protein occurs among 3, 4, 5, 6, or 7 of amino acids 259-265 of the ERG protein and the mSWI/SNF (BAF) chromatin remodeling complex protein.

In some embodiments, the interaction of the ETV1 protein and the mSWI/SNF (BAF) chromatin remodeling complex protein is among two or more of amino acids 355-360 (AWTGRG) of the ETV1 protein and the mSWI/SNF (BAF) chromatin remodeling complex protein. In some embodiments, the interaction of the ETV1 protein and the mSWI/SNF (BAF) chromatin remodeling complex protein occurs among 3, 4, 5, 6, or 7 of amino acids 355-360 (AWTGRG) of the ETV1 protein and the mSWI/SNF (BAF) chromatin remodeling complex protein.

In some embodiments, the interaction of the ETV4 protein and the mSWI/SNF (BAF) chromatin remodeling complex protein is among two or more of amino acids 322-327 (AWTGRG) of the ETV4 protein and the mSWI/SNF (BAF) chromatin remodeling complex protein. In some embodiments, the interaction of the ETV4 protein and the mSWI/SNF (BAF) chromatin remodeling complex protein occurs among 3, 4, 5, 6, or 7 of amino acids 322-327 (AWTGRG) of the ETV4 protein and the mSWI/SNF (BAF) chromatin remodeling complex protein.

In some embodiments, the interaction of the ETV5 protein and the mSWI/SNF (BAF) chromatin remodeling complex protein is among two or more of amino acids 387-392 (AWTGRG) of the ETV5 protein and the mSWI/SNF (BAF) chromatin remodeling complex protein. In some embodiments, the interaction of the ETV5 protein and the mSWI/SNF (BAF) chromatin remodeling complex protein occurs among 3, 4, 5, 6, or 7 of amino acids 387-392 (AWTGRG) of the ETV5 protein and the mSWI/SNF (BAF) chromatin remodeling complex protein.

In some embodiments, the determining the strength of the interaction between the ERG protein or the ETV protein and the mSWI/SNF (BAF) chromatin remodeling complex protein comprises chromatin immunoprecipitation of the ERG protein or the ETV protein. In some specific embodiments, the determining the interaction between the ERG protein or the ETV protein and the mSWI/SNF (BAF) chromatin remodeling complex protein comprises measuring of nuclear localization of the mSWI/SNF (BAF) chromatin remodeling complex protein. In some particular embodiments, the determining the interaction between the ERG protein or the ETV protein and the mSWI/SNF (BAF) chromatin remodeling complex protein comprises measuring positioning of the mSWI/SNF (BAF) chromatin remodeling complex protein on sites in the genome (genome-wide BAF Complex localization). In some embodiments, the measuring positioning of the mSWI/SNF (BAF) chromatin remodeling complex protein on sites in the genome (genome-wide BAF Complex localization) comprises chromatin immunoprecipitation sequencing (chIP-seq) of the ERG protein or the ETV protein, of the mSWI/SNF (BAF) chromatin remodeling complex protein, or of both the ERG protein or the ETV protein and the mSWI/SNF (BAF) chromatin remodeling complex protein. In some specific embodiments, the determining the interaction between the ERG protein or the ETV protein and the mSWI/SNF (BAF) chromatin remodeling complex protein comprises measuring of expression of at least one prostate cancer pathway gene or protein.

In some particular embodiments, the determining the interaction between the ERG protein or the ETV protein and the mSWI/SNF (BAF) chromatin remodeling complex protein comprises measuring of expression of one or more of FLI1, UBE2C, AR, and EZH2.

In some specific embodiments, the ETV protein is wild type ETV1.

In some particular embodiments, the interaction of the ETV protein and the mSWI/SNF (BAF) chromatin remodeling complex protein is between wild type ETV1 and BAF155/SMARCC1.

The present disclosure further provides a method of treating prostate cancer in a subject in need thereof comprising administering the candidate compound that interferes with interaction between an ERG protein or an ETV protein and a mSWI/SNF (BAF) chromatin remodeling complex protein according to any of the preceding claims. In some embodiments, the method comprises administering a candidate compound that interferes with interaction between an ERG protein and a mSWI/SNF (BAF) chromatin remodeling complex protein. In some embodiments, the method comprises administering a candidate compound that interferes with interaction between an ETV protein and a mSWI/SNF (BAF) chromatin remodeling complex protein. In some embodiments, the method comprises administering a candidate compound that interferes with interaction between an ETV1 protein and a mSWI/SNF (BAF) chromatin remodeling complex protein. In some embodiments, the method comprises administering a candidate compound that interferes with interaction between an ETV4 protein and a mSWI/SNF (BAF) chromatin remodeling complex protein. In some embodiments, the method comprises administering a candidate compound that interferes with interaction between an ETV5 protein and a mSWI/SNF (BAF) chromatin remodeling complex protein. In some embodiments, the interaction of the ERG protein and the mSWI/SNF (BAF) chromatin remodeling complex protein is among two or more of amino acids 259-265 of the ERG protein and the mSWI/SNF (BAF) chromatin remodeling complex protein. In some embodiments, the interaction of the ERG protein and the mSWI/SNF (BAF) chromatin remodeling complex protein occurs among 3, 4, 5, 6, or 7 of amino acids 259-265 of the ERG protein and the mSWI/SNF (BAF) chromatin remodeling complex protein. In some embodiments, the interaction of the ETV1 protein and the mSWI/SNF (BAF) chromatin remodeling complex protein is among two or more of amino acids 355-360 (AWTGRG) of the ETV1 protein and the mSWI/SNF (BAF) chromatin remodeling complex protein. In some embodiments, the interaction of the ETV1 protein and the mSWI/SNF (BAF) chromatin remodeling complex protein occurs among 3, 4, 5, 6, or 7 of amino acids 355-360 (AWTGRG) of the ETV1 protein and the mSWI/SNF (BAF) chromatin remodeling complex protein. In some embodiments, the interaction of the ETV4 protein and the mSWI/SNF (BAF) chromatin remodeling complex protein is among two or more of amino acids 322-327 (AWTGRG) of the ETV4 protein and the mSWI/SNF (BAF) chromatin remodeling complex protein. In some embodiments, the interaction of the ETV4 protein and the mSWI/SNF (BAF) chromatin remodeling complex protein occurs among 3, 4, 5, 6, or 7 of amino acids 322-327 (AWTGRG) of the ETV4 protein and the mSWI/SNF (BAF) chromatin remodeling complex protein. In some embodiments, the interaction of the ETV5 protein and the mSWI/SNF (BAF) chromatin remodeling complex protein is among two or more of amino acids 387-392 (AWTGRG) of the ETV5 protein and the mSWI/SNF (BAF) chromatin remodeling complex protein. In some embodiments, the interaction of the ETV5 protein and the mSWI/SNF (BAF) chromatin remodeling complex protein occurs among 3, 4, 5, 6, or 7 of amino acids 387-392 (AWTGRG) of the ETV5 protein and the mSWI/SNF (BAF) chromatin remodeling complex protein.

BRIEF DESCRIPTION OF THE DRAWINGS

FIG. 1A-D is a schematic of TMPRSS2-ERG fusion and protein (FIG. 1A), a schematic of the SILAC Mass Spectrometry experiment on VCaP cells (FIG. 1B), an enrichment plot of the anti-ERG enriched proteins from the Mass Spectrometry experiment on VCaP cells (FIG. 1C), and tables of the top 40 hits from the SILAC Mass Spectrometry experiment on VCaP cells and the mSWI/SNF (BAF) chromatin remodeling complex members (FIG. 1D, left and right).

FIG. 2A shows blots of immunoprecipitations using anti-ERG and anti-BRG1 in VCaP nuclear extracts (left) and of immunoprecipitation using an alternate anti-ERG antibody C-17. FIG. 2B shows immunoblots of ERG and mSWI/SNF (BAF) chromatin remodeling complex proteins in immunodepletion studies performed on VCaP cells using anti-BRG1 and anti-ERG antibodies. FIG. 2C shows anti-ERG immunoprecipitations on VCaP nuclear extract preparations treated with 0-2.5M urea. FIG. 2D shows immunoblots of ERG and mSWI/SNF (BAF) chromatin remodeling complex proteins in immunoprecipitations of nuclear extracts of LHS-AR cells expressing V5-ERG or control. FIG. 2E shows expression of ETV1 and ERG in LHS-AR cells overexpressing ERG, ETV1, or empty vector; and shows immunoblots of immunoprecipitation using anti-BRG1, anti-ETV1 or control antibodies on extracts from LHS-AR cells overexpressing ETV1.

FIG. 3A-H is a plot of overlap of ChIP-seq peaks of ERG, SMARCC1, and SMARCA4 in VCaP cells (FIG. 3A). FIG. 3B is a HTSeq plot of co-localization of ERG, SMARCC and SMARCA4 reads in VCaP cells. FIG. 3C shows the input blot of ERG protein levels in VCaP cells with ERG (shERG) and control knockdown (shCt), and the overlap of SMARCC1 ChIP-seq peaks in shERG and shCt conditions. FIG. 3D shows a HTSeq plot of ERG-SMARCC1 common peaks in shERG and shCt conditions. FIG. 3E is a HTSeq plot of co-localization of ERG, SMARCC and SMARCA4 reads in LHS-AR+ERG cells. FIG. 3F shows a HTSeq plot of co-localization of ERG, SMARCC1 and SMARCA4 reads in LHS-AR+ERG cells. FIG. 3G shows a blot of input ERG protein levels in LHS-AR cells overexpressing ERG or empty vector, RNA-seq RPKM levels of ERG transcript in LHS-AR cells overexpressing ERG or empty vector, and overlap of SMARCC1 ChIP-seq peaks in wild type and +ERG conditions. FIG. 3H shows motif enrichment of ERG over SMARCC1 sites in VCaP shCt and LHS-AR+ERG cells.

FIG. 4C is RPKM analysis of effect of ERG overexpression on expression of genes overexpressed in prostate cancer (FLI1, UBE2C) and decreased expression of genes suppressed in prostate cancer (AR, EZH2). FIG. 4D shows enrichment plots of genes involved in cancer-related mesenchymal transition and stem cell character. FIG. 4E shows localization of SMARCC1 to the UBE2C enhancer.

FIG. 6A-C is a schematic of full length ERG and TMPRSS2-ERG (FIG. 6A), a schematic of variant ERG proteins made to interrogate binding, and immunoblot of proteins immunoprecipitated by anti-V5 antibody in cells expressing empty vector, wild type ERG, or ERG variants.

FIG. 8A-D. FIG. 8A shows a SDS-PAGE protein gel stained with Coomassie showing 2 repeats (H/L and L/H) of the SILAC experiment (lanes 1, 2) and quality control (lanes 3, 4) samples of unmixed lysate to confirm label incorporation. SILAC lanes were cut into 8 segments for processing and mass spec analysis. FIG. 8B is a representation of all SILAC hits over the log 2-fold change of each experimental replicate. Highlighted in blue are peptides that did not meet the Bland Altman filter of 0.05; peptides in red have an adjusted p-value of 0.01. The upper right quadrant represents proteins enriched in the anti-ERG IP, while the lower left quadrant represents proteins enriched in the anti-IgG control IP (non-specific). FIG. 8C is a table of the top 40 proteins identified through anti-ERG SILAC experiments, indicating number of unique peptides, sequence coverage (%), associated p-values, and rank among enriched proteins. FIG. 8D is a representation of the top 40 anti-ERG SILAC hits over the log 2-fold change of each experimental replicate. High-lighted are: ERG (green dot), significant BAF complex members (red dots), known ERG interacting partners in the prostate (dark grey squares) and the remaining top 40 proteins identified through SILAC (orange squares).

FIG. 10A (middle) shows Coomassie-stained SDS-PAGE gel of IgG and anti-ERG (rabbit antibody) IPs in VCaP cells. FIG. 10A (right) is a table highlighting the BAF complex members enriched from the IgG, anti-ERG, anti-BRG1 and anti-BAF47 IPs. Protein identification was completed using the SEQUEST algorithm (Eng et al., 1994).

FIG. 11B shows ChIP-seq tracks of ERG, BAF155, and BRG1 at the KLK3 (PSA) gene locus in VCaP cells, a known ERG target gene in prostate cancer. FIG. 11C shows a Venn diagram illustrating overlap of ERG, BAF155, and BRG1 peaks in VCaP cells. FIG. 11D shows Centrimo motif enrichment plot of the ERG motif over BAF155 sites in VCaP cells. FIG. 11E shows Metagene plots of ERG sites in LHS-AR prostate epithelial cell line with overexpression of ERG, showing BAF complex enrichment at ERG sites. FIG. 11F shows ChIP-seq tracks of V5-ERG, BRG1 and BAF155 at the SOCS3 gene locus in LHS-AR cells. FIG. 11G shows Venn diagram illustrating overlap of V5 (V5-ERG), BAF155, and BRG1 peaks in LHS-AR cells containing overexpressed V5-ERG. FIG. 11H shows Centrimo motif enrichment plot of ERG motif over BAF155 sites in LHSAR+V5-ERG cells.

FIG. 12A shows the number of peaks for Peak A that overlap peaks for Peak B, as determined by direct overlap of peak intervals for peaks in VCaP shCt condition. FIG. 12D (bottom) Centrimo central enrichment plots of ERG motif enrichment over all ERG sites in VCaP cells. FIG. 12G (bottom) shows Centrimo central enrichment plots of ERG motif enrichment over all V5 sites in LHS-AR+V5-ERG cells.

FIG. 13A is a schematic depicting experiments in VCaP and LHS-AR cells to assess ERG-mediated genome-wide BAF complex occupancy and gene expression. FIG. 13B shows knockdown of ERG in VCaP cells as assessed by (left) western blot of ERG levels and (right) RPKM levels in RNA-seq experiment. Error bars=Mean±SEM (n=2). FIG. 13C is a Venn diagram illustrating overlap of BAF155 peaks in control (shCt) and ERG KD (shERG) settings, as well as ERG sites in control (shCt) setting. Shaded region indicates shCt-specific ERG-BAF155 sites. FIG. 13D shows Metagene plots of ERG and BAF155 over shCt-specific ERG-BAF155 sites (10993). FIG. 13E shows plots of ERG motif enrichment across shCt-specific and shERG-specific BAF155 sites in VCaP cells. FIG. 13F shows ERG-dependent BAF complex localization influences gene expression in VCaP (left) ChIP-seq tracks of ERG, BAF155, at HOXB13 intronic site; (right) RPKM values for PLAT in shCt and shERG conditions in VCaP cells. Error bars=Mean±SEM (n=2). (*** p<1e-6). FIG. 13G is a Venn diagram illustrating overlap of BAF155 sites in empty and +V5-ERG conditions, as well as V5 sites in the +V5-ERG condition in LHS-AR cells. Shaded region indicates ERG-specific V5-BAF155 sites. FIG. 13H is a Metagene plot over ERG-specific V5-BAF155 sites (3096). FIG. 13I shows plots of ERG motif enrichment across LHS-AR empty-specific and ERG-specific BAF155 sites. FIG. 13J shows the Intronic FLI1 ERG peak indicates ERG-dependent BAF complex localization and FLI1 gene expression: (left) ChIP-seq tracks of V5 (V5-ERG), BAF155, and BRG1 at FLI1 intronic site; (right) RPKM values for FLI1 in empty and ERG settings. Error bars=Mean±SEM (n=2). FIG. 103 shows ERG induces concordant gene expression changes in prostate cancer and prostate epithelial contexts: (left) Overlap of significantly-changed genes in LHS-AR and VCaP cell types between ERG conditions; (right) Genes significantly regulated (up/down) in both cell lines show significant concordance (p=0.018, Fisher exact test). FIG. 13L shows GO term enrichment of 232 upregulated ERG target genes from FIG. 13K show significant roles in cell cycle regulation.

FIG. 15A-I indicates ERG-BAF complex binding is required to regulate a distinct subset of ERG target genes. FIG. 15A shows V5-tagged ERG fragments used to define binding region of ERG to the BAF complex. FIG. 15B shows input and anti-V5 IP of ERG fragments expressed in 293T cells. FIG. 15C shows a ClustalW alignment of Exon 8 of ERG revealing amino acids 259-264 as a region that shows a high degree of similarity with oncogenic ETS-factors ETV1, ETV4, and ETV5. FIG. 15D is a schematic of ERG variants used to define narrow BAF binding region and a single amino acid point mutation (R367K) which disrupts ERG DNA binding (Verger et al., 2001). FIG. 15E shows input and anti-V5 IP for V5-tagged ERG-Δ259_265, R367K binding mutant and ERG-Δ225_271. FIG. 15F shows input and anti-V5 IP in LHS-AR cells with and without overexpressed V5-ETV1. FIG. 15G shows RPKM values for ETV1 in empty and +V5-ETV1 conditions in LHS-AR cells. Error bars=Mean±SEM (n=2). FIG. 15H shows GSEA over upregulated ERG target gene set (n=232 genes) showing strong positive enrichment upon ETV1 expression in LHS-AR cells. FIG. 15I shows ERG and ETV1 induce near-identical gene expression changes upon overexpression in prostate epithelial contexts: (left) Overlap of significantly-changed genes in LHS-AR cells with ERG overexpression and ETV1 overexpression; (right) Genes significantly regulated (up/down) in with ERG and ETV1 in LHS-AR cells show highly significant concordance (p<2.2e-16, Fisher exact test).

FIG. 16C shows a ClustalW alignment of Exon 8 (aa256-279) of ERG with oncogenic ETS-factors ETV1, ETV4, and ETV5 shows high degree of similarity. FIG. 16F (right) shows immunoprecipitation using anti-BRG or anti-ERG antibodies in shCtrl- (WT) or shBAF155-treated VCaP cells.

FIG. 17A shows Experimental schematic for RNAseq experiments in LHS-AR cells containing exogenously introduced ERG variants and ETV1. FIG. 17B shows a principal component analysis of top 5% most variable genes, normalized to log 2(RPKM+1) for LHS-AR cell–/+ERG variants or ETV1: PC1 underlies overexpression of all ERG variants and ETV1; PC2 underlies the difference between DNA and BAF binding mutants of ERG and wild-type ERG and ETV1. FIG. 17C shows loss of BAF binding ability of ERG differentially regulates a subset of ERG target genes: (left) Overlap of significantly-changed genes in LHS-AR cells, in empty vector vs. ERG conditions, as well as ERG-259_265 vs. ERG conditions to discern genes underlying PC2 difference in (B). (right) Of 390 overlapping genes, 247 are significantly upregulated by ERG compared to empty vector control, and also upregulated by ERG compared to ERG-!259_265 BAF binding variant, as well as 60 that are downregulated in both comparisons. These changes are significantly concordant (p<2.2e-16, Fisher exact test), demonstrating a requirement for BAF-binding ability in their regulation. FIG. 17D shows ERG-regulated EZH2 target genes SNCA, ADRB2, and MYC, and canonical ERG target genes PLAT, PLAU, AR, and EZH2 (Yu et al., 2010) expression is among the 247 differentially-regulated genes by wild-type, full-length ERG and ETV1, but not ERG BAF-binding or DNA binding mutants. Error bars=Mean±SEM (n=2). FIG. 17E shows immunoprecipitation of BRG1 and BAF155/170 by ETV1, ETV4, and ETV5.

FIG. 18C (left) shows overlap of significantly-changed genes in LHS-AR cells with ERG-Δ259_265 and ERG-R367K overexpression; FIG. 18C (right) shows genes significantly regulated (up/down) in with ERG-Δ259_265 and ERG-R367K in LHS-AR cells show highly significant concordance (p<2.2e-16, Fisher exact test).

FIG. 19A-E shows BAF complex binding is required for ERG-mediated proliferation in prostate cancer. FIG. 19A is an experimental schematic for proliferation experiments in LHS-AR−/+ERG variant conditions. FIG. 19B shows total nuclear protein levels of V5-ERG WT and mutant variants constitutively expressed in VCaP cells. FIG. 19C shows total nuclear protein levels of VCaP cells bearing either empty vector or wild-type ERG at day 0 and day 7 after introduction of 3'UTR shERG. FIG. 19D shows proliferation analyses over ERG knock-down time course in VCaP cells containing either empty vector or constitutively overexpressed ERG WT and mutant variants. FIG. 19E shows a model for ERG-BAF driven tumorigenesis in TMPRSS2-ERG prostate cancer.

DETAILED DESCRIPTION

Figure 1A:
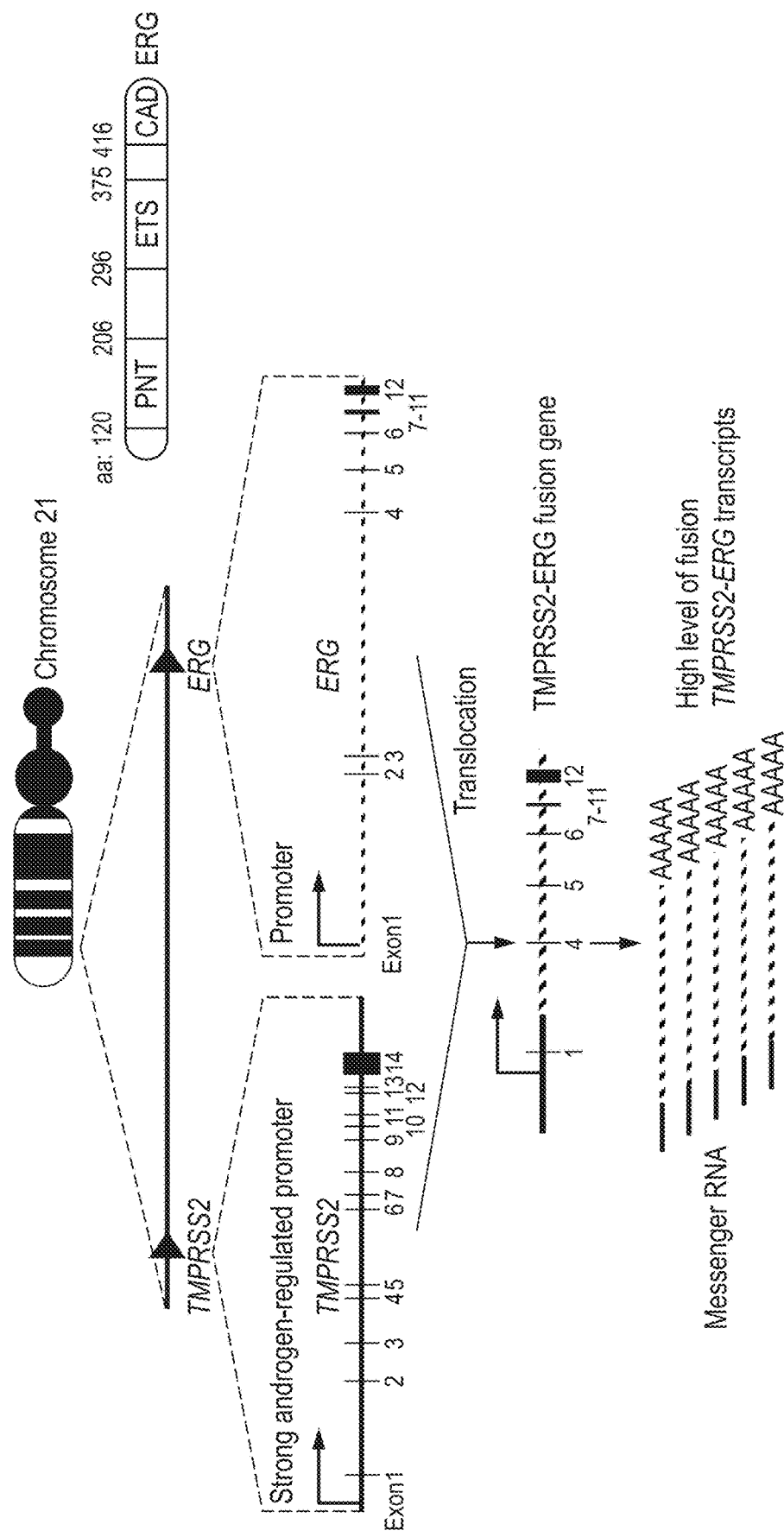

The disclosure provides that ERG and/or ETV1, ETV4 or ETV5 specifically bind mSWI/SNF (BAF) chromatin remodeling complexes of unique subunit composition (BAF complexes, not PBAF complexes with distinct subunit composition), and that this family of proteins represents the key (and most stable) binding interactions of ERG or an ETV protein in prostate cancer cells. The biochemical data presented herein support the fact that the majority of ERG is bound to mSWI/SNF (BAF) chromatin remodelling complexes (depletion studies), and that the interaction between ERG or an ETV protein and BAF is required for the oncogenic phenotype (by gene expression). In addition, it is shown that ERG is required for the (mis-) guidance of BAF complexes genome-wide. Knock down of ERG results in the relocalization of mSWI/SNF (BAF) chromatin remodeling complexes away from oncogenic sites.

A mechanism of TMPRSS2-ERG driven prostate cancer is presented and methods of treatment using this mechanism are also provided. Not to be limited by theory, it appears that ERG overexpression, which is considered to be an early and driving event in these cancers, acts by binding the BAF (mammalian SWI/SNF) complex and re-localizing mSWI/SNF (BAF) chromatin remodeling complexes to genomic loci, thereby altering gene expression levels at these sites, which drives tumorigenesis. It appears that ERG-driven mSWI/SNF (BAF) chromatin remodeling complex misguidance is the mechanism underpinning ERG overexpressed cancers. The binding regions on the ERG protein which are required for mSWI/SNF (BAF) chromatin remodeling complex binding were mapped. Importantly, the domain required for binding was the domain hallmark to several ETS factors, including ETV1, ETV4, ETV5, etc., corresponding to the product of Exon 8. On mSWI/SNF (BAF) chromatin remodeling complexes, the BAF155 subunit appears to be the most likely tethering point for ERG binding; knockdown of this subunit (or the complex) results in proliferative senescence in prostate cancer cell lines with the TMPRSS2-ERG fusion.

Based on this data, the disclosure provides methods of screening for compounds that interfere with interaction between an ERG protein or an ETV protein and mSWI/SNF (BAF) chromatin remodeling complex proteins. In certain embodiments, compounds that interfere with this interaction can be used as therapeutics in the treatment of prostate cancer.

By a "protein" is meant any two or more naturally occurring or modified amino acids joined by one or more peptide bonds. "Protein", "peptide" and "polypeptide" are used interchangeably herein.

By "RNA" is meant a sequence of two or more covalently bonded, naturally occurring or modified ribonucleotides. One example of a modified RNA included within this term is phosphorothioate RNA.

By "DNA" is meant a sequence of two or more covalently bonded, naturally occurring or modified deoxyribonucleotides.

By a "nucleic acid" is meant any two or more covalently bonded nucleotides or nucleotide analogs or derivatives. As used herein, this term includes, without limitation, DNA, RNA, and PNA. The term "nucleic acid" may include a modified nucleic acid, and, accordingly, nucleic acid and modified nucleic acid may be used interchangeably.

As used herein, the term "mSWI/SNF (BAF) chromatin remodeling complex protein" or "BAF complex protein" means a member or members of the chromatin remodeling complex of human proteins known as BRG1-associated factors (BAF). mSWI/SNF (BAF) chromatin remodeling complex proteins are mammalian analogs of SWI/SNF (Switch/Sucrose Non-Fermentable) proteins known as SWI/SNF-A. The mSWI/SNF (BAF) chromatin remodeling complex can contain one of two distinct ATPase subunits hBRM (human Brahma) or BRG1 (Brahma-related Gene 1). mSWI/SNF (BAF) chromatin remodeling complex proteins are also termed "Swi-Related, Matrix-associated, Actin Dependent Regulators of Chromatin," or SMARCs.

In some embodiments, a mSWI/SNF (BAF) chromatin remodeling complex protein can be BAF170/SMARCC2, BRG1/BAF190A/SMARCA4, BAF250a/ARID1A, BAF47/SNF5/SMARCB1, BAF155/SMARCC1, BAF53b/ACTL6A, BAF57/SMARCE1, BAF60b/SMARCD2, BAF45d/DPF2, BCL7B, hBRM/BAF190b/SMARCA2, BAF60a/SMARCD1, BAF60c/SMARCD3, PBRM1. BAF250b/ARID2, BRD7, ARID1B, BCL7A, BCL7B, BCL7C, BAF53a/ACTL6B or SS18L1. In particular embodiments, a mSWI/SNF (BAF) chromatin remodeling complex protein can be BAF170/SMARCC2, BRG1/BAF190A/SMARCA4, ARID1A, BAF47/SNF5/SMARCB1, or BAF155/SMARCC1. In specific embodiments, a mSWI/SNF (BAF) chromatin remodeling complex protein can be BAF155/SMARCC1. In other embodiments, the mSWI/SNF (BAF) chromatin remodeling complex protein can be BRD9, BAF45b/DPF1, BAF45c/DPF3, or BAF60c/SMARCD3.

As used herein, the term "ERG protein" means a wild type, variant or modified ETS-related gene (ERG) protein. ERG is a nuclear protein that functions as a transcriptional regulator, binding purine-rich sequences. It has an ETS DNA binding domain, a pointed (PNT) domain, and a c-terminal activation (CAD) domain. ERG can fuse with TMPRSS2 to form an oncogenic fusion protein that is found in human prostate cancer. In some embodiments, the ERG protein is wild type ERG, TMPRSS2-ERG, ERG: ΔPNT domain, ERG: ΔETS domain, ERG: ΔCAD domain, ERG-Δ225-271, ERG-Δ259-265, or ERG: R367K Mutant (DNA Binding mutant).

As used herein, the term "ETV protein" means a wild type, variant or modified ETS-variant gene (ETV) protein, and includes an ETV1 protein, an ETV4 protein and an ETV5 protein.

As used herein, the term "ETV1 protein" means a wild type, variant or modified ETS-variant gene 1 (ETV1) protein. ETV1 is a nuclear protein that functions as a transcriptional regulator, binding purine-rich sequences. It has an ETS DNA binding domain, and an N-terminal transactivation (TAD) domain. ETV1 can also fuse with TMPRSS2 to form an oncogenic fusion protein that is found in human prostate cancer. In some embodiments, the ETV1 protein is wild type ETV1, or TMPRSS2-ETV1.

As used herein, the term "ETV4 protein" means a wild type, variant or modified ETS-variant gene 4 (ETV4) protein. ETV4 is a nuclear protein that functions as a transcriptional regulator, binding purine-rich sequences. It has an ETS DNA binding domain, and an N-terminal transactivation (TAD) domain. ETV4 can also fuse with EWS (or EWSR1) to form an oncogenic fusion protein that is found in human prostate cancer. In some embodiments, the ETV4 protein is wild type ETV4, TMPRSS2-ETV4, or EWS-ETV4 (EWSR1-ETV4).

As used herein, the term "ETV5 protein" means a wild type, variant or modified ETS-variant gene 5 (ETV5) protein. ETV5 is a nuclear protein that functions as a transcriptional regulator, binding purine-rich sequences. It has an ETS DNA binding domain, and an N-terminal transactivation (TAD) domain. ETV5 can also fuse with TMRPSS2 or EWS (EWSR1) to form an oncogenic fusion protein that is found in human prostate cancer. In some embodiments, the ETV5 protein is wild type ETV5, TMPRSS2-ETV5, or EWS-ETV5 (EWSR1-ETV5).

TMPRSS2-ERG Fusion

ERG was identified as the most overexpressed proto-oncogene in prostate tumors (Petrovics et al.; "Frequent overexpression of ETS-related gene-1 (ERG1) in prostate cancer transcriptome," Oncogene 2005, 24(23):3847-3852). Such ERG overexpression is often the result of a fusion of the promoter region of the TMPRSS2 gene to one of a number of genes, including ERG (Tomlins et al., "Recurrent fusion of TMPRSS2 and ETS transcription factor genes in prostate cancer," Science 2005, 310(5748):644-648). These fusions may occur in a majority of prostate cancers.

The TMPRSS2-ERG fusion is present in late stage prostate cancer, as well as in benign prostatic hyperplasia. There are a large number of unique TMPRSS2-ERG transcripts, with the majority encoding null or truncated fusion proteins. The most common variant is the T1/E4 variant (see FIG. 1A and FIG. 6A). The TMPRSS2-ERG fusion is associated with an aggressive phenotype of prostate tumors (Rajput et al. "Frequency of the TMPRSS2:ERG gene fusion is increased in moderate to poorly differentiated prostate cancers", J Clin Pathol 2007, 60(11):1238-1243), prostate cancer progression and prostate cancer-specific death (Attard et al., "Duplication of the fusion of TMPRSS2 to ERG sequences identifies fatal human prostate cancer", Oncogene 2008, 27(3): 253-263; and Demichelis et al., "TMPRSS2:ERG gene fusion associated with lethal prostate cancer in a watchful waiting cohort", Oncogene 2007, 26(31):4596-4599), and prostate cancer recurrence (Nam et al. "Expression of the TMPRSS2:ERG fusion gene predicts cancer recurrence after surgery for localised prostate cancer", Br J Cancer 2007, 97(12):1690-1695). Both androgen-dependent and androgen-independent prostate tumors contain the TMPRSS2-ERG fusion gene, but only androgen-dependent tumors exhibit overexpression of fusion transcripts (and ERG).

ERG Protein and mSWI/SNF (BAF) Chromatin Remodeling Complex Protein Interaction/ETV Protein and mSWI/SNF (BAF) Chromatin Remodeling Complex Protein Interaction As used herein, the term "interaction between an ERG protein or an ETV protein and a mSWI/SNF (BAF) chromatin remodeling complex protein" means a binding or other interaction between an ERG protein or an ETV protein and a mSWI/SNF (BAF) chromatin remodeling complex protein. The interaction can occur between specific portions or domains of the ERG protein or the ETV protein and the mSWI/SNF (BAF) chromatin remodeling complex protein. The interaction can be between an ERG protein or an ETV protein and one mSWI/SNF (BAF) chromatin remodeling complex protein, or between an ERG protein or an ETV protein and more than one, for example two or more, mSWI/SNF (BAF) chromatin remodeling complex proteins.

The interaction of the ERG protein and the mSWI/SNF (BAF) chromatin remodeling complex protein can occur among two or more of amino acids 208-259 of the ERG protein and the mSWI/SNF (BAF) chromatin remodeling complex protein; in some instances, it can occur among 3, 4, 5, 6, 7, 8, 9, or 10 or more of amino acids 208-259 of the ERG protein and the mSWI/SNF (BAF) chromatin remodeling complex protein. The interaction of the ERG protein and the mSWI/SNF (BAF) chromatin remodeling complex protein can also occur among two or more of amino acids 208-235 of the ERG protein and the mSWI/SNF (BAF) chromatin remodeling complex protein; in some instances, it can occur among 3, 4, 5, 6, 7, 8, 9, or 10 or more of amino acids 208-235 of the ERG protein and the mSWI/SNF (BAF) chromatin remodeling complex protein. The interaction of the ERG protein and the mSWI/SNF (BAF) chromatin remodeling complex protein can occur among two or more of amino acids 224-272 of the ERG protein and the mSWI/SNF (BAF) chromatin remodeling complex protein; in some instances, it can occur among 3, 4, 5, 6, 7, 8, 9, or 10 or more of amino acids 224-272 of the ERG protein and the mSWI/SNF (BAF) chromatin remodeling complex protein.

The interaction of the ERG protein and the mSWI/SNF (BAF) chromatin remodeling complex protein can occur among two or more of amino acids 208-259 of the ERG protein and BAF155/SMARCC1; in some instances, it can occur among 3, 4, 5, 6, 7, 8, 9, or 10 or more of amino acids 208-259 of the ERG protein and BAF155/SMARCC1. The interaction of the ERG protein and the mSWI/SNF (BAF) chromatin remodeling complex protein can occur among two or more of amino acids 208-235 of the ERG protein and BAF155/SMARCC1; in some instances, it can occur among 3, 4, 5, 6, 7, 8, 9, or 10 or more of amino acids 208-235 of the ERG protein and BAF155/SMARCC1. The interaction of the ERG protein and the mSWI/SNF (BAF) chromatin remodeling complex protein can occur among two or more of amino acids 224-272 of the ERG protein and BAF155/SMARCC1; in some instances, it can occur among 3, 4, 5, 6, 7, 8, 9, or 10 or more of amino acids 224-272 of the ERG protein and BAF155/SMARCC1.

The interaction of the ERG protein and the mSWI/SNF (BAF) chromatin remodeling complex protein can occur among two or more of amino acids 259-265 of the ERG protein and the mSWI/SNF (BAF) chromatin remodeling complex protein; in some instances, it can occur among 3, 4, 5, 6, or 7, of amino acids 259-265 of the ERG protein and the mSWI/SNF (BAF) chromatin remodeling complex protein.

The interaction of the ERG protein and the mSWI/SNF (BAF) chromatin remodeling complex protein can occur among two or more of amino acids 259-265 of the ETV1 protein and the mSWI/SNF (BAF) chromatin remodeling complex protein; in some instances, it can occur among 3, 4, 5, 6, or 7 of amino acids 259-265 of the ETV1 protein and the mSWI/SNF (BAF) chromatin remodeling complex protein.

The interaction of the ERG protein and the mSWI/SNF (BAF) chromatin remodeling complex protein can occur among two or more of amino acids 259-265 of the ETV4 protein and the mSWI/SNF (BAF) chromatin remodeling complex protein; in some instances, it can occur among 3, 4, 5, 6, or 7 of amino acids 259-265 of the ETV4 protein and the mSWI/SNF (BAF) chromatin remodeling complex protein.

The interaction of the ERG protein and the mSWI/SNF (BAF) chromatin remodeling complex protein can occur among two or more of amino acids 259-265 of the ETV5 protein and the mSWI/SNF (BAF) chromatin remodeling complex protein; in some instances, it can occur among 3, 4, 5, 6, or 7 of amino acids 259-265 of the ETV5 protein and the mSWI/SNF (BAF) chromatin remodeling complex protein.

The strength of interaction between the ERG protein or the ETV protein and the mSWI/SNF (BAF) chromatin remodeling complex protein can be determined, for example by a method comprising measuring of binding of the ERG protein or the ETV protein to the mSWI/SNF (BAF) chromatin remodeling complex protein; in some cases, the measuring of binding of the ERG protein or the ETV protein to the mSWI/SNF (BAF) chromatin remodeling complex protein can comprise SILAC mass spectrometry; in some situations, the measuring of binding of the ERG protein or the ETV protein to the mSWI/SNF (BAF) chromatin remodeling complex protein can comprise the use of a yeast two hybrid system.

If the strength of the interaction between the ERG protein or the ETV protein and the mSWI/SNF (BAF) chromatin remodeling complex protein administered the first concentration of candidate compound is weaker than the strength of the interaction between the ERG protein or the ETV protein and the mSWI/SNF (BAF) chromatin remodeling complex protein administered the first concentration of candidate compound, then the candidate compound interferes with interaction between the ERG protein and the mSWI/SNF (BAF) chromatin remodeling complex protein. In some instances, the interaction between the ERG protein or the ETV protein and the mSWI/SNF (BAF) chromatin remodeling complex protein is at least 20% weaker when the first concentration of the candidate compound is administered than when the second concentration of the candidate compound is administered; in some instances, the interaction between the ERG protein or the ETV protein and the mSWI/SNF (BAF) chromatin remodeling complex protein is at least 30, 40, 50, 60, 70, 80 or 90% weaker when the first concentration of the candidate compound is administered than when the second concentration of the candidate compound is administered.

Interference with the interaction between the ERG protein or the ETV protein and the mSWI/SNF (BAF) chromatin remodeling complex protein is intended to refer to the characteristic of a candidate compound that blocks, inhibits, or diminishes binding of the ERG protein or the ETV protein to the mSWI/SNF (BAF) chromatin remodeling complex protein or blocks, inhibits, or diminishes a biological activity of the ERG protein or the ETV protein and/or the mSWI/SNF (BAF) chromatin remodeling complex protein or mSWI/SNF (BAF) chromatin remodeling complex. This blocking, inhibition or diminution of binding or activity can be assessed by measuring one or more indicators of activity known to the art, such as measuring chromatin immunoprecipitation of the ERG protein or the ETV protein, positioning of the mSWI/SNF (BAF) chromatin remodeling complex protein on sites in the genome (genome-wide BAF Complex localization), chromatin immunoprecipitation sequencing (chIP-seq) of the ERG protein or the ETV protein, of the mSWI/SNF (BAF) chromatin remodeling complex protein, or of both the ERG protein or the ETV protein and the mSWI/SNF (BAF) chromatin remodeling complex protein, or nuclear localization of mSWI/SNF (BAF) chromatin remodeling complex protein (see Examples below).

Cells

Cells used in the methods can be any cells, and in particular can be prostate cells or cell lines, such as normal prostate cells, prostate cancer cells, normal prostate cell line cells, or prostate cancer cell line cells. The cells can be VCaP cells, PC-3 cells or LNCaP cells. The cells can be also normal prostate epithelial cells, LHS-AR cells, LHS-AR cells ectopically expressing an ERG protein, or LHS-AR cells ectopically expressing an ETV protein.

Prostate Cancer Pathway Gene or Protein

The methods of the disclosure can comprise a measuring of expression of at least one prostate cancer pathway gene or protein. In some instances, the prostate cancer pathway gene or protein is one or more of FLI1, UBE2C, AR, and EZH2.

Definition of Candidate Compounds

The term "candidate compound" refers to a chemical to be tested by one or more screening method(s) of the invention as a putative compound that interferes with the interaction between an ERG protein or an ETV protein and a mSWI/SNF (BAF) chromatin remodeling complex protein or proteins. A candidate compound can be any chemical, such as an inorganic chemical, an organic chemical, a protein, a peptide, a carbohydrate, a lipid, or a combination thereof. Usually, various predetermined concentrations of candidate compounds are used for screening, such as 0.01 micromolar, 1 micromolar and 10 micromolar.

Identifying Modulators of ERG: or ETV: mSWI/SNF (BAF) Chromatin Remodeling Complex Protein Interaction The invention provides methods (also referred to herein as "screening assays") for identifying modulators, i.e., candidate or test compounds or agents (e.g., proteins, peptides, peptidomimetics, peptoids, small molecules or other drugs) which interfere with an interaction between an ERG protein or an ETV protein and a mSWI/SNF (BAF) chromatin remodeling complex protein or proteins. Compounds thus identified can be used to modulate the activity of target complex (e.g., TMPRSS2-ERG and BAF155) in a therapeutic protocol, to elaborate the biological function of the target complex, to identify compounds that disrupt normal ERG (or ETV):mSWI/SNF (BAF) chromatin remodeling complex interactions, or to identify compounds that interfere with the ERG-mediated misguidance of the mSWI/SNF (BAF) chromatin remodeling complex in TMPRSS2-ERG driven prostate cancers.

In one embodiment, the disclosure provides assays for screening candidate or test compounds that bind to or modulate an activity of an ERG protein or an ETV protein, or a mSWI/SNF (BAF) chromatin remodeling complex protein, or both.

The candidate compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) J Med. Chem. 37:2678-85); spatially addressable parallel solid phase or solution phase libraries; synthetic library methods requiring deconvolution: the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell at al. (1994) Angew. Chem. Int. Ed. Engl. 33:2061; and Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner, U.S. Pat. No. 5,223,409), spores (Ladner U.S. Pat. No. 5,223,409), plasmids (Cull et al. (1992) Proc Natl Acad Sci USA 89:1865-1869) or on phage (Scott and Smith (1990) Science 249:386-390; Devlin (1990) Science 249:404406; Cwirla et al. (1990) Proc. Natl. Acad. Sci. 87:6378-6382; Felici (1991) J. Mol. Biol. 222:301-310; Ladner supra.).

The ability of the candidate compound to interfere with an interaction between an ERG protein or ETV protein and a mSWI/SNF (BAF) chromatin remodeling complex protein can also be evaluated. This can be accomplished, for example, by coupling the compound, with a radioisotope or enzymatic label such that binding of the compound, to the ERG protein or ETV protein and/or the mSWI/SNF (BAF) chromatin remodeling complex protein can be determined by detecting the labeled compound, e.g., substrate, in a complex. Alternatively, the ERG protein or ETV protein and/or the mSWI/SNF (BAF) chromatin remodeling complex protein could be coupled with a radioisotope or enzymatic label to monitor the ability of a candidate compound to interfere with an interaction between an ERG protein or ETV protein and a mSWI/SNF (BAF) chromatin remodeling complex protein. For example, compounds can be labeled with 125I, 35S, 14C, or 3H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound to interfere with an interaction between an ERG protein or ETV protein and a mSWI/SNF (BAF) chromatin remodeling complex protein with or without the labeling of any of the interactants can be evaluated. For example, a microphysiometer can be used to detect the interaction of a compound with an ERG protein or ETV protein and/or a mSWI/SNF (BAF) chromatin remodeling complex protein without the labeling of either the compound or the ERG protein or ETV protein or a mSWI/SNF (BAF) chromatin remodeling complex protein. McConnell, H. M. et al. (1992) Science 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and an ERG protein or ETV protein and/or a mSWI/SNF (BAF) chromatin remodeling complex protein.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, measuring the interaction between an ERG protein or ETV protein and a mSWI/SNF (BAF) chromatin remodeling complex protein (in the presence or absence of a candidate compound) can be accomplished using real-time Biomolecular Interaction Analysis (BIA) (see, e.g., Sjolander, S. and Urbaniczky, C. (1991) Anal. Chem. 63:2338-2345 and Szabo et al. (1995) Curr. Opin. Struct. Biol. 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, one of the ERG protein or ETV protein or the mSWI/SNF (BAF) chromatin remodeling complex protein, or the candidate compound is anchored onto a solid phase. The ERG:BAF/candidate compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either the ERG protein or ETV protein, the mSWI/SNF (BAF) chromatin remodeling complex protein, an anti-ERG, anti-ETV or anti-mSWI/SNF (BAF) chromatin remodeling complex protein antibody to facilitate separation of complexed from uncomplexed forms of one or both of the proteins, as well as to accommodate automation of the assay. Binding of a candidate compound to a ERG protein or ETV protein or mSWI/SNF (BAF) chromatin remodeling complex protein, or interaction of the ERG protein or ETV protein and a mSWI/SNF (BAF) chromatin remodeling complex protein in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase/target fusion proteins can be adsorbed onto glutathione sepharose beads (Sigma Chemical, St. Louis, Mo.) or glutathione derivatized microtiter plates. Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of interaction determined using standard techniques.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with an ERG protein or ETV protein or a mSWI/SNF (BAF) chromatin remodeling complex protein but which do not interfere with binding of the ERG protein or ETV protein to the mSWI/SNF (BAF) chromatin remodeling complex protein. Such antibodies can be derivatized to the wells of the plate, and unbound mSWI/SNF (BAF) chromatin remodeling complex protein or ERG protein or ETV protein trapped in the wells by antibody conjugation. Methods for detecting such complexes, in addition to those described above for the GST-immobilized complexes, include immunodetection of complexes using antibodies reactive with the ERG protein or ETV protein or mSWI/SNF (BAF) chromatin remodeling complex protein, as well as enzyme-linked assays which rely on detecting an enzymatic activity associated with the ERG protein or ETV protein or mSWI/SNF (BAF) chromatin remodeling complex protein.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) Trends Biochem Sci 18:284-7); chromatography (gel filtration chromatography, ion-exchange chromatography); electrophoresis (see, e.g., Ausubel, F. et al., eds. Current Protocols in Molecular Biology 1999, J. Wiley: New York); and immunoprecipitation (see, for example, Ausubel. F. et al., eds. (1999) Current Protocols in Molecular Biology, J. Wiley: New York). Such resins and chromatographic techniques are known to one skilled in the art (see, e.g., Heegaard, N. H., (1998) J Mol Recognit 11:141-8; Hage, D. S., and Tweed, S. A. (1997) J Chromatogr B Biomed Sci Appl. 699:499-525). Further, fluorescence energy transfer may also be conveniently utilized, as described herein, to detect binding without further purification of the complex from solution.

To identify compounds that interfere with the interaction between the mSWI/SNF (BAF) chromatin remodeling complex protein and the ERG protein or ETV protein, a reaction mixture containing the mSWI/SNF (BAF) chromatin remodeling complex protein and the ERG protein or ETV protein is prepared, under conditions and for a time sufficient, to allow the two products to form complex. In order to test an inhibitory agent, the reaction mixture is provided in the presence and absence of the candidate compound. The candidate compound can be initially included in the reaction mixture, or can be added at a time subsequent to the addition of the ERG protein or ETV protein and the mSWI/SNF (BAF) chromatin remodeling complex protein. Control reaction mixtures are incubated without the candidate compound or with a placebo. The formation of any complexes between ERG protein or ETV protein and the mSWI/SNF (BAF) chromatin remodeling complex protein is then detected. The formation of a complex in the control reaction, but not in the reaction mixture containing the candidate compound, indicates that the compound interferes with the interaction of the ERG protein or ETV protein and the mSWI/SNF (BAF) chromatin remodeling complex protein. Additionally, complex formation within reaction mixtures containing the candidate compound and wild type ERG protein or ETV protein can also be compared to complex formation within reaction mixtures containing the candidate compound and mutant or variant ERG protein or ETV protein. This comparison can be important in those cases wherein it is desirable to identify compounds that disrupt interactions of mutant but not wild type ERG protein or ETV protein.

These assays can be conducted in a heterogeneous or homogeneous format. Heterogeneous assays involve anchoring either the ERG protein or ETV protein or mSWI/SNF (BAF) chromatin remodeling complex protein onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, candidate compounds that interfere with the interaction between the ERG protein or ETV protein and the mSWI/SNF (BAF) chromatin remodeling complex protein or proteins, e.g., by competition, can be identified by conducting the reaction in the presence of the candidate substance. Alternatively, candidate compounds that disrupt preformed complexes, e.g., compounds with higher binding constants that displace one of the components from the complex, can be tested by adding the candidate compound to the reaction mixture after complexes have been formed. The various formats are briefly described below.

In a heterogeneous assay system, either the ERG protein or ETV protein or the mSWI/SNF (BAF) chromatin remodeling complex protein is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the candidate compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, candidate compounds that inhibit complex formation or that disrupt preformed complexes can be detected.

Alternatively, the reaction can be conducted in a liquid phase in the presence or absence of the candidate compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, candidate compounds that inhibit complex or that disrupt preformed complexes can be identified.

In an alternate embodiment of the invention, a homogeneous assay can be used. For example, a preformed complex of the ERG protein or ETV protein and the mSWI/SNF (BAF) chromatin remodeling complex protein is prepared in that either the ERG protein or ETV protein or the mSWI/SNF (BAF) chromatin remodeling complex protein are labeled, but the signal generated by the label is quenched due to complex formation (see, e.g., U.S. Pat. No. 4,109,496 that utilizes this approach for immunoassays). The addition of a candidate substance that competes with and displaces one of the species from the preformed complex will result in the generation of a signal above background. In this way, test substances that disrupt ERG protein: mSWI/SNF (BAF) chromatin remodeling complex protein interaction or ETV protein: mSWI/SNF (BAF) chromatin remodeling complex protein interaction can be identified.

In yet another aspect, the ERG protein or ETV protein and/or the mSWI/SNF (BAF) chromatin remodeling complex protein can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other proteins, which bind to or interact with the ERG protein or ETV protein and/or the mSWI/SNF (BAF) chromatin remodeling complex protein and are involved in their activity. Such binding compounds can be activators or inhibitors of signals by the ERG protein or ETV protein and/or the mSWI/SNF (BAF) chromatin remodeling complex protein as, for example, downstream elements of an ERG-mediated pathway.

The two-hybrid system is based on the modular nature of most transcription factors, which consist of separable DNA-binding and activation domains. Briefly, the assay utilizes two different DNA constructs. In one construct, the gene that codes for an ERG protein or ETV protein or a mSWI/SNF (BAF) chromatin remodeling complex protein is fused to a gene encoding the DNA binding domain of a known transcription factor (e.g., GAL-4). In the other construct, a DNA sequence, from a library of DNA sequences that encodes an unidentified protein ("prey" or "sample") is fused to a gene that codes for the activation domain of the known transcription factor. (Alternatively the: ERG protein or ETV protein or mSWI/SNF (BAF) chromatin remodeling complex protein can be the fused to the activator domain.) If the "bait" and the "prey" proteins are able to interact, in vivo, forming a ERG-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the ERG protein or ETV protein and/or mSWI/SNF (BAF) chromatin remodeling complex protein.

Prostate Cancer

As used herein, a "subject" within the context of the present invention encompasses, but is not limited to, a mammal, e.g. a human, a domestic animal or a livestock including a cat, a dog, a cattle and a horse.

"A prostate cancer" encompasses, but is not limited to, a localized primary prostate tumor, a metastatic prostate cancer, a hormone-naïve prostate cancer, a hormone-sensitive prostate cancer, a castration-resistant prostate cancer, a prostate adenocarcinoma, and a neuroendocrine prostate cancer.

"A hormone-naïve prostate cancer" encompasses, but is not limited to, a prostate cancer that has not been treated with an androgen deprivation therapy (ADT).

"A hormone-sensitive prostate cancer" encompasses, but is not limited to, a prostate cancer whose growth can be inhibited by ADT.

"A castration-resistant prostate cancer" or "androgen-independent prostate cancer" encompasses, but is not limited to, a prostate cancer that is able to grow despite ADT.

"A metastatic prostate cancer" encompasses, but is not limited to, a cancer of prostate origin that spreads to one or more other parts of the body.

"A sample" encompasses, but is not limited to, a sample from a cancerous lesion, a sample from a cancer draining lymph node, a body fluid such as blood, serum, plasma, urine, semen, lymph, and peritoneal fluid.

"A cancerous lesion" encompasses, but is not limited to, a tissue, organ or structure wherein prostate cancer locates. It may be in or attached to a prostate, or at a metastatic site.

The methods of the disclosure include methods of treating prostate cancer in a subject in need thereof comprising administering a therapeutically effective amount of a candidate compound that interferes with interaction between an ERG protein or ETV protein and a mSWI/SNF (BAF) chromatin remodeling complex protein. A therapeutically effective amount is an amount that provides improvement in a subject to one or more symptoms of prostate cancer.

Symptoms of Prostate Cancer

"A symptom of a prostate cancer" encompasses, but is not limited to, difficulty urinating, blood in urine, erectile dysfunction, pain in the hips, pain in the back, pain the chest, weakness, numbness and incontinence.

"Improvement of a symptom of prostate cancer" includes, but is not limited to, alleviation of a symptom of a prostate cancer, a shrink of cancer size, a reduction of cancer-associated inflammation and/or cachexia, a reduction in Gleason Score, an absence of cancer growth during a period within which an untreated such cancer would grow, an absence of metastatic progression during a period within which an untreated such cancer would metastasize or expand, and an absence of increase in Gleason Score during a period within which the Gleason Score of an untreated such cancer would increase.

"Gleason Score" is a system of grading prostate cancer tissue based on its morphology under a microscope. Gleason scores range from 2 to 10 and indicate how likely it is that a tumor will spread. A low Gleason score means the cancer tissue is similar to normal prostate tissue and the tumor is less likely to spread; a high Gleason score means the cancer tissue is very different from normal and the tumor is more likely to spread.

The treatment(s) can be combined with other therapies appropriate for the treatment of prostate cancer. Treatments for prostate cancer include prostactomy, cryotherapy, radiation therapy, androgen deprivation therapy (ADT), chemotherapy and immunotherapy. Chemotherapy includes, but is not limited to, alkylating agents (e.g., nitrogen mustard, cyclophosphamide, melphalan, busulfan, dacarbazine, procarbazine, etc.), antimetabolites (e.g., methotrexate, mercaptopurine, thioguanine, fluorouracil, etc.), antibiotics (e.g., doxorubicin, daunorubicin, bleomycin, etc.) and alkaloids (e.g., vincristine, vinblastine, vindesine, taxanes, etc.). Immunotherapy includes, but is not limited to, an agent that increases an immune response (e.g. a T cell checkpoint inhibitor) and a cancer vaccine (e.g. Sipuleucel-T). Any of these compounds can be co-administered with any of the therapies disclosed herein.

Furthermore, in accordance with the present disclosure there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, New York (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

The present disclosure also provides recombinant expression vectors which include the synthetic, genomic, or cDNA-derived nucleic acid fragments of the invention, i.e. polynucleotides encoding the mabs of the invention. The nucleotide sequence coding for any of the sequences provided herein can be inserted into an appropriate expression vector, i.e., a vector that contains the necessary elements for the transcription and translation of the inserted protein-coding sequence. The necessary transcriptional and translational signals can also be supplied by the native or source gene and/or its flanking regions.

A variety of host vector systems may be utilized to express the recombinant expression vectors of the invention. These include, but are not limited to, mammalian cell systems infected with recombinant virus (e.g., vaccinia virus, adenovirus, retroviruses, etc.); mammalian cell systems transfected with recombinant plasmids; insect cell systems infected with recombinant virus (e.g., baculovirus); microorganisms such as yeast containing yeast expression vectors, or bacteria transformed with recombinant bacteriophage DNA, recombinant plasmid DNA, or cosmid DNA (see, for example. Goeddel, 1990).

Mammalian expression vectors may comprise non-transcribed elements such as origin of replication, a suitable promoter and enhancer linked to the recombinant nucleic acid to be expressed, and other 5' or 3' flanking sequences such as ribosome binding sites, a polyadenylation sequence, splice donor and acceptor sites, and transcriptional termination sequences.

The transcriptional and translational control sequences in mammalian expression vector systems to be used in transforming vertebrate cells may be provided by viral sources. For example, commonly used promoters and enhancers are derived from Polyoma virus, Adenovirus, Simian Virus 40 (SV40), and human cytomegalovirus, including the cytomegalovirus immediate-early gene 1 promoter and enhancer (CMV).

The following examples are provided to further elucidate the advantages and features of the present application, but are not intended to limit the scope of the application. The examples are for illustrative purposes only.

EXAMPLES

Examples: Section I

Example 1. Endogenous Anti-ERG SILAC Mass Spectrometry in VCaP Cells Reveals Interactions with Members of the mSWI/SNF (BAF) Chromatin Remodeling Complex Anti-ERG SILAC (stable isotope labeling by amino acids in cell culture) mass spectrometry was performed on nuclear extracts of VCaP cells, which express TMRPSS2-ERG fusion, and revealed that ERG interacts with members of the BAF chromatin remodeling complex.

Figure 1B:
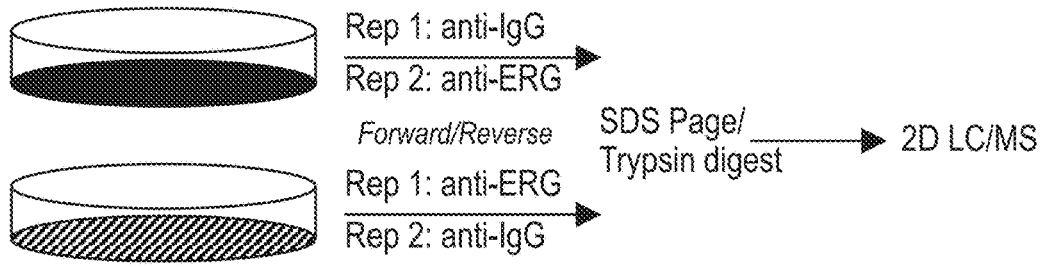

FIG. 1A shows a schematic of TMPRSS2-ERG fusions in prostate cancer (left), and a schematic of ERG protein in VCaP cells (right). The anti-ERG SILAC mass spectrometry proteomics assay is shown in FIG. 1B. Antibodies against ERG (C-20, Santa Cruz) or against IgG (as control) were used. Briefly, two populations of VCaP cells, which express TMPRSS2-ERG, were grown in culture media that are identical except that one contains amino acids with either "light" and the other a "heavy" form of a substituted stable isotopic nucleus. The labeled analog of the amino acid is incorporated into newly synthesized proteins in the cells. After a period of several cell divisions, the amino acid will be replaced with the labeled analog. Cells were harvested, proteins were subjected to SDS-PAGE resolution and trypsin digest. 2D LCMS was performed to identify proteins of the mSWI/SNF (BAF) chromatin remodeling complex interacting with ERG.

Figure 1C:
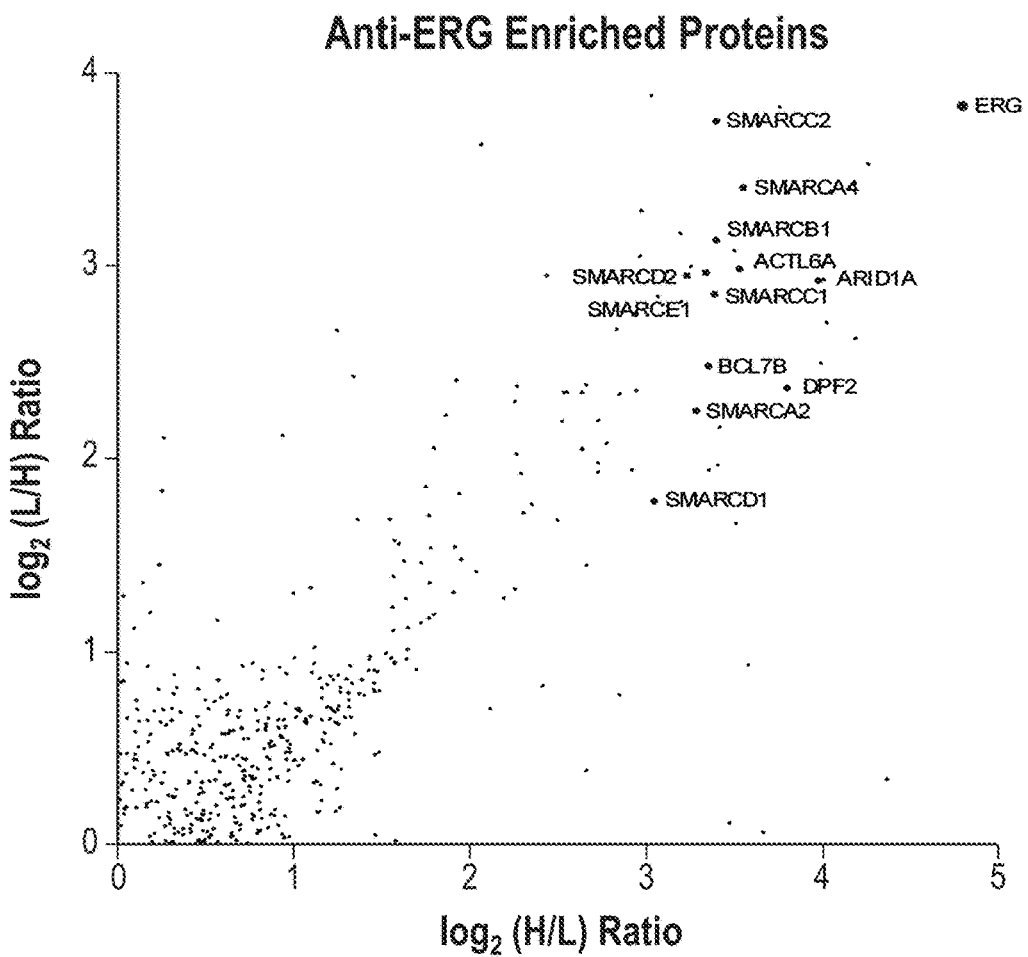

The top SILAC hits over the log 2 fold change of each replicate are represented in FIG. 1C. Highlighted are ERG and significant mSWI/SNF (BAF) chromatin remodeling complex members. mSWI/SNF (BAF) chromatin remodeling complex members are shown as anti-ERG enriched proteins from this analysis. These anti-ERG enriched proteins are indicated as including BAF170/SMARCC2, BRG1/BAF190A/SMARCA4, ARID1A, BAF47/SNF5/SMARCB1, BAF155/SMARCC1, ACTL6A, SMARCE1, SMARCD2, DPF2, BCL7B, SMARCA2, and SMARCD1.

The top 40 SILAC hits are shown in the table at left of FIG. 1D (and in Table 1). Of these top 40 hits, 11 are proteins associated with the BAF complex, and appear in the top 33 hits members identified in the screen. The right of FIG. 1D (and Table 2) shows a list of mSWI/SNF (BAF) chromatin remodeling complex members.

TABLE 1

Top 40 Anti-ERG SILAC hits

| Rank | Gene names | Razor + unique peptides | Sequence coverage [%] | P. Value |
|---|---|---|---|---|
| 1 | LBR | 8 | 16.4 | 1.35E−05 |
| 2 | ERG | 43 | 92.6 | 2.59E−07 |
| 3 | GSTP1 | 7 | 55.7 | 3.23E−06 |
| 4 | SRI | 7 | 39.9 | 7.73E−07 |
| 5 | TMEM160 | 10 | 37.2 | 9.13E−07 |
| 6 | SYNGR2 | 6 | 17.1 | 8.34E−07 |
| 7 | SUCLG2 | 5 | 14.1 | 3.97E−06 |
| 8 | SMARCC2 | 67 | 45.9 | 1.82E−06 |
| 9 | SMARCA4 | 79 | 41.3 | 2.41E−06 |
| 10 | USP40 | 65 | 55 | 4.19E−06 |
| 11 | ARID1A | 94 | 49.1 | 4.36E−06 |
| 12 | MAP3K4 | 107 | 65 | 8.67E−06 |
| 13 | CTNND2 | 8 | 9.4 | 7.53E−06 |
| 14 | SQSTM1 | 22 | 74.5 | 5.03E−06 |
| 15 | SMARCB1 | 21 | 65.4 | 5.22E−06 |
| 16 | SMARCC1 | 51 | 55.9 | 5.99E−06 |
| 17 | JPPAP2A | 6 | 32.7 | 1.40E−05 |
| 18 | OSBPL9 | 21 | 33 | 6.88E−06 |
| 19 | ACTL6A | 20 | 62.5 | 8.14E−06 |
| 20 | CDS2 | 2 | 9 | 8.63E−06 |
| 21 | PDE8A | 27 | 40.2 | 8.69E−06 |
| 22 | SMARCE1 | 16 | 36.7 | 9.78E−06 |
| 23 | SMARCD2 | 24 | 53.9 | 9.94E−06 |
| 24 | DPF2 | 29 | 70.3 | 2.28E−05 |
| 25 | GFPT1 | 37 | 63.2 | 1.30E−05 |
| 26 | E1F4G1 | 53 | 33.1 | 1.40E−05 |
| 27 | OSBPL11 | 15 | 33.2 | 1.55E−05 |
| 28 | OSBPL10 | 18 | 28.4 | 1.62E−05 |
| 29 | BCL7B | 5 | 41.1 | 2.55E−05 |
| 30 | APEH | 13 | 21.8 | 6.08E−05 |
| 31 | BAIAP2 | 31 | 62 | 2.47E−05 |
| 32 | ANXA7 | 19 | 40.2 | 5.57E−05 |
| 33 | SMARCA2 | 33 | 38.1 | 5.06E−05 |
| 34 | HNRNPK | 28 | 59.5 | 3.51E−05 |
| 35 | DAG1 | 17 | 19.8 | 4.84E−05 |
| 36 | FAM120C | 11 | 13.2 | 9.74E−05 |
| 37 | SPOP | 3 | 11.8 | 0.000109 |
| 38 | STAM | 19 | 46.7 | 5.99E−05 |
| 39 | PRKCI | 6 | 13.6 | 7.22E−05 |
| 40 | NDE1 | 9 | 33.8 | 0.000214 |

TABLE 2 mSWI/SNF (BAF) chiromatin remodeling complex members

| Rank | Gene Names | Razor + unique peptides | Sequence coverage [%] | P. Value |
|---|---|---|---|---|
| 8 | SMARCC2 | 67 | 45.9 | 1.82E−06 |
| 9 | SMARCA4 | 79 | 41.3 | 2.41E−06 |
| 11 | ARID1A | 94 | 49.1 | 4.36E−06 |
| 15 | SMARCB1 | 21 | 65.4 | 5.22E−06 |
| 16 | SMARCC1 | 51 | 55.9 | 5.99E−06 |
| 19 | ACTL6A | 20 | 62.5 | 8.14E−06 |
| 22 | SMARCE1 | 16 | 36.7 | 9.78E−06 |
| 23 | SMARCD2 | 24 | 53.9 | 9.94E−06 |
| 24 | DPF2 | 29 | 70.3 | 2.28E−05 |
| 29 | BCL7B | 5 | 41.1 | 2.55E−05 |
| 33 | SMARCA2 | 33 | 38.1 | 5.06E−05 |
| 48 | SMARCD1 | 18 | 50.7 | 0.000236321 |
| 289 | PBRM1 | 61 | 40.4 | 0.2738417 |
| 693 | ARID2 | 20 | 14.4 | 0.94347732 |
| 1096 | BRD7 | 3 | 4.8 | 0.146731109 |
| N/A | ARID1B | 4 | 3.9 | NA |
| N/A | BCL7A; BCL7B | 2 | 16.9 | NA |
| N/A | BCL7C | 4 | 51.2 | NA |
| N/A | ACTL6B | 2 | 16 | NA |
| N/A | SS18L1 | 6 | 15.4 | NA |

Figure 2A:
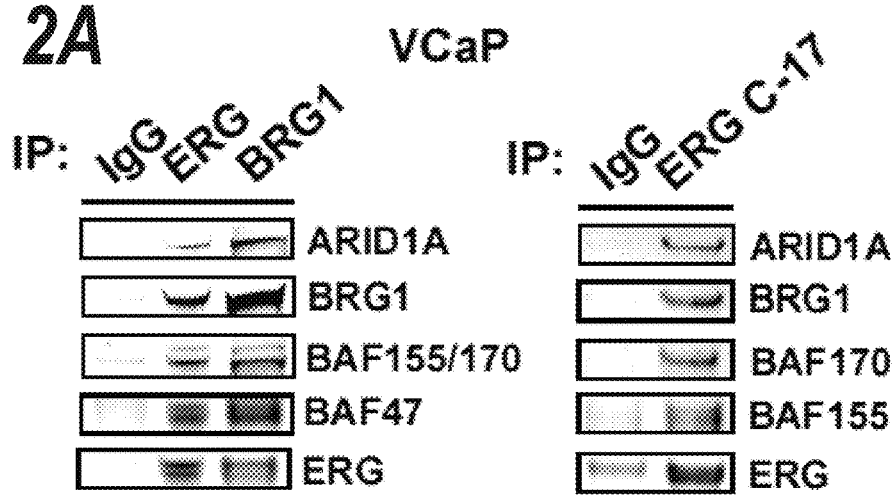
FIG. 2A-E shows immunoblots of ERG or BRG1 in VCaP cells and normal prostate epithelial cells with exogenously expressed ERG.

Example 2. ERG is Bound to BAF Complexes in VCaP Cells and in Normal Prostate Epithelial Cells with Exogenously Expressed ERG Reciprocal immunoprecipitation was performed on nuclear extracts of VCaP cells using anti-ERG and anti-BRG1 antibodies. Cells were grown and nuclear extracts prepared. Results are shown in FIG. 2A, left panel. Both anti-ERG (C-20, Santa Cruz) and anti-BRG1 antibodies precipitated ARID1A, BRG1, BAF155/170, BAF47 and ERG. In addition, an alternate anti-ERG antibody (C-17, Santa Cruz) was used for immunoprecipitation of VCaP nuclear extracts (see, FIG. 2A, right panel). This alternate anti-ERG antibody similarly precipitated ARID1A, BRG1, BAF155, BAF170, and ERG.

Figure 2B:
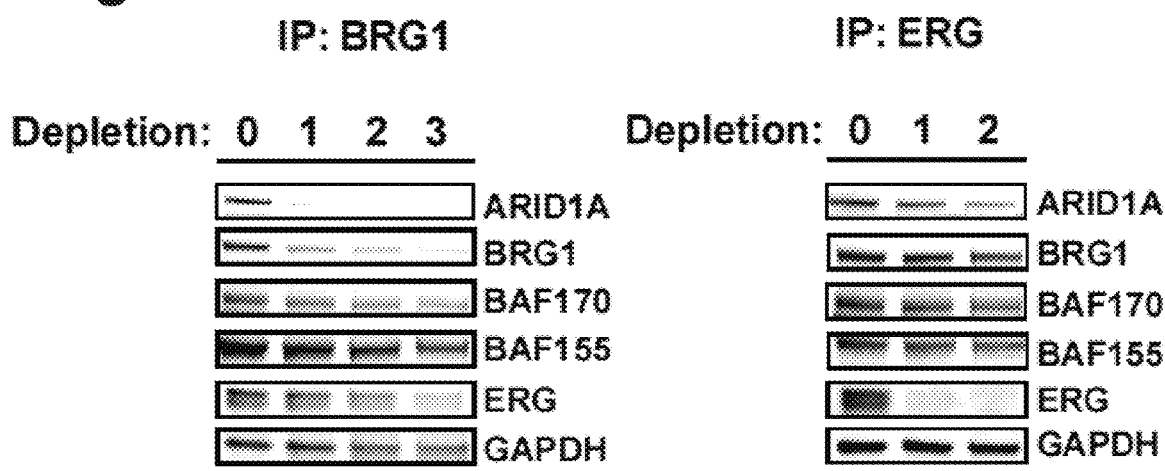

Immunodepletion studies were also performed nuclear extracts of VCaP cells using anti-BRG1 and anti-ERG antibodies. Results are shown in FIG. 2B.

Figure 2C:
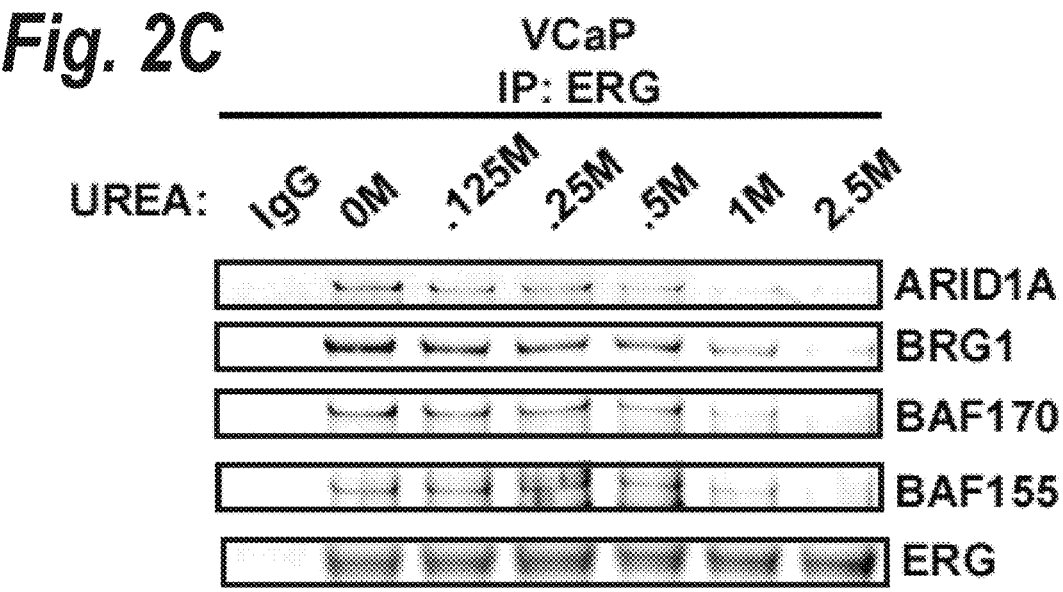

Urea denaturation studies were carried out by subjecting nuclear extracts from VCaP cells to partial urea denaturation, from 0.25 to 2.5M urea for 30 minutes at room temperature, prior to anti-BRG1 or anti-ERG immunoprecipitation. Co-precipitated proteins were analyzed by immunoblot (Western blot). Quantitative densitometry analyses were performed using Li-Cor Odyssey Imaging System (Li-Cor Biosciences, Lincoln, NE, USA). Results are shown in FIG. 2C.

Figure 2D:
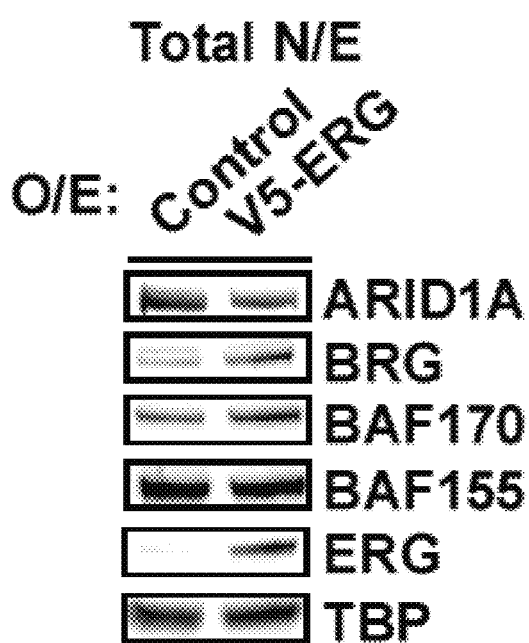
Figure 2D:
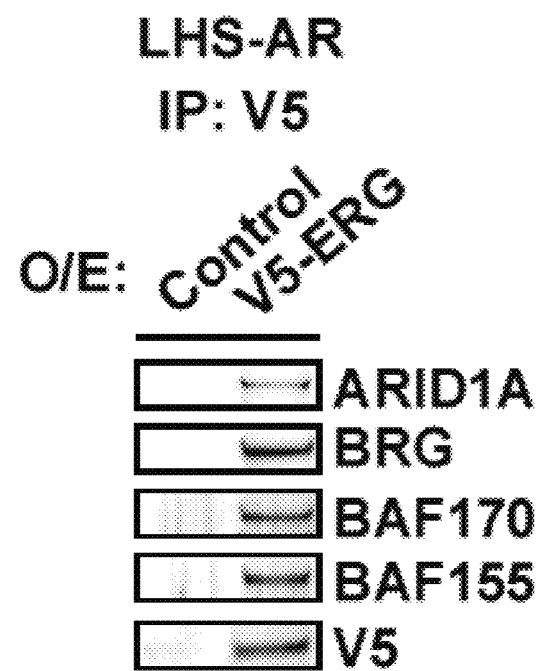

In addition, immunoprecipitation analysis was applied to LHS-AR cells with and without overexpression of V5-tagged ERG (V5-ERG). FIG. 2D shows results of this analysis. The left panel shows the amounts of BAF proteins and TBP control in total nuclear extracts of LHS-AR cells with and without ectopic expression of V5-ERG. Total nuclear extracts in these cells have levels of mSWI/SNF (BAF) chromatin remodeling complex members ARID1A, BRG1, BAF170, BAF155, and the V5-ERG cells have levels of ERG in the nuclear extracts. The right panel shows amounts of BAF proteins and V5 tag in anti-V5 antibody immunoprecipitates of nuclear extracts from LHS-AR cells with and without expression of V5-ERG. Anti-V5 precipitated mSWI/SNF (BAF) chromatin remodeling complex members ARID1A, BRG1, BAF170 and BAF155.

Figure 2E:
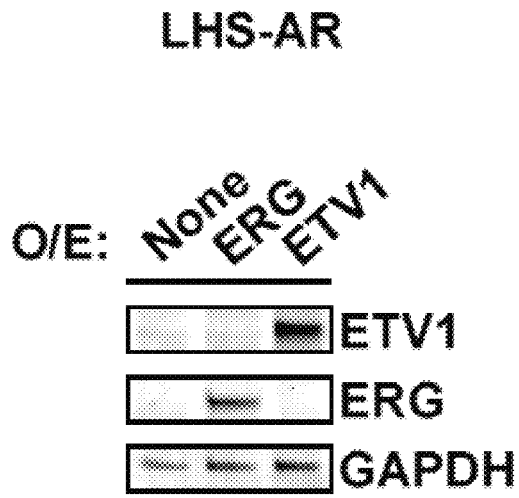
Figure 2E:
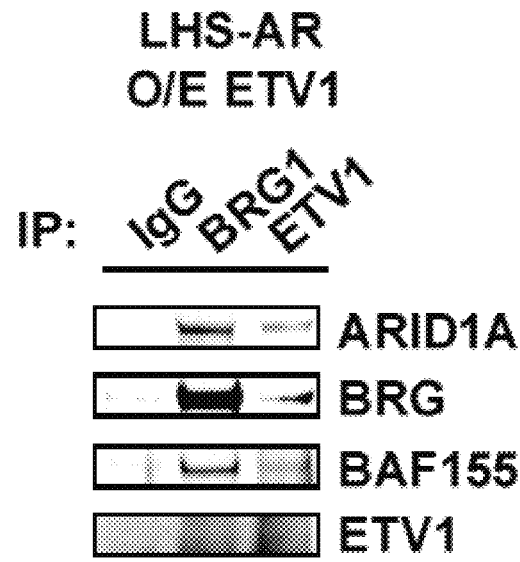

FIG. 2E shows immunoblots of ERG and ETV1 in LHS-AR cells overexpressing ERG, ETV1, or empty vector. The left panel shows that the LHS-AR cells transfected with ERG and with ETV1 expressed high levels of Erg and ETV1, respectively, and ERG-transfected cells did not express detectable levels of ETV1 (nor did ETV1-transfected cells express detectable levels of ERG). The right panel shows immunoblots of immunoprecipitation of LHS-AR cells overexpressing ETV1 by anti-BRG1, anti-ETV1, or control IgG antibody. Both anti-BRG1 and anti-ETV1 antibodies precipitated ARID1A, BRG, and BAF155 from these nuclear extracts.

Example 3. ERG Directs Genome-Wide mSWI/SNF (BAF) Chromatin Remodeling Complex Localization Genome-wide localization of mSWI/SNF (BAF) chromatin remodeling complex was analyzed by chromatin immunoprecipitation sequencing ("ChIP-seq") and high throughput sequencing ("HTseq") to determine co-localization of ERG with members of the BAF complex.

Figure 3C:
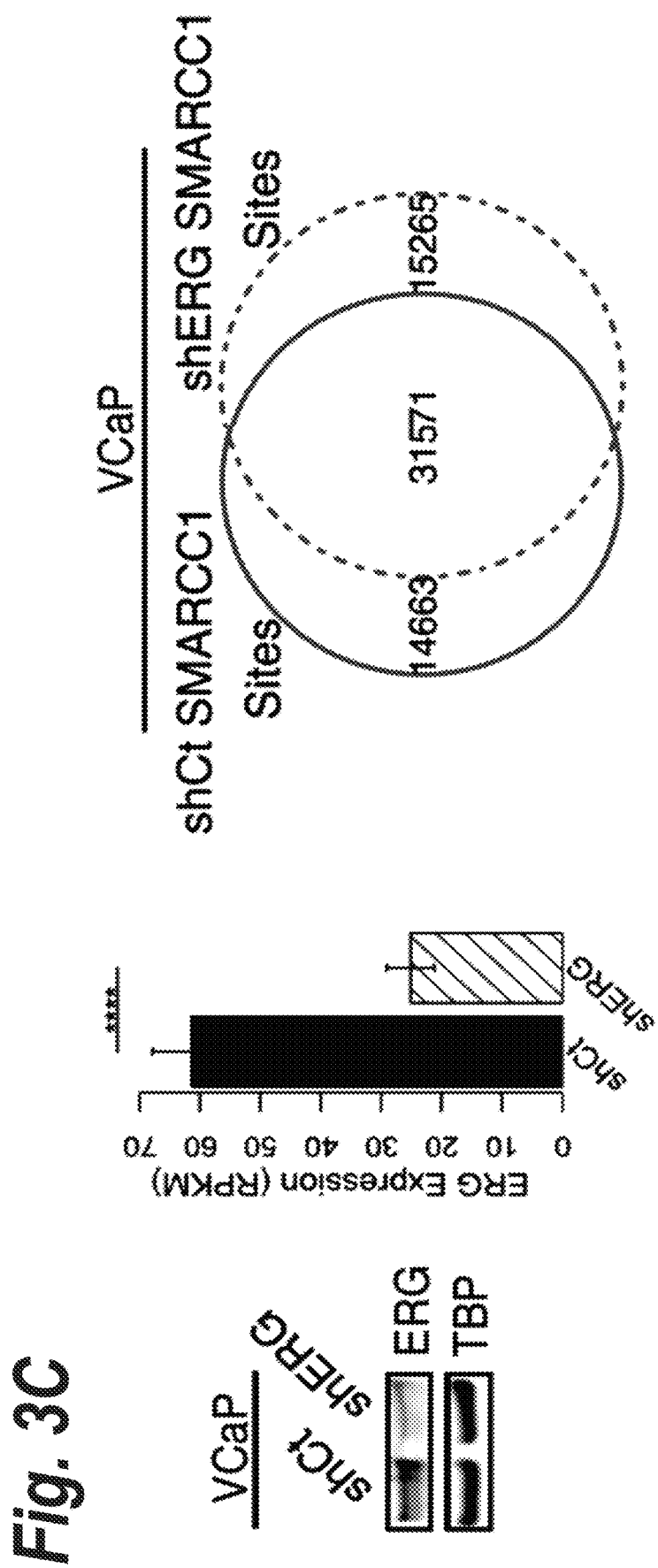

As shown in FIG. 3A, the overlap of ChIP-seq peaks of ERG, SMARCC1 and SMARCA4 demonstrates the degree of co-localization of ERG and these BAF members in VCaP cells. In the comparisons of the three sets of ChIP-seq peaks (ERG, SMARCC1 and SMARCA4), it was determined that ERG and SMARCC1 had 34,463 overlapping sites, with 36,452 non-overlapping ERG sites and 11,702 non-overlapping SMARCC1 sites. ERG and SMARCA4 had 28,551 overlapping sites, with 42,789 non-overlapping ERG sites and 11,733 non-overlapping SMARCA4 sites. SMARCC1 and SMARCA4 had 29,142 overlapping sites, with 17,500 non-overlapping SMARCC1 sites and 11,059 non-overlapping SMARCA4 sites.

The co-localization of ERG, SMARCC1, and SMARCA4 is further demonstrated in the HTseq plot of reads for these proteins in VCaP cells shown in FIG. 3B.

Knockdown of ERG in VCaP cells was found to affect genome-wide positioning of mSWI/SNF (BAF) chromatin remodeling complex (see, FIG. 3C). shERG in VCaP cells resulted in knockdown of levels of ERG protein and RNA. Overlap of SMARCC1 ChIP-seq peaks in shERG and control VCaP cells is shown. There were 15,265 non-overlapping shERG sites, with 14.663 non-overlapping shCt sites, and 31,571 overlapping sites between shERG and shCt.

Figure 3D:
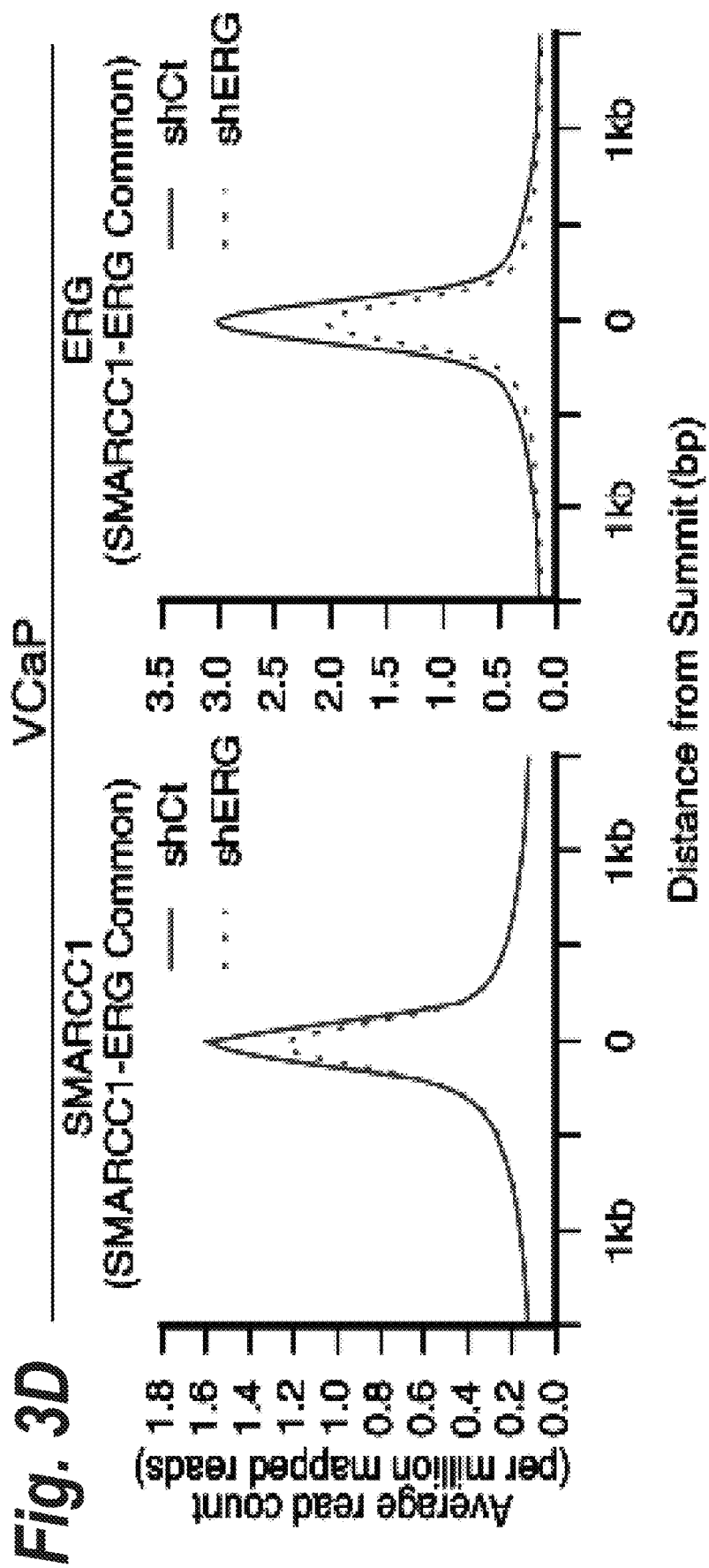

Furthermore, the effect of ERG knockdown on peaks common to both ERG and SMARCC1 was determined. Results are shown in FIG. 3D. Knockdown of ERG caused loss of ERG and SMARCC1 at ERG-SMARCC1 common peaks.

In addition, the overlap of ChIP-seq peaks of ERG, SMARCC1 and SMARCA4 was analyzed in prostate epithelial cell line LHS-AR cells transfected with ERG. As shown in FIG. 3E, in these LHS-AR+ERG cells, ERG and SMARCC1 had 23,637 overlapping sites, with 28,044 non-overlapping ERG sites and 9,879 non-overlapping SMARCC1 sites. ERG and SMARCA4 had 28,177 overlapping sites, with 25,294 non-overlapping ERG sites and 21,629 non-overlapping SMARCA4 sites. SMARCC1 and SMARCA4 had 26,179 overlapping sites, with 8,772 non-overlapping SMARCC1 sites and 23,641 non-overlapping SMARCA4 sites.

The co-localization of ERG, SMARCC1, and SMARCA4 is further demonstrated in the HTseq plot of reads for these proteins in LHS-AR+ERG cells shown in FIG. 3F.

Figure 3G:
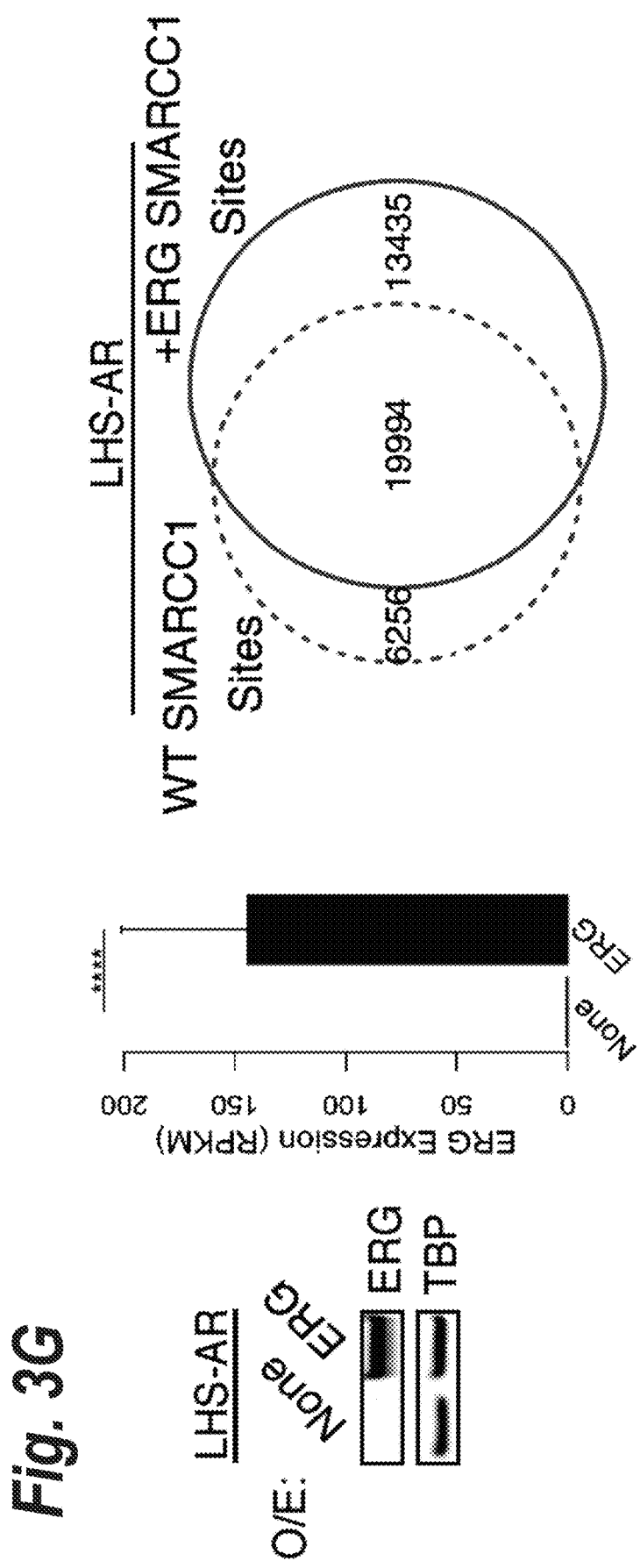

Further, ectopic expression of ERG in LHS-AR cells (LHS-AR+ERG cells) was found to direct BAF repositioning. See, FIG. 3G. Expression of ERG protein and RNA is shown for LHS-AR cells transfected with Erg, but not with empty vector. In these LHS-AR cells, overlap of SMARCC1 sites in wild type and ERG-overexpressing conditions was compared. There were 13,435 non-overlapping SMARCC1 sites in LHS-AR+ERG cells, 6,256 non-overlapping SMARCC1 sites in LHS-AR cells, and 19,994 overlapping SMARCC1 sites between LHS-AR+ERG cells and wild type LHS-AR cells.

Figure 3H:
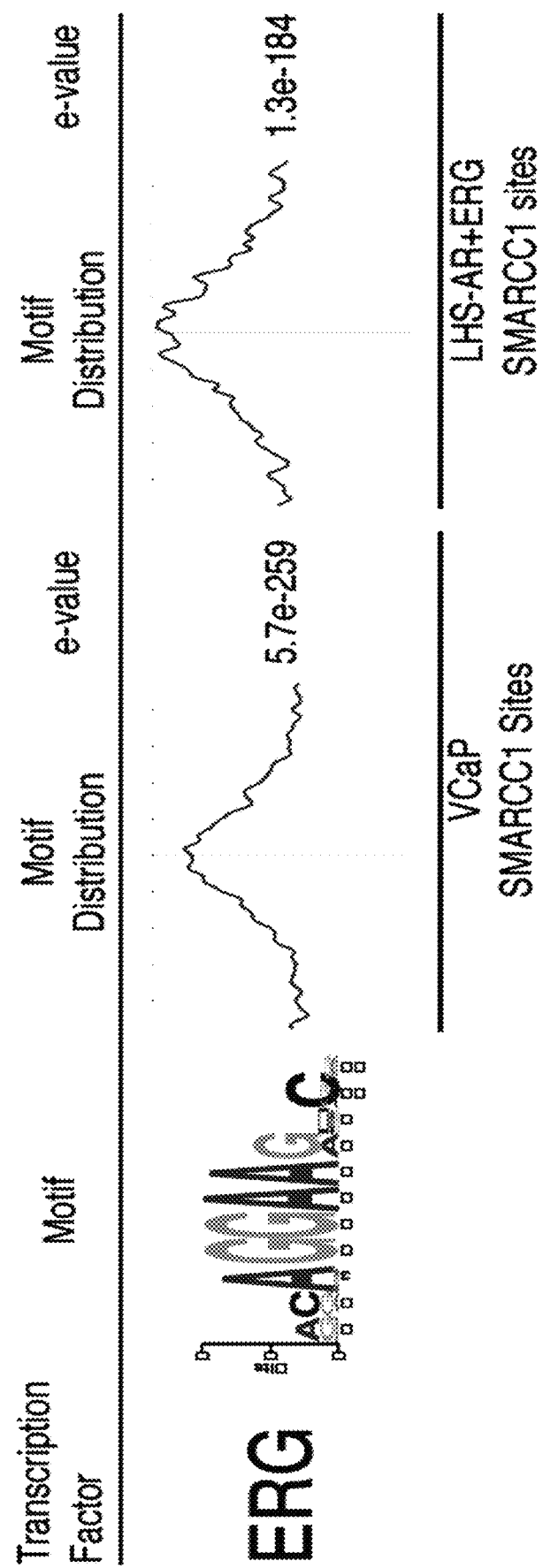

Motif enrichment of ERG over SMARCC1 sites in VCaP shCt and LHS-AR+ERG is shown in FIG. 3H.

Example 4. ERG Overexpression in LHS-AR Alters Gene Expression of Key Prostate Cancer Pathways Effects of overexpression of ERG in LHS-AR cells on gene expression was assessed, and found to affect expression of key prostate cancer pathways.

Figure 4A:
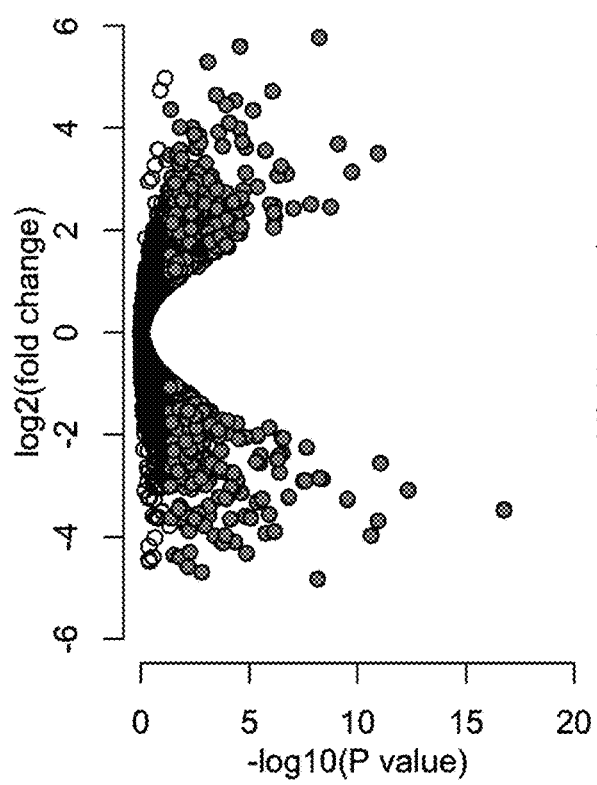
FIG. 4A-E is a plot of expression of all genes was plotted for VCaP cells (FIG. 4A) and for LHS-AR cells with ERG overexpression/knockdown (FIG. 4B). Genes significant (adjusted p-value <0.05 and |log 2(fold change)|>1) are filled light grey, and ERG is filled dark grey.
Figure 4B:
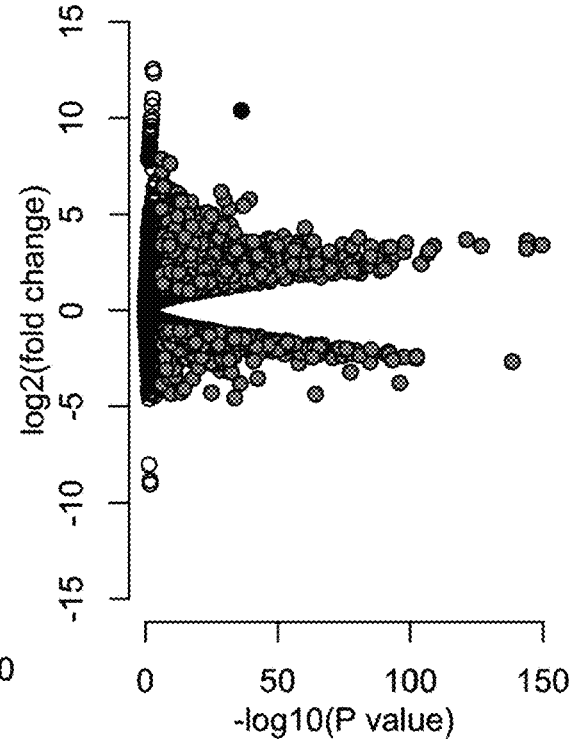

Expression of all genes was plotted for VCaP cells (FIG. 4A) and for LHS-AR cells with ERG overexpression/knockdown (FIG. 4B). Genes significant (adjusted p-value <0.05 and |log 2(fold change)|>1) are filled light grey, and ERG is filled dark grey.

Figure 4C:
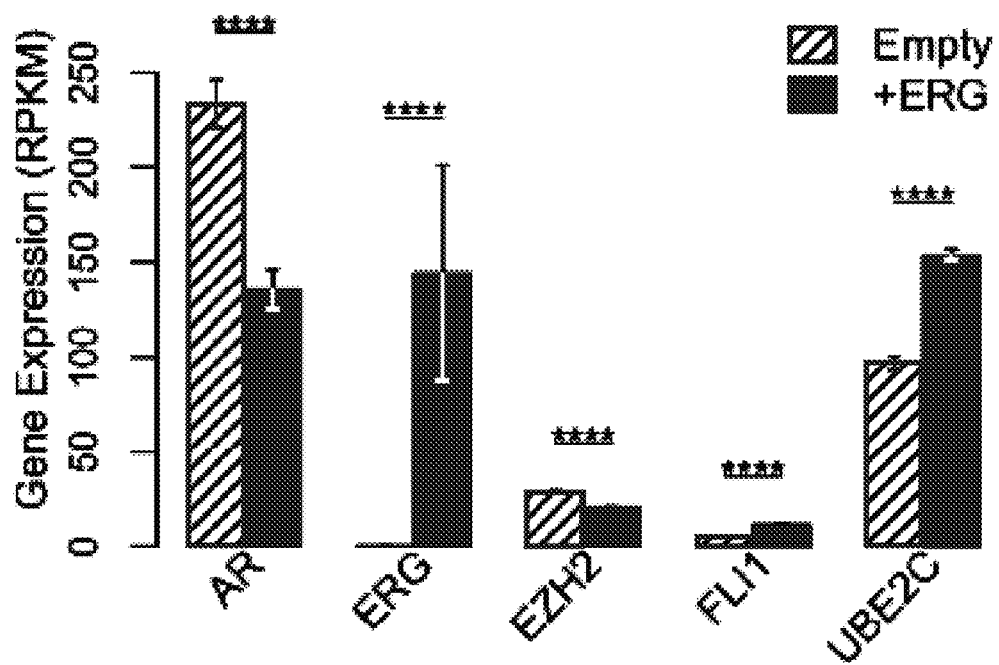

RPKM analysis showed ERG overexpression increased expression of genes overexpressed in prostate cancer (FLI1, UBE2C) and decreased expression of genes suppressed in prostate cancer (AR, EZH2). See, FIG. 4C.

Figure 4D:
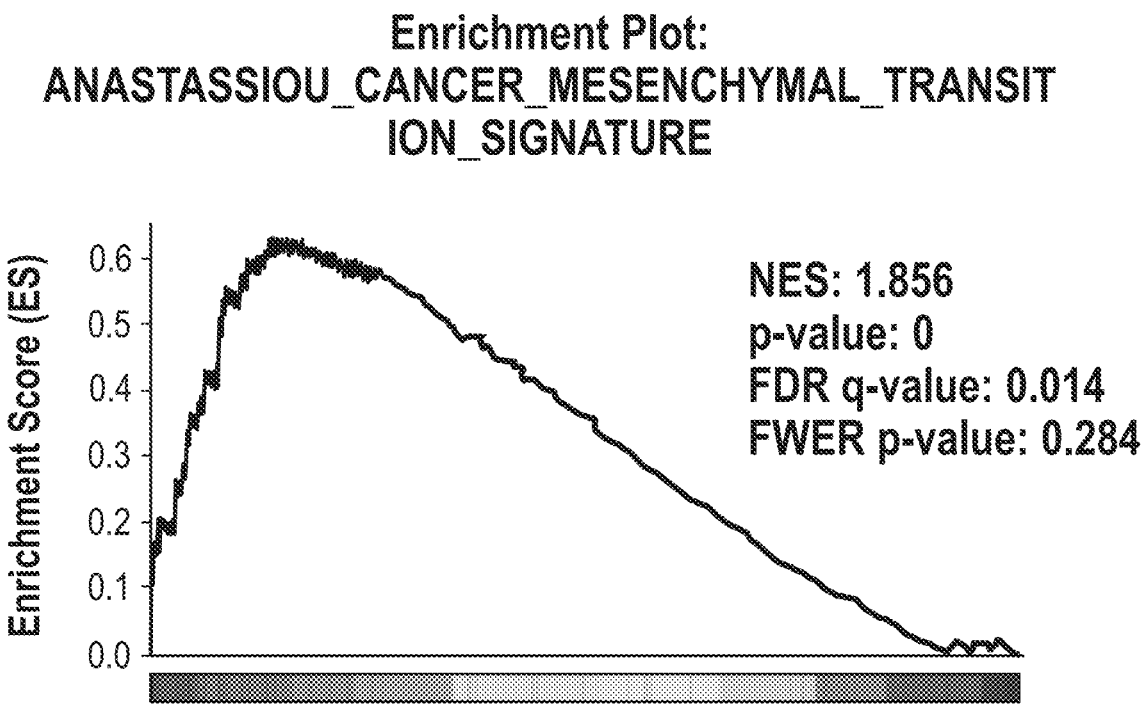
Figure 4D:
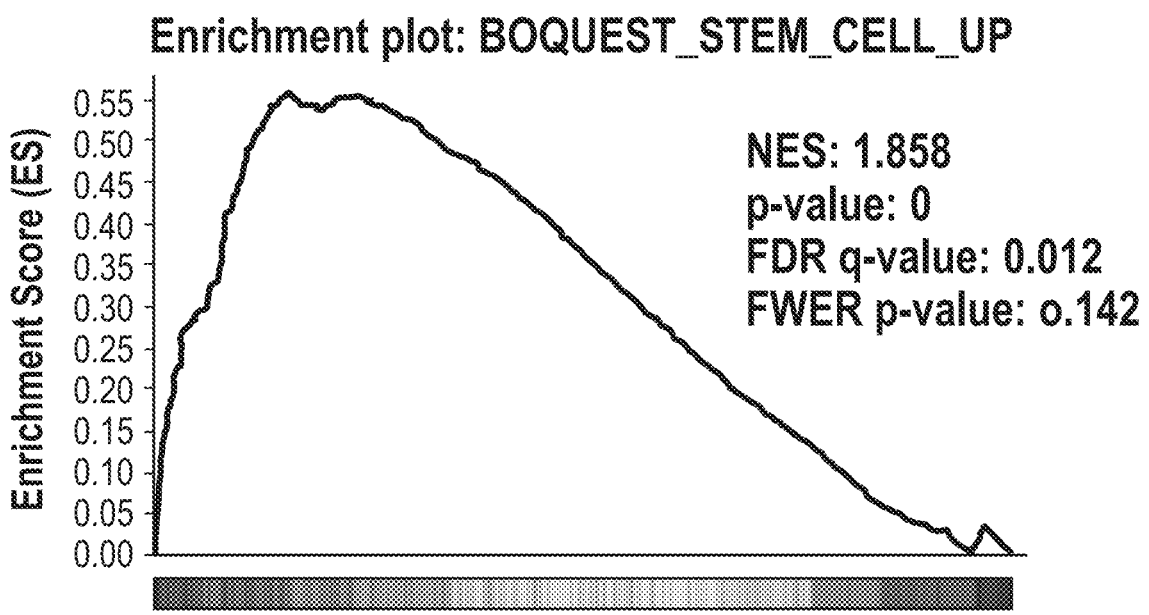

Pathways in stem cell-like qualities and cancer phenotypes are enriched with ERG overexpression in LHS-AR cell lines plus ERG. FIG. 4D shows enrichment plots of genes involved in cancer-related mesenchymal transition and stem cell character.

Figure 4E:
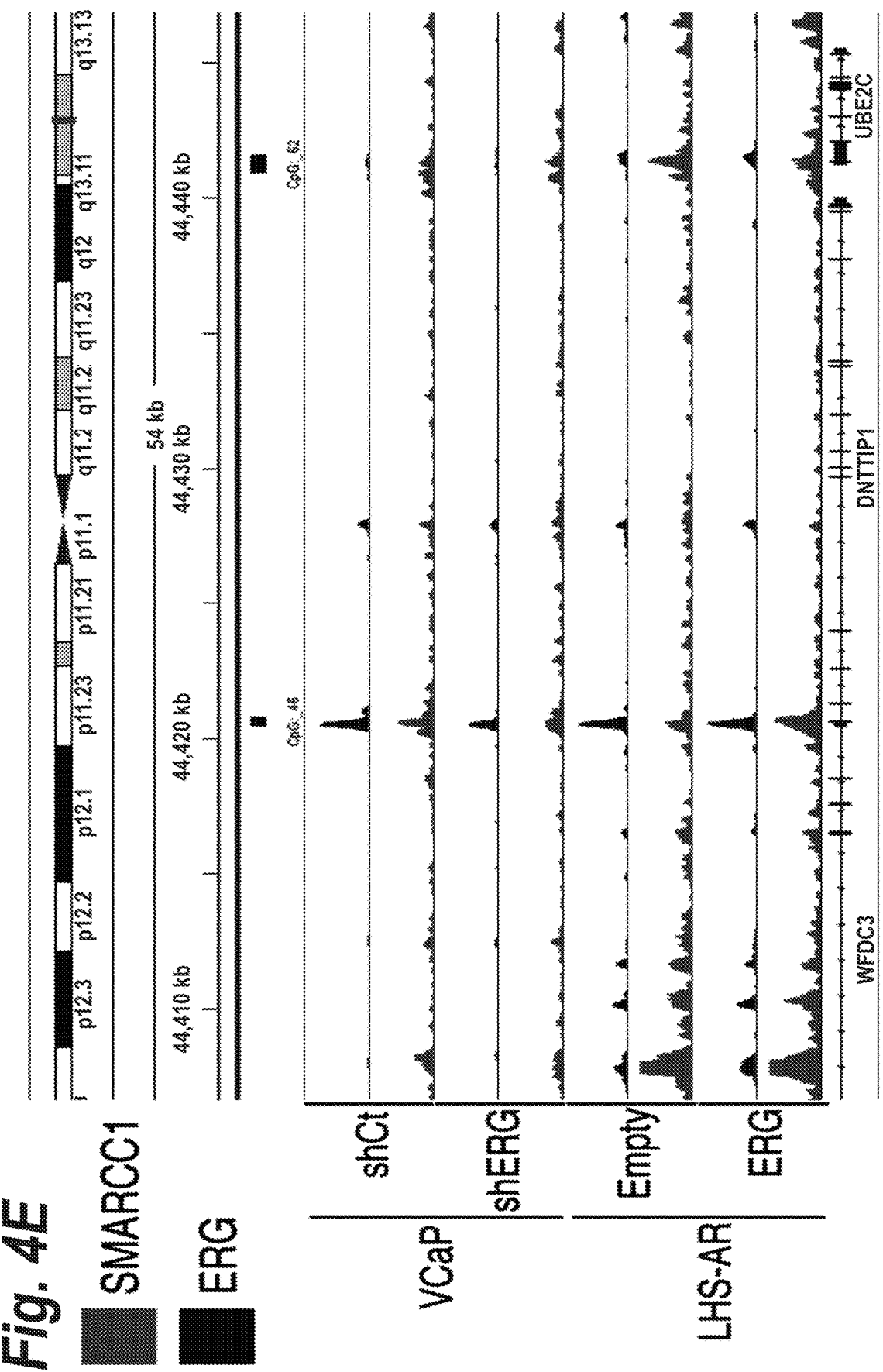

Furthermore, localization of SMARCC1 to the UBE2C enhancer was shown to exhibit ERG-dependence in these cells. (See, FIG. 4E)

Example 5. ERG Tethers to the mSWI/SNF (BAF) Chromatin Remodeling Complex Via BAF155

Figure 5A:
FIG. 5A-C shows immunoblots of immunoprecipitations using anti-BRG1, anti-ERG or control antibody on extracts from SKOV cells with and without ERG overexpression (FIG. 5A) and from VCaP cells with an without knockdown of BAF155.
Figure 5B:
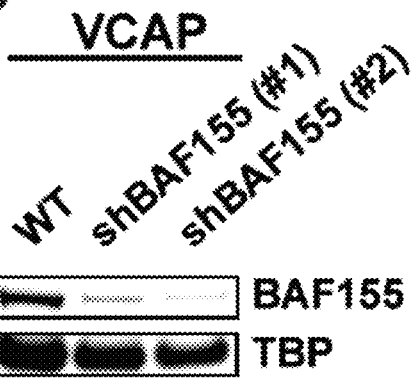
Figure 5C:
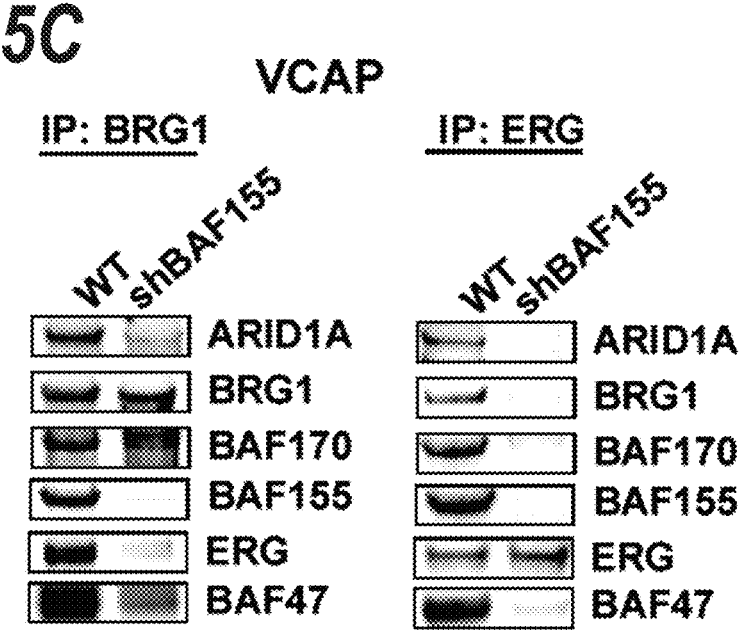

Using immunoprecipitation analysis, how ERG binds to the BAF complex was determined. FIG. 5 shows results of this analysis. VCaP cells with knockdown of BAF155 (FIGS. 5B and C) show loss of pulldown of the mSWI/SNF (BAF) chromatin remodeling complex in immunoprecipitation with anti-ERG antibodies (FIG. 5C, right side). Therefore, ERG tethers to the mSWI/SNF (BAF) chromatin remodeling complex in a manner that is dependent on BAF155.

Example 6. ERG Tethers to the mSWI/SNF (BAF) Chromatin Remodeling Complex Via Amino Acids 208-259 (Exons 7&8) of BAF155

To further characterize the tethering interaction between ERG and the mSWI/SNF (BAF) chromatin remodeling complex via BAF155, ERG variants were constructed and tested for interaction with BAF155 and other components of the BAF complex.

FIG. 6A shows a schematic of the full length (462aa long) ERG and the fusion expressed on VCaP cells, TMPRSS2-ERG. PNT=pointed domain (corresponding to about amino acids 120-206 of the full length protein); ETS=DNA binding domain (corresponding to about amino acids 296-375 of the full length protein); CAD=c-terminal activation domain (corresponding to about amino acids 416-462 of the full length protein).

FIG. 6B shows a schematic of variant ERG proteins developed to interrogate the binding interaction between ERG and the BAF complex:
ERG: ΔPNT domain (deletion of PNT domain),
ERG: ΔETS domain (deletion of ETS domain),
ERG: ΔCAD domain (deletion of CAD domain).
ERG: R367K Mutant (DNA Binding mutant),
ERG: ΔExon 4-8 (deletion of exons 4-8),
ERG: ΔExon 7 (deletion at about a.a. 208-235),
ERG: ΔExon 8 (deletion at about a.a. 236-259), and
ERG: ΔExon 7/8 (deletion at about a.a. 208-259).

These ERG variants were used to measure binding between ERG variants and the BAF complex, and in particular with BAF155. LHS-AR cells overexpressing ERG or ERG variants ERG: ΔExon 7, ERG: ΔExon 8, and ERG: ΔExon 7/8, were tested for their interaction with BAF155, BAF170 and BRG1. As shown in FIG. 6C, deletion of Exon 7, 8 or 7 and 8 resulted in a loss of pulldown of BAF155 via immunoprecipitation using anti-V5 antibody. Thus, Exons 7 and 8 mediate the tethering interaction between ERG and BAF155 of the BAF complex.

Examples 1-6: Materials and Methods

Nuclear Extract Preparation: Cell types were grown under standard conditions and lysed and homogenized in Buffer A (10 mM HEPES (pH 7.6), 25 mM KCL, 1 mM EDTA, 10% glycerol, 1 mM DTT, and protease inhibitors (Roche) supplemented with 1 mM PMSF) on ice. Nuclei were sedimented by centrifugation (1,200 rpm), resuspended in Buffer C (10 mM HEPES (pH 7.6), 3 mM MgCl2, 100 MM KCL, 0.1 mM EDTA, 10% glycerol, 1 mM DTT and protease inhibitors), and lysed by the addition of ammonium sulfate to a final concentration of 0.3M. Soluble nuclear proteins were separated by ultracentrifugation (100,000×g) and precipitated with 0.3 mg/ml ammonium sulfate for 20 mins on ice. Protein precipitate was isolated by ultracentrifugation (100,000×g) and resuspended in IP buffer (300 mM NaCl, 50 mM Tris-HCl [pH 8.0], 1% NP-40, 0.5% deoxycholate, 1 mM DTT, 1 mM PMSF with protease inhibitors) for immunoprecipitation analyses or HEMG-0 buffer (25 mM HEPES [pH 7.9], 0.1 mM EDTA, 12.5 mM MgCl2, 100 mM KCl, supplemented with DTT and PMSF) for analyses on glycerol gradient.

Immunoprecipitation: Nuclear extracts were resuspended in IP buffer and placed in protein LoBind tubes (Eppendorf). Protein concentration was determined using Bradford assay and adjusted to the final volume of 250 µl at a final concentration of 1.5 mg/ml with IP buffer. Each IP was incubated with 2.5 µg of antibody (Antibody specifications are found in Table 3) overnight at 4° C. and then for 1 h with 20 µl Protein G Sepharose beads. The beads were then washed five times at 4° C. with IP buffer and resuspended in 20 µl 2× gel loading buffer (4×LDS buffer: Invitrogen)+DTT and water.

TABLE 3

Antibody Specifications

| Antibody | Clone | Type | Peptide Region | Source | Catalog # |
|---|---|---|---|---|---|
| Brg | G7 | mouse monoclonal IgG1 | aa209-296; N-terminus | Santa Cruz Biotechnology | sc-17796 |
| Brg | J1 | Rabbit polyclonal | | generated in-house | N/A |
| BAF250 | C7 | mouse monoclonal IgG1 | aa1236-1325 | Santa Cruz Biotechnology | sc-373784 |
| BAF170 | H-116 | Rabbit polyclonal | aa1093-1208 | Santa Cruz Biotechnology | sc-10757 |
| BAF170 | G-12 | mouse monoclonal IgG1 | C-terminus | Santa Cruz Biotechnology | sc-166237 |
| BAF155 | | Rabbit polyclonal | aa924-1004; C-terminus | generated in-house | N/A |
| BAF155 | H-76 | Rabbit polyclonal | aa978-1073 | Santa Cruz Biotechnology | sc-10756 |
| BAF47 | A-5 | mouse monoclonal IgG1 | aa1-300 | Santa Cruz Biotechnology | sc-166165 |
| ERG | D-3 | mouse monoclonal IgG2a | aa101-120 | Santa Cruz Biotechnology | sc-271048 |
| ERG | C-17 | Rabbit polyclonal | internal | Santa Cruz Biotechnology | sc-354 |
| ERG | C-20 | Rabbit polyclonal | C-terminus | Santa Cruz Biotechnology | sc-353 |
| ERG | | Rabbit polyclonal | aa450 | abcam | ab92513 |
| ETV | | Rabbit polyclonal | C-terminus | abcam | ab81086 |
| V5 | | Rabbit polyclonal | V5 | abcam | ab15828 |
| V5 | | mouse monoclonal IgG1 | V5 | Invitrogen | 46-0705 |
| H3K27AC | | Rabbit polyclonal | | abcam | ab4729 |
| H3K273ME | | Rabbit polyclonal | | Millipore | 07-449 |
| BAF60a | 23 | mouse monoclonal IgG1 | | Santa Cruz Biotechnology | sc-15483 |
| BRM | | Rabbit polyclonal | aa100-150 | Bethyl | A301.015A |
| GAPDH | FL335 | Rabbit polyclonal | FL (h) | Santa Cruz Biotechnology | sc-25778 |
| TBP | | mouse monoclonal IgG1 | aa1-20 | abcam | ab818 |

Depletion Studies: Nuclear extracts were prepared to a final concentration of 2.5 mg/ml with IP buffer. Each IP was incubated with 2.5 µg of antibody overnight at 4° C. and then for 1 h with 15 µl Protein G Sepharose beads. After centrifugation (10,000 rpm for 1 min) 45 µl of the supernatant was either saved or used for another round of IP. In total 3 rounds of IP were performed.

Urea Denaturation Studies: NEs (150 mg) were subjected to partial urea denaturation, ranging from 0.25 to 2.5 M urea (in IP buffer), for 30 min at room temperature (RT) prior to anti-Brg1 or anti-Erg IP. The co-precipitated proteins were analyzed by immunoblot. Quantitative densitometry analyses were performed with the Li-Cor Odyssey Imaging System (Li-COR Biosciences, Lincoln, NE, USA).

Density Sedimentation Analyses: NE (500 mg) was resuspended in 200 ml of 0% glycerol HEMG buffer and carefully overlaid onto a 10 ml 10%-30% glycerol (in HEMG buffer) gradient prepared in a 14 3 89 mm polyallomer centrifuge tube (331327, Beckman Coulter, Brea, CA, USA). Tubes were centrifuged in an SW40 rotor at 4° C. for 16 hr at 40,000 rpm. Fractions (0.5 ml) were collected and used in analyses.

Transient Transfection Studies: Briefly, 293T cells were plated in 6-well plates to 80% confluence prior to transfection using polyethylenimine (PEI) in a 3:1 PEI:DNA ratio and were harvested after 48 h.

Lentiviral Generation: Lentivirus was produced by PEI (Polysciences Inc.) transfection of 293t LentiX cells (Clontech) with gene delivery vector cotransfected with packaging vectors pspax2 and pMD2.G as previously described (Kadoch and Crabtree, Cell 2013, 153(1): 71-85). Supernatants were harvested 72 h post transfection and centrifuged at 20,000 rpm for 2 h at 4° C. Virus containing pellets were resuspended in PBS and placed on cells dropwise. Selection of lentivirally-infected cells was achieved with either blasticydin or puromycin both used at 2 µg/ml. Overexpression or KD efficiency was determined by Western blot analysis.

Chromatin Immunoprecipitation: Chromatin immunoprecipitation (ChIP) experiments were performed per standard protocols (Millipore, Billerica, MA) with minor modifications. Briefly, cells were cross-linked for 10 min with 1% formaldehyde at 37° C. This reaction was subsequently quenched with 2.5M glycine for 5 min. Each ChIP was performed on soluble, sonicated chromatin from 5 million cells. DNA-protein complexes were immunoprecipitated with the following antibodies: anti-BRG1 (J1), anti-BAF155 (Dana Farber), anti-ERG (ab92513, Abcam, Cambridge, MA), anti-V5 (ab15828, Abcam), anti-H3K27AC (ab4729, Abcam) and anti-H3K273ME (07-449, Millipore, Billerica, MA); validation of the antibodies is provided on the manufacturers' websites.

Library Prep and Sequencing for Chip-Seq and RNA-Seq: All library prep and sequencing was performed in the Molecular Biology Core Facilities at Dana-Farber Cancer Institute.

SILAC: The SILAC (stable isotope labeling by amino acids in cell culture) mass spectrometry was performed on VCaP cells. Antibodies against ERG (C-20, Santa Cruz) or IgG as control were used. The mass spectrometry was then performed at the proteomics core at the Broad Institute.

Example 7. Identification of Endogenous TMPRSS2-ERG:BAF Interactions

Figure 7A:
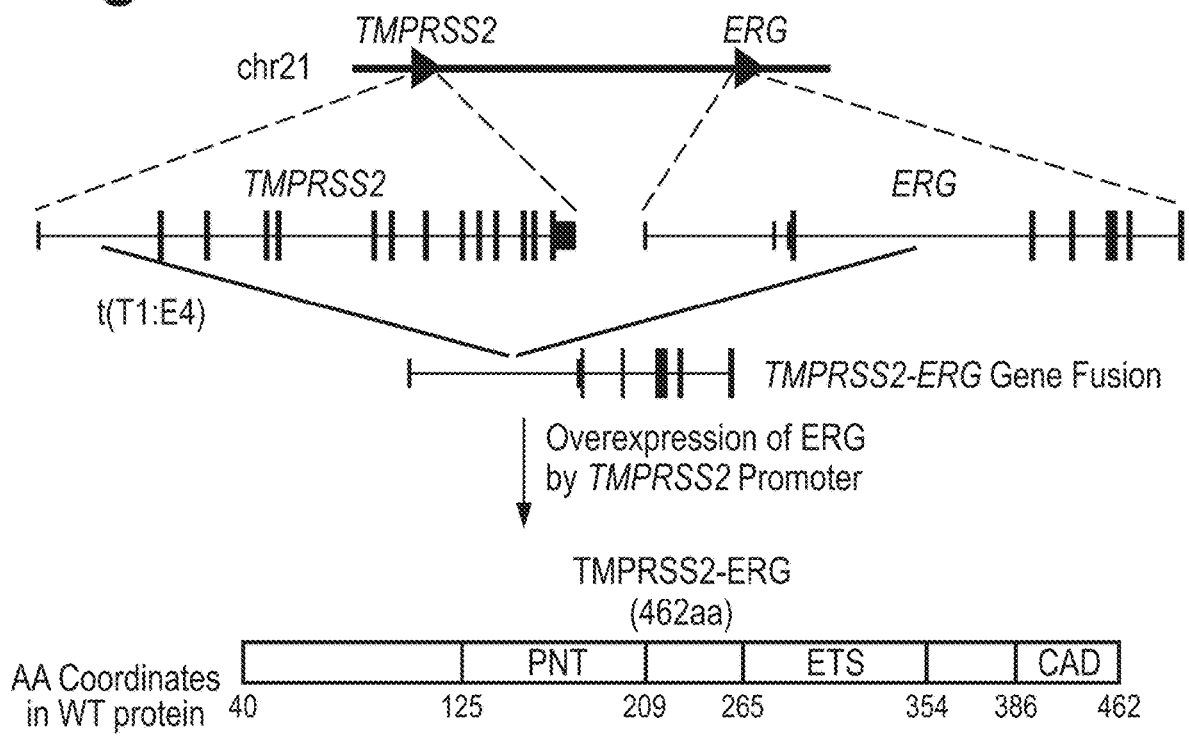
FIG. 7A-D shows a schematic of TMPRSS2-ERG fusion and protein (FIG. 7A), a schematic of the further SILAC Mass Spectrometry experiment on VCaP cells (FIG. 7B), an enrichment plot of the anti-ERG enriched proteins from the further Mass Spectrometry experiment on VCaP cells, representing top anti-ERG hits plotted as log 2-fold change for each experimental replicate (FIG. 7C), and a table of mSWI/SNF (BAF) complex protein subunits identified within the top 50 hits from the further SILAC Mass Spectrometry experiment on VCaP cells, indicating number of unique peptides, sequence coverage (%), associated p-values and rank among enriched proteins (FIG. 7D).
Figure 7B:
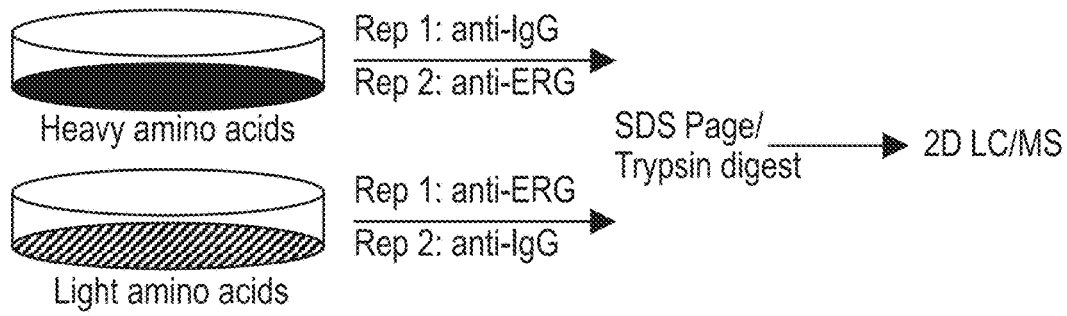
Figures 7C, 7D:
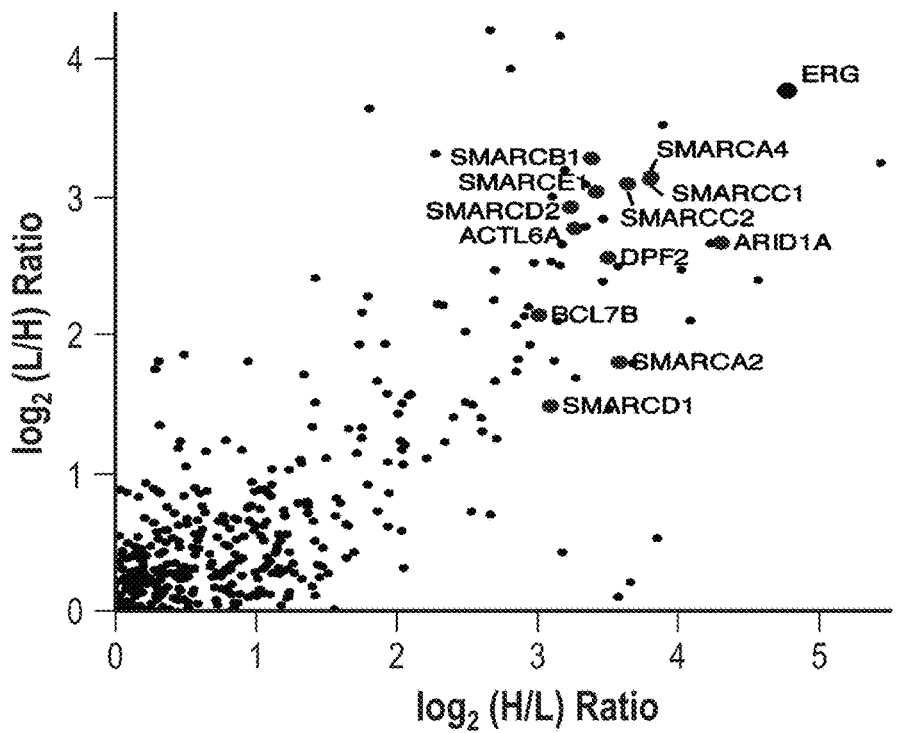
Figure 8A:
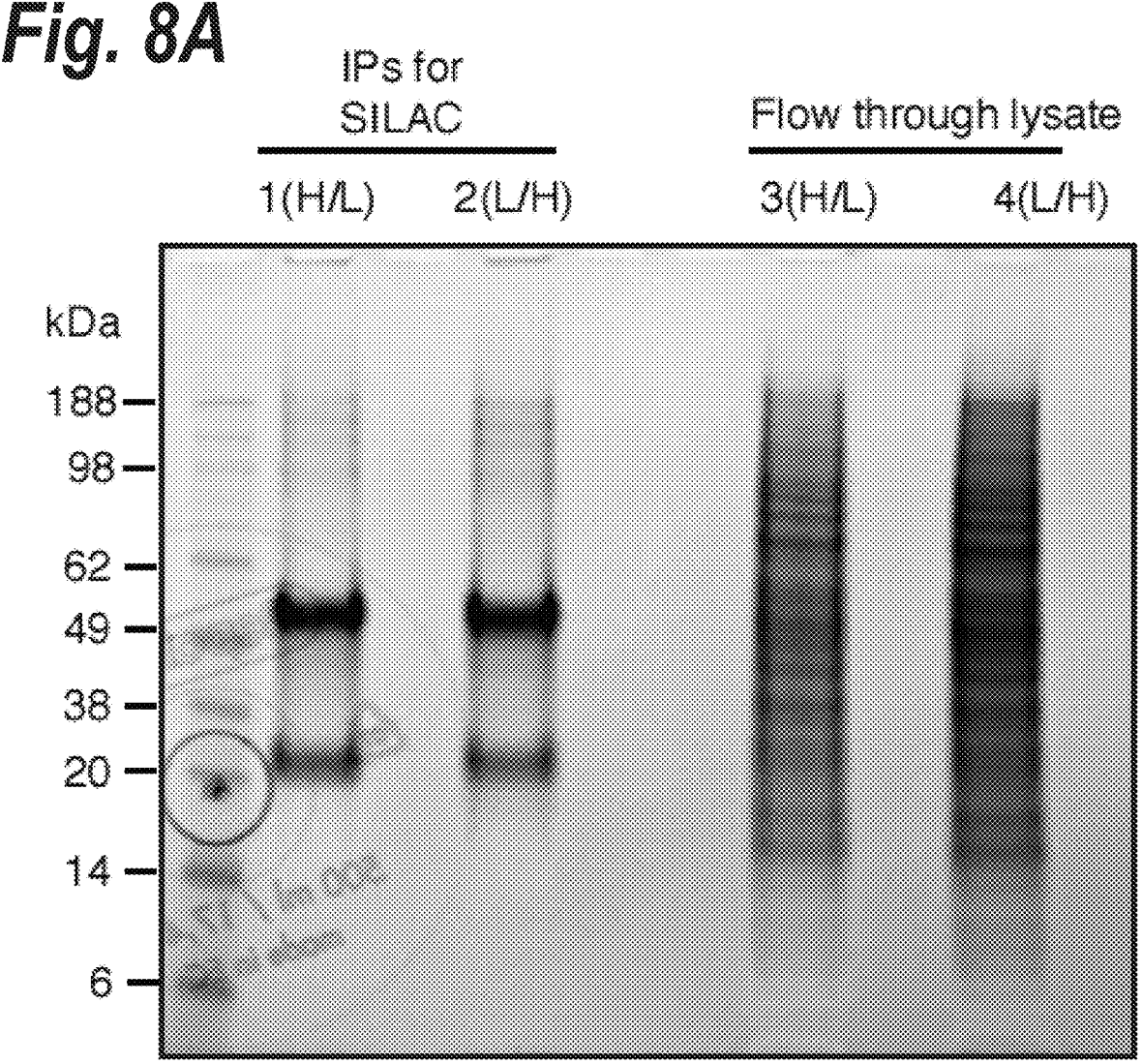
Figure 8B:
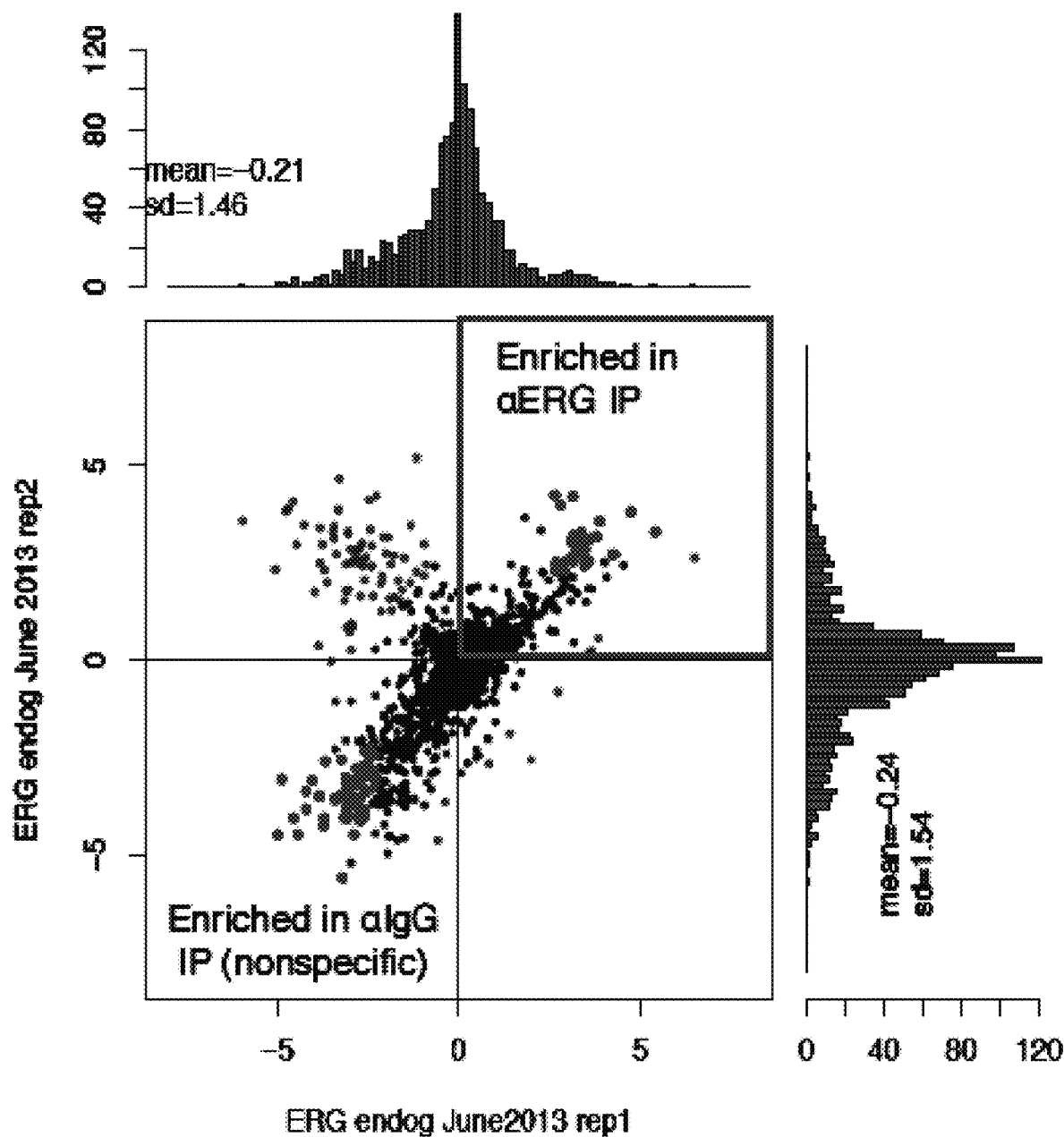
Figure 8D:
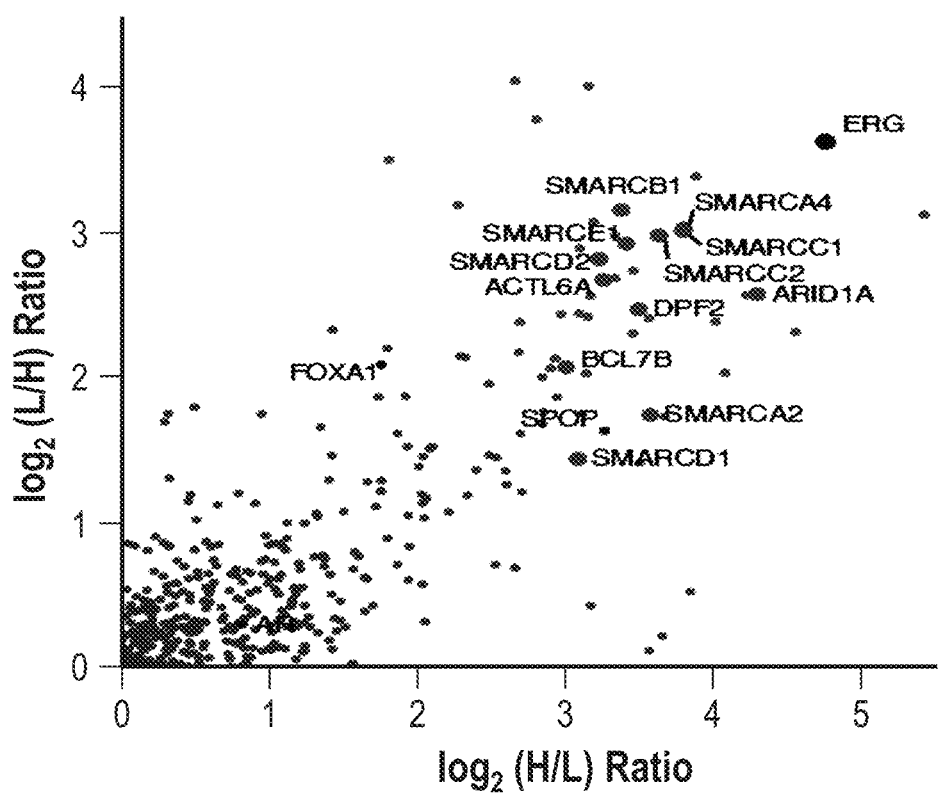

Several different TMPRSS2-ERG fusions occur in prostate cancer cases (Kumar-Sinha et al., 2008; Tomlins et al., 2005), the most of which involves the fusion of exon 1 of TMPRSS2 (non-coding region) to exon 4 of ERG (T1:E4) (FIG. 7A). To define the full constellation of ERG-specific interacting proteins, performed SILAC-based 2D-LC-MS mass spectrometric experiments was performed in VCaP cells, which harbor the T1:E4 TMPRSS2-ERG fusion, and express high levels of ERG mRNA and protein (Tomlins et al., 2005). Analysis of SILAC mass spectrometry performed on anti-ERG or control (IgG) immunoprecipitations from VCaP cells (FIG. 7B, FIG. 8A) uncovered peptides corresponding to several components of the mammalian SWI/SNF (BAF) complex within the top 50 differentially enriched peptides between ERG and control IgG conditions. These included 12 components of the canonical BAF complexes, including subunits such as ARID1A, BRG1 and BAF155 as well as more recently identified BAF complex components such as BCL7B (Kadoch et al., 2013) (FIG. 7C, 7D, 8B-D). Notably, significant enrichment of protein subunits specific to PBAF (polybromo-associated BAF) complexes was not found, indicating a potentially specific form of the combinatorially assembled family of BAF complexes to which ERG tethers.

Figure 9A:
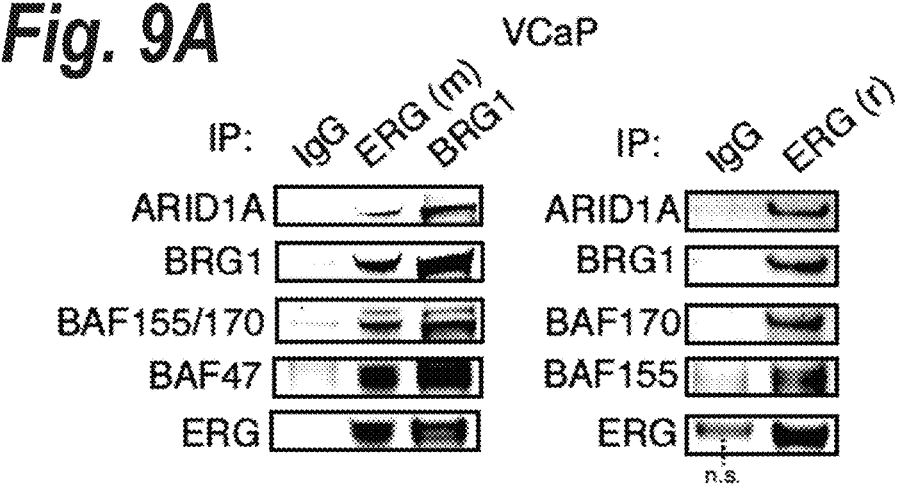
FIG. 9A-D shows immunoblots of immunoprecipitation using anti-ERG (mouse) and anti-BRG antibodies (FIG. 9A, left) and an alternate anti-ERG (rabbit) antibody (FIG. 9A, right) in VCap cell nuclear extracts; immunoblots of immunodepletion studies performed on VCaP cells using an anti-BRG1 antibody (FIG. 9B, left) and a graph depicting quantitative densitometry of immunodepletion blots (Error Mean±SEM) (FIG. 9B, right); urea denaturation analysis performed on anti-ERG IPs from VCaP nuclear extracts treated with 0-2.5M urea (FIG. 9C); and immunoblots showing total nuclear protein input (left) and anti-V5 IPs (right) in empty vector and V5-ERG overexpression conditions in LHS-AR prostate epithelial cells.
Figure 10A:
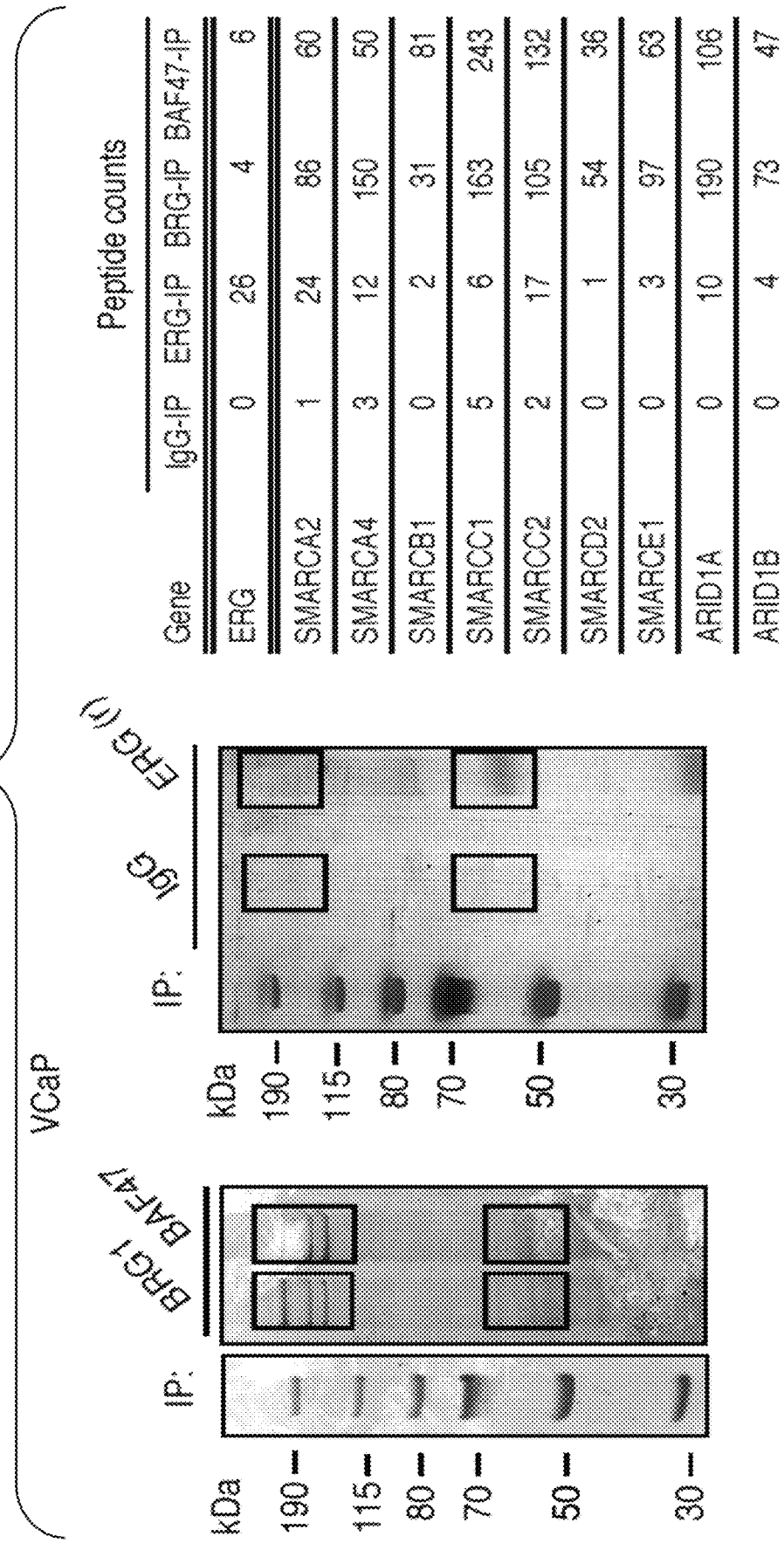
FIG. 10A shows (left) Coomassie-stained SDS-PAGE gel of anti-BRG1 and anti-BAF47 IPs in VCaP cells. Boxed sections indicate regions subjected to trypsin digest and subsequent mass spectrometric analysis.
Figure 10B:
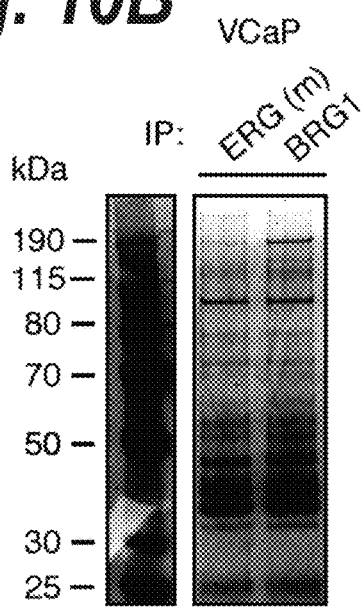
FIG. 10B shows silver stain analysis of anti-ERG and anti-BRG1 IPs in VCaP cells.

To confirm the ERG-BAF interaction, reciprocal immunoprecipitation studies were performed in nuclear extracts isolated from VCaP cells using an anti-ERG antibody and an antibody specific for the BRG1 ATPase subunit of BAF complexes (anti-BRG1) (FIG. 9A, left). Endogenous ERG and BAF complexes interaction was confirmed using antibodies directed to two different epitopes of the ERG protein (FIG. 9A, right). To further validate this interaction, reciprocal mass spectrometric analyses was performed on isolated regions of SDS-PAGE, Coomassie stained gels of BAF (BRG1 and BAF47), control IgG, and ERG immunoprecipitations, further confirming ERG-BAF interactions in VCaP cells (FIG. 10A). Moreover, immunoprecipitation using anti-BRG1 and anti-ERG antibodies in VCaP cell nuclear extracts revealed similar banding patterns upon silver stain analyses (FIG. 10B).

Figure 9B:
Figure 9B:
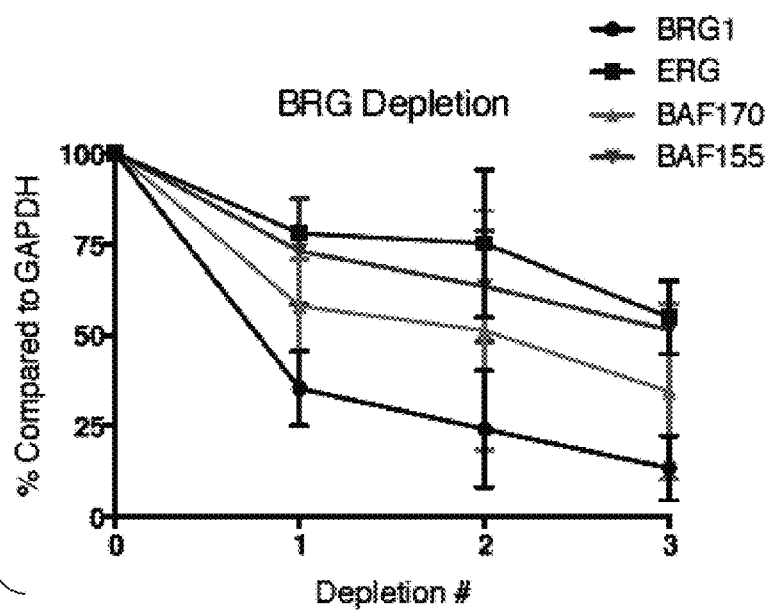
Figure 9C:
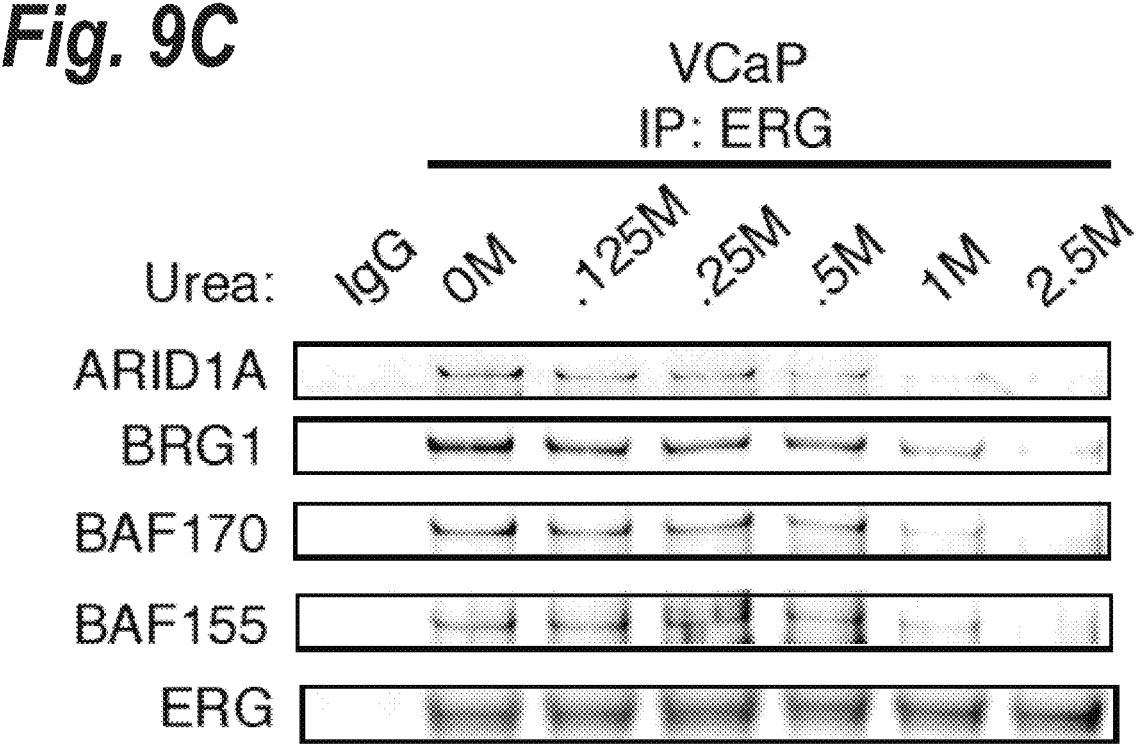
Figure 10C:
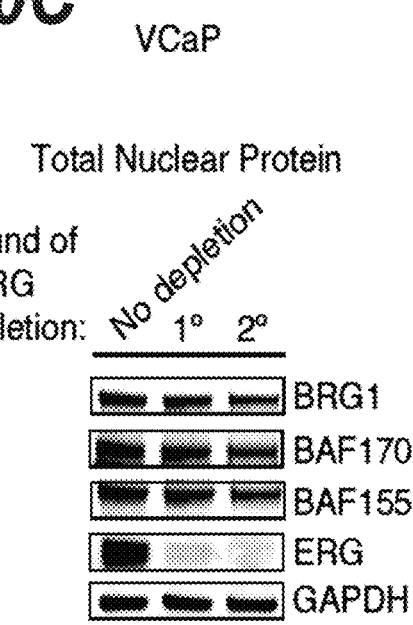
FIG. 10C shows results of immunodepletion studies performed on VCaP cells using an anti-ERG antibody; immunoblot for ERG and BAF complex components.
Figure 10D:
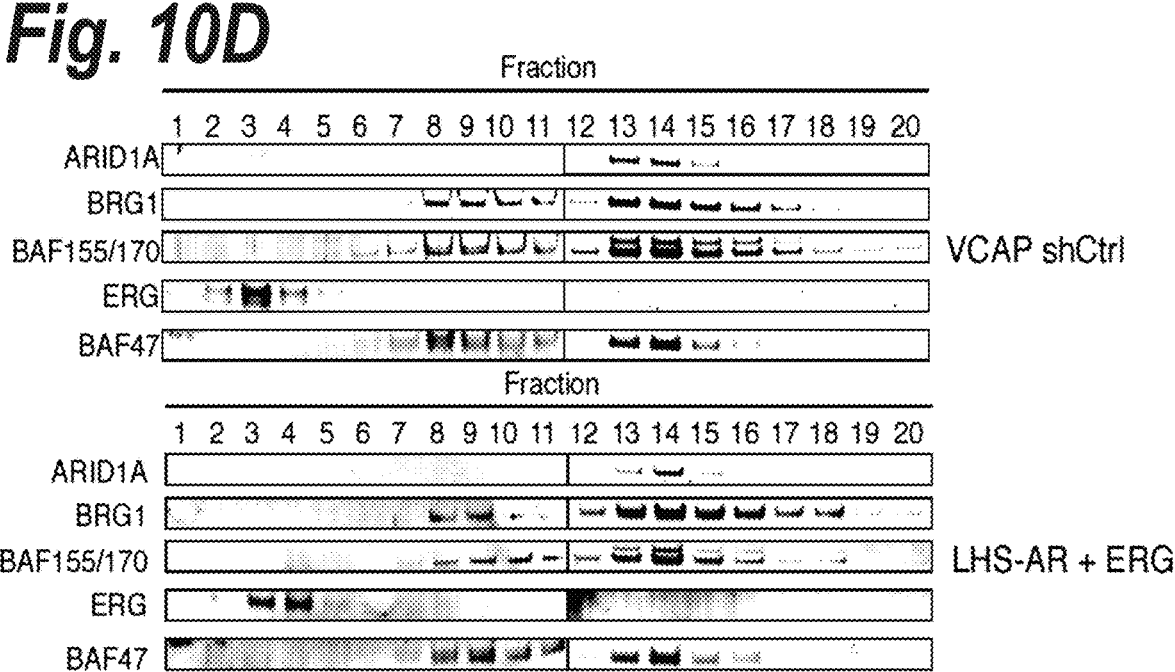
FIG. 10D shows results of density sedimentation studies using 10-30% glycerol gradient analyses of nuclear extracts from VCaP and LHS-AR cells expressing ERG; immunoblot for ERG and BAF complex subunits.

To determine the relative percentage of total nuclear ERG protein associated with BAF complexes, depletion studies were performed using an anti-BRG1 antibody which, over three rounds, sequentially depleted ERG from the nuclear extract, in addition to BAF complex subunits (FIG. 9B). Immunodepletion of ERG from VCaP nuclear extracts did not result in substantial depletion of BAF complex subunit proteins (FIG. 10C), suggesting that while the majority of nuclear ERG protein interacts with BAF complexes, a smaller percentage of total BAF complexes interact with ERG in solution (owing to the relative abundance of BAF complexes (estimated at ~300,000 molecules per cell) as compared to that of ERG). To determine the relative affinity of the ERG-BAF complex interaction, urea-based denaturation studies were performed, subjecting anti-ERG immunoprecipitations to increasing concentrations of urea and assessing BAF complex subunit binding. ERG was found to remain bound to the complex up to ~0.5M urea (FIG. 9C), indicative of a robust yet transient transcription factor interaction, and as expected, substantially weaker than stable, dedicated BAF complex subunits, which are stable at ≥2.5M urea (Kadoch and Crabtree, 2015). Density sedimentation studies using 10-30% glycerol gradients further revealed that ERG binds with low affinity and does not exhibit binding characteristics of a stable subunit. Specifically ERG was found to sediment in monomeric fractions (fractions 2-4) and did not overlap with any fractions containing fully formed BAF complexes (peak, fractions 13-15) (FIG. 10D).

Figure 9D:
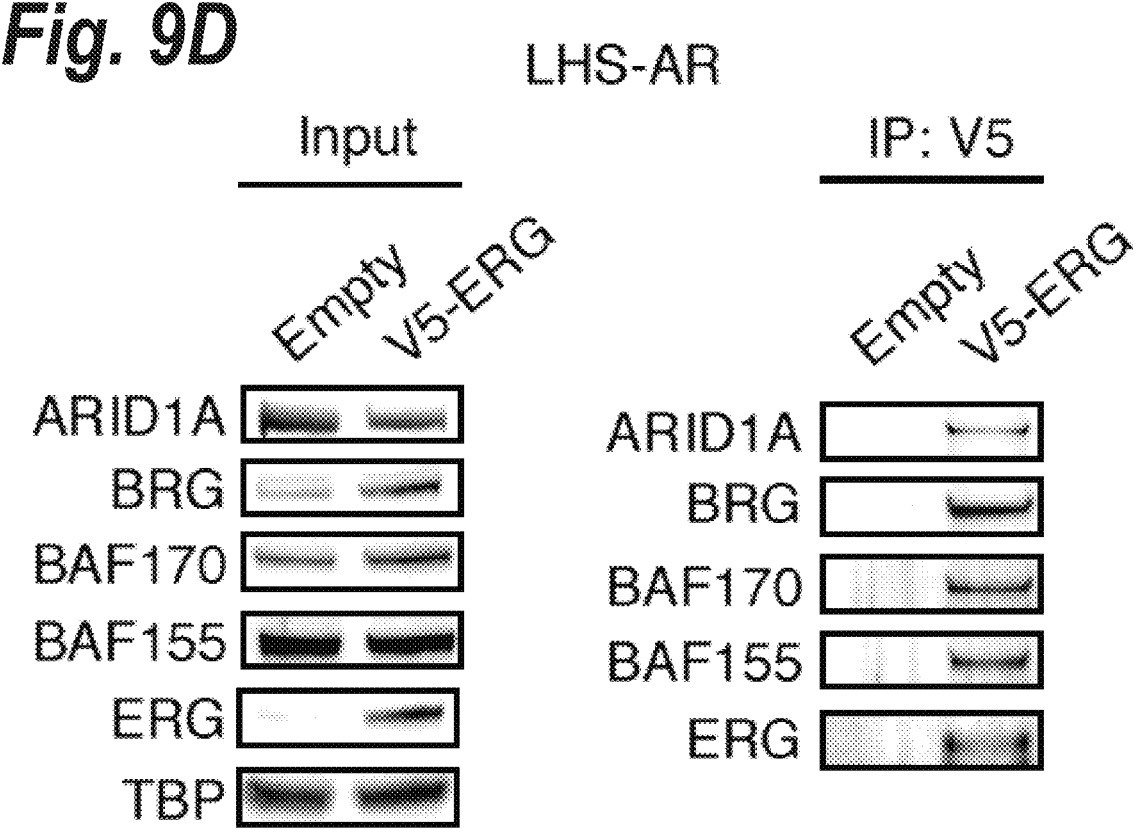
Figure 10E:
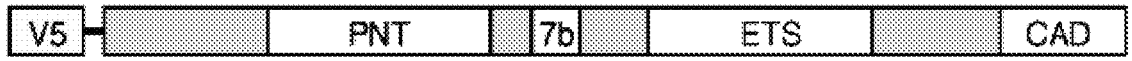
FIG. 10E is a schematic of the ERG variant overexpressed in LHS-AR cells, containing exon 7b.

To determine if the interaction between ERG and BAF complexes can be driven upon the introduction of ERG into cells lacking ERG expression, a V5-tagged ERG variant was introduced via lentiviral infection which mimics the T1:E4 fusion, the most common human TMPRSS2-ERG variant (FIG. 10E). This variant contains an additional exon (Exon 7b) not present in VCaP cells (Clark and Cooper, 2009). Introduction of V5-ERG into immortalized prostate epithelial cells, LHS-AR cells (Berger et al., 2004), a cell line lacking endogenous expression of ERG, resulted in robust co-immunoprecipitation of BAF complex subunits (FIG. 9D). Collectively, these results indicate that overexpression of ERG (by the TMPRSS2-ERG gene fusion or by exogenous introduction) results in a substantial and reproducible interaction with BAF complexes and validates results from anti-ERG SILAC mass spec experiments.

Example 8. ERG and BAF Co-Localize Genome-Wide in Prostate Cancer

Figure 11A:
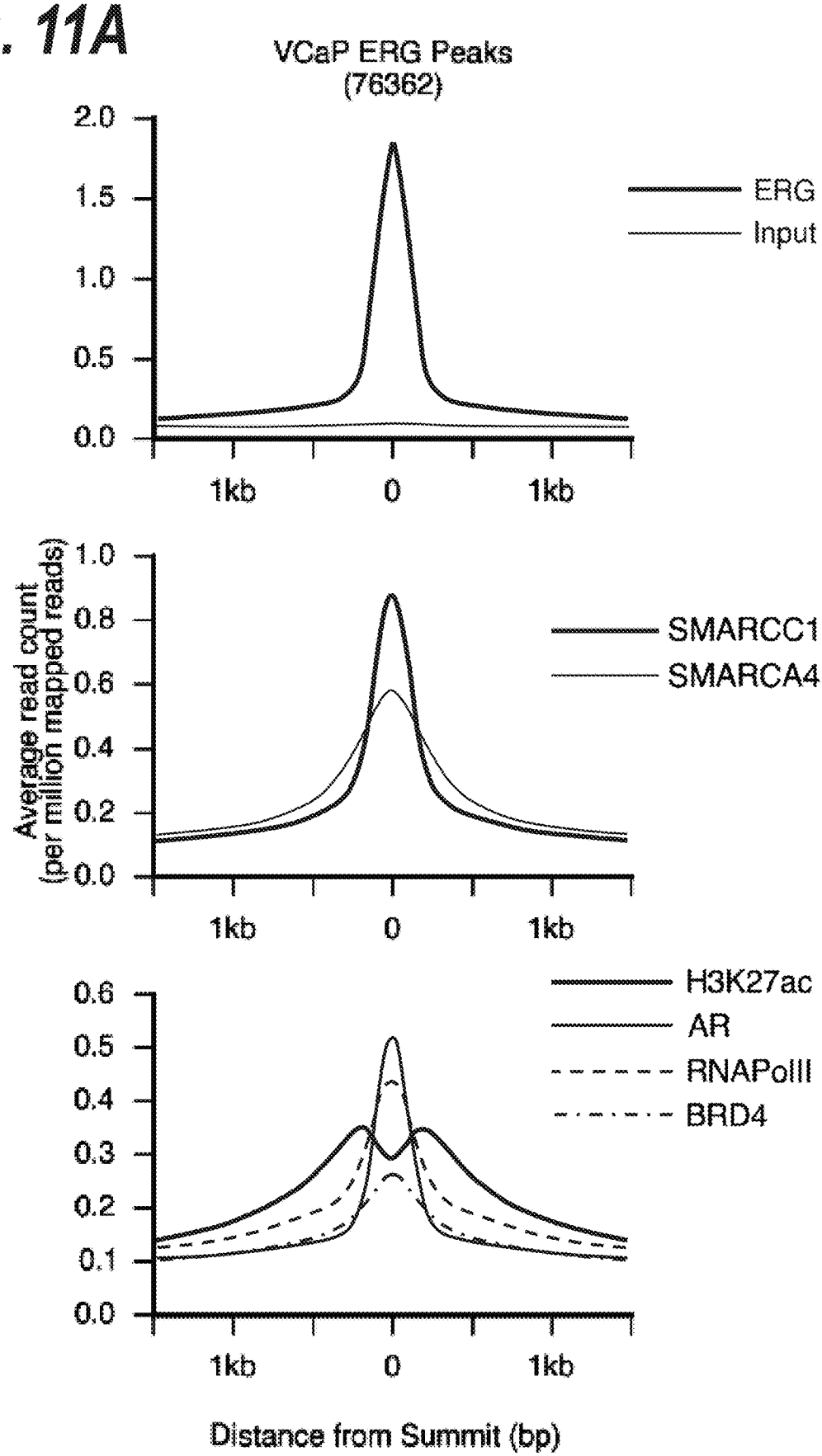
FIG. 11A-H shows Metagene plots over MACS-called ERG peaks in VCaP cells shows (FIG. 11A, top) ERG enrichment at target sites, (FIG. 11A, middle) BAF complex subunits BAF155 and BRG1 show targeted enrichment over ERG sites, and (FIG. 11A, bottom) published H3K27ac, AR, RNA Polymerase II, and BRD4 (Asangani et al., 2014), factors that are known to colocalize with ERG, co-occupy ERG sites (FIG. 11A).

Given this novel binding interaction, identification of the genome-wide occupancy patterns of BAF complexes and ERG was desired. Anti-ERG, anti-BRG1 (also known as SMARCA4) and anti-BAF155 (also known as SMARCC1) ChIP-seq experiments were performed in VCaP cells. Assessing metagene occupancy across all 76362 ERG peaks in VCaP cells, significant enrichment of BRG1 and BAF155 peaks as compared to unbound chromatin at ERG sites was found (FIG. 11A, top and middle panels). The anti-ERG ChIP-seq dataset was compared to published ChIP-seq datasets in VCaP cells for H3K27Ac, androgen receptor (AR), RNAPoIII, and BRD4 (Asangani et al., 2014) (FIG. 11A, bottom panel). Unexpectedly, these analyses indicated that BAF complex members, namely BRG1 and BAF155, exhibit greater average enrichment across all ERG sites than any of these proteins previously documented to co-localize with ERG, further suggesting a novel role for BAF complexes in TMPRSS2-ERG-mediated gene regulation.

Figure 11B:
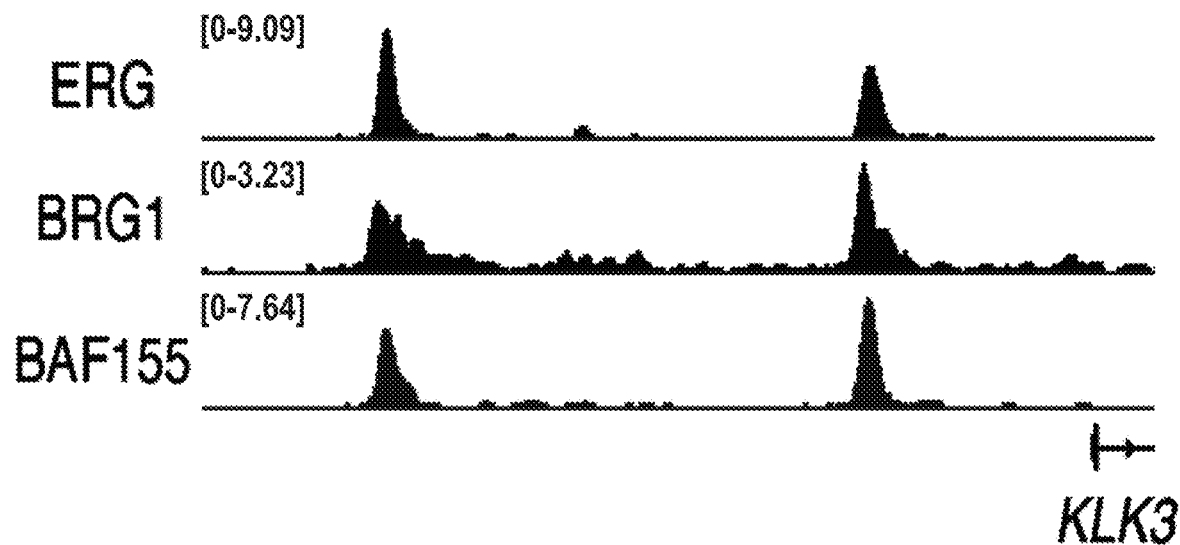
Figure 11C:
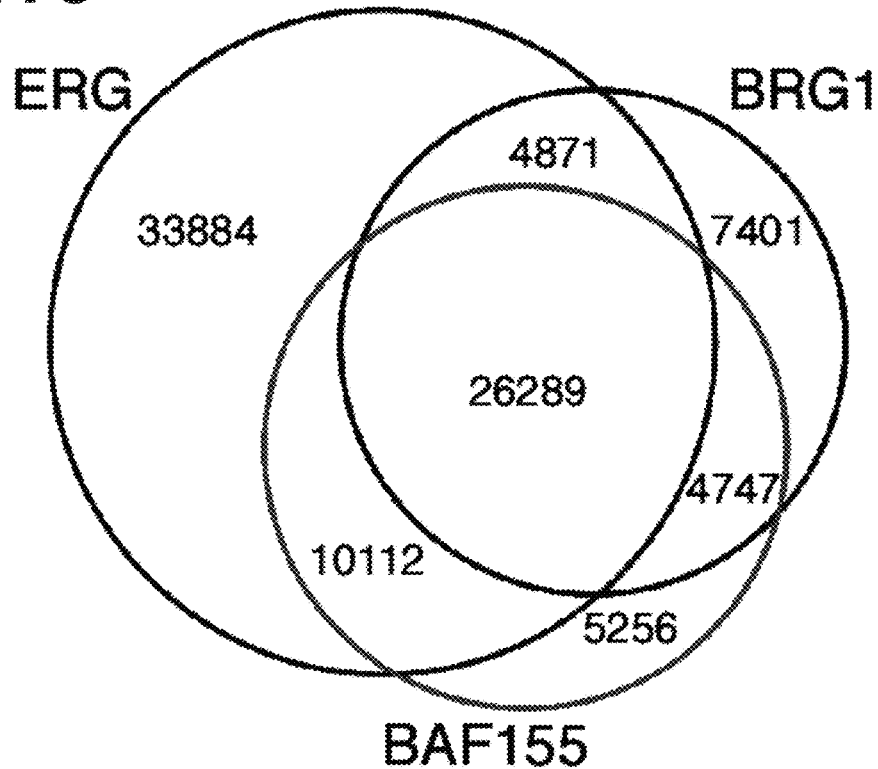
Figure 11D:
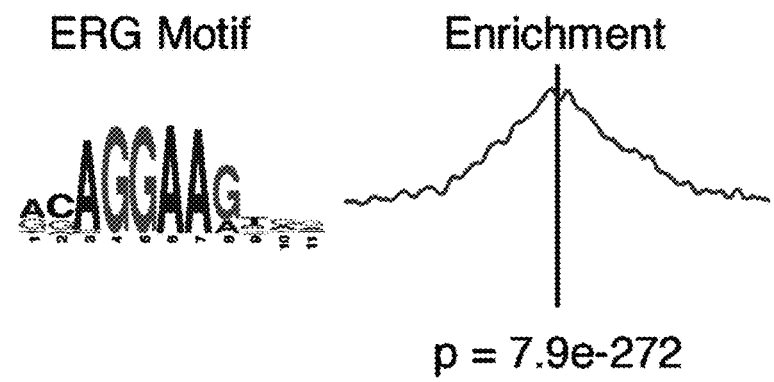
Figure 12B:
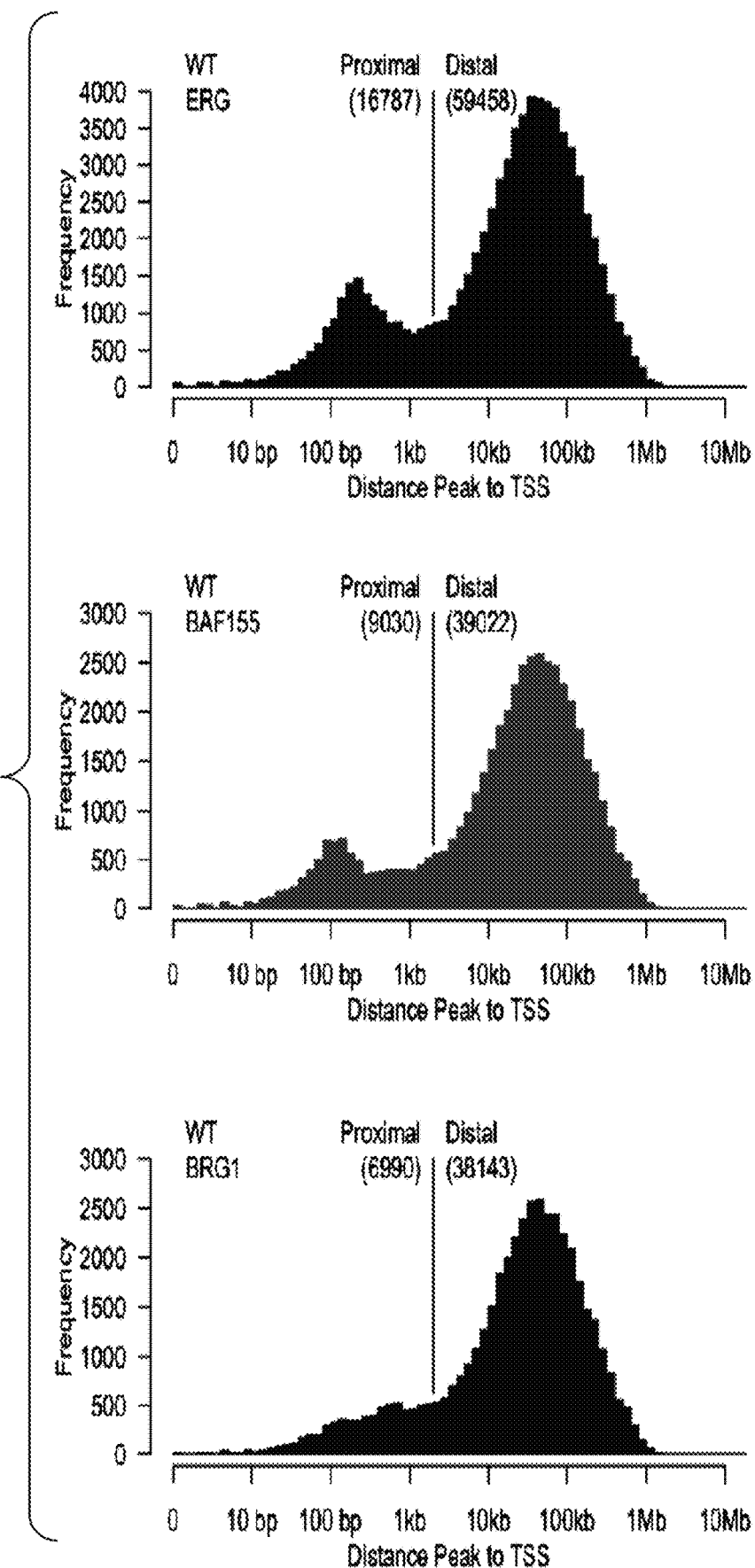
FIG. 12B shows a plot of the distance to TSS versus read frequency plots for ERG, BAF155, and BRG1 peaks in VCaP Cells.
Figure 12C:
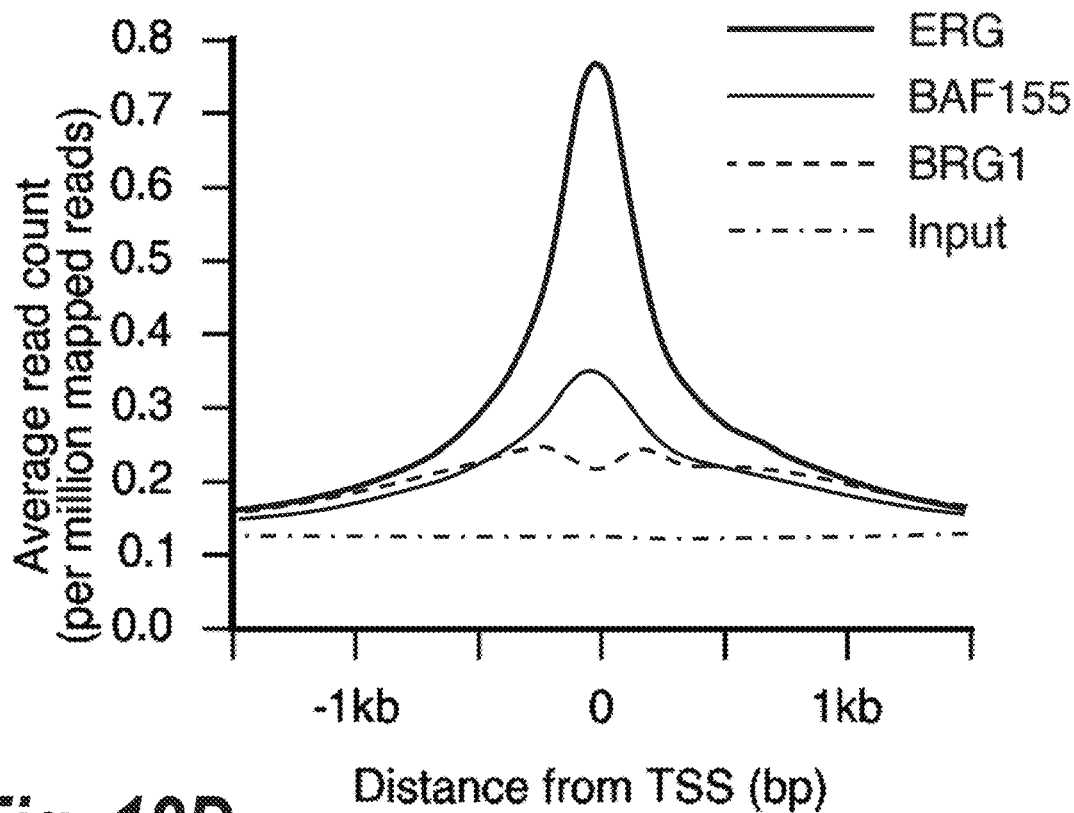
FIG. 12C is a TSS Enrichment plot across all RefSeq TSS for ERG, BAF155, and BRG1.
Figure 12D:
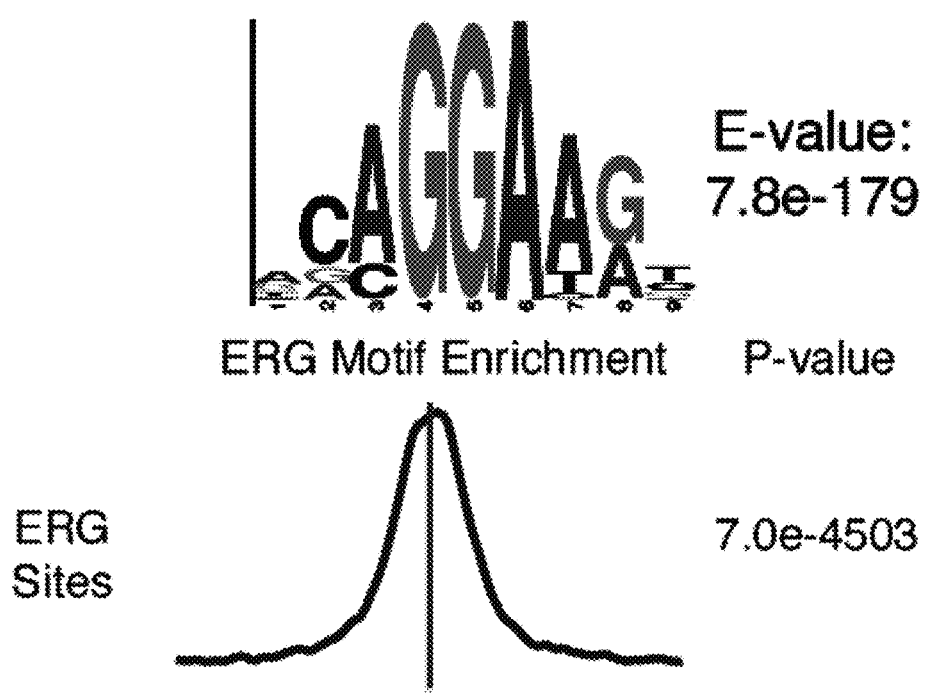
FIG. 12D (top) shows results of MEME motif discovery analysis at ERG sites in VCaP cells shows canonical ERG motif.

KLK3 (also known as prostate specific antigen (PSA)), an established ERG target gene, was considered and BRG1 and BAF155 were found to exhibit substantial co-occupancy with ERG at this site (FIG. 11B). Assessing the overlap of ERG, BRG1, and BAF155 peaks genome-wide, 26,289 peaks were found that are co-occupied by ERG, BRG1, and BAF155, with a majority of BAF155 (78.3%) and BRG1 (72.4%) peaks overlapping with ERG peaks, indicating a strong role for the BAF-ERG interaction in genomic regulation (FIG. 11C, FIG. 12A). ERG, BRG1, and BAF155 exhibit similar genomic distributions between distal and proximal TSS peaks (FIG. 12B), and exhibit significant promoter enrichment across all RefSeq TSS sites (FIG. 12C). Notably, a highly statistically significant central enrichment was found for the ERG motif at BAF155 sites (p=7.9e-272, FIG. 11D), demonstrating that BAF centrally localizes to the ERG motif in VCaP cells. The ERG motif was found to be centrally enriched at all ERG sites, and the ERG motif can be discovered de novo at these sites (FIG. 12D), confirming that the ERG ChIP-seq dataset adheres to expected sequence specificity observed in prior studies.

Figure 11E:
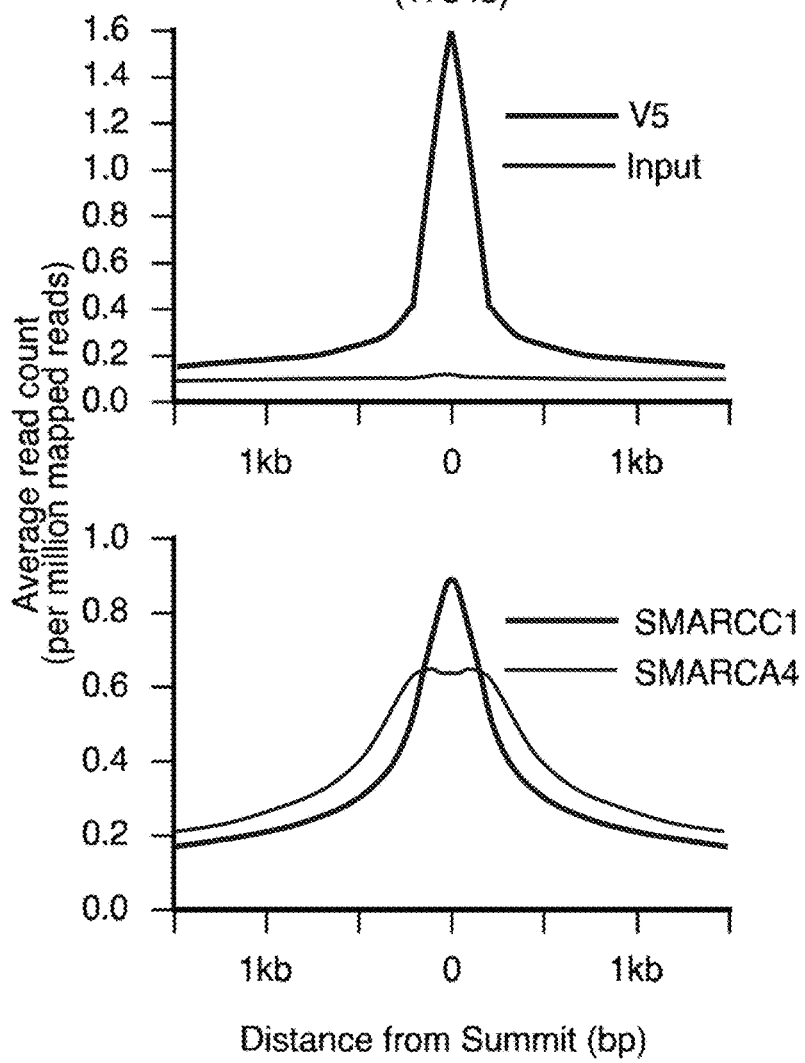
Figure 11F:
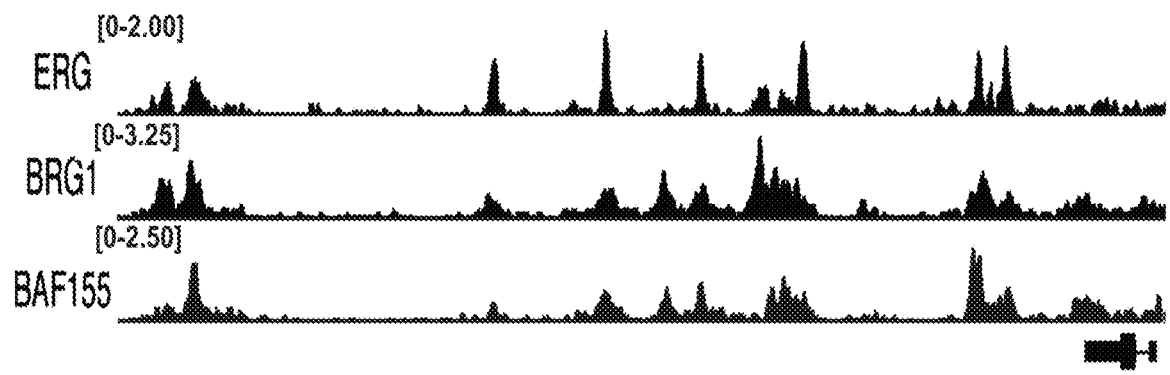
Figure 11G:
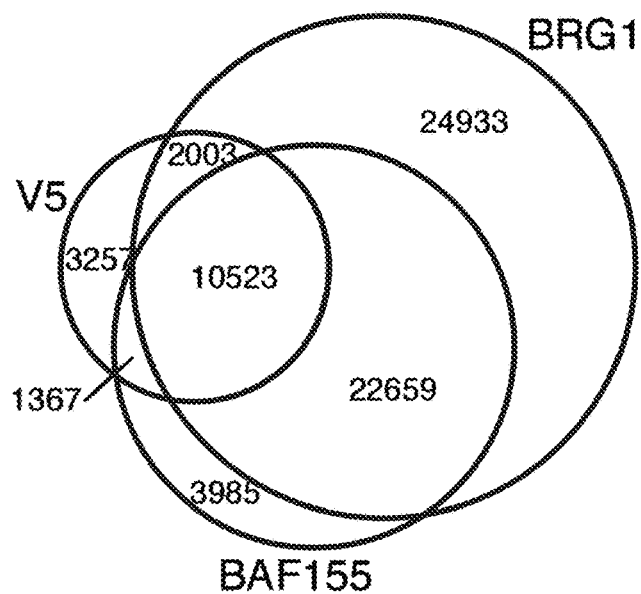
Figure 11H:
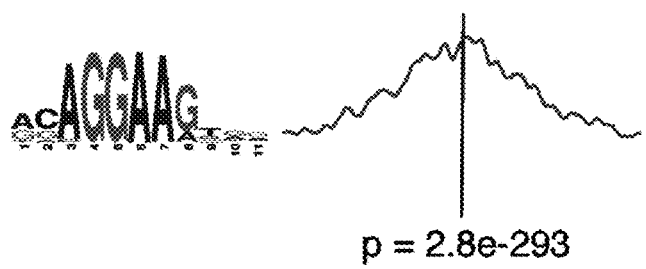
Figures 12E, 12F:
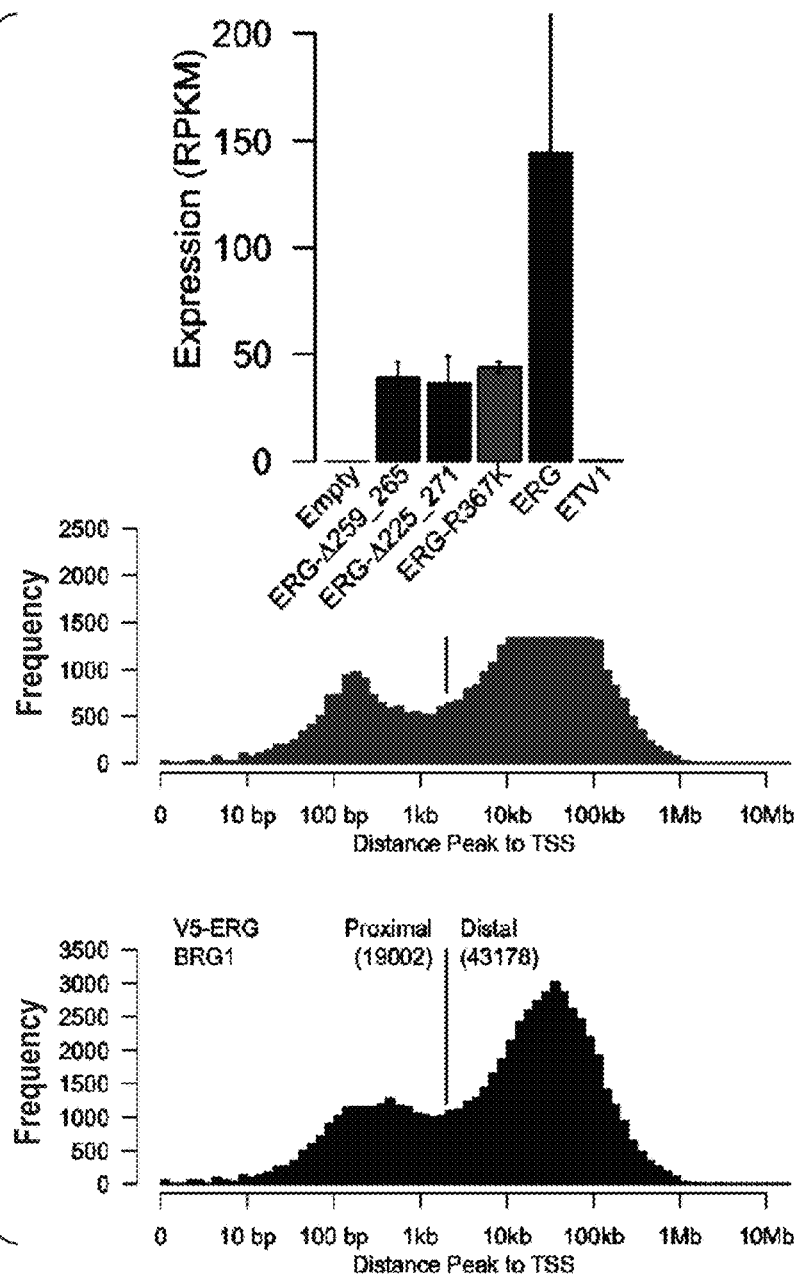
FIG. 12E shows the number of peaks for Peak A that overlap peaks for Peak B, as determined by direct overlap of peak intervals for peaks in LHS-AR+V5-ERG condition.
FIG. 12F shows plot of the distance to TSS versus read frequency for V5, BAF155, and BRG1 peaks in LHS-AR+V5-ERG Cells.
Figure 12G:
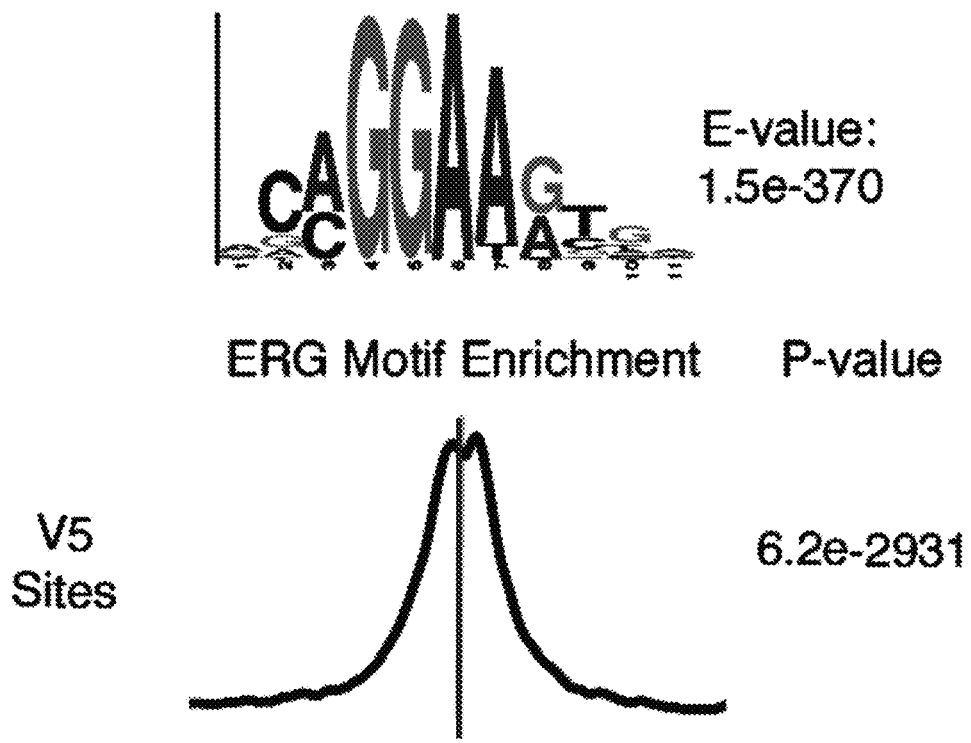
FIG. 12G (top) shows results of MEME motif discovery analysis at V5 sites in LHS-AR+V5-ERG cells shows canonical ERG motif.
Figure 12H:
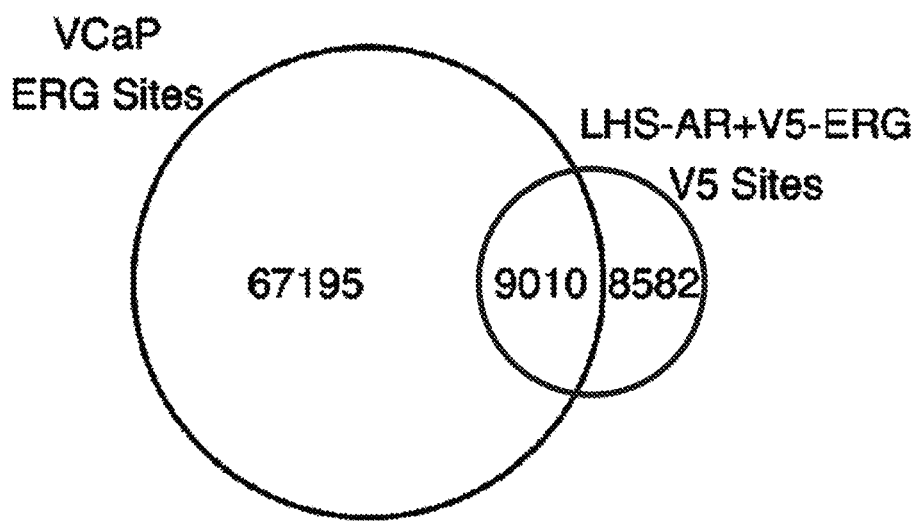
FIG. 12H represents overlap of ERG sites in VCaP and V5 sites in LHS-AR+V5-ERG, showing significant overlap.

ChIP-seq studies were subsequently performed in LHS-AR cells containing exogenously introduced V5-ERG, using anti-V5, anti-BRG1, and anti-BAF155 antibodies. Metagene analysis in LHS-AR cells revealed significant enrichment BRG1 and BAF155 ChIP-seq reads across ERG sites (FIG. 11E), further supporting data obtained in the VCaP cell setting. As an example, ERG, BRG1, and BAF155 co-occupy the SOCS3 genomic locus (FIG. 11F). Venn diagrams depicting the overlap of V5, BRG1, and BAF155 peaks show significant overlap between ERG and BAF, with a majority of V5 peaks overlapping with BAF155 (68.7%) and BRG1 (72.5%) (FIG. 11G, FIG. 12E), and similar genomic distribution of V5, BRG1, and BAF155 sites was found (FIG. 12F). V5 sites show de novo discovery of the ERG motif, as well as central enrichment of the canonical ERG motif (FIG. 12G), confirming that V5-specific peaks localize to the ERG target sequence. BAF155 peaks in LHS-AR+V5-ERG cells exhibit central enrichment of the ERG motif (p=2.8e-293), concordant with BAF155 peaks in VCaP cells (FIG. 11H), and significant overlap of ERG sites between VCaP cells and LHSAR cells containing V5-ERG was found, further underscoring the concordant regulation of ERG target sites in prostate cells (FIG. 12H).

Example 9. ERG Directs BAF Complexes to ERG Target Sites

Figure 13A:
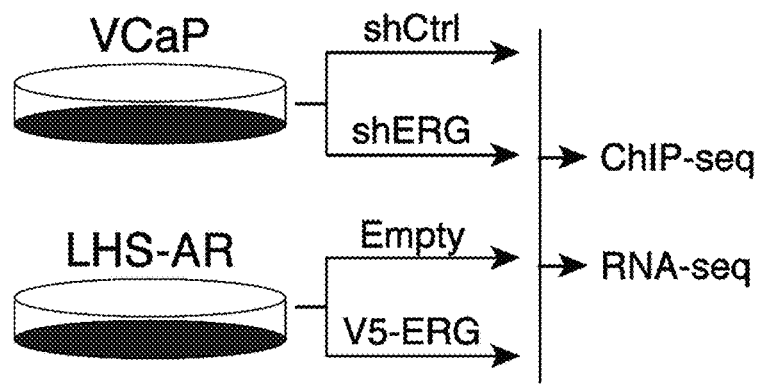
FIG. 13A-J shows ERG directs genome-wide BAF complex occupancy to ERG target genes.
Figure 13B:
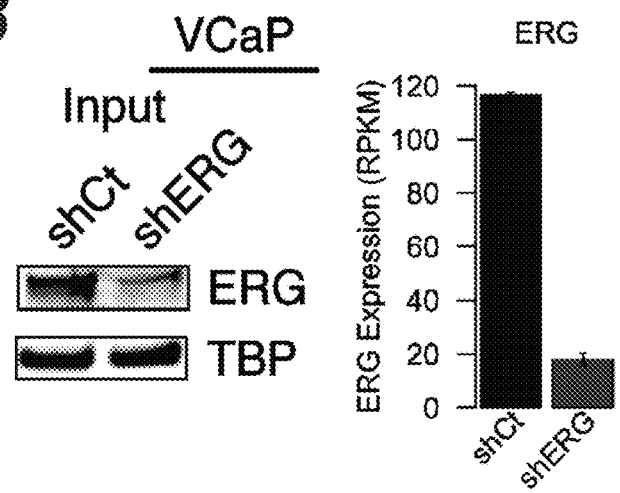
Figure 13C:
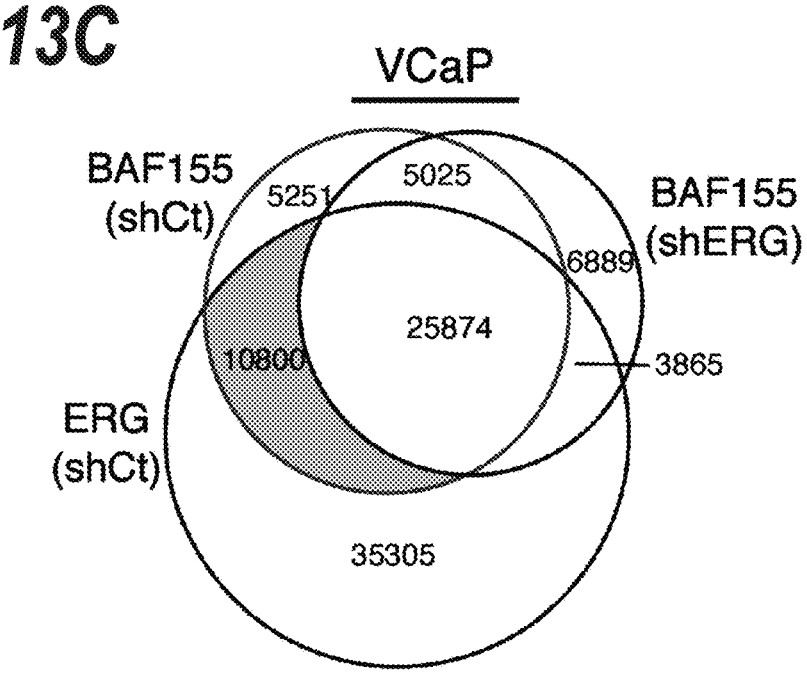
Figure 13D:
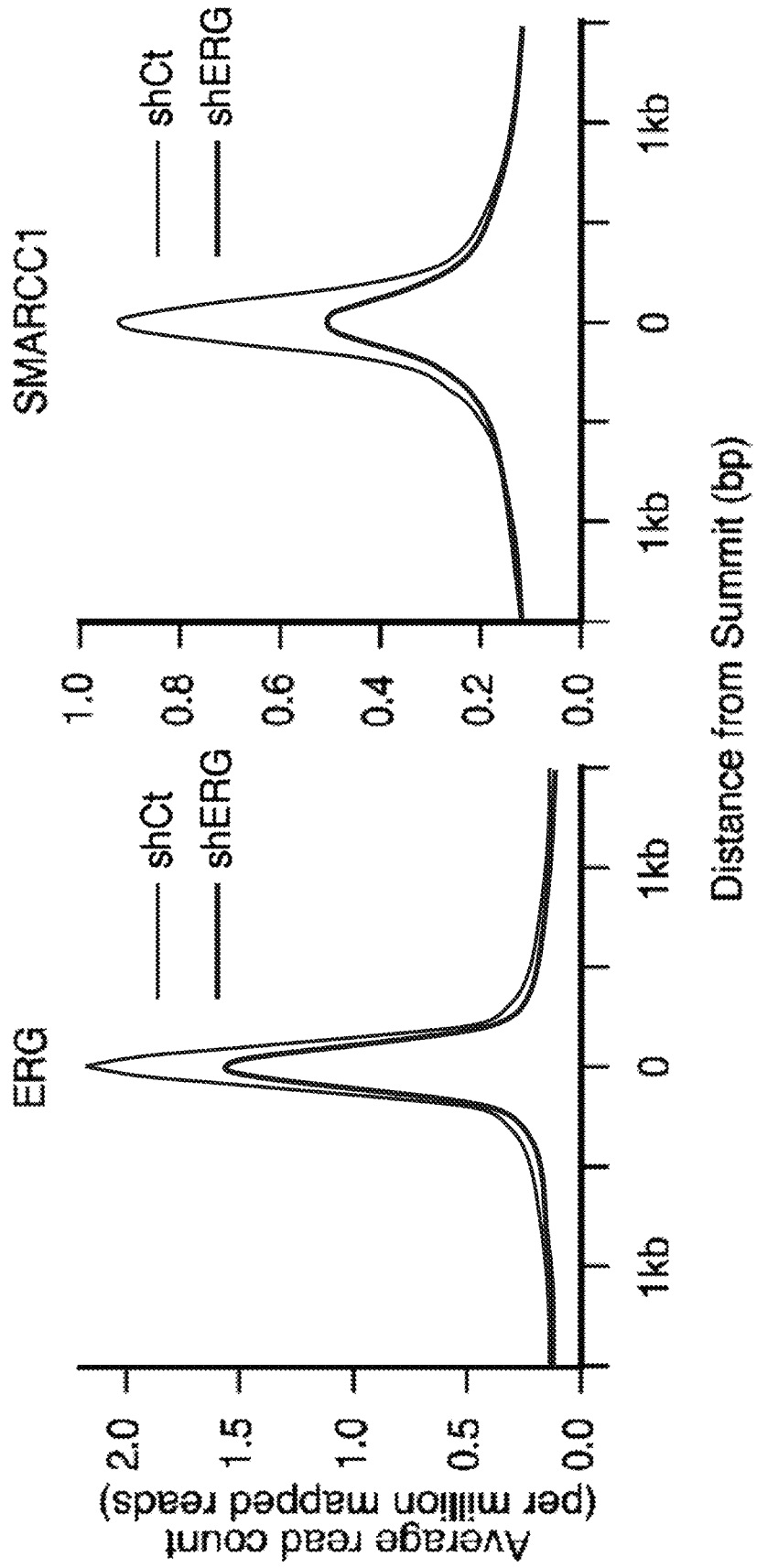
Figure 13E:
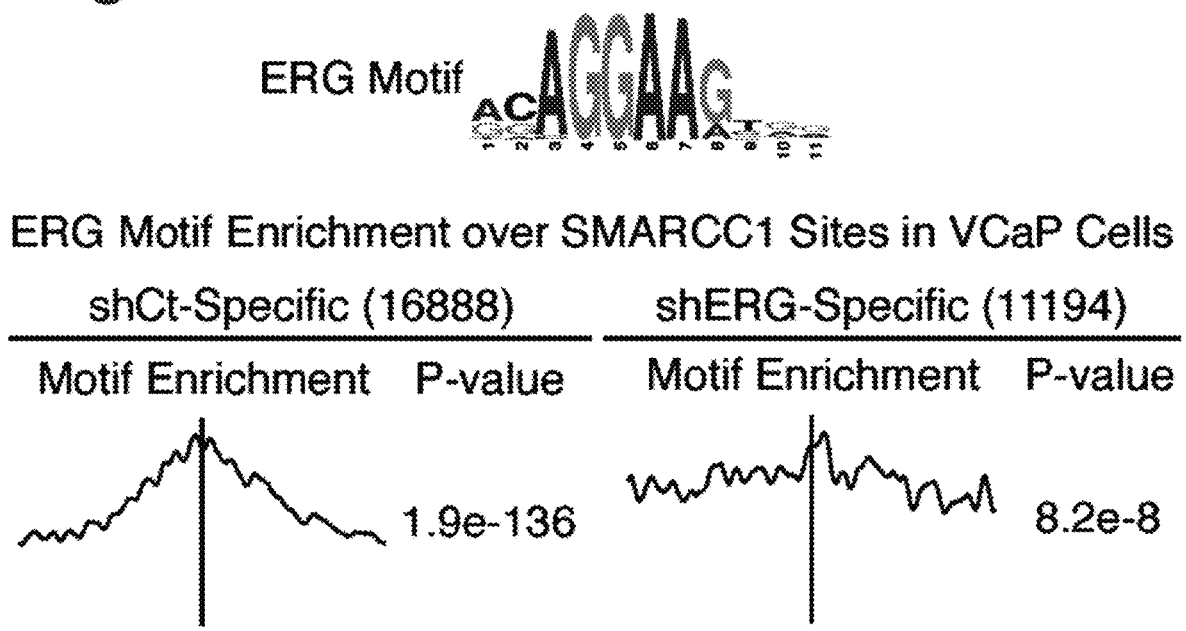
Figure 13F:
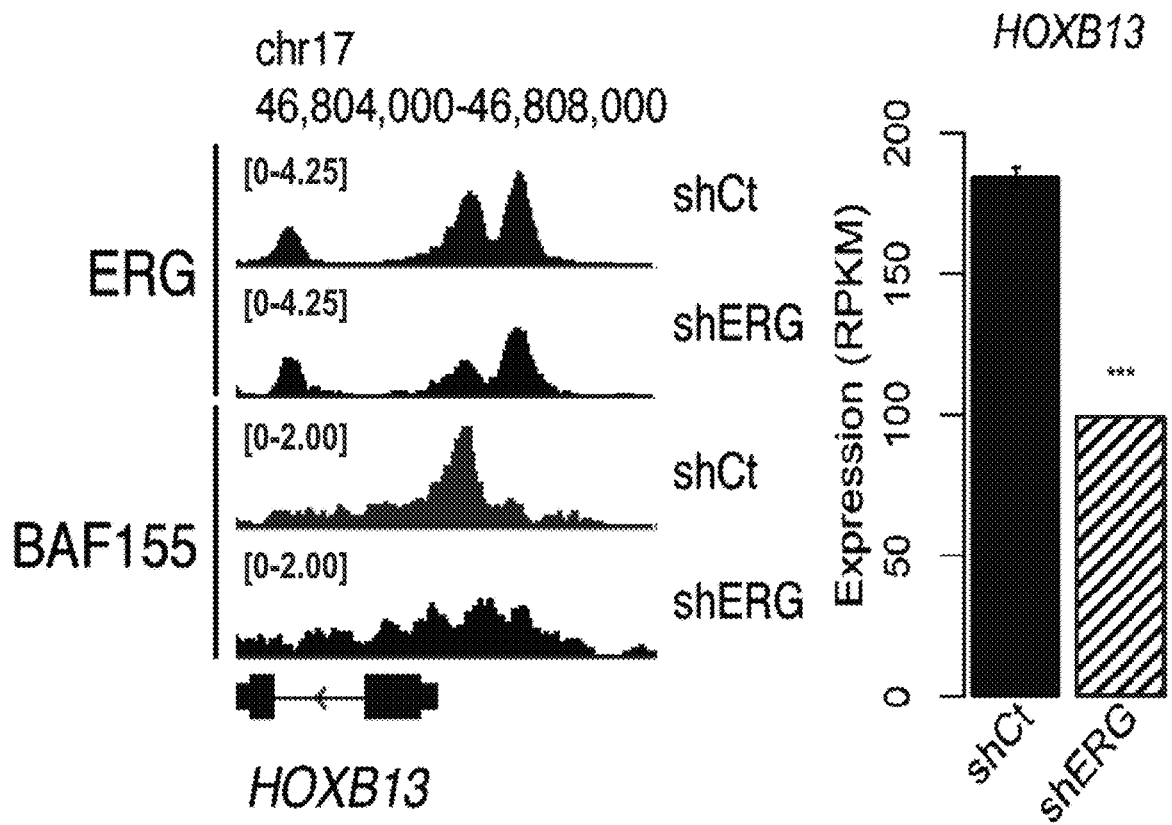
Figure 13G:
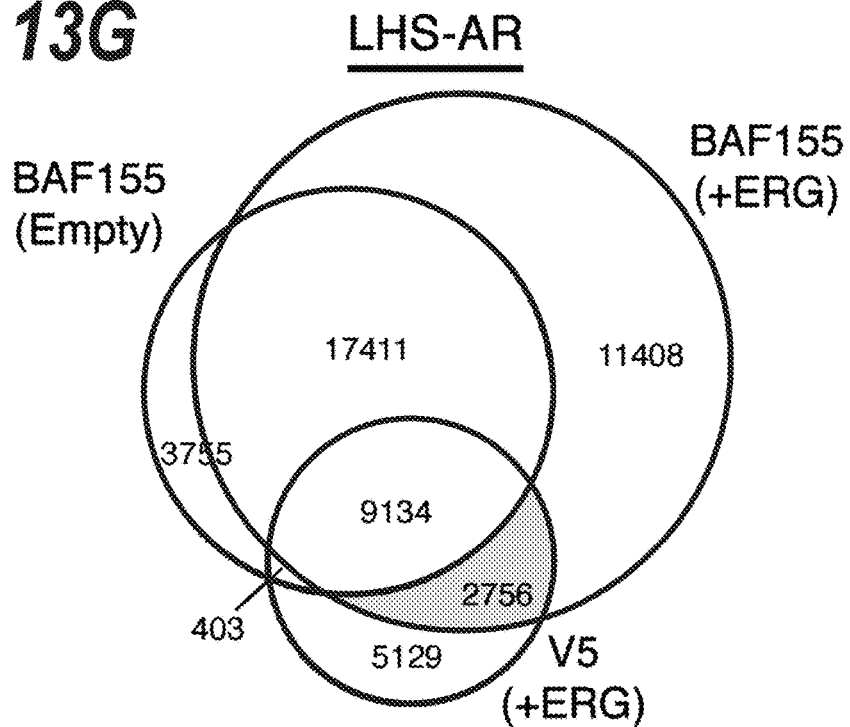
Figure 13H:
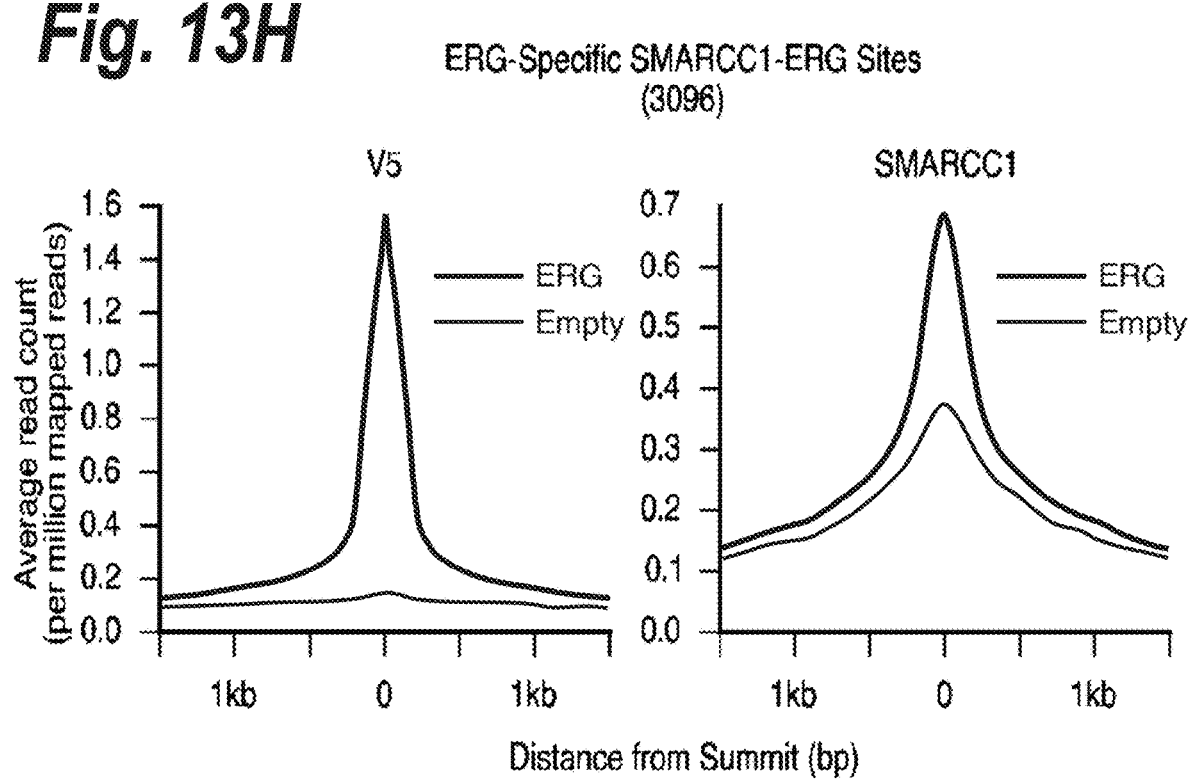
Figure 13I:
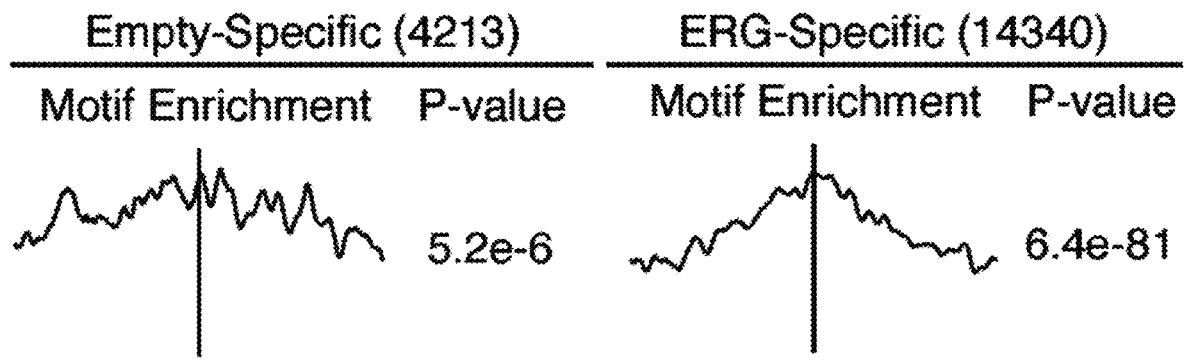
Figure 13J:
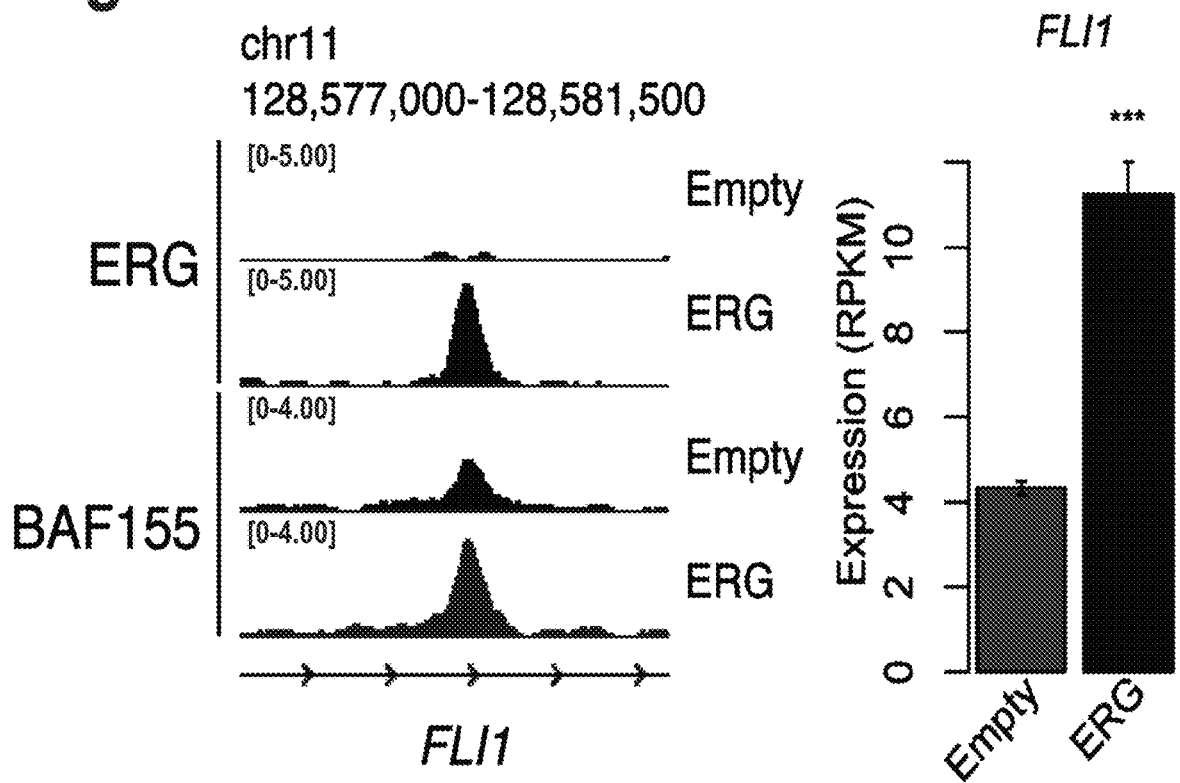
Figures 14A, 14B:
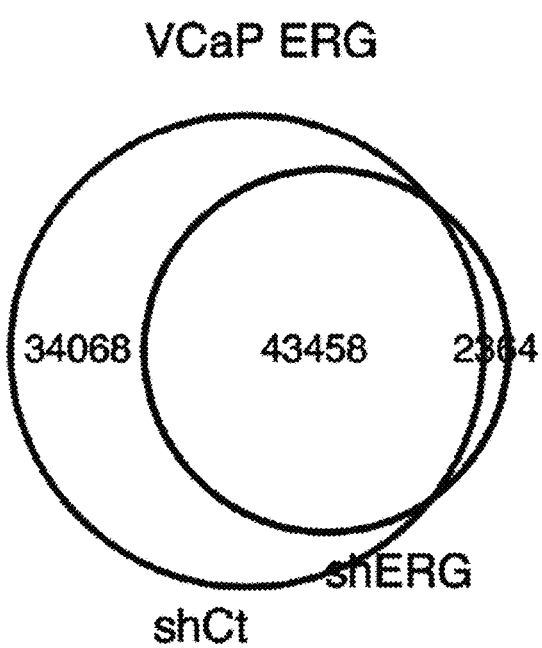
FIG. 14A is a Venn diagram of ERG peaks called in the shCt and shERG settings in VCaP cells, indicating loss of global ERG sites upon ERG knockdown.
FIG. 14B shows the top three ranked motifs enriched at shCt-specific and shERG-specific BAF155 sites in VCaP cells.
Figure 14C:
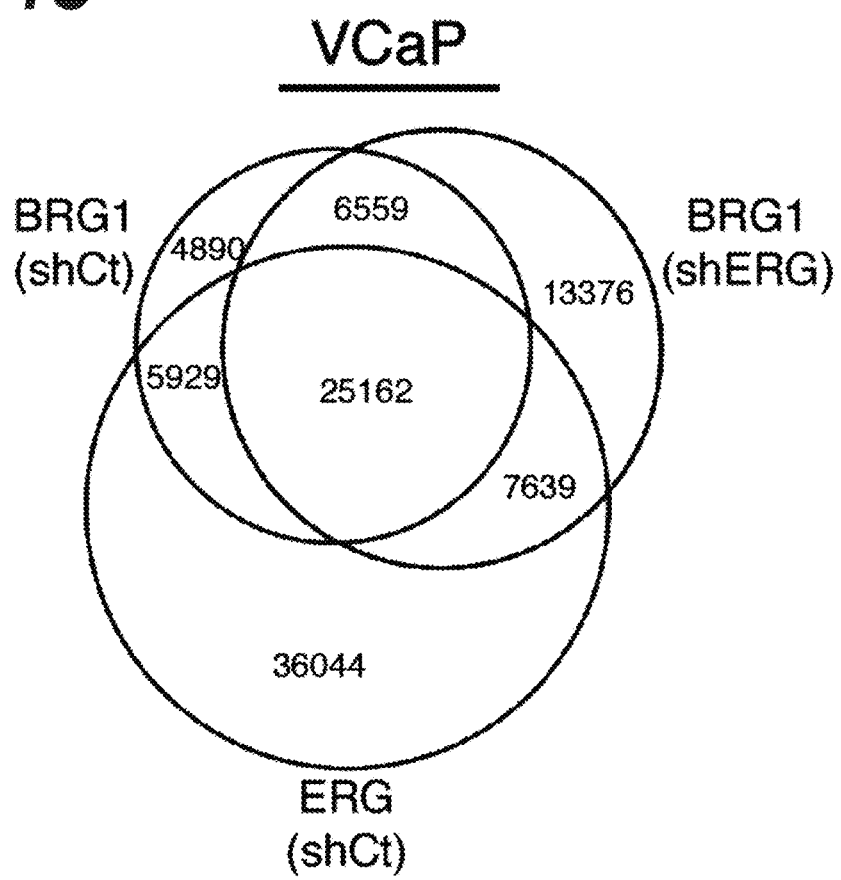
FIG. 14C is a Venn diagram illustrating overlap of BRG1 sites in shCt and shERG conditions, as well as ERG sites in the shCt condition in VCaP cells.
Figure 14D:
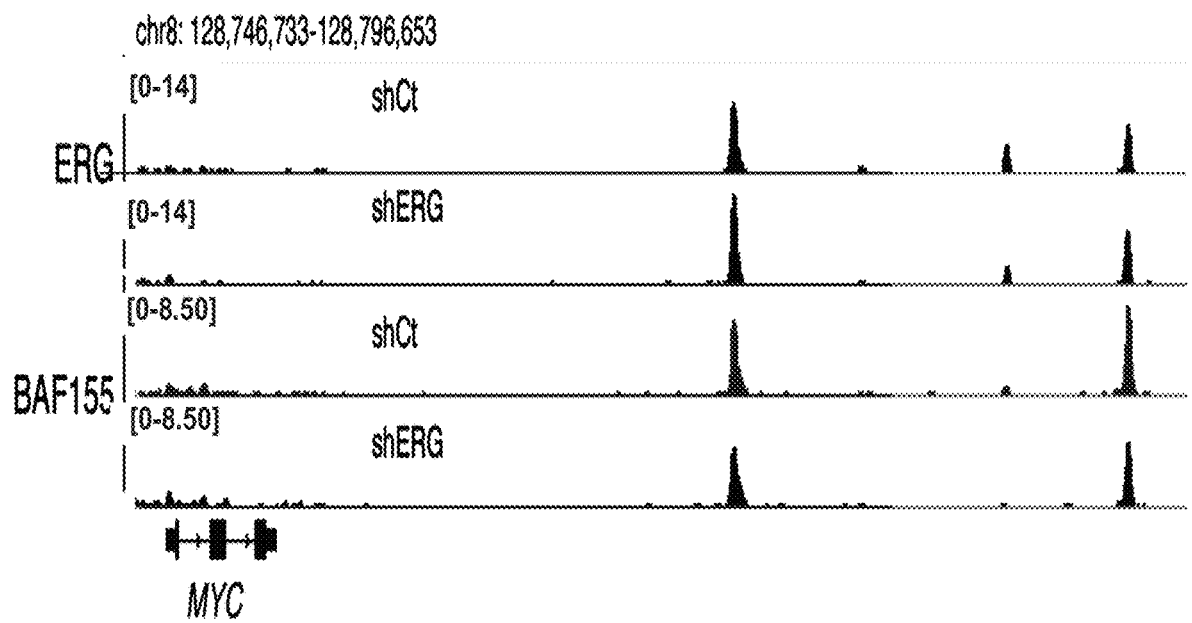
FIG. 14D-E show (left) ChIP-seq tracks over the MYC locus and (right) RPKM values for MYC, AR, and FOXA1 shows downregulation of key prostate cancer genes upon knockdown of ERG.
Figure 14E:
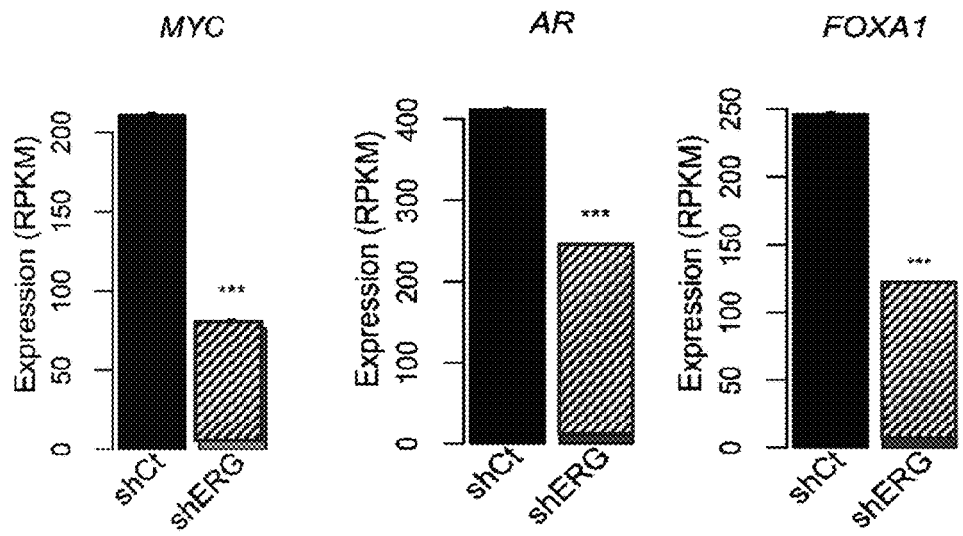
Figure 14F:
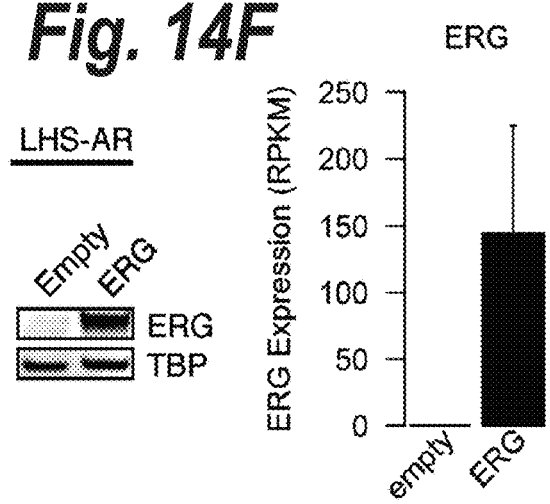
FIG. 14F indicates overexpression of ERG in LHS-AR cells as assessed by (left) western blot of ERG levels and (right) RPKM levels in RNA-seq experiment. Error bars=Mean±SEM (n=2).
Figure 14G:
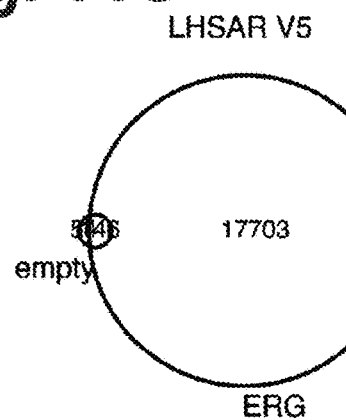
FIG. 14G is a Venn diagram of ERG peaks called in the empty vector and +V5-ERG settings, indicating gain of occupancy upon ERG overexpression in LHS-AR cells.
Figure 14H:
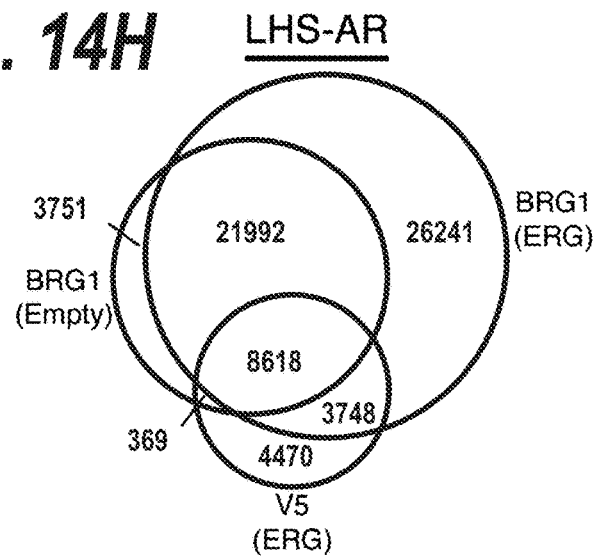
FIG. 14H is a Venn diagram illustrating overlap of BRG1 sites in empty and +V5-ERG conditions, as well as V5 sites in the +V5-ERG condition in LHS-AR cells.

To determine whether ERG has a direct, instructive role in dictating BAF complex localization genome-wide, the effect of suppressing ERG levels in TMPRSS2-ERG-expressing VCaP cells was examined (FIG. 13A-B, FIG. 14A) using shRNA-mediated knockdown. Knockdown of ERG in VCaP cells resulted in significant genomic retargeting of BAF complexes, as assessed by anti-BAF155 ChIP-seq (FIG. 13C): 16888 BAF155 sites are ERG-specific (not called in the shERG condition and hence are shCt-specific BAF155 sites) and 11194 BAF155 sites are only called upon knockdown of ERG (shERG-specific BAF155 sites). Notably, the shCt-specific sites show strongest enrichment of FOXA1, followed by CTCF and ERG motifs, whereas the shERG-specific sites show top enrichment of CTCF, followed by FOXA1 and AR motifs (Centrimo central enrichment p-value), pointing to an ERG-dependent differential sequence binding (FIG. 14S). Of these sites, 10800 (64.0%) shCt-specific BAF155 sites overlap with ERG sites, whereas only 3865 (34.5%) shERG-specific BAF155 sites overlap with ERG sites, demonstrating that the condition-dependent BAF155 sites are biased toward ERG sites when ERG is present, and not overlapping with ERG in a random manner (FIG. 13C). Similar analysis of condition-dependent BRG1 sites shows similar repositioning bias toward ERG sites in shCt condition (FIG. 14C). Of the subset of these 10800 shCt-specific BAF155 sites that overlap with ERG (shCt-specific BAF155-ERG sites, shaded in FIG. 13C), a major decrease in BAF155 occupancy was found upon ERG knockdown, further demonstrating an instructive role for ERG in directing BAF155 occupancy (FIG. 13D). shCt-specific BAF155 sites exhibit strong ERG motif enrichment (p=1.9e-136, FIG. 13E, left), whereas shERG-specific BAF155 sites show very weak ERG motif enrichment (p=8.2e-8, FIG. 13E, right). These data highlight differential occupancy of BAF complexes at ERG motifs in the shCt condition as compared to shERG condition, and indicate that BAF complex targeting to the ERG motif is gained upon ERG expression in LHS-AR cells, and not solely due to downstream ERG targets affecting BAF complex localization. This differential occupancy at the promoter of HOXB13, a key gene implicated in prostate oncogenesis, was found with knockdown of ERG inducing a loss of BAF155 occupancy and downregulated gene expression (FIG. 13F). In addition, downregulation of AR, MYC, and FOXA1 was found upon knockdown of ERG, concordant with decreased BAF complex occupancy, indicating a role for the BAF complex in the regulation of key target genes in prostate cancer (FIG. 14D-E) To examine the concordant effects of ERG on BAF complex localization, the overexpression of ERG in LHS-AR prostate epithelial lines was examined (FIG. 14F-G). BAF complexes are significantly retargeted upon overexpression of V5-ERG in LHS-AR prostate epithelial cells, with 4213 peaks lost upon ERG overexpression (empty-specific BAF155 sites) and 14340 sites gained upon ERG overexpression (ERG-specific BAF155 sites) (FIG. 13G). The increased number of gained sites in this setting is likely due to the super-stoichiometric overexpression of ERG. Of the empty vector-specific BAF155 sites, only 403 (9.6%) overlap with the V5 sites created by ERG overexpression, whereas 2756 (19.2%) ERG-specific BAF155 sites overlap with V5, further demonstrating the ERG-BAF genomic binding relationship concordant with that observed in VCaP cells (FIG. 13G), and similar analysis of condition-dependent BRG1 sites shows similar bias toward ERG sites (FIG. 14H). At these ERG-specific BAF155 sites that overlap with V5 (hence, ERG-specific BAF155-ERG sites, shaded region in FIG. 13G), a significant gain in BAF155 occupancy was found with gain of ERG occupancy, underscoring ERG-dependent BAF complex occupancy (FIG. 13H). Empty vector-specific BAF155 sites in LHS-AR cells display low enrichment of the ERG motif (p=5.2e-6, FIG. 13I, left), compared to the ERG-specific BAF155 sites, which show significant central enrichment of the ERG motif (p=6.4e-81, FIG. 13I, right). The FL1 gene locus contains a clear example of ERG-dependent BAF complex occupancy, with a gained V5-ERG peak and concordant gain of BAF complex occupancy, coupled with increased gene FL11 expression (FIG. 13J).

Figure 14I:
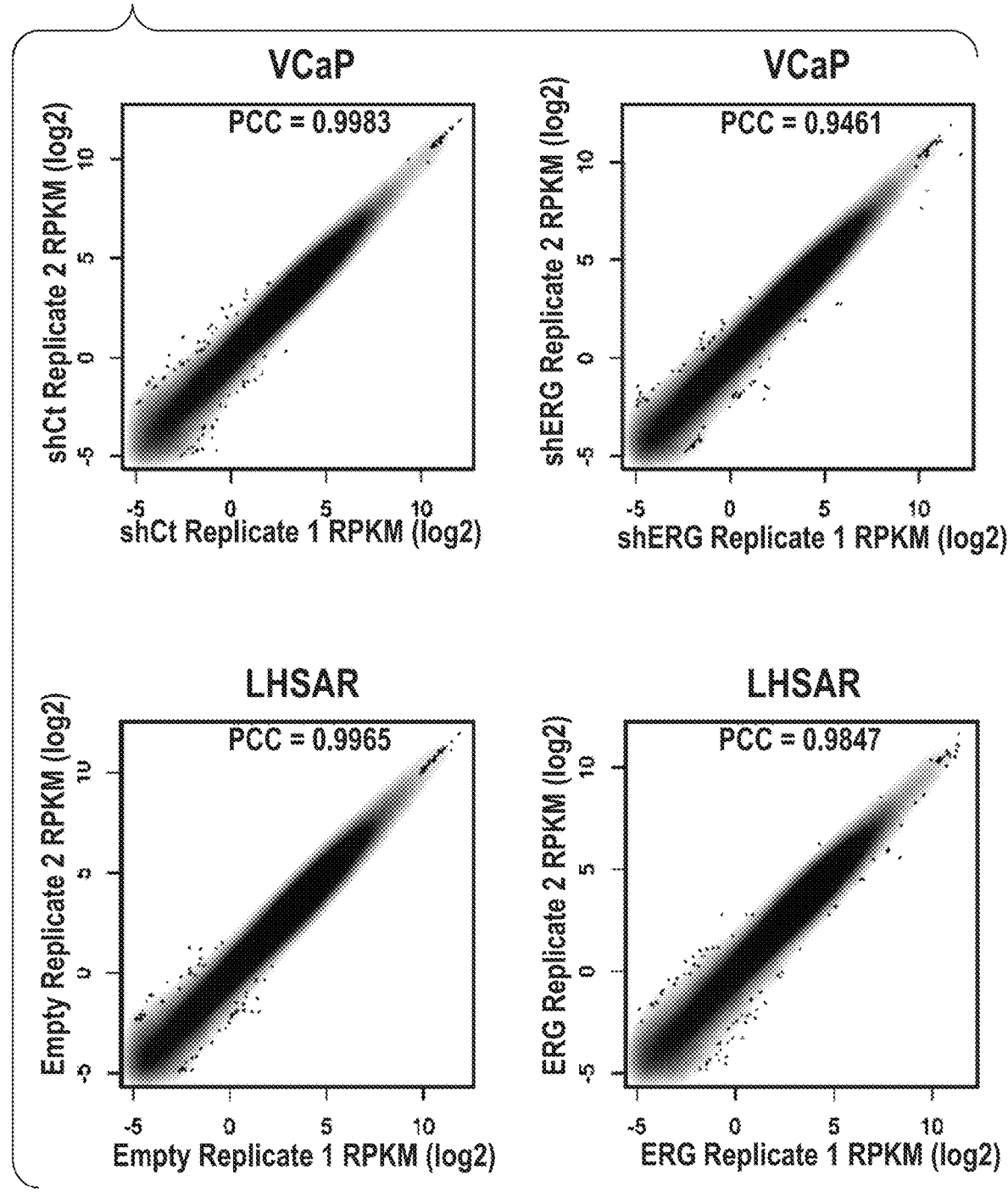
FIG. 14I shows concordance of replicate RNA-seq experiments in shCt and shERG conditions in VCaP cells, and empty and V5-ERG conditions in LHS-AR cells, with Pearson correlation coefficient (PCC) between replicates.

To determine if ERG overexpression results in similar target gene regulation across both cell settings (VCaP cells and LH-SAR cells), RNA-seq from each cell line ±ERG was compared (VCaP shCt vs. shERG, LHS-AR empty vs. ERG) (FIG. 13K, FIG. 14I). Of the 2128 significantly regulated genes in VCaP and 2949 significantly regulated genes in LHS-AR (as assessed by DESeq2 log 2FC >±1 and Bonfemr-corrected p-value <1e-3), 504 genes that exhibit significant regulation in both contexts were found. Of these, 232 are significantly upregulated and 79 are downregulated by ERG in both contexts (FIG. 13K, left). The effects of ERG in these two cell lines were significantly concordant (FIG. 13K, right, p=0.018, Fisher exact test), and these 232 genes were denoted significantly upregulated by ERG as our ERG target gene set for downstream analyses. Using GO term analysis, significant enrichment of cell cycle and cell division gene sets in the ERG target gene set was found (FIG. 13L).

Figure 15A:
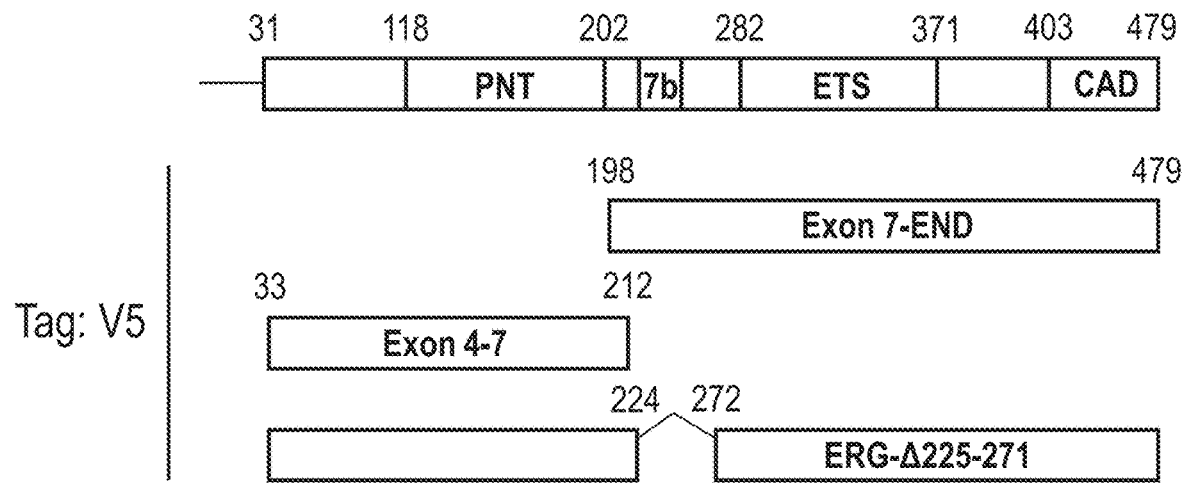
Figure 15B:
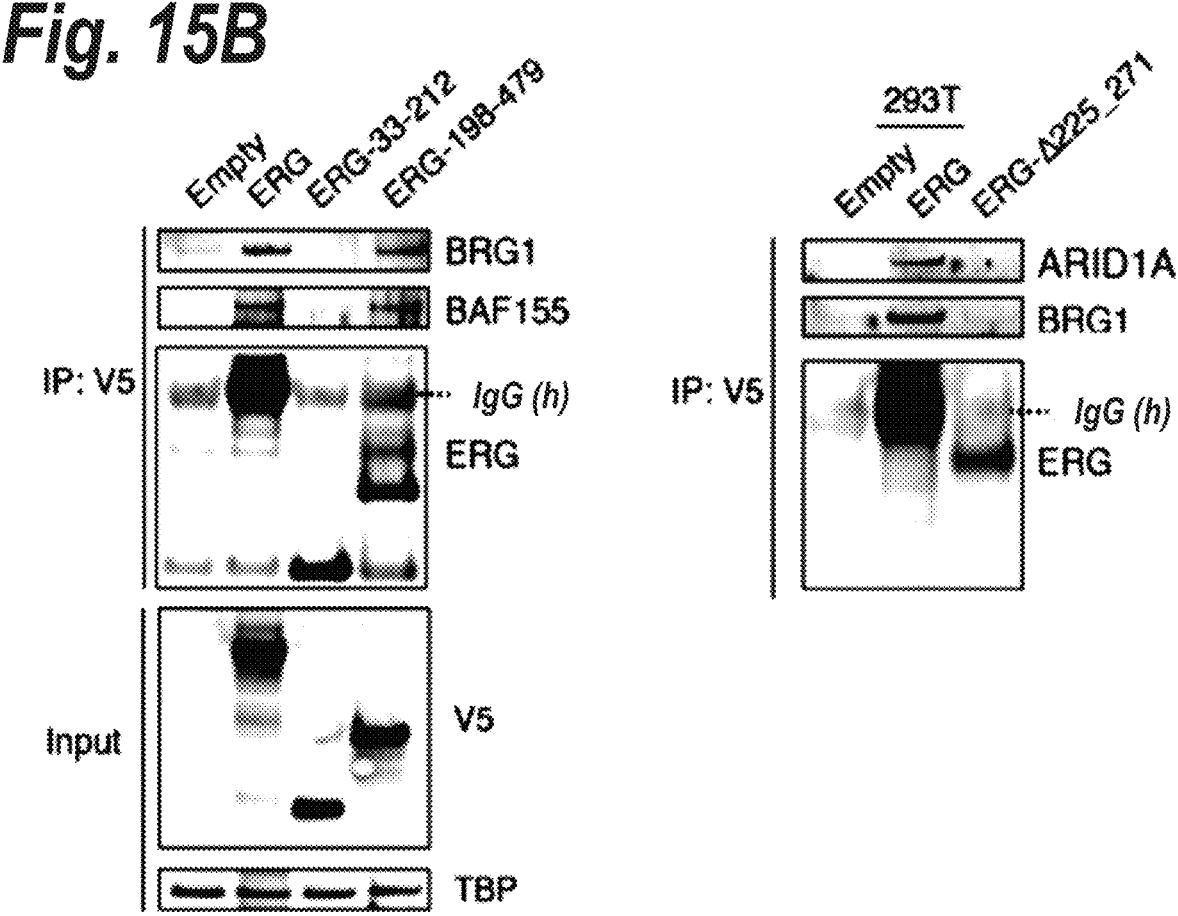
Figure 15F:
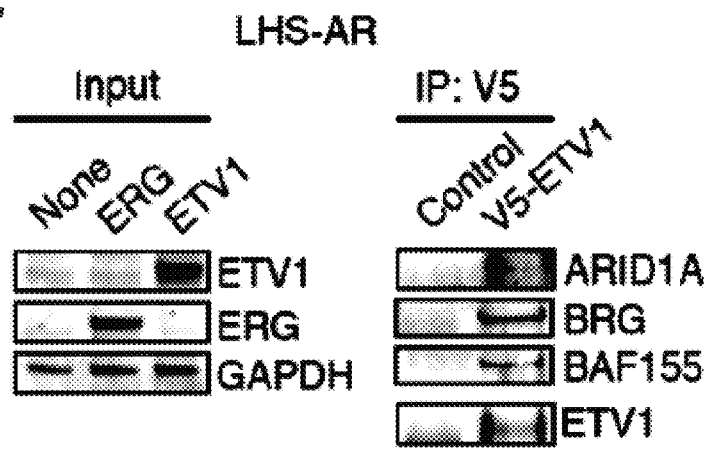
Figure 15G:
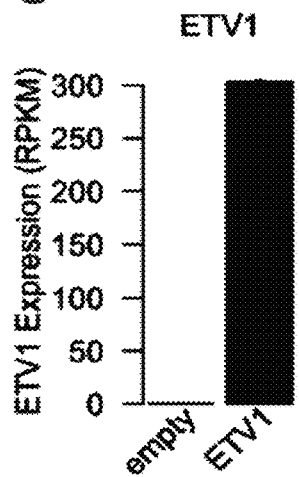
Figure 15H:
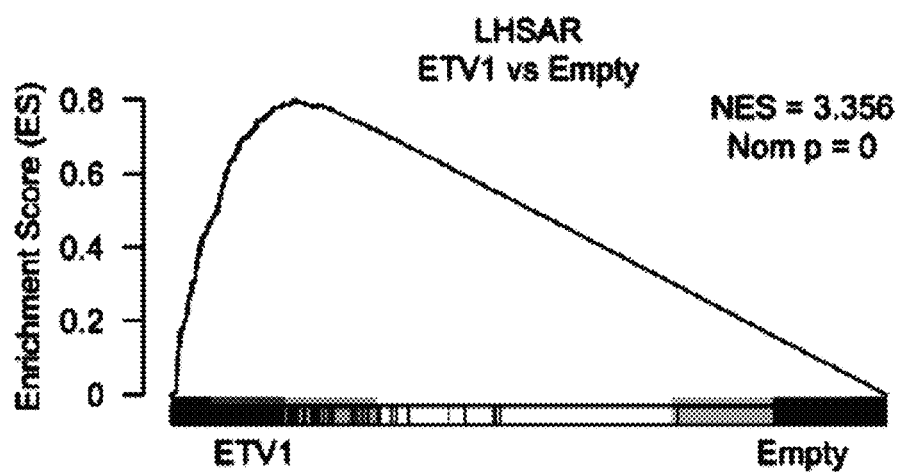
Figure 15I:
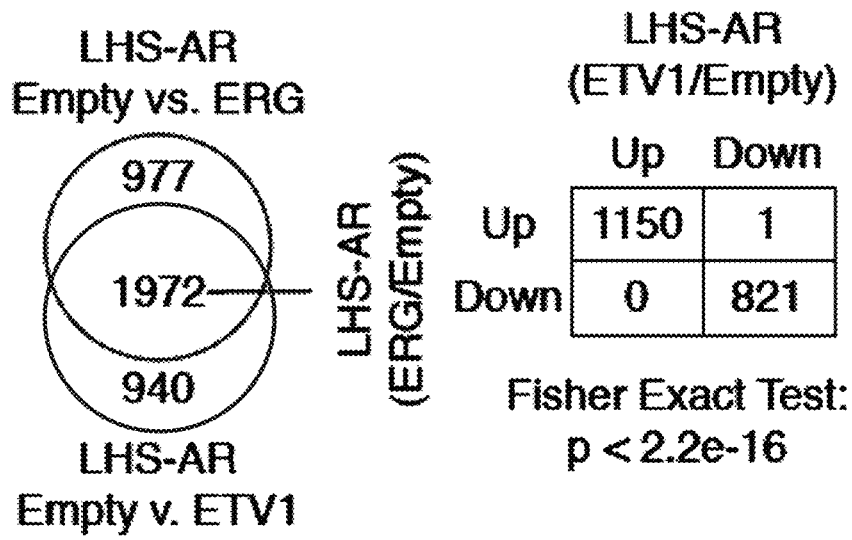
Figure 16A:
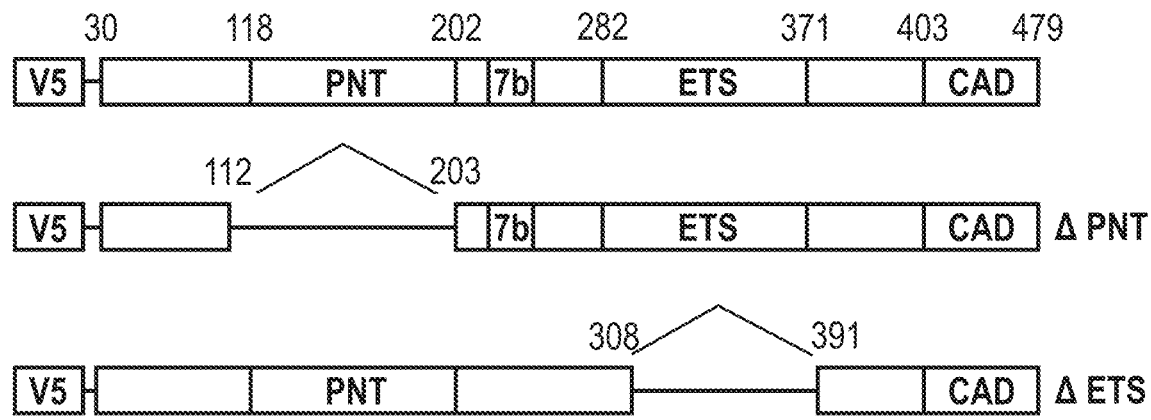
FIG. 16A shows ERG domain deletion variants used to define binding region of ERG to BAF complex.
Figure 16B:
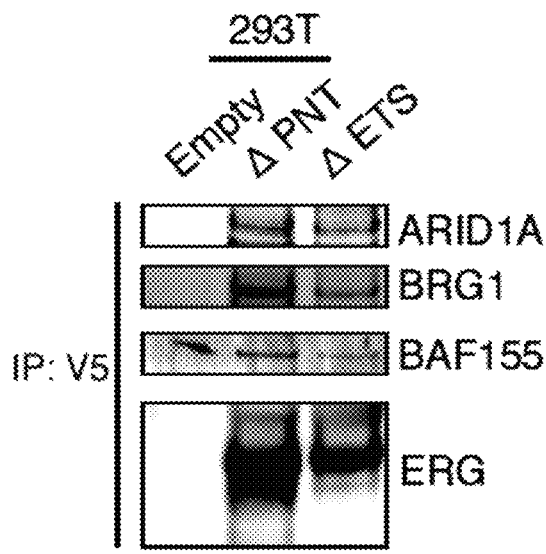
FIG. 16B shows results of Anti-V5 IPs of V5-tagged ERG domain deletion variants in 293T cells.
Figure 16D:
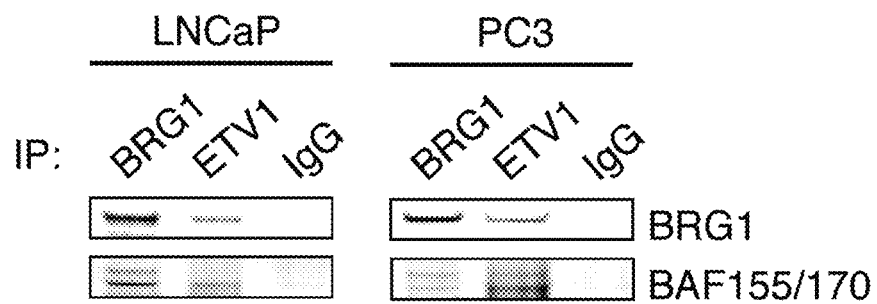
FIG. 16D shows immunoblot results of immunoprecipitation using anti-BRG, anti-ETV1 and anti-IgG antibodies in nuclear extracts isolated from LNCaP (right) and PC3 (left) prostate cancer cells confirms ETV1 binding to BAF complexes.
Figure 16E:
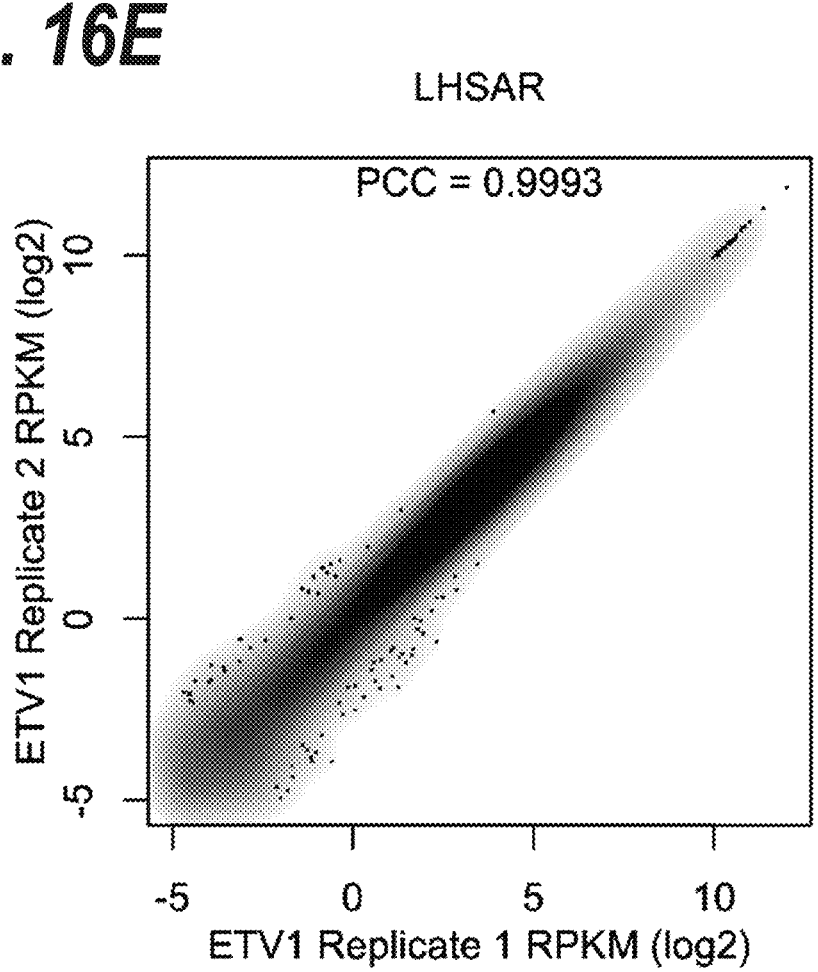
FIG. 16E shows concordance of replicate RNA-seq experiments in LHS-AR cells containing V5-ETV1, with Pearson correlation coefficient (PCC).
Figure 17A:
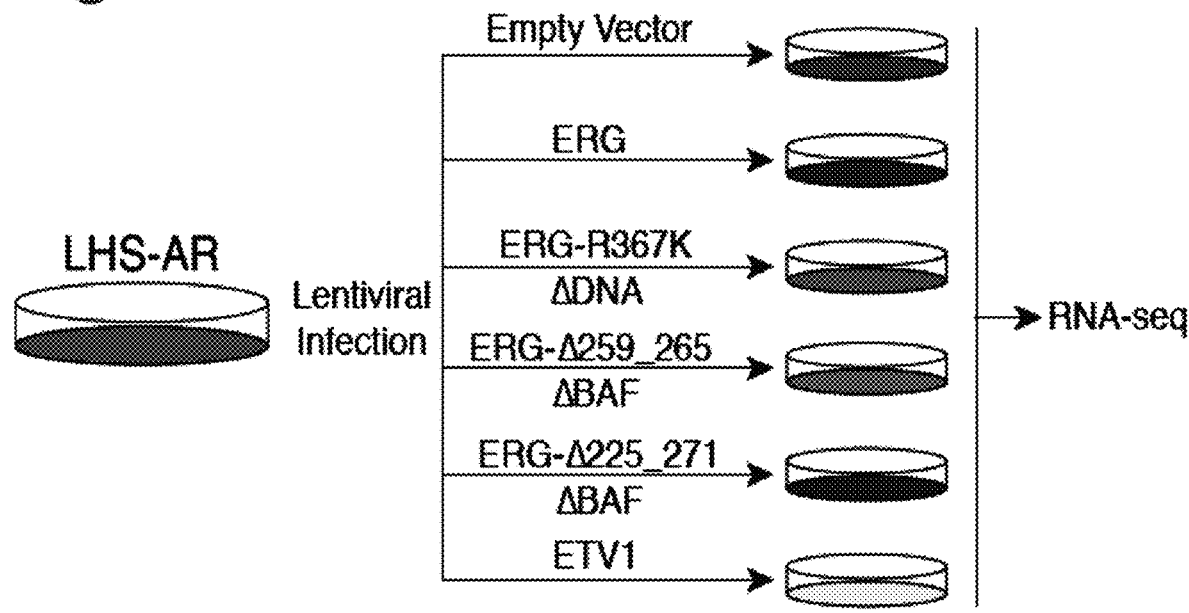
FIG. 17A-E show that ERG-BAF binding is required for TMPRSS2-ERG-driven gene expression signatures.
Figure 17B:
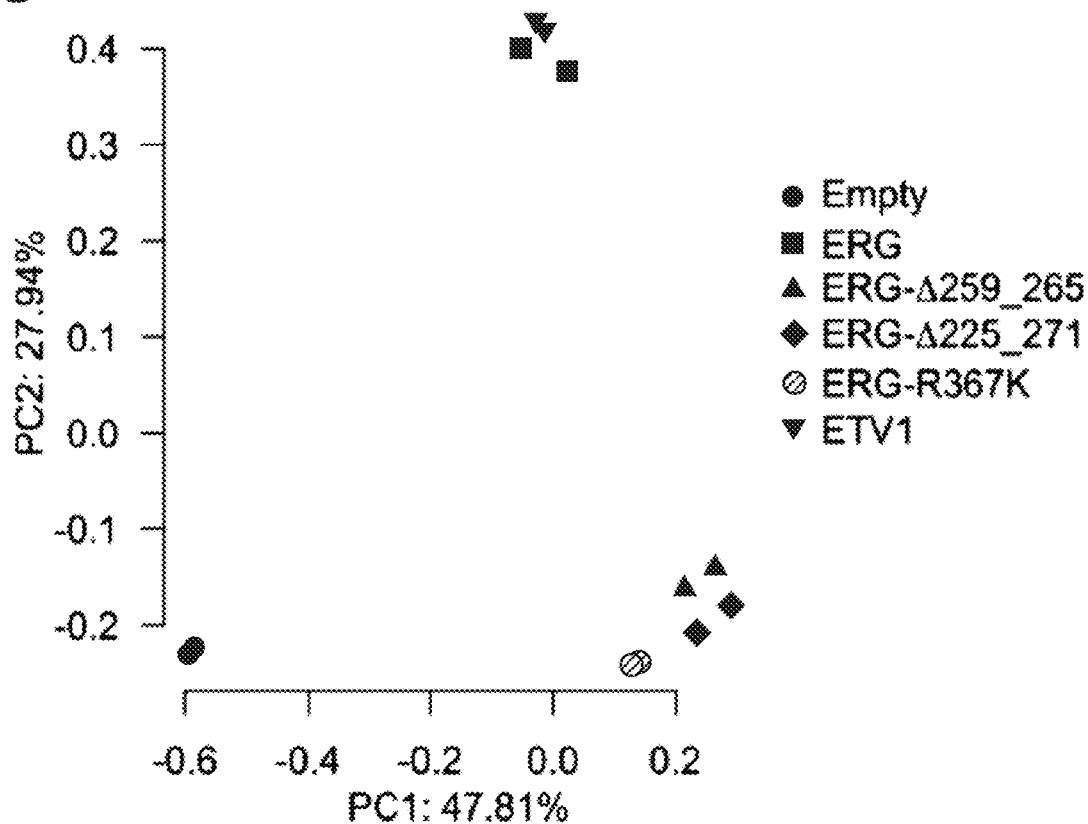
Figure 17C:
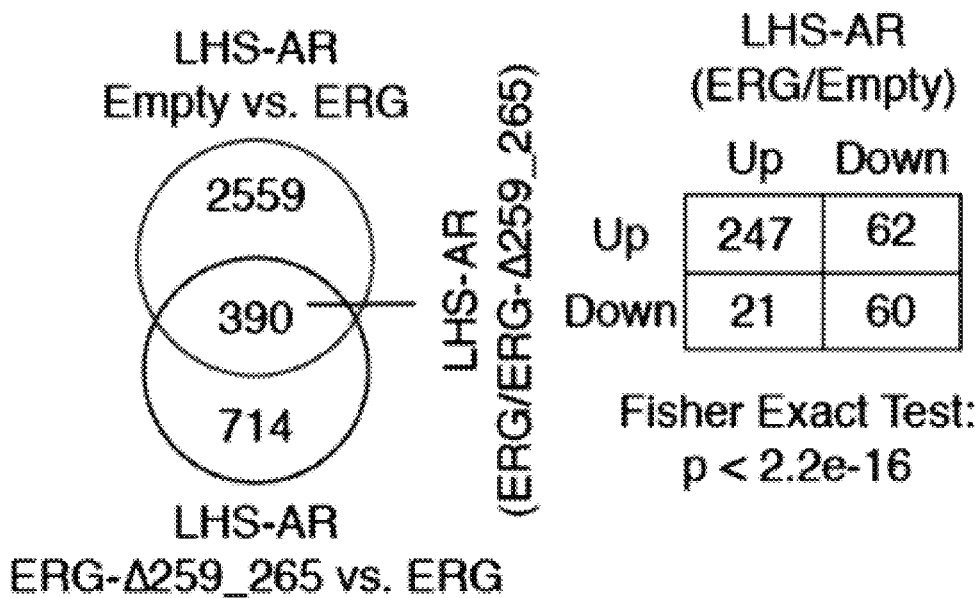
Figure 17D:
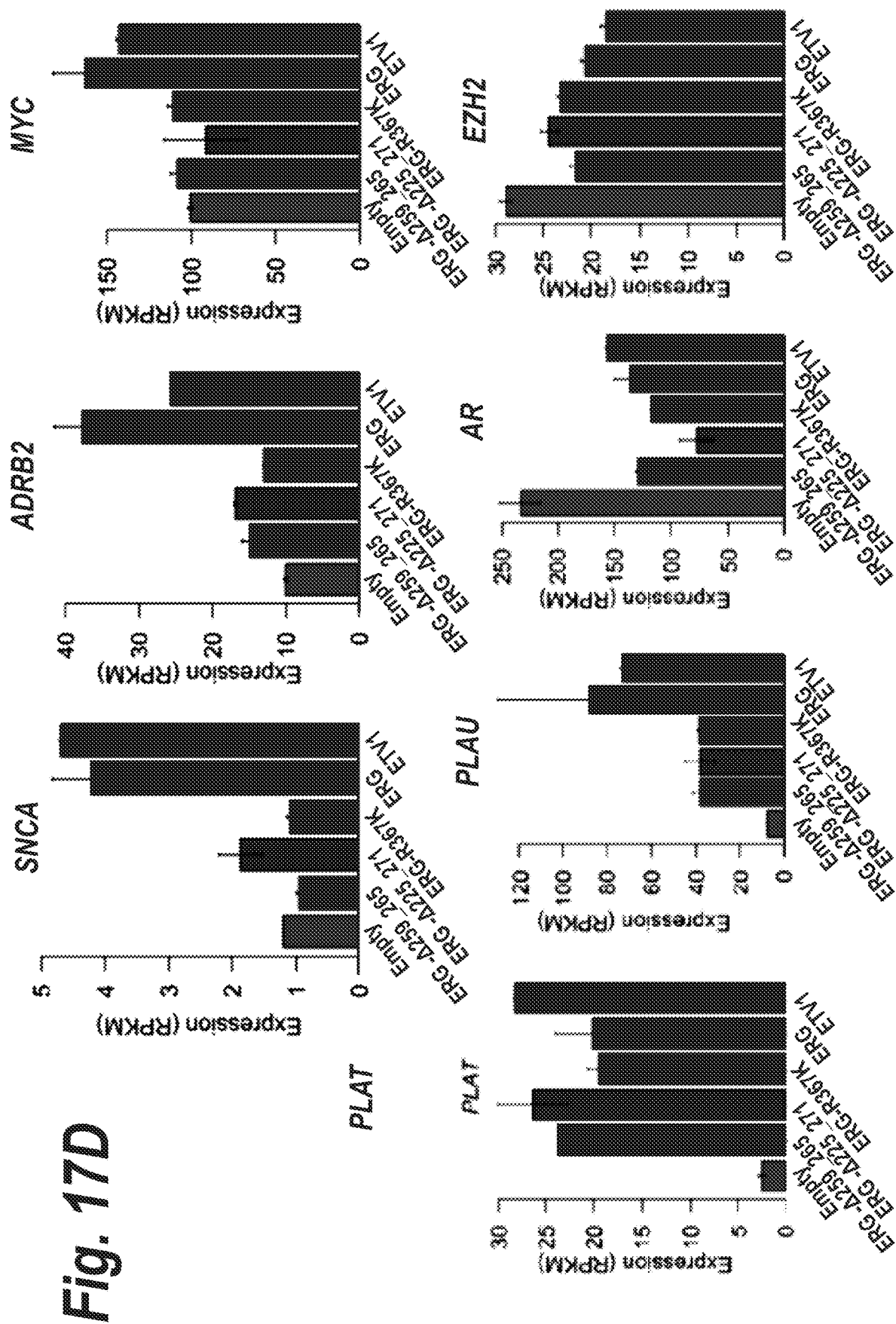
Figure 17E:
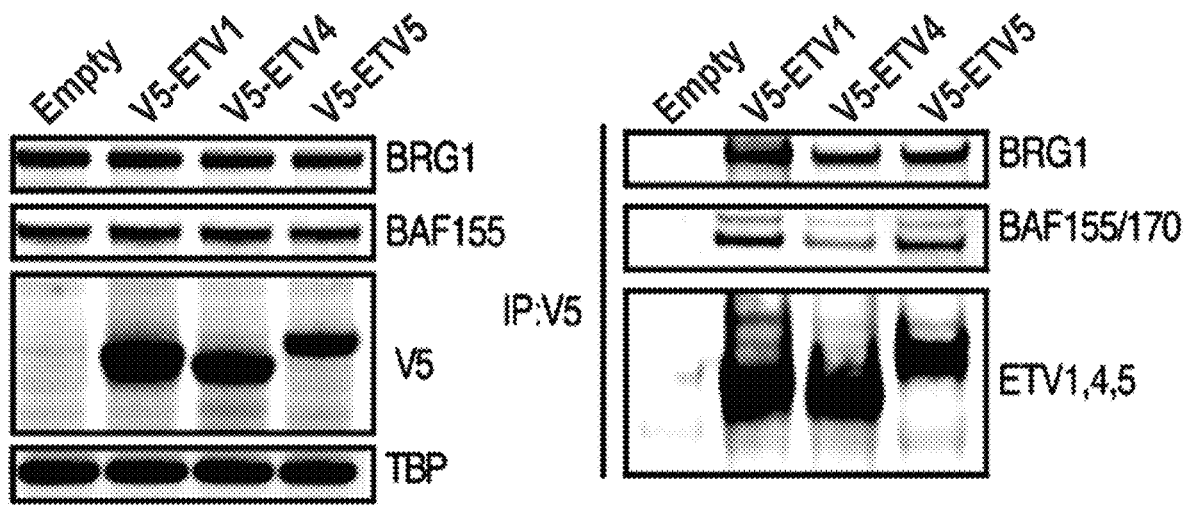

Example 10. The Region of the ERG Protein Required for BAF Complex Binding is Present in ETS Family Proteins Upregulated in Prostate Cancer The overexpression of various ETS factors is common in several cancer types, most often driven by specific translocations (Clark and Cooper, 2009; Delattre et al., 1992; Ichikawa et al., 1994; Tomlins et al., 2005). To determine the specific region of ERG required for BAF complex binding, and to map the region of ERG required to bind the BAF complex, tagged fragments of ERG containing aa30-212, aa198-479 and ERG-Δ225_271 were generated (FIG. 15A). Additional mutants lacking the major ERG protein domains (PNT and ETS domains) were generated (FIG. 16A). Neither the PNT nor the ETS domains were found to be necessary for binding BAF complexes, as assessed by anti-V5 IPs and subsequent immunoblot for BAF complex subunits (FIG. 16B). These domains have been shown to confer specific functions for ERG (as well as the ETS family), particularly the ETS domain which is required to tether to ERG motifs on DNA (Adamo and Ladomery, 2016; Basuyaux et al., 1997; Mackereth et al., 2004). Consistent with this, these results indicate that these two domains are not involved in BAF binding. Indeed, the only ERG fragment that bound to BAF contained amino acids 198-310 (FIG. 15B), that has been previously shown to be important for transactivation as well as binding various protein partners (Adamo and Ladomery, 2016). To focus on specific regions of ERG that bind BAF, protein alignment software was used to align amino acid sequences of this region of ERG with other ETS transcription factors, particularly those known to be involved in prostate cancer, such as ETV1, ETV4, and ETV5. ETV1, ETV4, and ETV5 are all capable of binding to BRG1 and BAF155, as demonstrated by immunoprecipitation (FIG. 17E). Surprisingly, all ETV variants expressed in prostate cancer were found to contain a highly conserved 7-amino acid region, aa 259-265, AWT-GRGH (FIGS. 15C and 16C). To further validate this binding region V5-tagged ERG constructs lacking this 7 amino acid region (ERG-Δ259_265) were generated, along with additional ERG variants in which the region containing exon 7b and exon 8 (ERG-Δ225_271) was deleted, and a mutant lacking ERG DNA binding activity, ERG R367K (Verger et al., 2001) (FIG. 15D). These results demonstrate that deletion of the 7 amino acid region aa 259-265 is sufficient to disrupt ERG-BAF complex binding (FIG. 15E). Moreover, because this 7 amino acid BAF binding region is present in ETV1, another ETS factor overexpressed in roughly 10% of prostate cancers, whether ETV1 can bind to the BAF complex was determined. Consistent with this region serving as the tether to BAF complexes, immunoprecipitation of overexpressed V5-ETV1 in LHS-AR cells revealed an interaction between ETV1 and BAF (FIG. 15F, 15G). In addition, the ETV1-BAF interaction can also be detected in both LNCaP and PC3 prostate cell lines, which contain overexpressed ETV1 (FIG. 16D). To characterize the effect of ETV1, RNA-seq was performed on LHS-AR cells overexpressing ETV1 (FIG. 15G, FIG. 16E). GSEA was performed using the 232 ERG target genes determined earlier, using the comparison of ETV1 to the empty vector control, and this ERG target gene set was significantly enriched upon ETV1 overexpression (FIG. 15H, NES=3.356, p=0). Of 1972 significantly regulated genes by both ERG and ETV1, only 1 is discordantly regulated, with 1150 concordantly upregulated and 821 concordantly downregulated (FIG. 15I, p<2.2e-16, Fisher exact test). This indicates that ERG and ETV1 drive highly concordant gene expression upon overexpression in prostate cells, indicating a convergent role in prostate cancer oncogenesis.

Figure 16F:
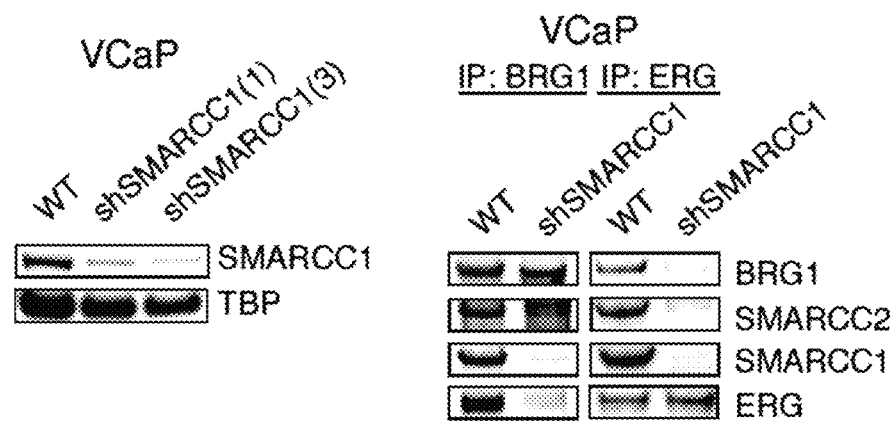
FIG. 16F (left) shows BAF155 nuclear protein levels in VCaP cells–/+BAF155 knock-down (shSMARCC1).
Figure 16G:
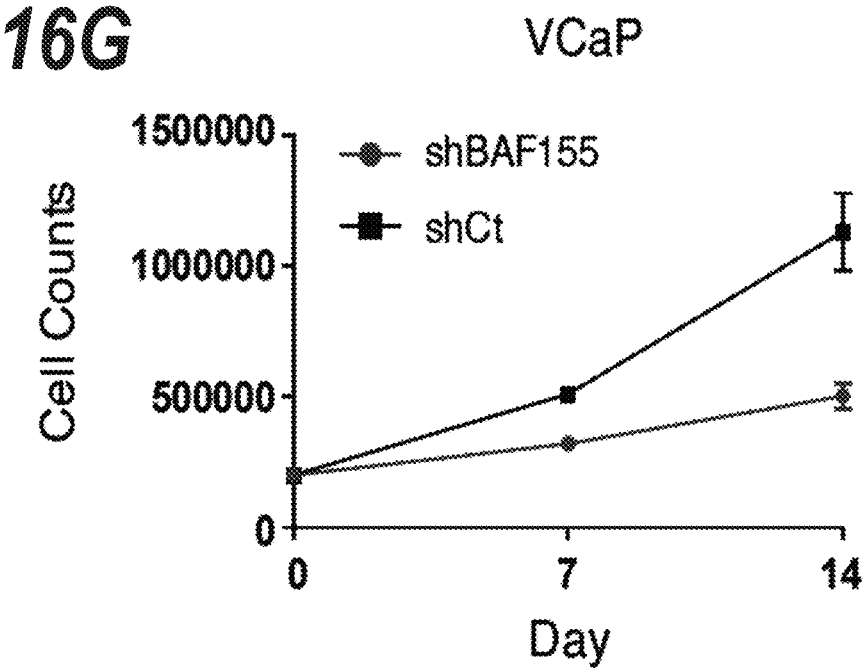
FIG. 16G shows shRNA-mediated knock down of BAF155 results in proliferative senescence of VCaP cells.

To determine whether disruption of BAF complex subunits (i.e. loss of specific subunits) results in reduced or absent ERG binding, the BAF155 subunit was knocked down in VCaP cells (FIG. 16F) and anti BRG1 and ERG immunoprecipitations were performed. In cells that lacked BAF155, ERG interaction was no longer observed (FIG. 16F). Moreover, loss of BAF155 severely impeded proliferation (FIG. 16G), suggesting that ERG-BAF interactions are important for proliferation of VCaP cells. These results collectively suggest that multiple ETS factors may promote oncogenesis in a similar manner via binding to the BAF complex family of ATP-dependent chromatin remodeling complexes.

Figure 18A:
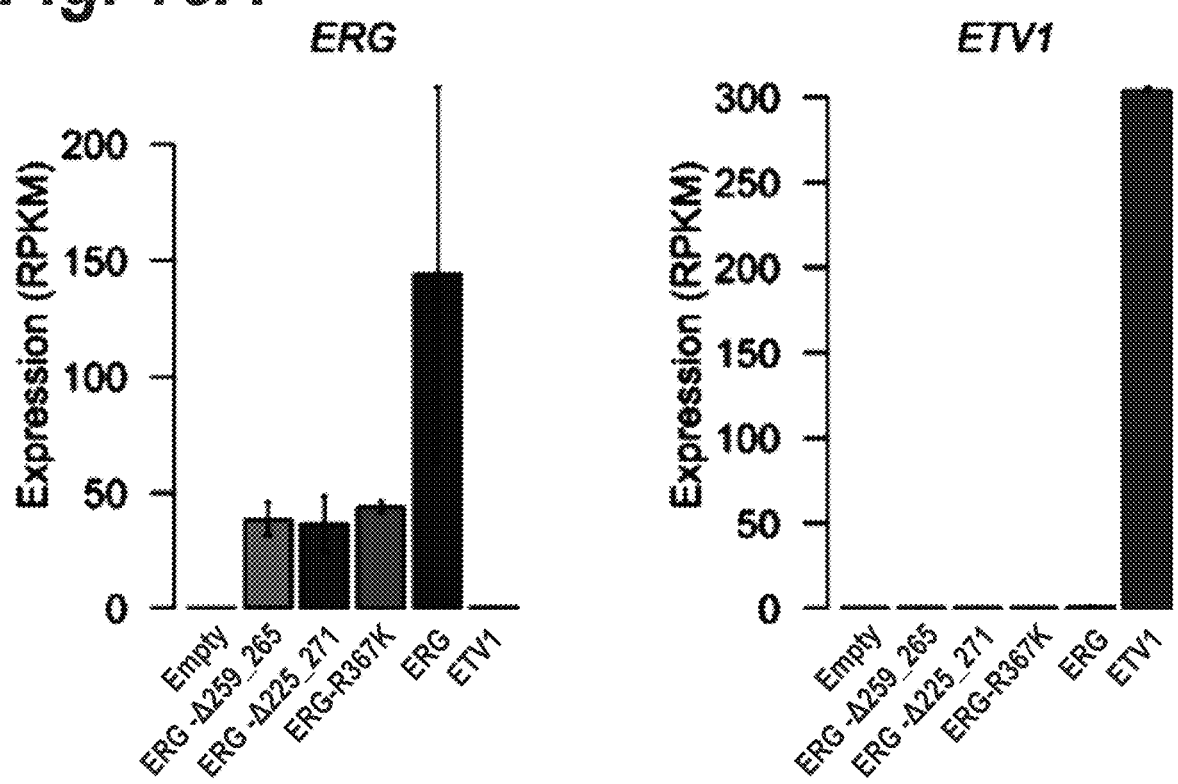
FIG. 18A shows RPKM values for (left) ERG and (right) ETV1 in each LHS-AR overexpression context. Error bars=Mean±SEM (n=2).
Figure 18B:
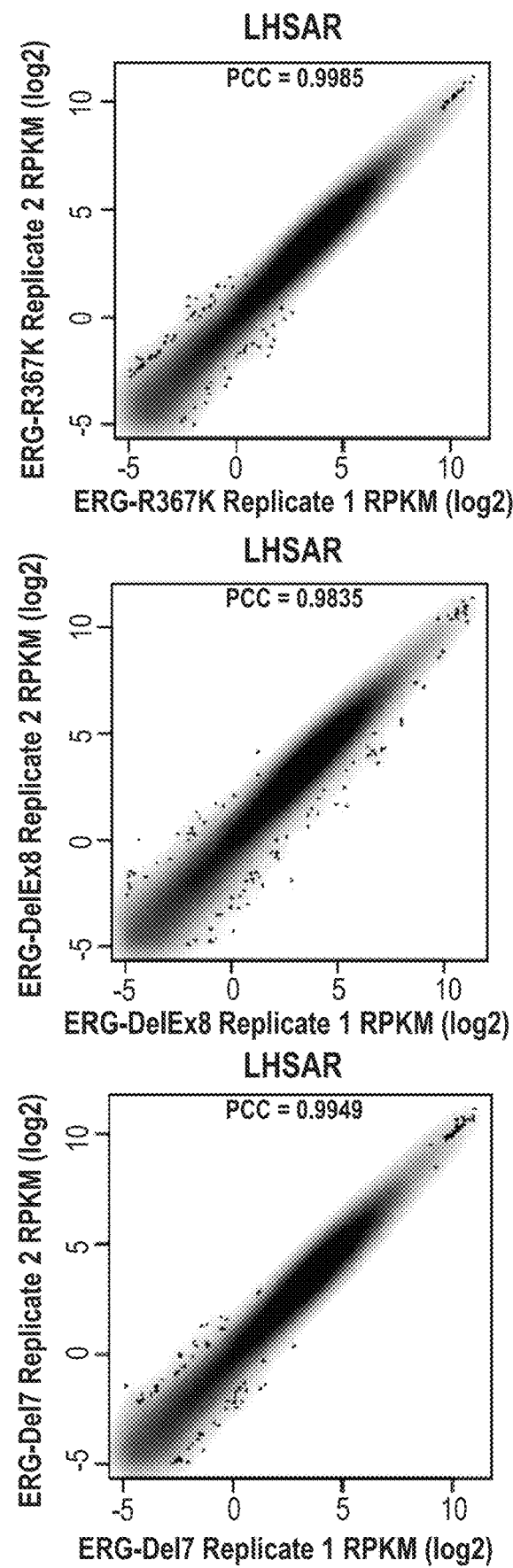
FIG. 18B shows concordance of replicate RNA-seq experiments for LHS-AR cells with introduced ERG-R367K, ERG-Δ225_271, and ERG- Δ259_265 (ERGΔ7aa) variants.
Figure 18C:
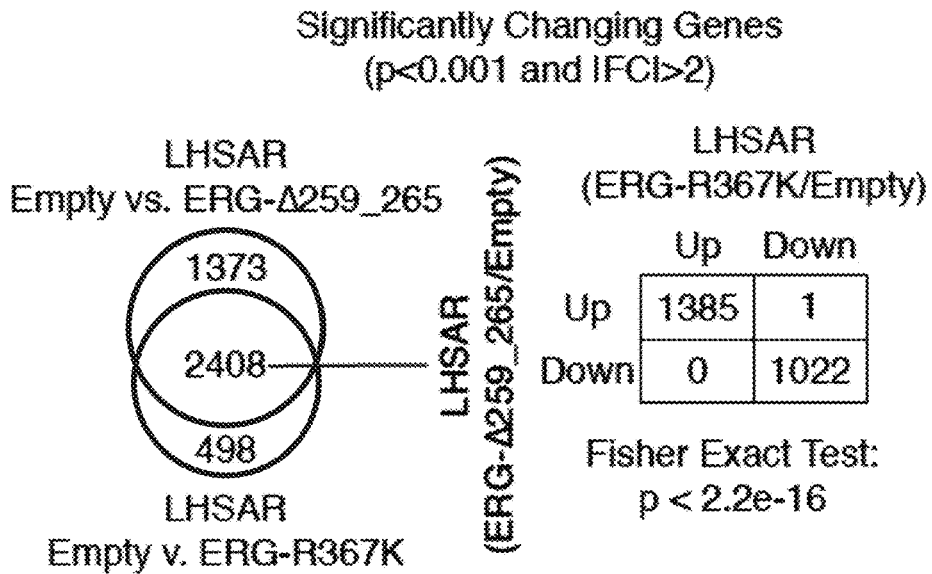
FIG. 18C shows BAF-binding and DNA-binding mutants of ERG induce near-identical gene expression changes upon overexpression in prostate epithelial contexts.
Figure 18D:
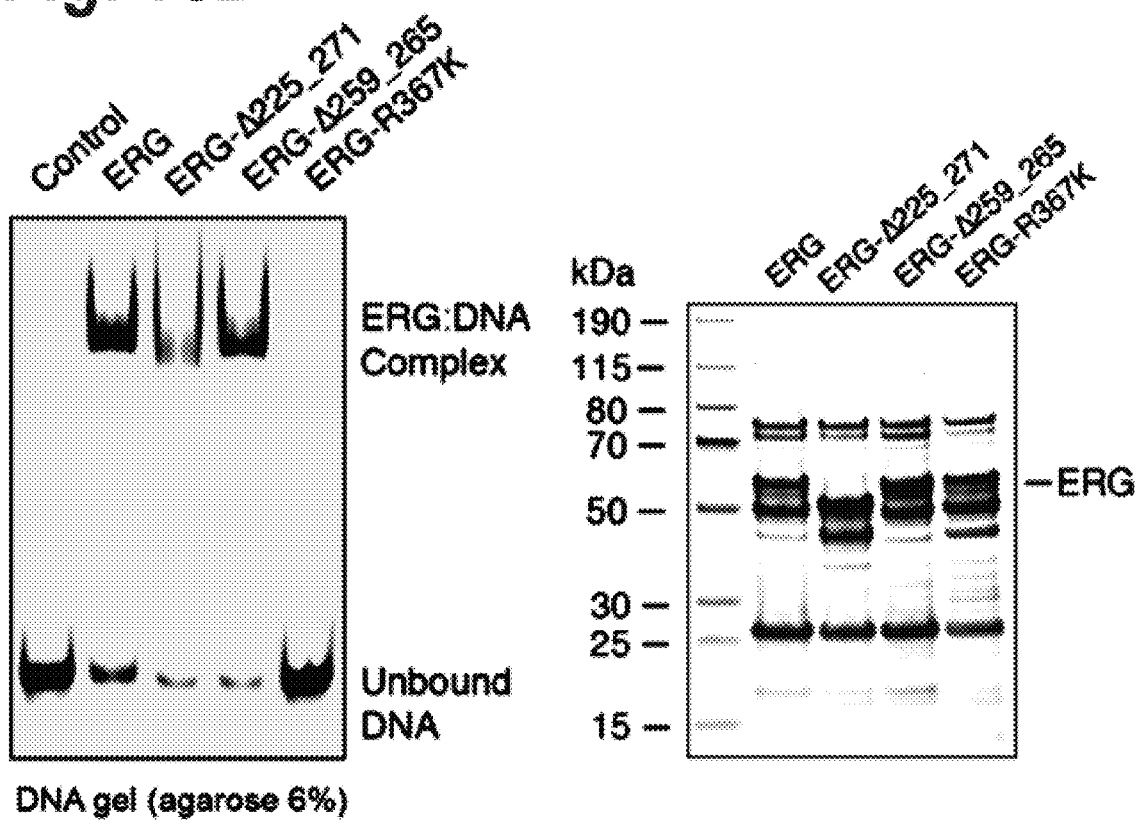
FIG. 18D shows the results of an electrophoretic mobility shift assay (EMSA) of ERG and ERG mutant variants, and a Commassie stain of SDS-PAGE of recombinant wild-type ERG and mutant variants expressed in and purified from E. coli cells.

Example 11. ERG Requires Both BAF Binding Regions and its DNA Binding Domain for Oncogenic Function To test the consequences of the ERG-BAF interaction on TMPRSS2-ERG-driven gene expression, a set of ERG variants was overexpressed in LHS-AR prostate epithelial cells (FIG. 17A, FIG. 18A-B). Using principal component analysis (PCA) of mRNA expression (RNA-seq) data, PC1 was found to underlie expressional differences induced upon expression of ERG, ETV1, and ERG variants compared to the empty setting, and PC2 was found to underlie an expressional distinction between the ERG variants and wild-type ERG (FIG. 17B). Notably, the ERG R367K DNA binding mutant variant was found to cluster together with the ERG-Δ225_271 (Exon 7b and 8 deletion) variant and the ERG-Δ259_265 (7aa deletion) BAF binding mutants, indicating a similar set of consequences mediated by loss of the DNA binding and BAF binding functionalities of ERG. Of 2408 genes significantly regulated by both ERG-Δ259_265 and ERG-R367K, only one gene was discordantly regulated, with 1385 genes upregulated in both contexts, and 1022 downregulated in both contexts (FIG. 18C, p<2.2e-16, Fisher exact test). In addition, both BAF-binding ERG mutants retain the ability to bind DNA, as assessed by electrophoretic mobility shift assays (EMSA) performed on purified recombinant ERG proteins (FIG. 18D), indicating that the BAF-binding region is separate from the region required for DNA-binding.

The concordant effect of the DNA and BAF binding mutant variants of ERG indicates that ERG requires the ETS domain to regulate its target genes, and that this ETS-dependent regulation also requires the BAF-binding ability, linking this novel BAF-binding ability to its canonical DNA-binding function.

Figure 17F:
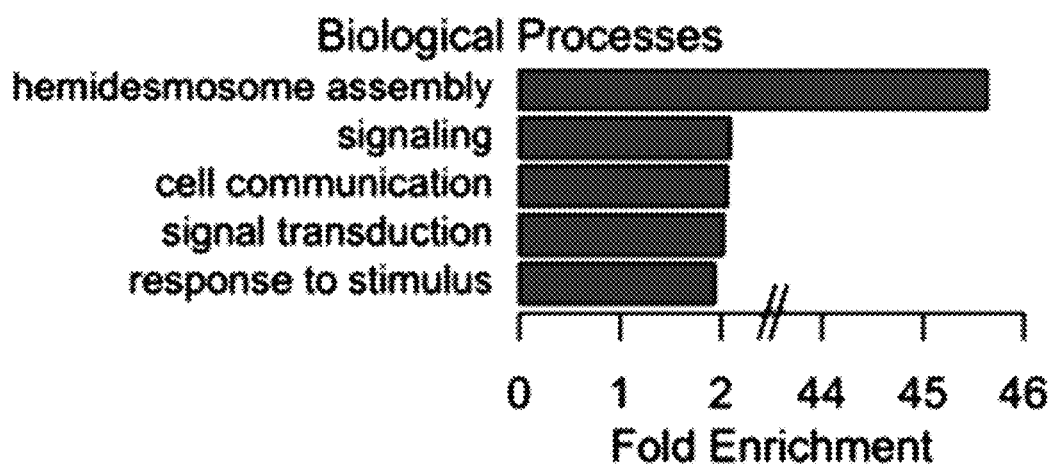
FIG. 17F shows GO term analysis of BAF-dependent upregulated ERG target genes demonstrating that cell signaling and cell communication processes are the biological pathways showing most significant enrichment.
Figure 18E:
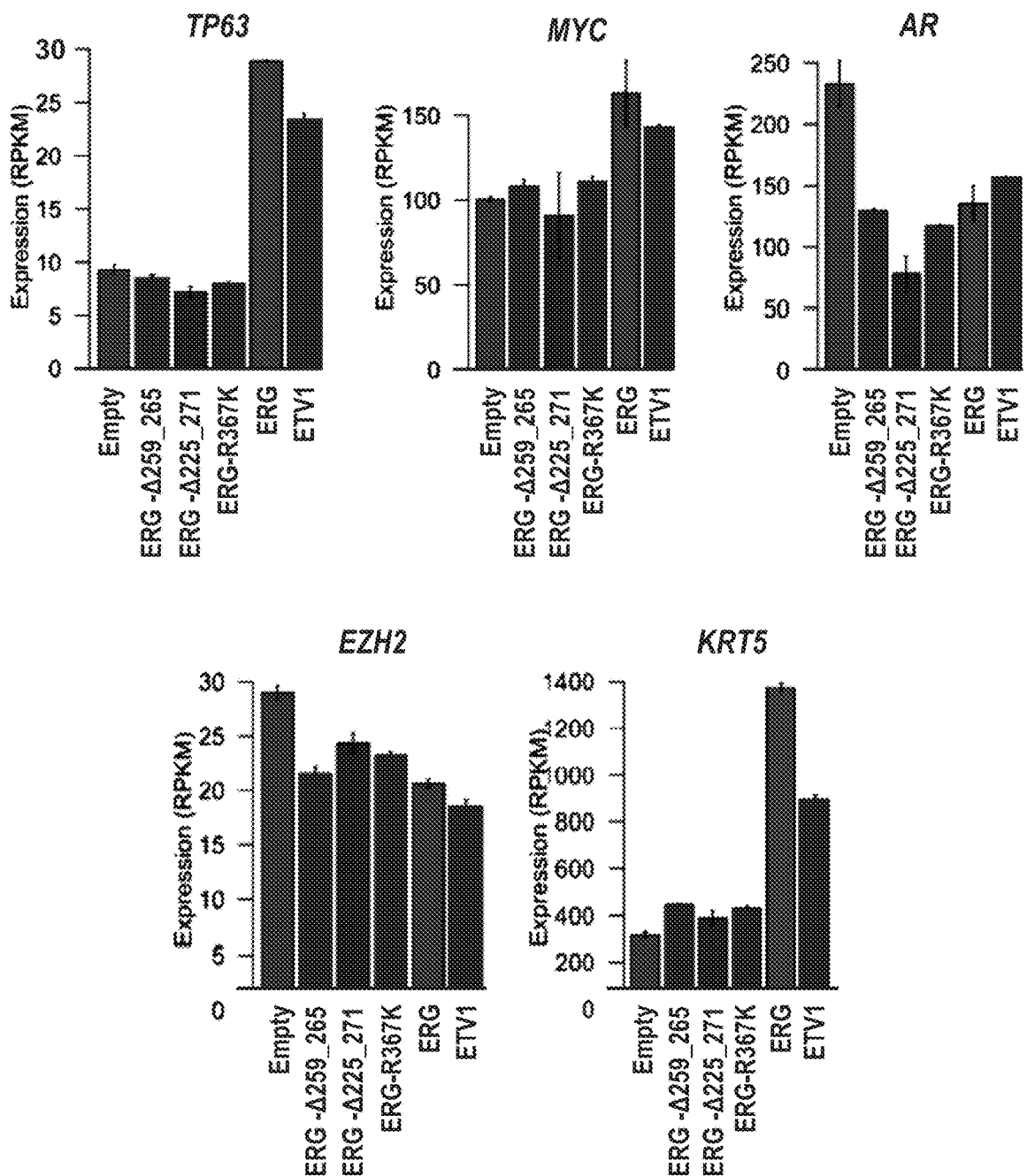
FIG. 18E shows additional genes such as TP63 and MYC showing differential expression by wild-type ERG and ERG variants, whereas genes such as EZH2 and AR are similarly regulated by wild-type ERG and ERG mutants.

The gene set uniquely regulated by wild-type ERG, but not by the ERG-Δ259_265 (7aa deletion) BAF-binding mutant, was determined, thereby determining a gene set regulated by this BAF-ERG interaction. Of the 2949 genes significantly changed between empty and ERG and the 1104 genes significantly changed between ERG-Δ259_265 and wild-type ERG, 390 genes were significantly altered in both comparisons (FIG. 17C, left). Among these, 247 genes were upregulated and 60 genes were downregulated only upon introduction of wild-type ERG, but not upon introduction of the BAF-binding mutant, indicating that the BAF-binding capability is required to regulate these genes (FIG. 17C). This differential gene regulation is exemplified by EZH2-target genes SNCA, ADRB2, and MYC (Yu et al., 2010) that is upregulated by ERG and ETV1 but not by the ERG mutants. Canonical ERG target genes PLAT and PLAU were similarly upregulated by ERG, ETV1, and all ERG BAF-binding and DNA-binding mutants, suggesting that ERG-mediated regulation of these specific genes were independent of both DNA and BAF complex binding. Similarly, AR and EZH2 showed downregulation by ERG, ETV1, and all ERG mutant variants (FIG. 17D). In addition, MYC, KRT5, and TP63 were differentially upregulated by wild-type ERG and ETV1, however key prostate cancer genes AR and EZH2 were downregulated independent of the DNA and BAF binding functions of ERG (FIG. 18E). Using GO term analysis on the 247 genes differentially upregulated by wild-type ERG relative to by ERG-Δ259_265, significant enrichment of hemidesmosome assembly and cell signaling genes was found (FIG. 17F). This contrasts with the overall enrichment of cell cycle genes characteristic of all ERG target genes, indicating that BAF plays a specific role in ERG-mediated regulation of signal transduction.

Figure 19D:
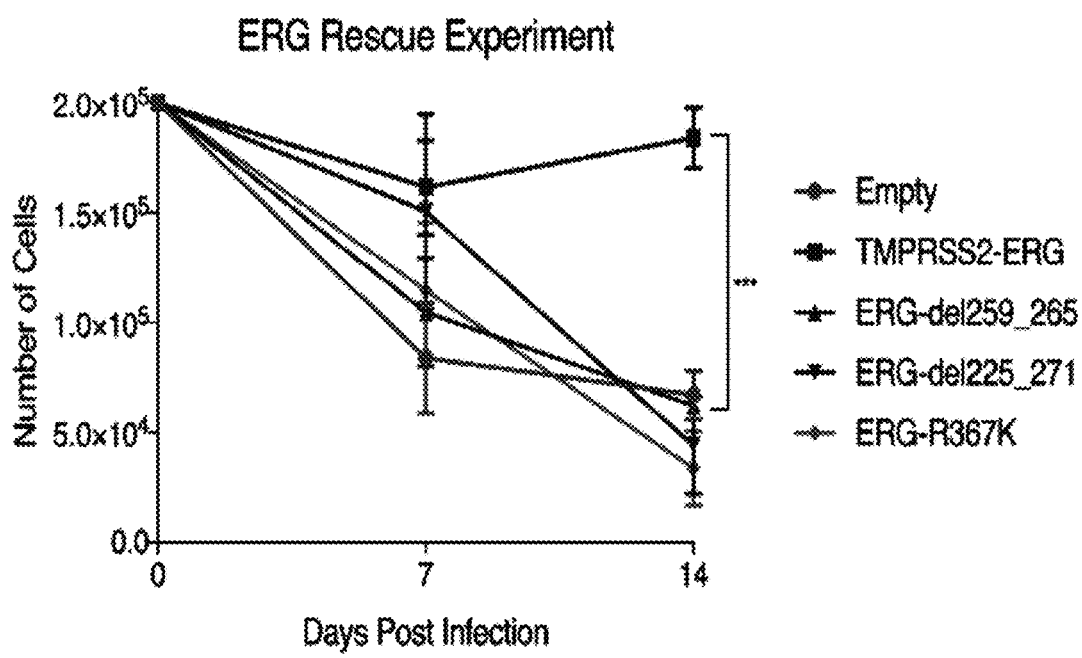
Figure 19E:
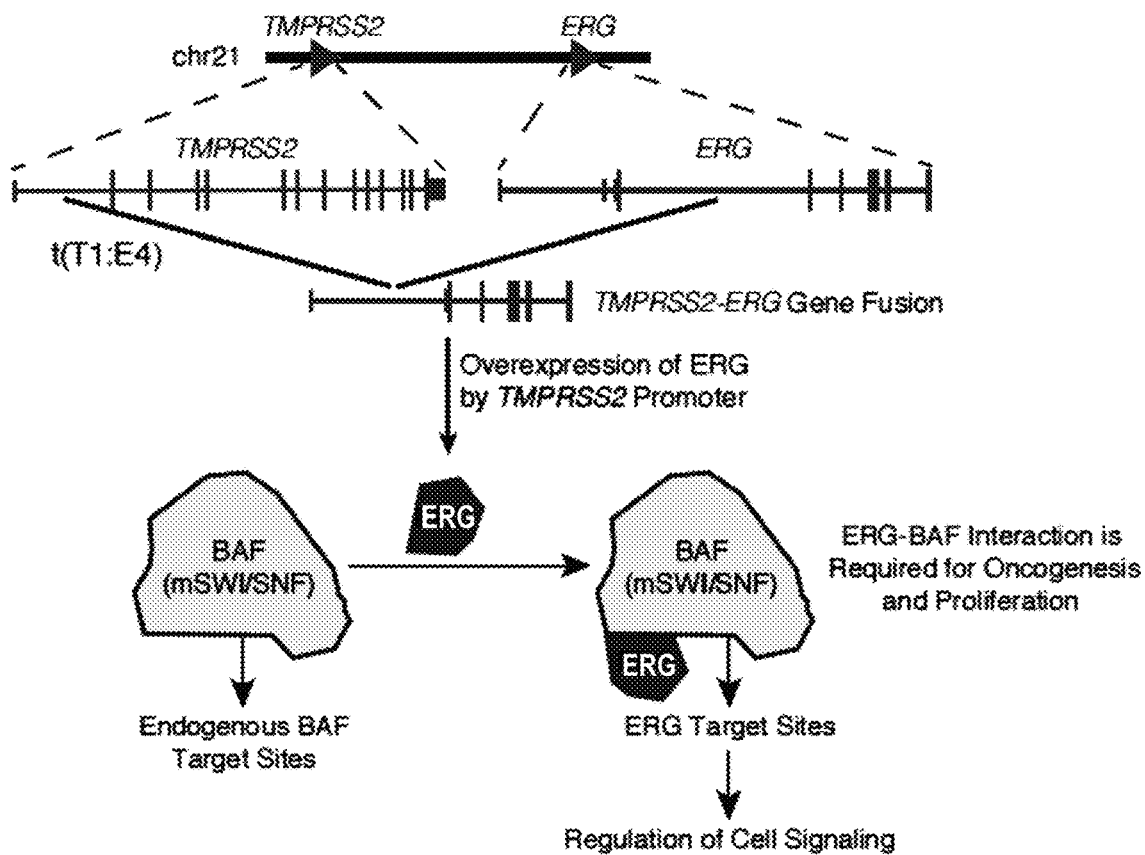

To test the functional importance of the ERG-BAF binding interaction and ERG-DNA binding interaction with respect to VCaP prostate cell proliferation, constitutively expressed ERG-BAF and DNA binding mutants were introduced in VCaP cells with and without concomitant suppression of endogenous ERG (via inducible ERG 3' UTR shRNA, to selectively deplete endogenous ERG and not exogenously overexpressed variants) (FIG. 19A, 19B). As demonstrated via western blot analysis, endogenous ERG is knocked down at the protein level in VCaP cells by t=7 days using this inducible construct (FIG. 19C). VCaP cells bearing overexpressed ERG variants and constitutive ERG 3'UTR shRNA were then seeded and proliferation was measured at time points indicated post induction of ERG 3'UTR shRNA. (FIG. 19D). Remarkably, exogenous overexpression of wild-type TMPRSS2-ERG was able to rescue the proliferative senescence resulting from endogenous ERG knockdown (Empty), while BAF and DNA binding mutant variants of ERG were unable to rescue (FIG. 19D, p-value=0.0001, unpaired two-sample t-test). Strikingly, these observations indicate two major roles for the ERG protein in oncogenesis: first is ERG must be able to bind to ETS DNA sequences to allow for transcription of its target genes, and secondly ERG must be able to interact with the BAF complex for maintenance of proliferation. Thus, the BAF binding and DNA binding activities of ERG are required for the maintenance of TMPRSS2-ERG driven prostate cancer cell (VCaP cell) proliferation. ERG also acts to disrupt normal BAF complex targeting, enabling increased proliferative capacity and oncogenic cell signaling pathways ushering in an oncogenic state. Disruption of this interaction results in slowed proliferation (FIG. 16G) or cell death (FIG. 19D, E).

Examples 7-11: Materials and Methods

SILAC media preparation and cell culture conditions: Standard SILAC media preparation and labeling steps were followed as previously described (Ong and Mann, 2006) with the addition of light proline to prevent the conversion of arginine to proline (Bendall et al., 2008). Briefly, L-methionine and 200 mg/L of L-Proline were added to base media according to standard formulations for DMEM (Caisson Labs). This base media was divided into three parts and to each was added either L-arginine (Arg0) and L-tysine (Lys0) (light), $^{13}C_6^{14}N_4$-L-arginine (Arg6) and 4,4,5,5-$D_4$-L-lysine (Lys4) (medium), or $^{13}C_6^{15}N_4$-L-arginine (Arg10) and $^{13}C_6^{15}N_2$L-Lysine (Lys8) (heavy) to generate the three SILAC labeling mediums. Each medium with the full complement of amino acids at the standard concentration for each media, was sterile filtered through a 0.22μ filter (Milipore, Bedford MA). VCaP cell line was grown in the corresponding labeling media, supplemented with 2 mM L-glutamine (Gibco), 10% dialyzed fetal bovine serum (Sigma) and antibiotics (Gibco), in a humidified atmosphere with 5% CO2. Cells were grown for at least eight cell divisions in labeling media.

ERG-Protein Interaction Studies: VCaP cells were grown for 3 weeks (8 cell doublings) in DMEM depleted of L-arginine and L-lysine (Caisson Labs Inc.) and supplemented with 10% dialyzed FBS (Sigma) and amino acids as described above to generate light- and heavy-labeled cells. Cells were lysed in low volume of IP lysis buffer (50 mM Tris-HCl, pH 7.5, 150 mM NaCl, 0.1% SDS, 1% NP-40, 0.1% sodium deoxycholate, 1 mM EDTA) supplemented with complete protease inhibitor cocktail (Roche) generating highly concentrated lysates (~10 mg/ml). For the immunoprecipitation reactions, lysates were diluted ten-fold into mild IP buffer (50 mM Tris-HCl, pH 7.5, 150 mM NaCl, 1% NP-40, protease inhibitors cocktail) to a concentration of 1 mg/ml. 5 mg of heavy-labeled protein lysate was incubated over night with 4 μg anti ERG (C20) antibody (Santa Cruz). 5 mg of light-labeled lysates were incubated with 4 μg isotype-matched IgG antibody (Santa Cruz) as a non-specific control for binding to antibody and/or to Protein A/G sepharose beads. The reactions were incubated with 50 μl of 50% beads slurry (pre-washed 3 times in PBS) for 2 hours at room temperature. Finally, the reactions were washed 3 times in IP buffer and one time in the same buffer lacking the NP40. The beads/antibody/ERG complex were eluted in 25 μl of 0.1% trifluoroacetic acid for 1 min at room temperature followed by immediate neutralization with 25 μl of 1M Tris HCl pH 8.0. The supernatants were subjected to mass spectrometric analysis, as described below. For a second replicate, labels were swapped such that heavy labeled lysates were incubated with control and light labeled lysates with anti-ERG antibody.

1D-SDS-PAGE and MS Analysis for ERG-Protein Interaction Studies: The beads from immunopurification samples were washed once with IP lysis buffer (Pierce), then the two different lysates of each replicate were combined, washed again and reduced and alkylated, on bead, in 2 mM DTT and 10 mM iodoacetamide respectively. One part LDS buffer (Invitrogen) was added to three parts sample (including beads) and tubes heated to 70° C. for 10 minutes. Proteins were resolved on a 4-12% gradient 1.5 mm thick Bis-Tris gel with MES running buffer (Nupage, Invitrogen) and Coomassie stained (Simply Blue, Invitrogen). Gel lanes were excised into eight pieces and then further cut into 1.5 mm cubes. The gel pieces were further destained in a solution containing 50% EtOH and 50% 50 mM ammonium bicarbonate, then dehydrated in 100% EtOH before addition of sufficient trypsin (12.5 ng/µL) to swell the gel pieces completely. An additional 100 µL of 50 mM ammonium bicarbonate was added before incubating at 37° C. overnight on a thermomixer (Eppendorf). Enzymatic digestion was stopped by the addition of 100 µL of 1% TFA to tubes. A second extraction with 300 µL of 0.1% TFA was combined with the first extract and the peptides from each gel slice cleaned up on C18 StageTips (Rappsilber et al., 2007). Peptides were eluted in 50 µL of 80% acetonitrile/0.1% TFA and dried down in an evaporative centrifuge to remove organic solvents. The peptides were then reconstituted with 3% ACN in 0.1% formic acid. Reconstituted peptides were separated on an online nanoflow EASY-nLC 1000 UHPLC system (Thermo Fisher Scientific) and analyzed on a benchtop Orbitrap Q Exactive mass spectrometer (Thermo Fisher Scientific). The peptide samples were injected onto a capillary column (Picofrit with 10 µm tip opening/75 µm diameter, New Objective, PF360-75-10-N-5) packed in-house with 20 cm 018 silica material (1.9 µm ReproSil-Pur C18-AQ medium, Dr. Maisch GmbH, r119.aq). The UHPLC setup was connected with a custom-fit microadapting tee (360 µm, IDEX Health & Science, UH-753), and capillary columns were heated to 50 C in column heater sleeves (Phoenix-ST) to reduce backpressure during UHPLC separation. Injected peptides were separated at a flow rate of 200 nL/min with a linear 80 min gradient from 100% solvent A (3% acetonitrile, 0.1% formic acid) to 30% solvent B (90% acetonitrile, 0.1% formic acid), followed by a linear 6 min gradient from 30% solvent B to 90% solvent B. Each sample was run for 150 min, including sample loading and column equilibration times. Data-dependent acquisition was obtained using Xcalibur 2.2 software in positive ion mode at a spray voltage of 2.00 kV. MS1 Spectra were measured with a resolution of 70,000, an AGC target of 3e6 and a mass range from 300 to 1800 m/z. Up to 12 MS2 spectra per duty cycle were triggered at a resolution of 17,500, an AGC target of 5e4, an isolation window of 2.5 m/z and a normalized collision energy of 25. Peptides that triggered MS2 scans were dynamically excluded from further MS2 scans for 20 s.

Identification and Quantification of Proteins for ERG-Protein Interaction Studies: All mass spectra were analyzed with MaxQuant software version 1.3.0.5(33) using a human Uniprot database. MS/MS searches for the proteome data sets were performed with the following parameters: Oxidation of methionine and protein N-terminal acetylation as variable modifications; carbamidomethylation as fixed modification. Trypsin/P was selected as the digestion enzyme, and a maximum of 3 labeled amino acids and 2 missed cleavages per peptide were allowed. The mass tolerance for precursor ions was set to 20 p.p.m. for the first search (used for nonlinear mass re-calibration) and 6 p.p.m. for the main search. Fragment ion mass tolerance was set to 20 p.p.m. For identification a maximum FDR of 1% was applied separately on protein, peptide and PTM-site level. 2 or more unique/razor peptides were required for protein identification and a ratio count of 2 or more for protein quantification per replicate measurement. To assign interacting proteins the Limma package in the R environment was used to calculate moderated t-test p, as described previously (N. D. Udeshi et al., Refined preparation and use of anti-diglycine remnant (K-epsilon-GG) antibody enables routine quantification of 10,000 s of ubiquitination sites in single proteomics experiments. Mol Cell Proteomics 12, 825 (March, 2013)).

Mass Spectrometry: VCaP nuclear extracts were immunoprecipitated with cross-linked antibodies against either IgG (Cell Signaling Technology) or ERG (C-17, Santa-Cruz). Samples were then run on a 4%-12% Bis-Tris Gel (Thermo Scientific) and subjected to Coomassie staining. Bands were then cut from each IP from the 40-60 KDa and 140-200 KDa regions and submitted to the Taplin Biological Mass Spectrometry Facility (Harvard Medical School) for analysis.

Nuclear Extract Preparation: Cell types were grown under standard conditions and lysed and homogenized in Buffer A (10 mM HEPES (pH 7.6), 25 mM KCL, 1 mM EDTA, 10% glycerol, 1 mM DTT, and protease inhibitors (Roche) supplemented with 1 mM PMSF) on ice. Nuclei were sedimented by centrifugation (1,200 rpm), resuspended in Buffer C (10 mM HEPES (pH 7.6), 3 mM MgCl2, 100 MM KCL, 0.1 mM EDTA, 10% glycerol, 1 mM DTT and protease inhibitors), and lysed by the addition of ammonium sulfate to a final concentration of 0.3M. Soluble nuclear proteins were separated by ultracentrifugation (100,000×g) and precipitated with 0.3 mg/ml ammonium sulfate for 20 mins on ice. Protein precipitate was isolated by ultracentrifugation (100,000×g) and resuspended in IP buffer (300 mM NaCl, 50 mM Tris-HCl [pH 8.0], 1% NP-40, 0.5% deoxycholate, 1 mM DTT, 1 mM PMSF with protease inhibitors) for immunoprecipitation analyses or HEMG-0 buffer (25 mM HEPES [pH 7.9], 0.1 mM EDTA, 12.5 mM MgCl2, 100 mM KCl, supplemented with DTT and PMSF) for analyses on glycerol gradient.

Immunoprecipitation: Nuclear extracts were resuspended in IP buffer and placed in protein lo-bind tubes (Eppendorf). Protein concentration was determined using Bradford assay and adjusted to the final volume of 250 µl at a final concentration of 1.5 mg/ml with IP buffer. Each IP was incubated with 2.5 µg of antibody (Antibody specifications are found in Table 3 above as for Examples Section I) overnight at 4° C. and then for 1 h with 20 µl Protein G Sepharose beads. The beads were then washed five times at 4° C. with IP buffer and resuspended in 20 µl 2× gel loading buffer: (4×LDS buffer; Invitrogen)+DTT and water.

Depletion Studies: Nuclear extracts were prepared to a final concentration of 2.5 mg/ml with IP buffer. Each IP was incubated with 2.5 µg of antibody overnight at 4° C. and then for 1 h with 15 µl pre-washed Protein G Sepharose beads. After centrifugation (10,000 rpm for 1 min), 45 µl of the supernatant was either saved or used for another round of IP. In total, 3 rounds of IP were performed.

Urea Denaturation Studies: Nuclear extracts (150 µg) were subjected to partial urea denaturation, ranging from 0.25 to 2.5 M urea (in IP buffer), for 30 min at room temperature (RT) prior to anti-BRG1 or anti-ERG IP. The co-precipitated proteins were analyzed by immunoblot. Quantitative densitometry analyses were performed with the Li-Cor Oddessy Imaging System (Li-COR Biosciences, Lincoln, NE, USA).

Density Sedimentation Analyses: Nuclear extract (500 µg) was resuspended in 200 ml of 0% glycerol HEMG buffer and carefully overlaid onto a 10 ml 10%-30% glycerol (in HEMG buffer) gradient prepared in a 14×89 mm polyallomer centrifuge tube (331327, Beckman Coulter, Brea, CA, USA). Tubes were centrifuged in an SW40 rotor at 4° C. for 16 hr at 40,000 rpm. Fractions (0.5 ml) were collected and used in analyses.

Transient Transfection Studies: Briefly, 293T cells were plated in 6-well plates to 80% confluence prior to transfection using polyethylenimine (PEI) in a 3:1 PEI:DNA ratio and were harvested after 48 h.

Lentiviral Generation: Lentivirus was produced by PEI (Polysciences Inc.) transfection of 293t LentiX cells (Clontech) with gene delivery vector co-transfected with packaging vectors pspax2 and pMD2.G as previously described (Kadoch and Crabtree, Cell 2013). Supernatants were harvested 72 h post-transfection and centrifuged at 20,000 rpm for 2 h at 4° C. Virus containing pellets were resuspended in PBS and placed on cells dropwise. Selection of letntivirally-infected cells was achieved with either blasticydin or puromycin, both used at 2 µg/ml. Overexpression or KD efficiency was determined by Western blot analysis.

Chromatin Immunoprecipitation: Chromatin immunoprecipitation (ChIP) experiments were performed per standard protocols (Millipore, Billerica, MA) with minor modifications. Briefly, cells were cross-linked for 10 min with 1% formaldehyde at 37° C. This reaction was subsequently quenched with 2.5M glycine for 5 min. Each ChIP was performed on soluble, sonicated chromatin from 5 million cells. DNA-protein complexes were immunoprecipitated with the following antibodies: anti-BRG1 (J1), anti-BAF155 (Homemade), anti-ERG (ab92513, Abcam, Cambridge, MA), anti-V5 (ab15828, Abcam). Validation of the antibodies is provided on the manufacturers' websites.

RNA Preparation: All RNA was produced using the RNeasy Mini Kit (Qiagen).

Library Prep and Sequencing for ChIp-Seq and RNA-Seq: All library prep and sequencing (75 bp single end on Illuminia Nextseq 500) was performed in the Molecular Biology Core Facilities at the Dana-Farber Cancer Institute.

Sequence Data Processing: ChIP-seq reads were mapped to the human reference genome (hg19) using Bowtie2 (Langmead and Salzberg, 2012) version 2.1.0 with parameters-k 1. RNA-seq reads were mapped to the human reference genome (hg19) using STAR (Dobin et al., 2013) version 2.3.1 with default parameters. All sequence data is deposited in the Sequence Read Archive under SRP074422.

ChIP-Seq Data Analysis: Peaks were called against input reads using MACS2 (Zhang et al., 2008) version 2.1.0 at q=1e-3. Peaks were filtered to remove peaks that overlap with ENCODE blacklisted regions. Duplicate reads were removed using samtools rmdup for all downstream analyses. ChIP-seq track densities were generated per million mapped reads with MACS2 2.1.0 using parameters -B -SPMR. Metagene average read densities were generated using HTSeq (Anders et al., 2015), with fragment length extended to 200 bp to account for the average 200 bp fragment size selected in sonication, centered on narrow peak summits from MACS2 peak calls. Total read counts were normalized by the number of peak sites and the number of mapped reads to give reads per site per million mapped reads. For motif enrichment analysis, 500 bp core sequences centered on peak summits were submitted to MEME-ChIP analysis (Machanick and Bailey, 2011). Determinations of peak overlap and condition-specific sites were made using BEDTools (Quinlan and Hall, 2010) version 2.21.0 parameter -A. Distance to TSS for ChIP-seq peaks was determined using hg19 refFlat annotation for nearest edge of peak to annotated start site.

RNA-Seq Data Analysis: RPKM values for biological duplicate RNA-seq samples were generated using GFold (Feng et al., 2012) version 1.1.0. All error bars represent MeantSEM. Significance was assessed using the R package DESeq2 (Love et al., 2014) using raw read counts generated with Rsubread featureCounts against the hg19 refFlat annotation. Significantly changing genes were assessed with a Bonferri-corrected p-value of less than 1e-3 and a two-fold gene expression change (|log 2FC|>1) to determine set of significantly changing genes. ERG target gene set was determined using genes significantly upregulated by ERG in VCaP (shCt vs. shERG) and LHS-AR (ERG vs. Empty). BAF-Dependent ERG target gene set was determined using genes significantly upregulated in LHS-AR ERG vs. Empty and LHS-AR ERG vs. ERG-Δ259_265 comparisons. GSEA was performed on the Log 2FC values using the GSEA Preranked function of the JAVA program (http://www.broadinstitute.org/gsea) as described previously (Subramanian et al., 2005). GO Term analysis was performed on the target gene sets using biological processes annotation (Gene Ontology. 2015). For clustering analysis, RPKM values were normalized to log 2(RPKM+1), and the 5% most variable genes were analyzed with the R package corpcor to determine principle components. Pairwise correlation was determined using a Pearson correlation coefficient between normalized expression values.

Published Data Sets: ChIP-seq data sets were obtained for H3K27ac in VCaP cells for H3K27ac from GSM1328982, for AR from GSM1328945 and GSM1328947, for BRD4 from GSM1328959, for RNA Polymerase II from GSM1328964 (Asangani et al., 2014).

TABLE 4

Number of raw, mapped, and enriched regions for all high-throughput sequencing data

| Type | Sample | Total Number Raw Reads | Total Number Mapped Reads | Percent Mapped Reads | Total Number Nonredundant Reads | Number of Peaks | Fraction of Non Redundant Reads in Peaks |
|---|---|---|---|---|---|---|---|
| ChIP | VCaP_shCt_ERG | 41535836 | 39838522 | 95.9 | 29405521 | 76362 | 0.209 |
| ChIP | VCaP_shCt_SMARCC1 | 22872610 | 21972960 | 96.1 | 16138697 | 48118 | 0.103 |
| ChIP | VCaP_shCt_SMARCA4 | 23090167 | 22215428 | 96.2 | 18245321 | 45174 | 0.099 |
| ChIP | VCaP_shCt_Input | 31717626 | 30110206 | 94.9 | 27313594 | NA | NA |
| ChIP | VCaP_shERG_ERG | 22837813 | 21800258 | 95.5 | 15663801 | 45602 | 0.137 |
| ChIP | VCaP_shERG_SMARCC | 22974010 | 22150742 | 96.4 | 15543867 | 42538 | 0.09 |

TABLE 4-continued

Number of raw, mapped, and enriched regions for all high-throughput sequencing data

| Type | Sample | Total Number Raw Reads | Total Number Mapped Reads | Percent Mapped Reads | Total Number Nonredundant Reads | Number of Peaks | Fraction of Non Redundant Reads in Peaks |
|---|---|---|---|---|---|---|---|
| ChIP | VCaP_shERG_SMARCA | 22673220 | 21997312 | 97 | 17056416 | 55704 | 0.119 |
| ChIP | VCaP_shERG_Input | 33171111 | 31643837 | 95.4 | 29963973 | NA | NA |
| ChIP | LHSAR_empty_V5 | 25622249 | 24397188 | 95.2 | 15259614 | 194 | 0.006 |
| ChIP | LHSAR_empty_SMARC | 39111951 | 38178743 | 97.6 | 24461156 | 31738 | 0.074 |
| ChIP | LHSAR_empty_SMARCA | 51766963 | 50719806 | 98 | 16497175 | 39021 | 0.11 |
| ChIP | LHSAR_empty_Input | 139522580 | 134215051 | 96.2 | 115885927 | NA | NA |
| ChIP | LHSAR_ERG_V5 | 26959464 | 25653132 | 95.2 | 16895539 | 17845 | 0.045 |
| ChIP | LHSAR_ERG_SMARCC | 52637361 | 51388581 | 97.6 | 26152170 | 41465 | 0.093 |
| ChIP | LHSAR_ERG_SMARCA4 | 50429513 | 49459989 | 98.1 | 29521869 | 62300 | 0.153 |
| ChIP | LHSAR_ERG_Input | 130198453 | 123638593 | 95 | 99318114 | NA | NA |
| RNA | LHSAR_empty_1 | 57592337 | 56570579 | 98.2 | NA | NA | NA |
| RNA | LHSAR_empty_2 | 67861485 | 66472970 | 98 | NA | NA | NA |
| RNA | LHSAR_ERG_1 | 58121362 | 57204118 | 98.4 | NA | NA | NA |
| RNA | LHSAR_ERG_2 | 65450667 | 64231956 | 98.1 | NA | NA | NA |
| RNA | LHSAR_ERG- | 44843260 | 44233606 | 98.6 | NA | NA | NA |
| RNA | LHSAR_ERG- | 54059093 | 53278501 | 98.6 | NA | NA | NA |
| RNA | LHSAR_ERG- | 55914683 | 54956726 | 98.3 | NA | NA | NA |
| RNA | LHSAR_ERG- | 56479915 | 55516640 | 98.3 | NA | NA | NA |
| RNA | LHSAR_ERG-R367K_1 | 74709546 | 72071927 | 96.5 | NA | NA | NA |
| RNA | LHSAR_ERG-R367K_2 | 33377939 | 32247344 | 96.6 | NA | NA | NA |
| RNA | LHSAR_ETV1_1 | 28038632 | 26985292 | 96.2 | NA | NA | NA |
| RNA | LHSAR_ETV1_2 | 35049138 | 33935450 | 96.8 | NA | NA | NA |
| RNA | VCaP_shCt_1 | 33232416 | 31004895 | 93.3 | NA | NA | NA |
| RNA | VCaP_shCt_2 | 36669217 | 34309864 | 93.6 | NA | NA | NA |
| RNA | VCaP_shERG_1 | 52490697 | 49921163 | 95.1 | NA | NA | NA |
| RNA | VCaP_shERG_2 | 56808834 | 54011802 | 95.1 | NA | NA | NA |

Electrophoretic Mobility Shift Assay (EMSA): The DNA-protein binding reaction was carried out as described previously 18 with following modifications. We used the polyomavirus enhancer (Py) probe 5'/IRD800/ GATCTTTAAGCAGGAAGTGACTAACTGACCGCAGGTGG ATC-3' (SEQ ID NO: 1) modified at the 5' end with the infrared fluorescent dye IRD800 (IRD800-Py) for facile detection on the Odyssey CLx imaging system from LI-COR. Duplex DNA formation was carried out on a thermocycler with the complement of IRD800-Py. The DNA binding assay was assessed in a total volume of 10 uL of binding buffer at room temperature for 20 min. ERG/duplex IRD800-Py complex was analyzed on a 6% DNA Retardation Gel in 0.5×TBE (ThermoFisher Scientific).

The methods of the present disclosure are not to be limited in scope by the specific embodiments described herein. Indeed, various modifications of the invention in addition to those described herein will become apparent to those skilled in the art from the foregoing description. Such modifications are intended to fall within the scope of the appended claims.

REFERENCES

Adamo, P., and Ladomery, M. R. (2016). The oncogene ERG: a key factor in prostate cancer. Oncogene 35, 403-414.

Anders, S., Pyl. P. T., and Huber, W. (2015). HTSeq—a Python framework to work with high-throughput sequencing data. Bioinformatics (Oxford, England) 31, 166-169.

Asangani, I. A., Dommeti, V. L., Wang, X., Malik, R., Cieslik, M., Yang, R., Escara-Wilke, J., Wilder-Romans, K., Dhanireddy, S., Engelke, C., et al. (2014). Therapeutic targeting of BET bromodomain proteins in castration-resistant prostate cancer. Nature 510, 278-282.

Basuyaux, J. P., Ferreira, E., Stehelin, D., and Buttice. G. (1997). The Ets transcription factors interact with each other and with the c-Fos/c-Jun complex via distinct protein domains in a DNA-dependent and -independent manner. J Biol Chem 272, 26188-26195.

Bendall, S. C., Hughes, C., Stewart, M. H., Doble, B., Bhatia, M., and Lajoie, G. A. (2008). Prevention of amino acid conversion in SILAC experiments with embryonic stem cells. Mol Cell Proteomics 7. 1587-1597.

Berger, R., Febbo, P. G., Majumder, P. K., Zhao, J. J., Mukherjee, S., Signoretti, S., Campbell, K. T., Sellers, W. R., Roberts, T. M., Loda, M., et al. (2004). Androgen-induced differentiation and tumorigenicity of human prostate epithelial cells. Cancer Res 64, 8867-8875.

Bormo, S. T., Fischer, A., Kerick, M., Faith, M., Laible, M., Brase, J. C., Kuner, R., Dahl, A., Grimm, C., Sayanjali, B., et al. (2012). Genome-wide DNA methylation events in TMPRSS2-ERG fusion-negative prostate cancers implicate an EZH2-dependent mechanism with miR-26a hypermethylation. Cancer Discov 2, 1024-1035.

Cancer Genome Atlas Research, N. (2015). The Molecular Taxonomy of Primary Prostate Cancer. Cell 163, 1011-1025.

Chen, Y., Chi, P., Rockowitz, S., Iaquinta, P. J., Shamu, T., Shukla, S., Gao, D., Sirota, I., Carver, B. S., Wongvipat, J., et al. (2013). ETS factors reprogram the androgen receptor cistrome and prime prostate tumorigenesis in response to PTEN loss. Nat Med 19, 1023-1029.

Chng, K. R., Chang, C. W., Tan, S. K., Yang, C., Hong, S. Z., Sng, N. Y., and Cheung, E. (2012). A transcriptional repressor co-regulatory network governing androgen response in prostate cancers. EMBO J 31, 2810-2823.

Clark, J., Attard, G., Jhavar, S., Flohr, P., Reid, A., De-Bono, J., Eeles, R., Scardino, P., Cuzick, J., Fisher, G., et al.

(2008). Complex patterns of ETS gene alteration arise during cancer development in the human prostate. Oncogene 27, 1993-2003.

Clark, J. P., and Cooper, C. S. (2009). ETS gene fusions in prostate cancer. Nat Rev Urol 6, 429-439.

Delattre, O., Zucman, J., Plougastel, B., Desmaze, C., Melot, T., Peter, M., Kovar, H., Joubert, I., de Jong, P., Rouleau, G., et al. (1992). Gene fusion with an ETS DNA-binding domain caused by chromosome translocation in human tumours. Nature 359, 162-165.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics (Oxford, England) 29. 15-21.

Donaldson, L. W., Petersen, J. M., Graves, B. J., and McIntosh, L. P. (1996). Solution structure of the ETS domain from murine Ets-1: a winged helix-turn-helix DNA binding motif. EMBO J 15, 125-134.

Feng, J., Meyer, C. A., Wang, Q., Liu, J. S., Shirley Liu, X., and Zhang, Y. (2012). GFOLD: a generalized fold change for ranking differentially expressed genes from RNA-seq data. Bioinformatics (Oxford, England) 28, 2782-2788.

Gene Ontology, C. (2015). Gene Ontology Consortium: going forward. Nucleic Acids Res 43, D1049-1056.

Helgeson, B. E., Tomlins, S. A., Shah, N., Laxman, B., Cao, Q., Prensner, J. R., Cao, X., Singla. N., Montie, J. E., Varambally, S., et al. (2008). Characterization of TMPRSS2:ETV5 and SLC45A3:ETV5 gene fusions in prostate cancer. Cancer Res 68, 73-80.

Ho, L., Jothi, R., Ronan, J. L., Cui, K., Zhao, K., and Crabtree, G. R. (2009). An embryonic stem cell chromatin remodeling complex, esBAF, is an essential component of the core pluripotency transcriptional network. Proceedings of the National Academy of Sciences of the United States of America 106, 5187-5191.

Ichikawa, H., Shimizu, K., Hayashi, Y., and Ohki, M. (1994). An RNA-binding protein gene, TLS/FUS, is fused to ERG in human myeloid leukemia with t(16; 21) chromosomal translocation. Cancer Res 54, 2865-2868.

Kadoch, C., and Crabtree, G. R. (2015). Mammalian SWI/SNF chromatin remodeling complexes and cancer Mechanistic insights gained from human genomics. Sci Adv 1, e1500447.

Kadoch, C., Hargreaves, D. C., Hodges, C., Elias, L., Ho, L., Ranish, J., and Crabtree, G. R. (2013). Proteomic and bioinformatic analysis of mammalian SWI/SNF complexes identifies extensive roles in human malignancy. Nat Genet 45, 592-601.

Klezovitch, O., Risk, M., Coleman, I., Lucas, J. M., Null, M., True, L. D., Nelson, P. S., and Vasioukhin, V. (2008). A causal role for ERG in neoplastic transformation of prostate epithelium. Proceedings of the National Academy of Sciences of the United States of America 105, 2105-2110.

Kumar-Sinha, C., Tomlins, S. A., and Chinnaiyan, A. M. (2008). Recurrent gene fusions in prostate cancer. Nat Rev Cancer 8, 497-511.

Kunderfranco. P., Mello-Grand, M., Cangemi, R., Pellini, S., Mensah. A., Albertini, V., Malek, A., Chiorino, G., Catapano, C. V., and Carbone, G. M. (2010). ETS transcription factors control transcription of EZH2 and epigenetic silencing of the tumor suppressor gene Nkx3.1 in prostate cancer. PLoS One 5, e10547.

Langmead, B., and Salzberg, S. L. (2012). Fast gapped-read alignment with Bowtie 2. Nature methods 9, 357-359.

Link, K. A., Balasubramaniam, S., Sharma. A., Comstock, C. E., Godoy-Tundidor, S., Powers, N., Cao, K. H., Haelens, A., Claessens, F., Revelo, M. P., et al. (2008). Targeting the BAF57 SWI/SNF subunit in prostate cancer a novel platform to control androgen receptor activity. Cancer Res 68, 4551-4558.

Love, M. I., Huber, W., and Anders, S. (2014). Moderated estimation of fold change and dispersion for RNA-seq data with DESeq2. Genome biology 15, 550.

Lupien, M., Eeckhoute, J., Meyer, C. A., Wang, Q., Zhang, Y., Li, W., Carroll, J. S., Liu, X. S., and Brown, M. (2008). FoxA1 translates epigenetic signatures into enhancer-driven lineage-specific transcription. Cell 132, 958-970.

Machanick, P., and Bailey, T. L. (2011). MEME-ChIP: motif analysis of large DNA datasets. Bioinformatics (Oxford, England) 27, 1696-1697.

Mackereth, C. D., Scharpf, M., Gentile, L. N., Macintosh, S. E., Slupsky, C. M., and McIntosh, L. P. (2004). Diversity in structure and function of the Ets family PNT domains. J Mol Biol 342, 1249-1264.

Mele, M., Ferreira, P. G., Reverter, F., DeLuca, D. S., Monlong, J., Sammeth, M., Young, T. R., Goldmann, J. M., Pervouchine, D. D., Sullivan, T. J., et al. (2015). Human genomics. The human transcriptome across tissues and individuals. Science 348, 660-665.

Mounir, Z., Korn, J. M., Westerling, T., Lin, F., Kirby, C. A., Schirle, M., McAllister, G., Hoffman, G., Ramadan, N., Hartung, A., et al. (2016). ERG signaling in prostate cancer is driven through PRMT5-dependent methylation of the androgen receptor. Elife 5.

Nagaich, A. K., Walker, D. A., Wolford, R., and Hager, G. L. (2004). Rapid periodic binding and displacement of the glucocorticoid receptor during chromatin remodeling. Mol Cell 14, 163-174.

Ong, S. E., and Mann, M. (2006). A practical recipe for stable isotope labeling by amino acids in cell culture (SILAC). Nat Protoc 1, 2650-2660.

Paulo, P., Barros-Silva, J. D., Ribeiro, F. R., Ramalho-Carvalho, J., Jeronimo, C., Henrique, R., Lind, G. E., Skotheim, R. I., Lothe, R. A., and Teixeira, M. R. (2012). FLI1 is a novel ETS transcription factor involved in gene fusions in prostate cancer. Genes Chromosomes Cancer 51, 240-249.

Pomerantz, M. M., Li, F., Takeda, D. Y., Lenci, R., Chonkar, A., Chabot, M., Cejas, P., Vazquez, F., Cook, J., Shivdasani, R. A., et al. (2015). The androgen receptor cistrome is extensively reprogrammed in human prostate tumorigenesis. Nat Genet 47, 1346-1351.

Prensner, J. R., Iyer, M. K., Sahu, A., Asangani, I. A., Cao, Q., Patel, L., Vergara, I. A., Davicioni, E., Erho, N., Ghadessi, M., et al. (2013). The long noncoding RNA SChLAP1 promotes aggressive prostate cancer and antagonizes the SWI/SNF complex. Nat Genet 45, 1392-1398.

Quinlan, A. R., and Hall, I. M. (2010). BEDTools: a flexible suite of utilities for comparing genomic features. Bioinformatics (Oxford, England) 26, 841-842.

Rappsilber, J., Mann, M., and Ishihama, Y. (2007). Protocol for micro-purification, enrichment, pre-fractionation and storage of peptides for proteomics using StageTips. Nat Protoc 2, 1896-1906.

Roberts, C. W., and Orkin, S. H. (2004). The SWI/SNF complex-chromatin and cancer. Nat Rev Cancer 4, 133-142.

Shen, H., Powers, N., Saini, N., Comstock, C. E., Sharma, A., Weaver, K., Revelo, M. P., Gerald, W., Williams, E., Jessen, W. J., et al. (2008). The SWI/SNF ATPase Brm is a gatekeeper of proliferative control in prostate cancer. Cancer Res 68, 10154-10162.

Siegel, R. L., Miller, K. D., and Jemal, A. (2015). Cancer statistics, 2015. CA Cancer J Clin 65, 5-29.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proceedings of the National Academy of Sciences of the United States of America 102, 15545-15550.

Sun, C., Dobi, A., Mohamed, A., Li, H., Thangapazham, R. L., Furusato, B., Shaheduzzaman, S., Tan, S. H., Vaidyanathan, G., Whitman, E., et al. (2008). TMPRSS2-ERG fusion, a common genomic alteration in prostate cancer activates C-MYC and abrogates prostate epithelial differentiation. Oncogene 27, 5348-5353.

Tomlins, S. A., Laxman, B., Varambally, S., Cao, X., Yu, J., Helgeson, B. E., Cao, Q., Prensner, J. R., Rubin, M. A., Shah, R. B., et al. (2008). Role of the TMPRSS2-ERG gene fusion in prostate cancer. Neoplasia 10, 177-188.

Tomlins, S. A., Mehra, R., Rhodes, D. R., Smith, L. R., Roulston, D., Helgeson, B. E., Cao, X., Wei, J. T., Rubin, M. A., Shah, R. B., et al. (2006). TMPRSS2:ETV4 gene fusions define a third molecular subtype of prostate cancer. Cancer Res 66, 3396-3400.

Tomlins, S. A., Rhodes, D. R., Perner, S., Dhanasekaran, S. M., Mehra, R., Sun, X. W., Varambally, S., Cao, X., Tchinda, J., Kuefer, R., et al. (2005). Recurrent fusion of TMPRSS2 and ETS transcription factor genes in prostate cancer. Science 310, 644-648.

Varambally, S., Dhanasekaran, S. M., Zhou, M., Barrette. T. R., Kumar-Sinha, C., Sanda, M. G., Ghosh, D., Pienta, K. J., Sewalt, R. G., Otte, A. P., et al. (2002). The polycomb group protein EZH2 is involved in progression of prostate cancer. Nature 419, 624-629.

Verger, A., Buisine, E., Carrere, S., Wintjens. R., Flourens, A., Coill, J., Stehelin, D., and Duterque-Coquillaud, M. (2001). Identification of amino acid residues in the ETS transcription factor Erg that mediate Erg-Jun/Fos-DNA ternary complex formation. J Biol Chem 276, 17181-17189.

Yang, Y. A., and Yu, J. (2013). EZH2, an epigenetic driver of prostate cancer. Protein Cell 4, 331-341.

Yu, J., Yu, J., Mani, R. S., Cao, Q., Brenner, C. J., Cao, X., Wang, X., Wu, L., Li, J., Hu, M., et al. (2010). An integrated network of androgen receptor, polycomb, and TMPRSS2-ERG gene fusions in prostate cancer progression. Cancer Cell 17, 443-454.

Yu, M., Mazor, T., Huang, H., Huang, H. T., Kathrein, K. L., Woo, A. J., Chouinard, C. R., Labadorf, A., Akie, T. E., Moran, T. B., et al. (2012). Direct recruitment of polycomb repressive complex 1 to chromatin by core binding transcription factors. Mol Cell 45, 330-343.

Zhang, Y., Liu, T., Meyer, C. A., Eeckhoute, J., Johnson, D. S., Bernstein, B. E., Nusbaum, C., Myers, R. M., Brown, M., Li, W., et al. (2008). Model-based analysis of ChIP-Seq (MACS). Genome biology 9, R137.

Zong, Y., Xin, L., Goldstein, A. S., Lawson, D. A., Teitell, M. A., and Witte, O. N. (2009). ETS family transcription factors collaborate with alternative signaling pathways to induce carcinoma from adult murine prostate cells. Proceedings of the National Academy of Sciences of the United States of America 106, 12465-12470.

The invention claimed is:

1. A method of identifying a compound that interferes with the physical interaction between an erythroblast transformation specific (ETS)-related gene (ERG) protein, and a mouse Switch/Sucrose Non-Fermentable (mSWI/SNF) (BRG1-associated factors (BAF)) chromatin remodeling complex protein, wherein i) the ERG protein is ERG: ΔPNT domain (deletion of pointed domain), ERG: ΔETS domain (deletion of ETS domain), ERG: ΔCAD domain (deletion of C-terminal Activation domain), ERG-Δ225-271, ERG-Δ259-265, or ERG: R367K Mutant (R367K DNA Binding mutant) and ii) the mSWI/SNF (BAF) chromatin remodeling complex protein is BAF155, the method comprising:

a) administering a candidate compound at a first concentration to a first set of one or more cells;

b) directly determining the strength of the protein-protein interaction between the ERG protein and the mSWI/SNF (BAF) chromatin remodeling complex protein in the first set of one or more cells using mass spectrometry;

c) administering the candidate compound at a second concentration to a second set of one or more cells;

d) directly determining the strength of the protein-protein interaction between the ERG protein and the mSWI/SNF (BAF) chromatin remodeling complex protein in the second set of one or more cells using mass spectrometry; and e) comparing the strength of the interaction between the ERG protein and the mSWI/SNF (BAF) chromatin remodeling complex protein of the first set of one or more cells to the strength of the interaction between the ERG protein and the mSWI/SNF (BAF) chromatin remodeling complex protein of the second set of one or more cells, wherein if the strength of the interaction between the ERG protein and the mSWI/SNF (BAF) chromatin remodeling complex protein in the first set of one or more cells is weaker than the strength of the interaction between the ERG protein and the mSWI/SNF (BAF) chromatin remodeling complex protein in the second set of one or more cells, then the candidate compound interferes with interaction between the ERG protein and the mSWI/SNF (BAF) chromatin remodeling complex protein.

2. The method of claim 1, wherein the first and second sets of one or more cells are normal prostate cells, prostate cancer cells, normal prostate cell line cells, or prostate cancer cell line cells.

3. The method of claim 2, wherein the first and second sets of one or more cells are vertebral-cancer of the prostate (VCaP) cells, prostate cancer-3 (PC-3) cells, prostate epithelial cells ectopically expressing simian virus 40 (SV40) large T antigen (LT), SV40 small T antigen (ST), telomerase reverse transcriptase (TERT), and androgen receptor (AR) (LHS-AR cells), LHS-AR cells ectopically expressing an ERG protein, or LHS-AR cells ectopically expressing an ETV1 protein.

4. The method of claim 1, wherein the interaction between the ERG protein and the mSWI/SNF (BAF) chromatin remodeling complex protein of the first set of one or more cells is at least 20%, 30%, 40%, 50%, 60%, 70%, 80%, or 90% weaker than the ERG protein and the mSWI/SNF (BAF) chromatin remodeling complex protein of the second set of one or more cells.

5. The method of claim 1, wherein the determining the strength of the interaction between the ERG protein and the mSWI/SNF (BAF) chromatin remodeling complex protein comprises stable isotope labeling by amino acids in cell culture (SILAC) mass spectrometry.

6. The method of claim 1, wherein the determining the interaction between the ERG protein and the mSWI/SNF (BAF) chromatin remodeling complex protein further comprises measuring of expression of at least one prostate cancer pathway gene or protein selected from the group consisting of FLI1 (Friend leukemia integration 1 transcription factor), UBE2C (Ubiquitin-conjugating enzyme E2C), AR (androgen receptor), and EZH2 Enhancer of zeste homolog 2).

* * * * *

SEQUENCE LISTING

```
<160> NUMBER OF SEQ ID NOS: 1

<210> SEQ ID NO 1
<211> LENGTH: 41
<212> TYPE: DNA
<213> ORGANISM: Artificial Sequence
<220> FEATURE:
<223> OTHER INFORMATION: polyomavirus enhancer (Py) probe IRD800

<400> SEQUENCE: 1
gatctttaag caggaagtga ctaactgacc gcaggtggat c                          41
```